US009688689B2

(12) United States Patent
Choi et al.

(10) Patent No.: US 9,688,689 B2
(45) Date of Patent: Jun. 27, 2017

(54) COMPOUNDS AND COMPOSITIONS FOR INDUCING CHONDROGENESIS

(71) Applicants: Ha-Soon Choi, San Diego, CA (US); James Paul Lajiness, San Diego, CA (US); Srinivasa Reddy Natala, San Diego, CA (US); Bao Nguyen, San Diego, CA (US); Hank Michael James Petrassi, Cardiff, CA (US); Zhicheng Wang, San Diego, CA (US)

(72) Inventors: Ha-Soon Choi, San Diego, CA (US); James Paul Lajiness, San Diego, CA (US); Srinivasa Reddy Natala, San Diego, CA (US); Bao Nguyen, San Diego, CA (US); Hank Michael James Petrassi, Cardiff, CA (US); Zhicheng Wang, San Diego, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/709,852

(22) Filed: May 12, 2015

(65) Prior Publication Data

US 2015/0329554 A1 Nov. 19, 2015

Related U.S. Application Data

(60) Provisional application No. 61/992,815, filed on May 13, 2014.

(51) Int. Cl.

| | |
|---|---|
| *C07D 493/08* | (2006.01) |
| *A61K 31/443* | (2006.01) |
| *A61K 31/4245* | (2006.01) |
| *A61K 31/4155* | (2006.01) |
| *A61K 31/506* | (2006.01) |
| *A61K 31/34* | (2006.01) |
| *A61K 31/4439* | (2006.01) |
| *A61K 31/5377* | (2006.01) |
| *A61K 31/351* | (2006.01) |
| *A61K 31/4545* | (2006.01) |
| *A61K 31/4525* | (2006.01) |
| *A61K 31/497* | (2006.01) |
| *A61K 31/444* | (2006.01) |
| *A61K 45/06* | (2006.01) |
| *C07D 491/18* | (2006.01) |

(52) U.S. Cl.

CPC ............ *C07D 493/08* (2013.01); *A61K 31/34* (2013.01); *A61K 31/351* (2013.01); *A61K 31/4155* (2013.01); *A61K 31/4245* (2013.01); *A61K 31/443* (2013.01); *A61K 31/444* (2013.01); *A61K 31/4439* (2013.01); *A61K 31/4525* (2013.01); *A61K 31/4545* (2013.01); *A61K 31/497* (2013.01); *A61K 31/506* (2013.01); *A61K 31/5377* (2013.01); *A61K 45/06* (2013.01); *C07D 491/18* (2013.01)

(58) Field of Classification Search

None

See application file for complete search history.

(56) References Cited

U.S. PATENT DOCUMENTS

| | | | |
|---|---|---|---|
| 3,925,554 A | 12/1975 | Tottori et al. | |
| 4,707,494 A | 11/1987 | Varma et al. | |
| 5,126,370 A | 6/1992 | Misra | |
| 5,618,946 A | 4/1997 | Poss et al. | |
| 6,384,281 B1 * | 5/2002 | Keenan | C07C 211/30 546/139 |
| 2004/0077605 A1 | 4/2004 | Salvati et al. | |
| 2005/0203086 A1 | 9/2005 | Constan et al. | |
| 2006/0223832 A1 | 10/2006 | Salvati et al. | |
| 2010/0256385 A1 | 10/2010 | Woodward et al. | |

FOREIGN PATENT DOCUMENTS

| | | |
|---|---|---|
| CN | 101628951 | 1/2010 |
| DE | 2354873 | 5/1974 |
| EP | 248435 | 12/1987 |
| EP | 453960 | 10/1991 |
| JP | 4275182 | 9/1992 |
| JP | 2005097195 | 4/2005 |

(Continued)

OTHER PUBLICATIONS

Ranise, A. Farmaco Sci. 37(2) (1982) 94-104.*
Minkin, Vladimir I. Molecular Crystals and Liquid Crystals Science and Technology, Section A: Molecular Crystals and Liquid Crystals (1994), 246, 151-4.*
Gorgues, A. Tetrahedron (1986), 42(1), 351-70.*
Dong, Jing-Chao. Bioorganic & Medicinal Chemistry Letters 13 (2003) 4327-4329.*
Yatham, et al., "1,4-Bis-Dipp/Mes-1,2,4-Triazolylidenes: Carbene Catalysts That Efficiently Overcome Steric Hindrance in the Redox Esterification of α- and β-Substituted α, β-Enals", Journal of the American Chemical Society, Jan. 21, 2016, pp. 2670-2677, vol. 138, American Chemical Society.

(Continued)

*Primary Examiner* — Golam M M Shameem
*Assistant Examiner* — Laura Daniel
(74) *Attorney, Agent, or Firm* — Emily Tongco Wu; Genomics Institute of the Novartis Research Foundation

(57) ABSTRACT

The present invention provides compounds of formula I:

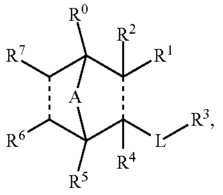

or a pharmaceutically acceptable salt, tautomer, or stereoisomer thereof, wherein the variables are as defined herein. The present invention further provides pharmaceutical compositions comprising such compounds, and methods of using such compounds for treatment of joint damage or joint injury in a mammal, and for inducing differentiation of mesenchymal stem cells into chondrocytes.

28 Claims, No Drawings

(56) References Cited

FOREIGN PATENT DOCUMENTS

| | | | |
|---|---|---|---|
| JP | 2011051945 | | 3/2011 |
| WO | 9507078 | A1 | 3/1995 |
| WO | 9515331 | A1 | 6/1995 |
| WO | 9518103 | A1 | 7/1995 |
| WO | 9526338 | A1 | 10/1995 |
| WO | 9600214 | A1 | 1/1996 |
| WO | 9740825 | A1 | 11/1997 |
| WO | 9830566 | A1 | 7/1998 |
| WO | 1999012921 | A1 | 3/1999 |
| WO | 00066577 | A1 | 11/2000 |
| WO | 0147510 | A2 | 7/2001 |
| WO | 0242310 | A2 | 5/2002 |
| WO | 02066469 | A2 | 8/2002 |
| WO | 2004014842 | A1 | 2/2004 |
| WO | 2004078169 | A1 | 9/2004 |
| WO | 2005009468 | A1 | 3/2005 |
| WO | 2005047383 | A1 | 5/2005 |
| WO | 2005049621 | A1 | 6/2005 |
| WO | 2007058156 | A1 | 5/2007 |
| WO | 2007071396 | A1 | 6/2007 |
| WO | 2007106330 | A1 | 9/2007 |
| WO | 2008097561 | A1 | 8/2008 |
| WO | 2010014141 | A1 | 2/2010 |
| WO | 2010014220 | A1 | 2/2010 |
| WO | 2010014254 | A1 | 2/2010 |
| WO | 2010099573 | A1 | 9/2010 |
| WO | 2010134014 | A1 | 11/2010 |
| WO | 2011059763 | A1 | 5/2011 |
| WO | 2011103135 | A1 | 8/2011 |
| WO | 2011163502 | A1 | 12/2011 |
| WO | 2012066488 | A1 | 5/2012 |
| WO | 2012129562 | A2 | 9/2012 |
| WO | 2012162535 | A1 | 11/2012 |
| WO | 2013171687 | A1 | 11/2013 |
| WO | 2013171694 | A1 | 11/2013 |
| WO | 2014005080 | A1 | 1/2014 |
| WO | 2014005084 | A1 | 1/2014 |
| WO | 2014168941 | A1 | 10/2014 |
| WO | 2014206966 | A1 | 12/2014 |
| WO | 2015007830 | A1 | 1/2015 |

OTHER PUBLICATIONS

Salminen, et al., "Biomass to value added chemicals: Isomerisation of 8-pinene oxide over supported ionic liquid catalysts (SILCAs) containing Lewis acids", Catalysis Today, Jun. 30, 2014, pp. 318-321, vol. 257, Elsevier B.V.

Gao, et al., "Synthesis and Insecticidal Activity of Acylthiourea Derivatives from β-pinene", Letters in Drug Design & Discovery, 2015, pp. 241-249, vol. 12, Bentham Science Publishers.

Kong, et al., "Probing the origin of carobxylate migration selectivity in Rh2(II)-catalyzed N-heterocyle formation from trisubstituted styryl azides", Tetrahedron Letters, 2015, pp. 3262-3264, vol. 56, Elsevier Ltd.

Verma, et al., "Essential oil composition of Himalayan Peony (*Paeonia emodi* Royle)", Journal of Essential Oil Research, 2015, pp. 477-480, vol. 27, No. 6, Taylor & Francis.

O'Connor, et al., "Synthesis of Amathaspiramides by Aminocyanation of Enoates", Angew. Chem. Int. Ed., 2015, pp. 9963-9966, vol. 54, Wiley-VCH Verlag GMBH & Co.

Miladinovic, et al., "Chemical Composition of the Essential Oil of Geum coccineum", Chemistry of Natural compounds, Jul. 2015, pp. 785-786, vol. 51, No. 4, Springer Science & Business Media New York.

Ardashov, et al., "The First Synthesis of (4S,5R,6R)-5,6-Dihydroxy-4-(prop-1-3n-2-yl)cyclohex-1-ene-1-carboxylic Acid", Helvetica Chimica Acta, 2015, pp. 1442-1455, vol. 98.

Pachuta-Stec, et al., "New Norcantharidin Analogs: Synthesis and Anticancer Activity", Arch. Pharm. Chem. Life Sci., 2015, pp. 897-907, vol. 348, Wiley-VCH Verlag GmbH & Col., KGaA, Weinheim.

Li, et al., "Synthesis and in vitro antitumor activity of some tetraphenylantimony derivatives of exo-7-oxa-bicyclo[2,2,1] heptane (ene)-3-arylamide-2-acid", Applied Organometallic Chemistry, Jan. 8, 2001, pp. 639-645, vol. 15, John Wiley & Sons, Ltd.

Li, et al., "Synthesis , Spectroscopic Characterization, and in vitro Antitumor Activity of Tetraphenylantimony Derivatives of Analogues of Demethylcantharidin and Demethyldehydrogen-Cantharidin", Synthesis and Reactivity in Inorganic and Metal-Organic Chemistry, 2002, pp. 583-593, vol. 32, No. 3, Taylor & Francis Informa Ltd., England.

Joshi, et al., "Synthesis & Anticonvulsant Activity of 7-Oxabicyclo[2.2.1] heptane Derivatives: Part II-N-Alkyl, N-Aryl & N-Heteroaryl Derivatives of 3,6-Epoxyhexahydrophthalic Acid Amide", Indian Journal of Chemistry, Feb. 1983, pp. 136-139, vol. 22B.

Hopkins, et al., "Synthesis and Herbicidal Activity of Small-Ring Compounds", J. Agr. Food Chem., May-Jun. 1967, pp. 501-507, vol. 15, No. 3.

Zhao, et al., "Dual suppression of estrogenic and inflammatory activities for targeting of endometriosis", Science Translational Medicine, Jan. 21, 2015, Corrected Feb. 11, 2015, see Erratum; pp. 1-15, vol. 7, Issue 271, American Association for the Advancement of Science, US.

Parella, et al., "Palladium-Catalyzed Double Activation and Arylation of 2o and 3o C(sp3)-H Bonds of the Norborane System: Formatio of a C—C and at the Bridgehead Carbon and Bridgehead Quaternary Stereocenter", Synlett, Apr. 29, 2014, pp. 1395-1402, vol. 25, Georg Thieme Verlag, Stuttgart—New York.

Baghwat, et al., "Thromboxane Receptor Antagonism Combined with Thromboxane Synthase Inhibition", J. Med. Chem., Jun. 1, 1991, pp. 1790-1797, vol. 34, No. 6, American Chemical Society.

Singh, et al., "Chemistry, Design and Structure-Activity Relationship of Cocaine Antagonists", Chem. Rev., Mar. 1, 2000, pp. 925-1024, vol. 100, No. 3, American Chemical Society.

Christensen, et al., "QSAR studies and pharmacophore identification for arylsubstituted cycloalkenecarboxylic acid methyl esters with affinity for the human dopamine transporter", Bioorganic & Medicinal Chemistry, Jun. 8, 2007, pp. 5262-5274, vol. 15, No. 15, Elsevier.

* cited by examiner

COMPOUNDS AND COMPOSITIONS FOR INDUCING CHONDROGENESIS

CROSS-REFERENCED TO RELATED APPLICATIONS

This application claims the benefit of priority to U.S. Provisional Patent Application No. 61/992,815 filed 13 May 2014; the full disclosure of which is incorporated herein by reference in its entirety and for all purposes.

BACKGROUND OF THE INVENTION

Field of the Invention

The present invention relates to the identification of a class of compounds, pharmaceutical compositions comprising such compounds and methods of using such compounds to treat joint damage resulting from joint injury and arthritis in a mammal.

Background

Osteoarthritis (OA) represents the most common musculoskeletal disorder. Approximately 40 million Americans are currently affected and this number is predicted to increase to 60 million within the next twenty years as a result of the aging population and an increase in life expectancy, making it the fourth leading cause of disability. OA is characterized by a slow degenerative breakdown of the joint including both the articular cartilage (containing the cells and matrix which produce lubrication and cushioning for the joint) and the subchondral bone underlying the articular cartilage. OA can be considered a consequence of various etiologic factors. For example, it can be caused by abnormal biomechanical stress or genetic or acquired abnormalities of articular cartilage or bone. Current OA therapies include pain relief with oral NSAIDs or selective cyclooxygenase 2 (COX-2) inhibitors, intra-articular (IA) injection with agents such as corticorsteroids and hyaluronan, and surgical approaches.

Joint damage, e.g., acute joint injury, such as a meniscal or ligament tear, or an intra-articular fracture can also lead to arthritis, e.g., posttraumatic arthritis. Because articular cartilage has a limited ability to repair, even small undetectable damage can often get worse over time and lead to OA. Current treatments for joint injury can include surgery and other invasive procedures focused on regeneration of damaged joints as well as treatment with agents to reduce pain and inflammation.

Mesenchymal stem cells (MSCs) are present in adult articular cartilage and upon isolation can be programmed in vitro to undergo differentiation to chondrocytes and other mesenchymal cell lineages, and may be used for cartilage regeneration. In part, the process is regulated by growth factors (TGFβs, BMPs), serum conditions and cell-cell contact. WO2011/008773 describes peptide compositions and use of those compositions for treating or preventing arthritis and joint injury and for inducing differentiation of mesenchymal cells into chondrocytes. Additionally, WO2012/129562 describes small molecule compounds, compositions and use of those compositions for amelioration of arthritis and joint injury and for inducing differentiation of mesenchymal cells into chondrocytes.

Though surgical techniques, and regenerative technology have made some progress in restoration of cartilage, slowing degeneration, and improved repair of joint damage, a continued need exists for improvement of compositions and methods for effective cartilage regeneration, treatment of joint damage and amelioration or prevention of OA.

BRIEF SUMMARY OF THE INVENTION

The invention therefore relates to a compound of the formula (I):

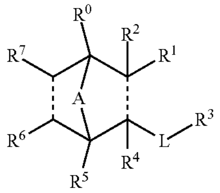

I or a pharmaceutically acceptable salt, or stereoisomer thereof; wherein

"- - - - -" represents a single or double bond;

A is $CR^{8a}R^{8b}$, $NR^9$, or O; wherein $R^{8a}$, $R^{8b}$ and $R^9$ are each independently hydrogen or $C_{1-6}$alkyl;

L is *—C(O)$NR^{10}$— or *—C(O)O—, wherein "*" represents the point of attachment of L to the bicyclic ring containing A, and $R^{10}$ is hydrogen or $C_{1-6}$alkyl;

$R^0$ is selected from hydrogen and $C_{1-6}$alkyl;

$R^1$ is selected from halo, cyano, —C(O)$R^{11}$, —C(O)$NR^{12a}R^{12b}$, —C(O)O$NR^{12a}R^{12b}$, 5- and 6-membered heterocycloalkyl, 5- and 6-membered heterocyclyl, phenyl, and 5- to 9-membered heteroaryl, wherein $R^{11}$ is hydrogen or $C_{1-6}$alkyl;

$R^{12a}$ and $R^{12b}$ are each independently hydrogen or $C_{1-6}$alkyl;

the heterocycloalkyl, heterocyclyl, phenyl, or heteroaryl of $R^1$ is unsubstituted or substituted by 1 to 2 substituents independently selected from halo, cyano, $C_{1-6}$alkyl, $C_{1-6}$haloalkyl, —C(O)$R^{13}$, —C(O)O$R^{13}$, —$NR^{14a}R^{14b}$, 5- and 6-membered heterocycloalkyl, phenyl, and 5- and 6-membered heteroaryl; wherein $R^{13}$ is selected from hydrogen, $C_{1-6}$alkyl, $C_{1-6}$haloalkyl, amino, and $C_{1-6}$alkylamino;

$R^{14a}$ and $R^{14b}$ are each independently selected from hydrogen, $C_{1-6}$alkyl, —C(O)$R^{15}$, —C(O)O$R^{15}$, and —S(O)$_2R^{15}$, wherein $R^{15}$ is hydrogen or $C_{1-6}$alkyl; and the heterocycloalkyl, phenyl or heteroaryl substituent of $R^1$ is further substituted by 1 to 2 substituents independently selected from halo, $C_{1-6}$alkyl, $C_{1-6}$haloalkyl, and hydroxy;

$R^3$ is selected from $C_{1-6}$alkyl, $C_{1-6}$haloalkyl, 3- to 6-membered cycloalkyl, (159), 4- to 7-membered heterocycloalkyl, 5- to 10-membered heterocyclyl, phenyl, and 5- to 9-membered heteroaryl, wherein the cycloalkyl, heterocycloalkyl, heterocyclyl, phenyl, or heteroaryl of $R^3$ is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, —S(O)$_2R^{16}$, 5 and 6 membered heterocycloalkyl, and pheny; wherein $R^{16}$ is hydrogen or $C_{1-6}$alkyl;

the phenyl or heterocycloalkyl substituent or $R^3$ is unsubstituted or further substituted by 1 to 2 substituents independently selected from halo, cyano, $C_{1-6}$alkyl, and $C_{1-6}$haloalkyl; and $R^2$ and $R^4$ are each hydrogen or $C_{1-6}$alkyl; or $R^2$ and $R^4$ taken together form a cyclopropyl ring fused to the bicyclic ring containing A; or $R^2$ and $R^4$ taken together form a bond producing a double bond between the two carbons to which $R^2$ and $R^4$ are attached; and $R^5$ is hydrogen or $C_{1-6}$alkyl, or $R^5$ and $R^{10}$ taken with the atoms to which they are linked form a 5- or 6-membered ring fused to the bicyclic ring containing A; and $R^6$ and $R^7$ are each hydrogen or $C_{1-6}$alkyl; or $R^6$ and $R^7$ taken together form a bond producing a double bond between the two carbons to which $R^6$ and $R^7$ are attached.

In a second aspect, the present invention provides a pharmaceutical composition containing a compound of Formula I, or a sub-formula thereof, where the compound is present in a single stereoisomer or a mixture of stereoisomers thereof; or a pharmaceutically acceptable salt thereof, in admixture with one or more suitable excipients.

In a third aspect, the present invention relates to a pharmaceutical composition formulated for intra-articular delivery, the composition including a pharmaceutically effective amount of a compound of Formula I, or a a sub-formula thereof, where the compound is present as a single stereoisomer or a mixture of stereoisomers thereof; or a pharmaceutically acceptable salt thereof, and a pharmaceutically acceptable excipient.

In a fourth aspect, the present invention provides methods of treating a subject comprising administering a therapeutically effectively amount of a compound of Formula I, or a sub-formula thereof, a pharmaceutical salt thereof, or a pharmaceutical composition thereof. Provided methods include treating a subject having or at risk of having joint damage and/or arthritis, comprising administering to the subject a therapeutically effective amount of one or more compounds of the invention or a pharmaceutical composition thereof.

In a fifth aspect, the present invention further provides a method for treating, ameliorating or preventing arthritis or joint damage in a mammal in need thereof, where the method comprises administering to a joint of a patient a therapeutically effective amount of a compound of formula I, or a sub-formula thereof, a pharmaceutical salt thereof, or a pharmaceutical composition thereof. Examples of conditions that can benefit from such methods include, but are not limited to arthritis (e.g., osteoarthritis, traumatic arthritis), and joint damage (e.g., acute joint injury).

In a sixth aspect, the present invention relates to a method of inducing differentiation of mesenchymal stem cells into chondrocytes, the method including contacting mesenchymal stem cells with a sufficient amount of a compound of Formula I or a sub-formula thereof, a pharmaceutical salt thereof, or a pharmaceutical composition thereof.

In a seven aspect, the present invention relates to a method of increasing production of collagen in fibroblast, the method including contacting fibroblast with a sufficient amount of a compound of Formula I or a sub-formula thereof, a pharmaceutical salt thereof, or a pharmaceutical composition thereof.

In a eighth aspect, the present invention relates to the use of a compound Formula I or a sub-formula thereof, a pharmaceutically acceptable salt thereof, or a pharmaceutical composition thereof, in the manufacture of a medicament for treating joint injury.

In a ninth aspect, the present invention provides a process for preparing compounds of Formula I, or a sub-formula thereof, salts and prodrug derivatives, thereof, or pharmaceutical composition thereof.

Unless specified otherwise, the term "compounds of the present invention" refers to compounds of Formula (I) and subformulae thereof, salts of the compound, hydrates or solvates of the compounds, salts, as well as all stereoisomers (including diastereoisomers and enantiomers), tautomers and isotopically labeled compounds (including deuterium substitutions). Compounds of the present invention further comprise polymorphs of compounds of formula I (or subformulae thereof) and salts thereof.

DETAILED DESCRIPTION OF THE INVENTION

The present invention is based, at least in part, on the identification of a novel class of compounds that stimulate chondrocyte differentiation of mesenchymal stem cells. WO2012/129562, describes compounds and compositions and the use of same for treating or preventing arthritis and joint injury and for inducing differentiation of mesenchymal cells into chondrocytes. Accordingly, the present invention provides a different class of compounds and compositions for repairing cartilage. Also provided are compositions and methods to treat, prevent or ameliorate arthritis or joint injury by administering a compound or composition of the invention into a joint, a cartilage tissue or a cartilage proximal tissue, or systemically. Further, the invention provides compositions and methods for induction of mesenchymal stem cell differentiation into chondrocytes.

DEFINITIONS

For purposes of interpreting this specification, the following definitions will apply and whenever appropriate, terms used in the singular will also include the plural and vice versa.

"Alkoxy" as used herein refers the radical —O-alkyl, wherein the alkyl is as defined herein. $C_X$alkoxy and $C_{X-Y}$alkoxy as used herein describe alkoxy groups where X and Y indicate the number of carbon atoms in the alkyl chain. Representative examples of $C_{1-10}$alkoxy include, but are not limited to, methoxy, ethoxy, propoxy, 2-propoxy, butoxy, tert-butoxy, pentyloxy, hexyloxy, heptyloxy, octyloxy and decyloxy. The alkyl portion of the alkoxy may be optionally substituted, and the substituents include those described for the alkyl group below.

"Alkyl" as used herein refers to a fully saturated branched or unbranched hydrocarbon chain having up to 10 carbon atoms. $C_X$ alkyl and $C_{X-Y}$ alkyl as used herein describe alkyl groups where X and Y indicate the number of carbon atoms in the alkyl chain. For example, $C_{1-10}$ alkyl refers to an alkyl radical as defined above containing one to ten carbon atoms. $C_{1-6}$ alkyl includes, but is not limited to, methyl, ethyl, n-propyl, iso-propyl, n-butyl, sec-butyl, iso-butyl, tert-butyl, n-pentyl, isopentyl, neopentyl, n-hexyl, and the like. Alkyl represented along with another radical like arylalkyl, heteroarylalkyl, alkoxyalkyl, alkoxyalkyl, alkylamino, where the alkyl portion shall have the same meaning as described for alkyl and is bonded to the other radical. For example, $(C_{6-10})$aryl$(C_{1-3})$alkyl includes, benzyl, phenylethyl, 1-phenylethyl, 3-phenylpropyl, 2-thienylmethyl, 2-pyridinylmethyl and the like.

Unless stated otherwise specifically in the specification, an alkyl group may be unsubstituted or substituted by one or more substituents to the extent that such substitution makes sense chemically. Typical substituents include, but are not limited to halo, hydroxyl, alkoxy, cyano, amino, acyl, aryl, arylalkyl, and cycloalkyl, or an heteroforms of one of these groups, and each of which can be substituted by the substituents that are appropriate for the particular group.

"Amino" as used herein refers to the radical —$NH_2$. When an amino is described as "substituted" or "optionally substituted", the term includes NR'R" wherein each R' and R" is independently H, or is an alkyl, alkenyl, alkynyl, acyl, aryl, aryl, cycloalkyl, arylalkyl cycloalkylalkyl group or a heteroform of one of these groups, and each of the alkyl, alkenyl, alkynyl, acyl, aryl, arylalkyl or groups or heteroforms of one of these groups, each of which is optionally substituted with the substituents described herein as suitable for the corresponding group.

Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Alkylamino" as used herein refers to the radical —$NR_aR_b$, where at least one of, or both, $R_a$ and $R_b$ are an alkyl group as described herein. An $C_{1-4}$alkylamino group includes —$NHC_{1-4}$alkyl and —$N(C_{1-4}alkyl)_2$; e.g., —$NHCH_3$, —$N(CH_3)_2$, —$NH(CH_2CH_3)$, —$N(CH_2CH_3)_2$, and the like.

"Aromatic" as used herein refers to a moiety wherein the constituent atoms make up an unsaturated ring system, where all atoms in the ring system are $sp^2$ hybridized and the total number of pi electrons is equal to 4n+2. An aromatic ring may be such that the ring atoms are only carbon atoms or may include carbon and non-carbon atoms (see Heteroaryl).

"Aryl" as used herein refers to a monocyclic or polycyclic aromatic ring assembly containing 6-14 ring atoms where all the ring atoms are carbon atoms. Typically, the aryl is a 6-membered (ring atoms) monocyclic, a 10- to 12-membered bicyclic or a 14-membered fused tricyclic aromatic ring system. Six to fourteen membered aryls include, but are not limited to, phenyl, biphenyl, naphthyl, azulenyl, and anthracenyl.

An aryl may be unsubstituted or substituted by 1-5 (such as one, or two, or three) substituents independently selected from the group consisting of hydroxy, thiol, cyano, nitro, $C_{1-4}$alkyl, $C_{1-4}$alkenyl, $C_{1-4}$alkynyl, $C_{1-4}$alkoxy, thio$C_{1-4}$ alkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$ alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl, aryl, heteroaryl, cycloalkyl and heterocycloalkyl, wherein each of the afore-mentioned substitutents may be further substituted by one or more substituents independently selected from halogen, alkyl, hydroxyl or $C_{1-4}$alkoxy groups.

When an "aryl" is represented along with another radical like "arylalkyl", "aryloxyalkyl", "aryloxycarbonyl", "aryloxy-carbonylalkyl", the aryl portion shall have the same meaning as described in the above-mentioned definition of "aryl".

"Aryloxy" as used herein, refers to the radical —O-aryl, wherein aryl is as defined herein.

"Bicyclic" or "bicyclyl" as used here in refers to a ring assembly of two rings where the two rings are fused together, linked by a single bond or linked by two bridging atoms. The rings may be a carbocyclyl, a heterocyclyl, or a mixture thereof.

"Bridging ring" as used herein refers to a polycyclic ring system where two ring atoms that are common to two rings are not directly bound to each other. One or more rings of the ring system may also comprise heteroatoms as ring atoms. Non-exclusive examples of bridging rings include norbornanyl, oxabicyclo[2.2.1]heptanyl, azabicyclo[2.2.1]heptanyl, adamantanyl, and the like.

"Cycloalkyl", as used herein, means a radical comprising a non-aromatic, saturated monocyclic, bicyclic, tricyclic, fused, bridged or spiro polycyclic hydrocarbon ring system of 3- to 14-ring members where all the ring members are carbon atoms. Exemplary monocyclic cycloalkyl include, but are not limited to, cyclopropyl, cyclobutyl, cyclopentyl, cyclohexyl, cycloheptanyl, cyclooctanyl, and the like. Exemplary bicyclic cycloalkyls include bicyclo[2.2.1]heptane, bicyclo[3.2.1]octanyl, bornyl, norbornanyl, decahydronaphthyl, bicyclo[2.1.1]hexyl, bicyclo[2.2.1]heptyl, bicyclo[3.1.1]heptyl, bicyclo[2.2.2]octyl. Exemplary tricyclic cycloalkyl groups include, for example, adamantanyl.

A cycloalkyl may be unsubstituted or substituted by one, or two, or three, or more substituents independently selected from the group consisting of hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

"Cyano", as used herein, refers to the radical —CN.

"$EC_{50}$", refers to the molar concentration of an inhibitor or modulator that produces 50% efficacy.

"$IC_{50}$", refers to the molar concentration of an inhibitor or modulator that produces 50% inhibition.

"Fused ring", as used herein, refers to a multi-ring assembly wherein the rings comprising the ring assembly are so linked that the ring atoms that are common to two rings are directly bound to each other. The fused ring assemblies may be saturated, partially saturated, aromatics, carbocyclics, heterocyclics, and the like. Non-exclusive examples of common fused rings include decalin, naphthalene, anthracene, phenanthrene, indole, benzofuran, purine, quinoline, and the like.

"Halo" or "halogen" as used herein refers to fluoro, chloro, bromo, and iodo.

"Haloalkyl", or halo-substituted-alkyl" as used herein, refers to an alkyl as defined herein, which is substituted by one or more halo atoms defined herein. The haloalkyl can be mono-haloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. $C_X$haloalkyl and $C_{X-Y}$haloalkyl are typically used where X and Y indicate the number of carbon atoms in the alkyl chain. Non-limiting examples of $C_{1-4}$haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A $C_{1-4}$perhaloalkyl group refers to a $C_{1-4}$alkyl group having all hydrogen atoms replaced with halo atoms.

"Heteroaryl", as used herein, refers to a 5-14 membered aromatic ring assembly (e.g., a 5-7 membered monocycle, an 8-10 membered bicycle, or a 13-14 membered tricyclic ring system) having 1 to 8 heteroatoms selected from N, O and S as ring atoms and the remaining ring atoms are carbon atoms. The nitrogen atoms of such heteroaryl rings can be optionally quaternerized and the sulfur atoms of such heteroaryl rings can be optionally oxidized. Typical 5- to 7-membered heteroaryl groups include thienyl, furanyl, imidazolyl, pyrazolyl, pyrrolyl, pyrrolinyl, thiazolyl, 1,3,4-thiadiazolyl, isothiazolyl, oxazolyl, oxadiazole isoxazolyl, triazolyl, tetrazolyl, pyridyl, pyridazinyl, pyrazinyl, pyrazinyl, pyrimidinyl, and the like. Bicyclic or tricyclic 8- to 14-membered heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, quinazolinyle, pteridinyl, indolizine, imidazo[1,2a]pyridine, quinoline, quinolinyl, isoquinoline, phthalazine, quinoxaline, naphthyridine, naphthyridinyl, quinolizine, indole, isoindole, indazole, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo [1,5-a]pyrimidine, imidazo[1,5-c]pyrimidine, pyrrolo[2,3-b] pyridine, pyrrolo[2,3-c]pyridine, pyrrolo[3,2-c]pyridine, pyrrolo[3,2-b]pyridine, pyrrolo[2,3-d]pyrimidine, pyrrolo [3,2-d]pyrimidine, pyrrolo[2,3-b]pyrazine, pyrazolo[1,5-a] pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, purinyl, carbazole, acridine, phenazine, phenothiazene, phenoxazine, 1,2-dihydropyrrolo[3,2,1-hi]indole, indolizine, pyrido[1,2-a]indole and 2(1H)-pyridinone.

A heteroaryl may be unsubstituted or substituted with one or more substituents independently selected from hydroxyl, thiol, cyano, nitro, $C_{1-4}$alkyl, $C_{1-4}$alkenyl, $C_{1-4}$alkynyl, $C_{1-4}$alkoxy, thio$C_{1-4}$alkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

When a heteroaryl is represented along with another radical like "heteroaryloxy", "heteroaryloxyalkyl", "heteroaryloxycarbonyl", the heteroaryl portion shall have the same meaning as described in the above-mentioned definition of "heteroaryl".

"Heteroatom", as used herein, refers to an atom that is not a carbon atom. Particular examples of heteroatoms include, but are not limited to nitrogen, oxygen, and sulfur.

"Heterocycloalkyl", as used herein, refers to a 4-15 membered, saturated monocyclic or polycyclic ring system, comprising 1-8 heteroatoms as ring atoms and that the remaining ring atoms are carbon atoms. The heteroatoms are selected from N, O, and S, preferably O and N. The nitrogen atoms of the heterocycloalkyl can be optionally quaternerized and the sulfur atoms of the heterocycloalkyl can be optionally oxidized. The heterocycloalkyl can include fused or bridged rings as well as spirocyclic rings. Typically, the heterocycloalkyl is 4- to 8-membered monocyclic ring containing 1 to 3 heteroatoms, a 7- to 12-membered bicyclic ring system containing 1-5 heteroatoms, or a 10- to 15-membered tricyclic ring system containing 1 to 7 heteroatoms. Examples of 4- to 6-membered heterocycloalkyl include those derived from azetidine, tetrahydrofuran (THF), 1,4-dioxane, morpholine, 1,4-dithiane, piperazine, piperidine, 1,3-dioxolane, imidazolidine, pyrazolidinyl, pyrrolidine, tetrahydropyran, oxathiolane, dithiolane, 1,3-dioxane, 1,3-dithiane, oxathiane, thiomorpholine. Examples of bicyclic heterocycloalkyl include, but not limited to, oxabicyclo[2.2.1]heptane, azabicyclo[2.2.1]heptane, and the like.

A heterocycloalkyl may be unsubstituted or substituted with 1-5 substituents (such as one, or two, or three) each independently selected from hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups. When a heterocycloalkyl forms part of other groups like "heterocycloalkyl-alkyl", "heterocycloalkoxy", "heterocycloalkyl-aryl", the heteroaryl portion shall have the same meaning as described in the above-mentioned definition of "heteroaryl"

"Heterocyclyl" or "heterocycle" as used herein, refers to a partially saturated or partially unsaturated 3-14 membered, monocyclic or polycyclic ring system containing at least one heteroatom moiety selected from the group consisting of N, O, SO, $SO_2$, (C═O), and S, and preferably N, O, S, optionally containing one to four additional heteroatoms in each ring. Heterocyclyl as defined herein also includes polycyclic ring systems that contain a fully saturated ring fused to a fully unsaturated ring. Examples of monocyclic heterocyclyl include those derived from pyrroline, imidazoline, 1,2,3,6-tetrahydropyridine, 2H-pyran, 4H-pyran, 3,6-dihydro-2H-pyran, and the like. Examples of polycyclic heterocyclyl include those derived from indoline, 3H-indole, carbazole, indene, dihydrobenzo[b][1,4]dioxine fluorene, phenoxazine, and the like.

Hydroxy, as used herein, refers to the radical —OH.

"Protected derivatives" means derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, β-methoxyethoxymethyl ether, ρ-methoxybenzyl, methylthiomethyl ether, pivaloyl, silyl ether, carbobenzyloxy, benzyl, tert-butoxycarbonyl, ρ-methoxyphenyl, 9-fluorenylmethyloxycarbonyl, acetals, ketals, acylals, dithianes, methylesters, benzyl esters, tert-butyl esters, and silyl esters. A comprehensive list of suitable protecting groups can be found in T. W. Greene, *Protecting Groups in Organic Synthesis,* 3rd edition, John Wiley & Sons, Inc. 1999.

"Unsubstituted or substituted" or "optionally substituted" as used herein indicate the substituent bound on the available valance of a named group or radical. "Unsubstituted" as used herein indicates that the named group or radical will have no further non-hydrogen substituents. "Substituted" or "optionally substituted" as used herein indicates that at least one of the available hydrogen atoms of named group or radical has been (or may be) replaced by a non-hydrogen substituent.

Unless otherwise specified, examples of substituents may include, but are not limited to, halo, nitro, cyano, thio, oxy, hydroxy, carbonyloxy, $C_{1-6}$alkoxy, 6- to 10-membered aryloxy, 5- to 10-membered heteroaryloxy, carbonyl, oxycarbonyl, aminocarbonyl, amino, $C_{1-6}$alkylamino, sulfonamido, imino, sulfonyl, sulfinyl, $C_{1-6}$alkyl, $C_{1-6}$haloalkyl, hydroxy$C_{1-6}$alkyl, carbonyl$C_{1-6}$alkyl, thiocarbonyl$C_{1-10}$ alkyl, sulfonyl$C_{1-6}$alkyl, sulfinyl$C_{1-6}$alkyl, $C_{1-10}$azaalkyl, imino$C_{1-6}$alkyl, 3- to 12-membered cycloalkyl$C_{1-6}$alkyl, 4- to 15-membered heterocycloalkyl$C_{1-6}$alkyl, 6- to 10-membered aryl$C_{1-6}$alkyl, 5- to 10-membered heteroaryl$C_{1-6}$alkyl, 10- to 12-membered bicycloaryl$C_{1-6}$alkyl, 9- to 12-membered heterobicycloaryl$C_{1-6}$alkyl, 3- to 12-membered cycloalkyl, 4- to 12-membered heterocycloalkyl, 9- to 12-membered bicycloalkyl, 3- to 12-membered heterobicycloalkyl, 6- to 12-membered aryl, and 5- to 12-membered heteroaryl, "Sulfonyl", as used herein, means the radical —$S(O)_2$—. It is noted that the term "sulfonyl" when referring to a monovalent substituent can alternatively refer to a substituted sulfonyl group, —$S(=O)_2R$, where R is hydrogen or a non-hydrogen substituent on the sulfur atom forming different sulfonyl groups including sulfonic acids, sulfonamides, sulfonate esters, and sulfones.

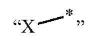 and 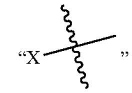

are symbols denoting the point of attachment of the radical X, to other part of the molecule.

Any definition herein may be used in combination with any other definition to describe a composite structural group. By convention, the trailing element of any such definition is that which attaches to the parent moiety. For example, the composite group alkoxyalkyl would represent an alkoxy group attached to the parent molecule through an alkyl group.

It is noted in regard to all of the definitions provided herein that the definitions should be interpreted as being open ended in the sense that further substituents beyond those specified may be included. Hence, a $C_1$alkyl indicates that there is one carbon atom but does not indicate what are the substituents on the carbon atom. Hence, a $C_1$alkyl comprises methyl (i.e., —$CH_3$) as well as —$CR_aR_bR_c$ where $R_a$, $R_b$, and $R_c$ may each independently be hydrogen or any other substituent where the atom attached to the carbon is not a hydrogen atom. Hence, —$CF_3$, —$CH_2OH$ and —$CH_2CN$, for example, are all $C_1$alkyls.

"Chondrocytes" refers to cartilage cells. Chondrocytes produce and maintain the cartilaginous matrix which is composed of collagen and proteoglycans. Chondrocytes are derived from the differentiation of mesenchymal stem cells (MSCs). MSCs are multipotent stem cells that can differentiate into several different types of cells including, but not limited to, osteoblasts, chondrocytes and adipocytes. Differentiation is the process a specialized cell type is formed from a less specialized cell type, for example, a chondrocyte from a MSC.

"Hyaluronic acid" refers to derivatives of hyaluronic acid that include esters of hyaluronic acid, salts of hyaluronic acid and also includes the term hyaluronan. The designation also includes both low and high molecular weight forms of hyaluronans and crosslinked hyaluronans or hylans. Examples of such hyaluronans are Synvisc™ (Genzyme Corp. Cambridge, Mass.), ORTHOVISC™ (Anika Therapeutics, Woburn, Mass.), and HYALGAN™ (Sanofi-Synthelabo Inc., Malvern, Pa.).

DESCRIPTION OF THE PREFERRED EMBODIMENTS

The invention provides a novel class of compounds, pharmaceutical compositions comprising such compounds and methods of using such compounds to treat or prevent joint damage resulting from joint injury and arthritis. In particular, the compounds can be used to treat acute joint damage, osteoarthritis, traumatic arthritis, degenerative disc disease, and systemic rheumatoid arthritis.

I. Compounds of the Invention

In the first embodiment, the compound of the invention is of Formula I

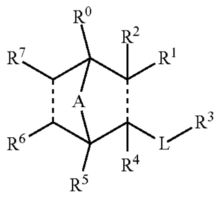

I or a pharmaceutically acceptable salt, or stereoisomer thereof; wherein

"- - - - -" represents a single or double bond;

A is $CR^{8a}R^{8b}$, $NR^9$, or O; wherein $R^{8a}$, $R^{8b}$ and $R^9$ are each independently hydrogen or $C_{1-6}$alkyl;

L is *—$C(O)NR^{10}$— or *—C(O)O—, wherein "*" represents the point of attachment of L to the bicyclic ring containing A, and $R^{19}$ is hydrogen or $C_{1-6}$alkyl;

$R^0$ is selected from hydrogen and $C_{1-6}$alkyl;

$R^1$ is selected from halo, cyano, —$C(O)R^{11}$, —C(O)$NR^{12a}$, $R^{12b}$, —$C(O)ONR^{12a}R^{12b}$, 5- and 6-membered heterocycloalkyl, 5- and 6-membered heterocyclyl, phenyl, and 5- to 9-membered heteroaryl, wherein $R^{11}$ is hydrogen or $C_{1-6}$alkyl;

$R^{12a}$ and $R^{12b}$ are each independently hydrogen or $C_{1-6}$alkyl;

the heterocycloalkyl, heterocyclyl, phenyl, or heteroaryl of $R^1$ is unsubstituted or substituted by 1 to 2 substituents independently selected from halo, cyano, $C_{1-6}$alkyl, $C_{1-6}$haloalkyl, —$C(O)R^{13}$, —C(O)$OR^{13}$, —$NR^{14a}R^{14b}$, 5- and 6-membered heterocycloalkyl, phenyl, and 5- and 6-membered heteroaryl; wherein $R^{13}$ is selected from hydrogen, $C_{1-6}$alkyl, $C_{1-6}$haloalkyl, amino, and $C_{1-6}$alkylamino;

$R^{14a}$ and $R^{14b}$ are each independently selected from hydrogen, $C_{1-6}$alkyl, —$C(O)R^{15}$, —$C(O)OR^{15}$, and —$S(O)_2R^{15}$, wherein $R^{15}$ is hydrogen or $C_{1-6}$alkyl; and the heterocycloalkyl, phenyl or heteroaryl substituent of $R^1$ is further substituted by 1 to 2 substituents independently selected from halo, $C_{1-6}$alkyl, $C_{1-6}$haloalkyl, and hydroxy;

$R^3$ is selected from $C_{1-6}$alkyl, $C_{1-6}$haloalkyl, 3- to 6-membered cycloalkyl, (159), 4- to 7-membered heterocycloalkyl, 5- to 10-membered heterocyclyl, phenyl, and 5- to 9-membered heteroaryl, wherein the cycloalkyl, heterocycloalkyl, heterocyclyl, phenyl, or heteroaryl of $R^3$ is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, —$S(O)_2R^{16}$, 5 and 6 membered heterocycloalkyl, and pheny; wherein $R^{16}$ is hydrogen or $C_{1-6}$alkyl;

the phenyl or heterocycloalkyl substituent or $R^3$ is unsubstituted or further substituted by 1 to 2 substituents independently selected from halo, cyano, $C_{1-6}$alkyl, and $C_{1-6}$haloalkyl; and $R^2$ and $R^4$ are each hydrogen or $C_{1-6}$alkyl; or $R^2$ and $R^4$ taken together form a cyclopropyl ring fused to the bicyclic ring containing A; or $R^2$ and $R^4$ taken together form a bond producing a double bond between the two carbons to which $R^2$ and $R^4$ are attached; and $R^5$ is hydrogen or $C_{1-6}$alkyl, or $R^5$ and $R^{10}$ taken with the atoms to which they are linked form a 5- or 6-membered ring fused to the bicyclic ring containing A; and $R^6$ and $R^7$ are each hydrogen or $C_{1-6}$alkyl; or $R^6$ and $R^7$ taken together form a bond producing a double bond between the two carbons to which $R^6$ and $R^7$ are attached.

In another embodiment, the compound is of Formula IA:

IA

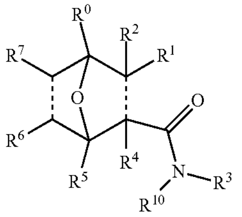

"- - - - -" represents a single or double bond;

$R^0$ is hydrogen or $C_{1-6}$alkyl;

$R^1$ is selected from cyano, —C(O)$NR^{12a}R^{12b}$, 6-membered heterocycloalkyl, 6-membered heterocyclyl, phenyl, and 5- to 9-membered heteroaryl, wherein $R^{12a}$ and $R^{12b}$ are each independently hydrogen or $C_{1-6}$alkyl;

the heterocycloalkyl, heterocyclyl, phenyl, or heteroaryl of $R^1$ is unsubstituted or substituted by 1 to 2 substituents independently selected from halo, cyano, $C_{1-6}$alkyl, $C_{1-6}$haloalkyl, —C(O)$R^{13}$, —C(O)O$R^{13}$, —$NR^{14a}R^{14b}$, 5- and 6-membered heterocycloalkyl, phenyl, and 5- and 6-membered heteroaryl; wherein $R^{13}$ is selected from $C_{1-6}$alkyl, amino, and $C_{1-6}$alkylamino;

$R^{14a}$ and $R^{14b}$ are each independently selected from hydrogen, $C_{1-6}$alkyl, —C(O)$R^{15}$, —C(O)O$R^{15}$, and —$S(O)_2R^{15}$, wherein $R^{15}$ is hydrogen or $C_{1-6}$alkyl; and the heterocycloalkyl, phenyl or heteroaryl substituent of $R^1$ is unsubstituted or further substituted by 1 to 2 substituents independently selected from halo, hydroxy, $C_{1-6}$alkyl, and $C_{1-6}$haloalkyl, $R^3$ is selected from $C_{1-6}$alkyl, $C_{1-6}$haloalkyl, 5- and 6-membered cycloalkyl, (159), 5- and 6-membered heterocycloalkyl, 6- and 10-membered heterocyclyl, phenyl, and 5- and 6-membered heteroaryl, wherein the cycloalkyl, heterocycloalkyl, heterocyclyl, phenyl, or heteroaryl of $R^3$ is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, —$S(O)_2R^{16}$, 5- and 6-membered heterocycloalkyl, and pheny; wherein $R^{16}$ is hydrogen or $C_{1-6}$alkyl;

the phenyl or heterocycloalkyl substituent of $R^3$ is unsubstituted or further substituted by 1 to 2 substituents independently selected from halo, and cyano; and $R^2$ and $R^4$ are independently hydrogen or $C_{1-6}$alkyl; or $R^2$ and $R^4$ taken together form a cyclopropyl ring fused to the bicyclic ring; or $R^2$ and $R^4$ taken together form a bond producing a double bond between the two carbons to which $R^2$ and $R^4$ are attached; and $R^5$ is hydrogen or $C_{1-6}$alkyl, or $R^5$ and $R^{10}$ taken with the atoms to which they are linked form a 5- or 6-membered ring fused to the bicyclic ring, and $R^6$ and $R^7$ are independently hydrogen or $C_{1-6}$alkyl; or $R^6$ and $R^7$ taken together form a bond producing a double bond between the two carbons to which $R^6$ and $R^7$ are attached.

In another embodiment of the compound of the invention, in accordance to the embodiments above, $R^6$ is hydrogen.

In another embodiment of the compound of the invention, in accordance to any one of the embodiments above, $R^7$ is hydrogen.

In another embodiment, in accordance to any one of the embodiments above, the compound of the invention is of a formula selected from one of the formulae below:

IA1

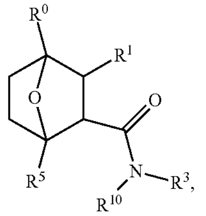

IA2

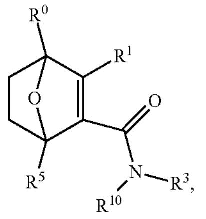

IA3

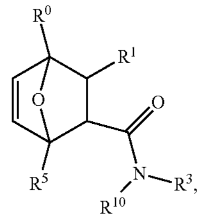

and

-continued

IA4

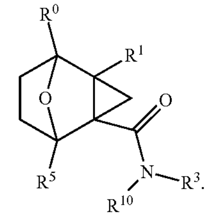

In another embodiment, in accordance to the first or second embodiment, the compound of the invention is of Formula IA1:

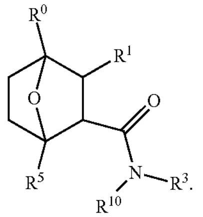

In yet another embodiment, in accordance to the first or second embodiment, the compound of the invention is of Formula IA2:

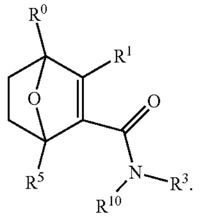

In a yet another embodiment, in accordance to the first or second embodiment, the compound of the invention is of Formula IA3:

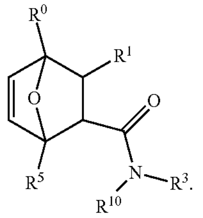

In still another embodiment, in accordance to the first or second embodiment, the compound of the invention is of Formula IA4:

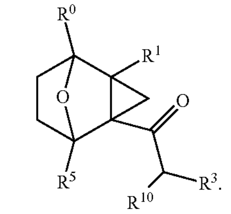

In yet another embodiment of the compound of the invention, in accordance to any one of the embodiments above, $R^0$ is hydrogen.

In yet another embodiment of the compound of the invention, in accordance to any one of the embodiments above, $R^5$ is hydrogen.

In yet another embodiment of the compound of the invention, in accordance to any one of the above embodiments, $R^1$ is selected from 6-membered heterocycloalkyl, 6-membered heterocyclyl, phenyl, and 5- to 9-membered heteroaryl, wherein the heterocycloalkyl, heterocyclyl, phenyl, or heteroaryl is unsubstituted or substituted by 1 to 2 substituents independently selected from halo, cyano, $C_{1-6}$alkyl, $C_{1-6}$haloalkyl, —C(O)$R^{13}$, —C(O)O$R^{13}$, —N$R^{14a}R^{14b}$, 5- and 6-membered heterocycloalkyl, phenyl, and 5- to 6-membered heteroaryl; wherein $R^{13}$ is selected from $C_{1-6}$alkyl, amino, and $C_{1-6}$alkylamino;

$R^{14a}$ and $R^{14b}$ are each independently selected from hydrogen, $C_{1-6}$alkyl, —C(O)$R^{15}$, —C(O)O$R^{15}$, and —S(O)$_2R^{15}$, wherein $R^{15}$ is $C_{1-6}$alkyl; and the heterocycloalkyl, phenyl or heteroaryl substituent of $R^1$ is unsubstituted or further substituted by 1 to 2 substituents independently selected from halo, hydroxy, $C_{1-6}$alkyl and $C_{1-6}$haloalkyl.

In another embodiment of the compound of the invention, in accordance to any one of the above embodiments, $R^1$ is phenyl, 5- or 6-membered heteroaryl, wherein the phenyl or heteroaryl is unsubstituted or substituted by 1 to 2 substituents independently selected from halo, cyano, $C_{1-6}$alkyl, $C_{1-6}$haloalkyl, —C(O)$R^{13}$, —C(O)O$R^{13}$, —N$R^{14a}R^{14b}$, 5- and 6-membered heterocycloalkyl, phenyl, and 5- and 6-membered heteroaryl, wherein $R^{13}$ is selected from $C_{1-6}$alkyl, amino, and $C_{1-6}$alkylamino;

$R^{14a}$ and $R^{14b}$ are each independently selected from hydrogen, $C_{1-6}$alkyl, —C(O)$R^{15}$, and —C(O)O$R^{15}$, wherein $R^{15}$ is $C_{1-6}$alkyl; and the heterocycloalkyl, phenyl or heteroaryl substituent of $R^1$ is unsubstituted or further substituted by 1 to 2 substituents independently selected from hydroxy, halo, $C_{1-6}$alkyl, and $C_{1-6}$haloalkyl.

In another embodiment of the compound of the invention, in accordance to any one of the above embodiments, $R^1$ is selected from cyano, —C(O)N$H_2$, piperidinyl, tetrahydropyridinyl, dihydropyranyl, phenyl, pyrazoyl, oxadiazolyl, pyridinyl, pyrimidinyl, pyrazinyl, and Indazolyl, wherein the piperidinyl, tetrahydropyridinyl, dihydropyranyl, phenyl, pyrazoyl, oxadiazolyl, pyridinyl, pyrimidinyl, pyrazinyl, or Indazolyl is unsubstituted or substituted by 1 to 2 substituents independently selected from halo, cyano, $C_{1-6}$alkyl, $C_{1-6}$haloalkyl, —C(O)$R^{13}$, —C(O)O$R^{13}$, —N$R^{14a}R^{14b}$, 5- and 6-membered heterocycloalkyl, phenyl, and 5- and 6-membered heteroaryl, wherein $R^{13}$ is selected from $C_{1-6}$alkyl, amino, and $C_{1-6}$alkylamino;

$R^{14a}$ and $R^{14b}$ are each independently selected from hydrogen, $C_{1-6}$alkyl, —C(O)$R^{15}$, —C(O)O$R^{15}$, and —S(O)$_2R^{15}$, wherein $R^{15}$ is $C_{1-6}$alkyl; and the heterocycloalkyl, phenyl or heteroaryl substituent of $R^1$ is unsubstituted or further substituted by 1 to 2 substituents independently selected from hydroxy, halo, $C_{1-6}$alkyl, and $C_{1-6}$haloalkyl.

In another embodiment of the compound of the invention, in accordance to any one of the above embodiments, $R^1$ is selected from pyrazoyl, oxadiazolyl, pyridinyl, pyrimidinyl, and pyrazinyl, wherein the pyrazoyl, oxadiazolyl, pyridinyl, pyrimidinyl, or pyrazinyl is unsubstituted or substituted by 1 to 2 substituents independently selected from halo, cyano, $C_{1-6}$alkyl, $C_{1-6}$haloalkyl, —C(O)$R^{13}$, —C(O)O$R^{13}$, —N$R^{14a}R^{14b}$, 5- and 6-membered heterocycloalkyl, and phenyl, wherein $R^{13}$ is selected from $C_{1-6}$alkyl, amino, and $C_{1-6}$alkylamino;

$R^{14a}$ and $R^{14b}$ are each independently selected from hydrogen, $C_{1-6}$alkyl, —C(O)$R^{15}$, and —C(O)O$R^{15}$, wherein $R^{15}$ is $C_{1-6}$alkyl; and the heterocycloalkyl or phenyl substituent of $R^1$ is unsubstituted or further substituted by 1 to 2 substituents independently selected from hydroxy, halo, $C_{1-6}$alkyl, and $C_{1-6}$haloalkyl.

In still another embodiment of the compound of the invention, in accordance to any one of the above embodiments, $R^1$ is selected from pyrazoyl, pyridinyl, pyrimidinyl, and pyrazinyl, each of which is unsubstituted or substituted by 1 to 2 substituents independently selected from halo, cyano, $C_{1-6}$alkyl, $C_{1-6}$haloalkyl, —C(O)$R^{13}$, —C(O)O$R^{13}$, N$R^{14a}R^{14b}$, tetrahydropyranyl, hydroxy substituted pyrrolidinyl, wherein $R^{13}$ is $C_{1-6}$alkyl, amino, or $C_{1-6}$alkylamino;

$R^{14a}$ and $R^{14b}$ are each independently selected from hydrogen, $C_{1-6}$alkyl, —C(O)$R^{15}$, and —C(O)O$R^{15}$, wherein $R^{15}$ is $C_{1-6}$alkyl.

In still another embodiment of the compound of the invention, in accordance to any one of the above embodiments, $R^1$ is selected from

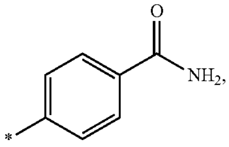 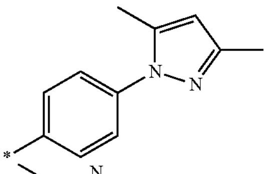 ,

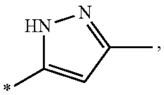 , 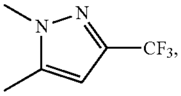

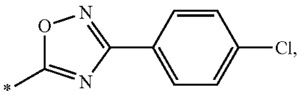 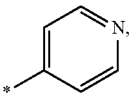

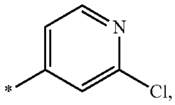 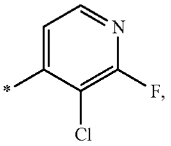 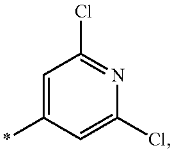

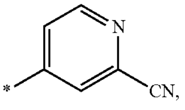 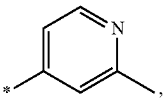 , 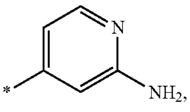

-continued

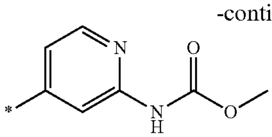 , 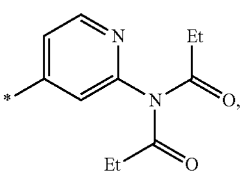

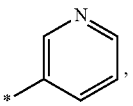 , 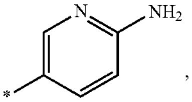 , 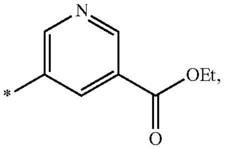

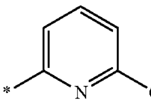 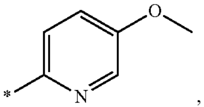 ,

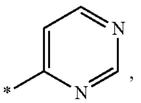 , 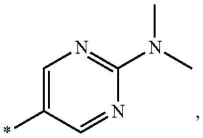 , and 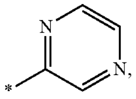

wherein "*" represents the point of attachment of $R^1$ to the bicyclic core ring.

In still another embodiment of the compound of the invention, in accordance to any one of the above first to eleventh embodiments, $R^1$ is selected from

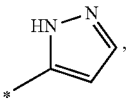 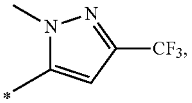

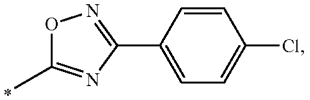 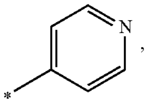

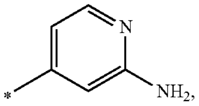 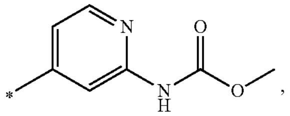 ,

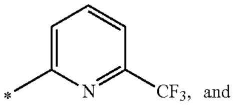 and 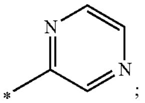 ;

wherein "*" represents the point of attachment of $R^1$ to the bicyclic core ring.

In still another embodiment of the compound of the invention, in accordance to any one of the above embodiments, $R^1$ is

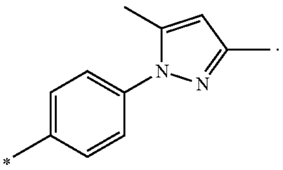

In still another embodiment of the compound of the invention, in accordance to any one of the above embodiments, $R^1$ is

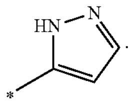

In still another embodiment of the compound of the invention, in accordance to any one of the above embodiments, $R^1$ is

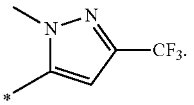

In Still another embodiment of the compound of the invention, in accordance to any one of the above embodiments, $R^1$ is

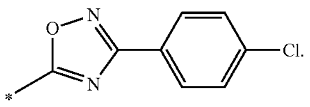

In another embodiment of the compound of the invention, in accordance to any one of the above embodiments, $R^1$ is

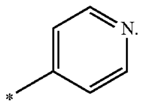

In another embodiment of the compound of the invention, in accordance to any one of the above embodiments, $R^1$ is

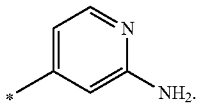

In another embodiment of the compound of the invention, in accordance to any one of the above embodiments, $R^1$ is

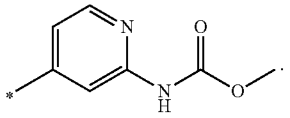

In still another embodiment of the compound of the invention, in accordance to any one of the above embodiments, $R^1$ is

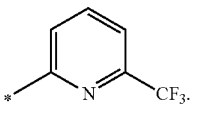

In still another embodiment of the compound of the invention, in accordance to any one of the above embodiments, $R^1$ is

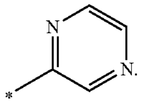

In still another embodiment of the compound of the invention, in accordance to any one of the above embodiments, $R^3$ is phenyl, 5- or 6-membered heteroaryl, wherein the phenyl, or heteroaryl of $R^3$ is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, —S(O)$_2R^{16}$, 5- and 6-membered heterocycloalkyl, and pheny; wherein $R^{16}$ is $C_{1-6}$alkyl; and the phenyl or heterocycloalkyl substituent or $R^3$ is unsubstituted or further substituted by 1 to 2 substituents independently selected from halo or cyano.

In still another embodiment of the compound of the invention, in accordance to any one of the above embodiments, $R^3$ is selected from cyclohexyl, piperidinyl, 2,3-dihydrobenzo[b][1,4]dioxinyl, phenyl, pyrazolyl, pyridinyl, pyrimidinyl, wherein the cyclohexyl, piperidinyl, 2,3-dihydrobenzo[b][1,4]dioxinyl, phenyl, pyrazolyl, pyridinyl, or pyrimidinyl is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, —S(O)$_2R^{16}$, 5- and 6-membered heterocycloalkyl, and phenyl; wherein $R^{16}$ is $C_{1-6}$alkyl; and the phenyl or heterocycloalkyl substituent or $R^3$ is unsubstituted or further substituted by 1 to 2 substituents independently halo or cyano.

In still another embodiment of the compound of the invention, in accordance to any one of the embodiments, $R^3$ is selected from:

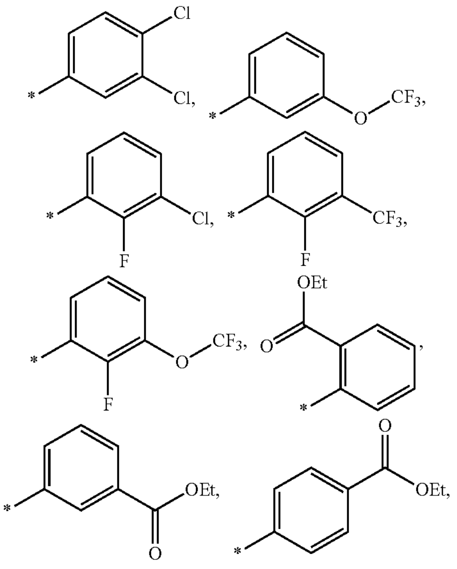

-continued

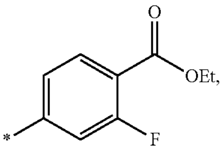
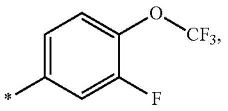
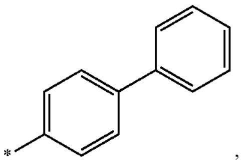
,
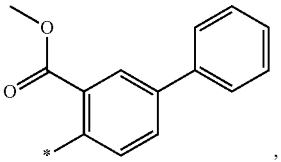
,
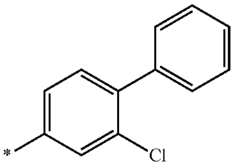
,
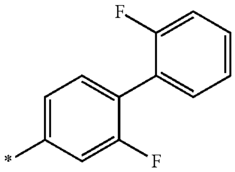
,
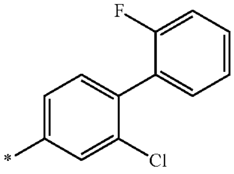
,
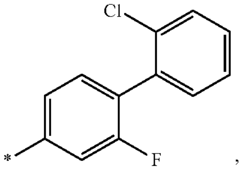
,
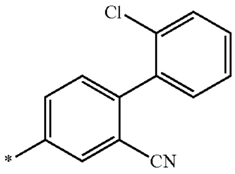
,
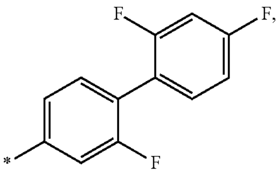
and
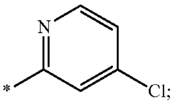

wherein "*" represents the point of attachment of $R^3$ to the bicyclic ring.

In still another embodiment of the compound of the invention, in accordance to any one of the above embodiments, $R^3$ is selected from:

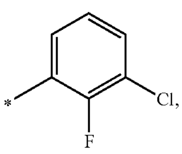
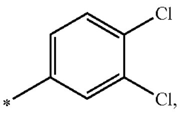
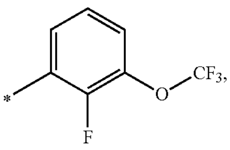
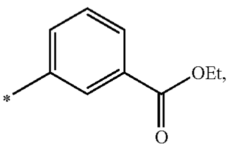
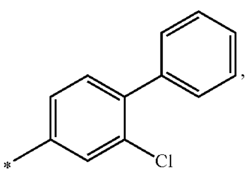
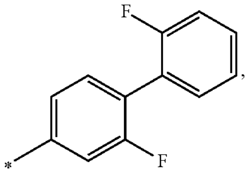

-continued

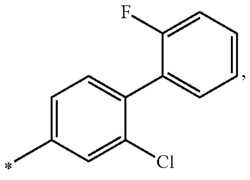
and
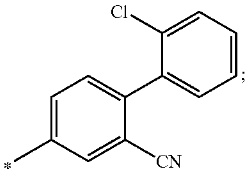

wherein "*" represents the point of attachment of $R^1$ to the bicyclic core ring.

In still another embodiment of the compound of the invention, in accordance to any one of the above embodiments, $R^3$ is

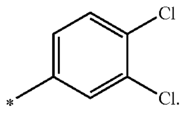

In still another embodiment, $R^3$ is

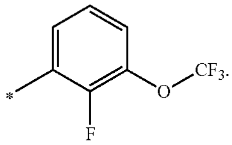

In still another embodiment, $R^3$ is

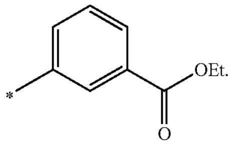

In still another embodiment, $R^3$ is

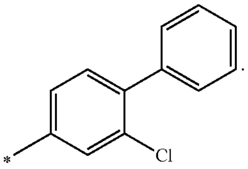

In still another embodiment, $R^3$ is

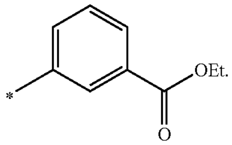

In still another embodiment, $R^3$ is

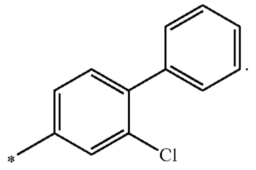

In still another embodiment, $R^3$ is

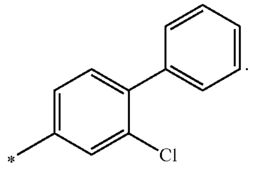

In still another embodiment, $R^3$ is

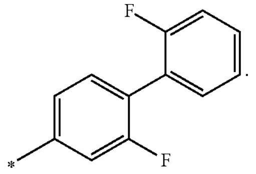

In still another embodiment, $R^3$ is

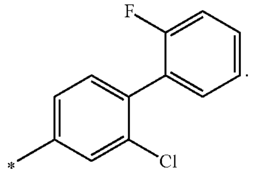

In still another embodiment, $R^3$ is

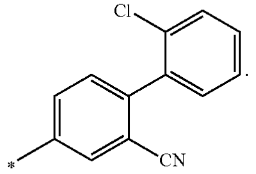

In still another embodiment of the compound of the invention, in accordance to any one of the above first to forty-first embodiments, $R^{10}$ is hydrogen.

In a special embodiment, the compound of the invention is of Formula IB:

IB

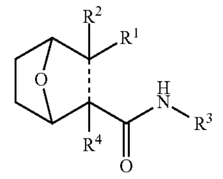

or a pharmaceutically acceptable salt, or an enantiomer thereof, or a mixture of the respective enantiomers thereof, wherein "- - - - -" represents a single or double bond;

$R^1$ is phenyl, 5- or 6-membered heteroaryl, wherein the phenyl or heteroaryl of $R^1$ is unsubstituted or substituted by 1 to 2 substituents independently selected from halo, cyano, $C_{1-6}$alkyl, $C_{1-4}$haloalkyl, —C(O)$R^{13}$, —C(O)O$R^{13}$, —N$R^{14a}R^{14b}$, 5- and 6-membered heterocycloalkyl, phenyl, and 5- and 6-membered heteroaryl, wherein $R^{13}$ is $C_{1-6}$alkyl or amino;

$R^{14a}$ and $R^{14b}$ are independently is selected from hydrogen, $C_{1-6}$alkyl, —C(O)$R^{15}$, and —C(O)O$R^{15}$, wherein $R^{15}$ is $C_{1-4}$alkyl; and the heterocycloalkyl, phenyl, or heteroaryl substituent of $R^1$ is unsubstituted or substituted by 1 to 2 substituents independently selected from halo, hydroxy, and $C_{1-6}$alkyl;

$R^3$ is phenyl, 5- or 6-membered heteroaryl, wherein the phenyl or heteroaryl is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, 5- and 6-membered heterocycloalkyl, and phenyl, wherein $R^{16}$ is $C_{1-6}$alkyl; and the heterocycloalkyl or phenyl is unsubstituted or substituted by 1 to 2 substituents selected from halo and cyano;

$R^2$ and $R^4$ are independently hydrogen or $C_{1-6}$alkyl, or $R^2$ and $R^4$ taken together form a cyclopropyl fused to the bicyclic ring, or $R^2$ and $R^4$ taken together form a bond, producing a double bond between the two carbons to which $R^2$ and $R^4$ are attached.

In some embodiment according to the special embodiment above, the compound of the invention is of a formula selected from Formulae:

IB1

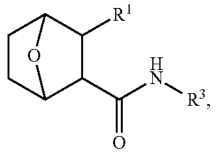

IB2

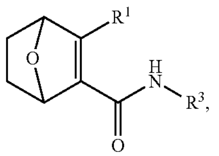

and

-continued

IB3

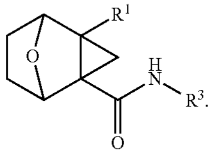

It is noted that the compounds of the invention may possess asymmetric carbon atoms (optical centers) or double bonds; the enantiomers, diastereomers, geometric isomers and individual stereoisomers, and mixtures of the stereoisomers are all intended to be encompassed within the scope of the present invention. Particularly, the present invention contemplates that the compounds of the invention may be obtained and used as individual diastereomers which may be obtained and used as enantiomerically enriched mixtures of two enantiomers, or occasionally as a single enantiomer. In some embodiments of the invention, a formula shown herein as a single stereoisomer includes the enantiomer of the depicted compound and mixtures of the enantiomers unless otherwise specified. Where a compound is described as a single diastereomer or a single enantiomer, it is understood that a sample of the compound may still contain small amounts of other diastereomers or of the opposite enantiomer. Typically, where a compound is described as a single isomer, diastereomer or enantiomer, the specified structure accounts for at least 90% by weight of total weight of depicted compound plus its isomers; preferably, the specified isomer, diastereomer or enantiomer accounts for at least 95% by weight of the total weight including other isomers.

The compounds of the invention In the present application, the stereoisomers are identified by their structural formula, a diastereomer identifier and an enantioisomer identifier. For example, Formula IB1a' identifies the compound is of Formula IB1 (see supra), the “a” denotes a specific diastereomer, and the “'” or “"” denotes a specific enantiomer. Further, for ease of presentation, the compounds are represented by the structure or name of one of the enantiomers, but unless otherwise indicated, the structure or name designates an enantiomeric mixture.

In some embodiments according to the special embodiment above, the compound of the invention is selected from the stereoisomers of Formula IB1 including:

IB1a'

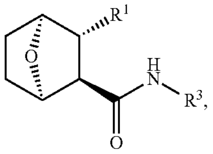

IB1a"

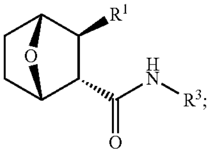

-continued

IB1b'

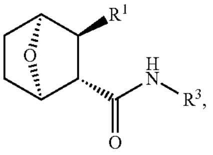

IB1b"

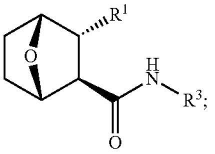

IB1c'

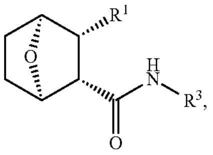

IB1c"

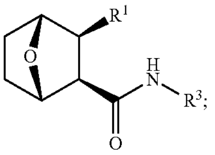

IB1d'

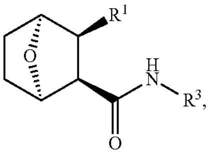

IB1d"

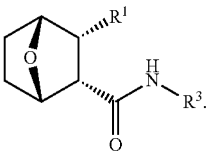

In some other embodiments according to the above special embodiment, the compound of the invention is selected from the stereoisomers of Formula IB2 including:

IB2a'

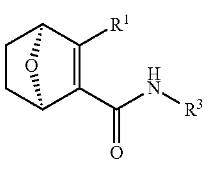

and

IB2"

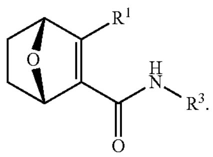

In some other embodiments according to the above special embodiment, the compound of the invention is selected from the stereoisomer of Formula IB3 including:

IB3a′
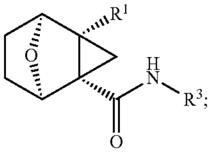
IB3a″
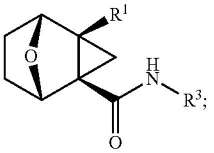
IB3b′
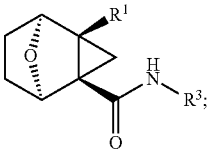
IB3b″
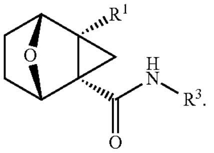
In some other embodiments, the compound of the invention is selected from the single stereoisomer of Formula IB including:
IB1a″
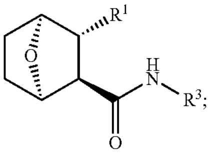
IB1b′
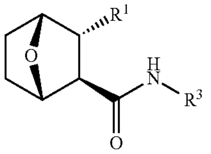
IB1b″
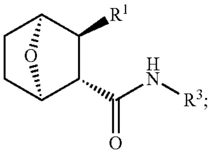
IB1c″
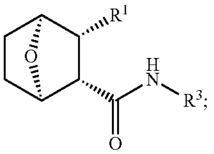
-continued
IB1d′
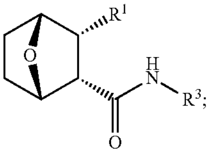
IB1d″
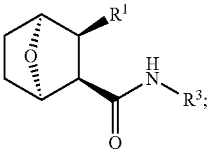
IB2a′
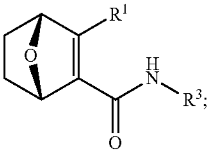
IB2a″
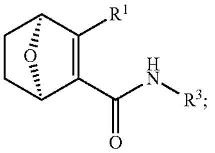
IB3b′
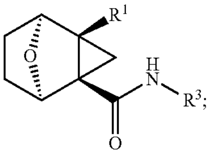
and
IB3b″
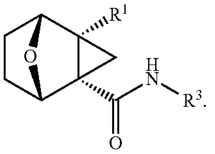
In some other embodiments, the compound of the invention is selected from a single stereoisomer of Formula IB including:
IB1a″
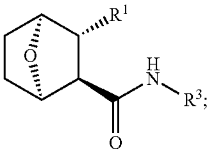
IB1c″
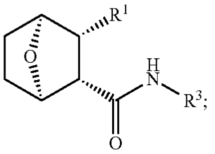

-continued

IB1d''

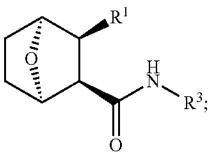

IB3b'

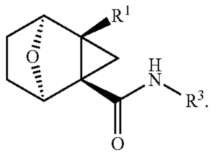

In an embodiment according to the above special embodiment, the compound of the invention is a single stereoisomer of Formula IB1a''

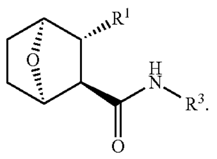

In another embodiment, the compound of the invention is a single stereoisomer of Formula IB1 b'

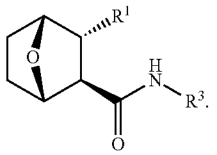

In another embodiment, the compound of the invention is a single stereoisomer of Formula IB1b''

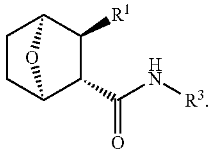

In another embodiment, the compound of the invention is a single stereoisomer of Formula IB1c'

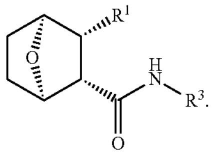

In another embodiment, the compound of the invention is a single stereoisomer of Formula IB1d'

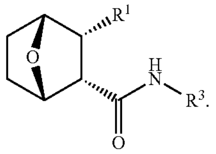

In another embodiment, the compound of the invention is a single stereoisomer of Formula IB1d''

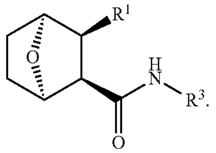

In another embodiment, the compound of the invention is a single stereoisomer of Formula IB2'

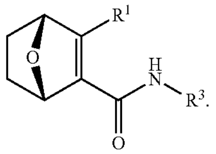

In another embodiment, the compound of the invention is a single stereoisomer of Formula IB2''

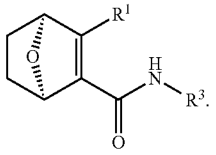

In another embodiment, the compound of the invention is of Formula IB3b'

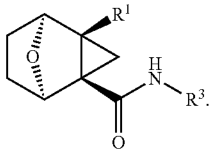

In another embodiment, the compound of the invention is a single stereoisomer of Formula IB3b''

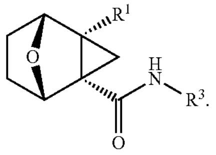

In one embodiment of the compound of the invention, according to any one of the above special embodiment and other embodiments, $R^1$ is a 5 or 6 membered heteroaryl, unsubstituted or substituted by 1 to 2 substituents independently selected from halo, $C_{1-4}$alkyl, $C_{1-4}$haloalkyl, and $NHR^{14b}$, wherein $R^{14b}$ is hydrogen or $C_{1-4}$alkyl.

In another embodiment of the compound of the invention according to any one of the above special embodiment and other embodiments, $R^1$ is selected from pyrazolyl, oxadiazolyl, pyridinyl, pyrimidinyl and pyrazinyl, wherein the pyrazolyl, pyridinyl, pyrimidinyl or pyrazinyl is unsubstituted or substituted by $—NH_2$, $—NHC(O)OCH_3$ or trifluoromethyl.

In another embodiment of the compound of the invention according to any one of the above special embodiment and other embodiments, $R^1$ is selected from

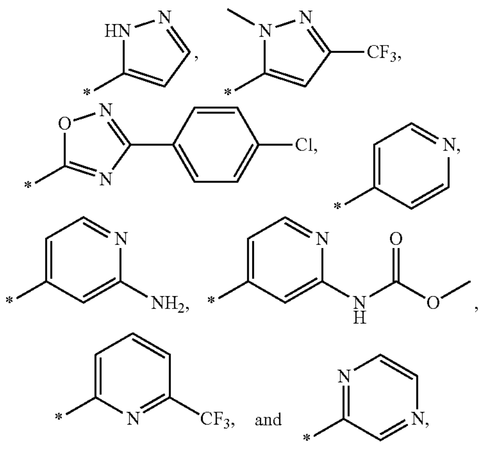

wherein "*" represents the point of attachment of $R^1$ to the bicyclic core ring.

In still another embodiment of the compound of the invention according to any one of the above special embodiment and other embodiments, $R^3$ is phenyl substituted by 1 to 2 substituents independently selected from halo, cyano, $C_{1-6}$alkyl, $C_{1-6}$haloalkyl, $C_{1-6}$alkoxy, $C_{1-6}$haloalkoxy, and phenyl, $C_{1-6}$alkyl, $C_{1-6}$haloalkyl, $C_{1-6}$alkoxy, $C_{1-6}$haloalkoxy, $—C(O)R^{16}$, $—C(O)OR^{16}$, wherein $R^{16}$ is $C_{1-6}$alkyl, and the phenyl substituent of $R^3$ is unsubstituted or further substituted by 1 to 2 substituents independently selected from halo and cyano.

In still another embodiment of the compound of the invention according to any one of the above special embodiment and embodiments, $R^3$ is selected from

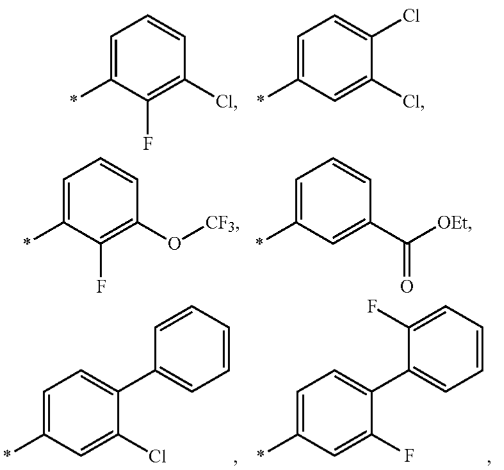

-continued

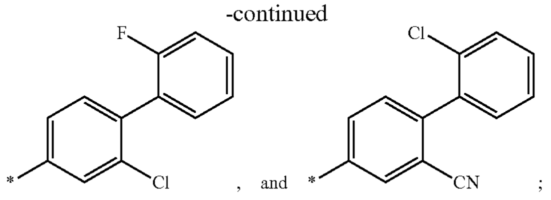

wherein "*" represents the point of attachment of $R^1$ to the bicyclic core ring.

Particular examples of the compounds, or a pharmaceutically acceptable salt thereof, or the corresponding enantiomer thereof, according to the present invention include, but are not limited to: (1R,2R,3S,4S)—N-(3,4-dichlorophenyl)-3-(2-(ethylsulfonamido)pyridin-4-yl)-7-oxabicyclo[2.2.1]heptane-2-carboxamide; ethyl 2-((1R,2S,3R,4S)-3-(3-(4-chlorophenyl)-1,2,4-oxadiazol-5-yl)-7-oxabicyclo[2.2.1]heptane-2-carboxamido)benzoate; (1R,2R,3S,4S)—N-(3,4-dichlorophenyl)-3-(1H-pyrazol-4-yl)-7-oxabicyclo[2.2.1]heptane-2-carboxamide; (1R,2R,3S,4S)—N-(3,4-dichlorophenyl)-3-(1-methyl-1H-pyrazol-5-yl)-7-oxabicyclo[2.2.1]heptane-2-carboxamide; (1R,2R,3S,4S)-3-(2-aminopyridin-4-yl)-N-(3,4-dichlorophenyl)-7-oxabicyclo[2.2.1]heptane-2-carboxamide; (1R,2S,3S,4S)—N-(3,4-dichlorophenyl)-3-(1-methyl-1H-pyrazol-4-yl)-7-oxabicyclo[2.2.1]heptane-2-carboxamide; (1R,2R,3S,4S)—N-(3,4-dichlorophenyl)-3-(1-methyl-1H-pyrazol-4-yl)-7-oxabicyclo[2.2.1]heptane-2-carboxamide; (1S,2R,3R,4R)—N-(3,4-dichlorophenyl)-3-(pyridin-4-yl)-7-oxabicyclo[2.2.1]heptane-2-carboxamide; methyl 4-((1R,2S,3R,4S)-3-(3-(4-chlorophenyl)-1,2,4-oxadiazol-5-yl)-7-oxabicyclo[2.2.1]heptane-2-carboxamido)-[1,1'-biphenyl]-3-carboxylate; (1S,2S,3R,4R)-3-(2-aminopyridin-4-yl)-N-(3,4-dichlorophenyl)-7-oxabicyclo[2.2.1]heptane-2-carboxamide; (1R,2S,3S,4S)—N-(3,4-dichlorophenyl)-3-(pyridin-4-yl)-7-oxabicyclo[2.2.1]heptane-2-carboxamide; (1R,2R,3S,4S)—N-(3,4-dichlorophenyl)-3-(1-methyl-1H-pyrazol-3-yl)-7-oxabicyclo[2.2.1]heptane-2-carboxamide; (1R,2S,3S,4S)—N-(3,4-dichlorophenyl)-3-(1-methyl-1H-pyrazol-5-yl)-7-oxabicyclo[2.2.1]heptane-2-carboxamide; (1R,2R,3S,4S)—N-(3,4-dichlorophenyl)-3-(2-(N-propionylpropionamido)pyridin-4-yl)-7-oxabicyclo[2.2.1]heptane-2-carboxamide; methyl (4-((1S,2S,3R,4R)-3-((3,4-dichlorophenyl)carbamoyl)-7-oxabicyclo[2.2.1]heptan-2-yl)pyridin-2-yl)carbamate; (1R,2R,3S,4S)—N-(3,4-dichlorophenyl)-3-(2-propionamidopyridin-4-yl)-7-oxabicyclo[2.2.1]heptane-2-carboxamide; ethyl 4-((1R,2S,3R,4S)-3-(3-(4-chlorophenyl)-1,2,4-oxadiazol-5-yl)-7-oxabicyclo[2.2.1]heptane-2-carboxamido)benzoate; (1R,2R,3R,4S)—N-(4-chloro-3-fluorophenyl)-3-(pyridin-4-yl)-7-oxabicyclo[2.2.1]heptane-2-carboxamide; (1R,2R,3S,4S)—N-(3,4-dichlorophenyl)-3-(2-(dimethylamino)pyrimidin-5-yl)-7-oxabicyclo[2.2.1]heptane-2-carboxamide; (1R,2R,3R,4S)-3-(2-cyanopyridin-4-yl)-N-(2,2'-difluoro-[1,1'-biphenyl]-4-yl)-7-oxabicyclo[2.2.1]heptane-2-carboxamide; (1S,4S)—N-(2-chloro-2'-fluoro-[1,1'-biphenyl]-4-yl)-3-(1H-pyrazol-5-yl)-7-oxabicyclo[2.2.1]hept-2-ene-2-carboxamide; (1R,2R,3S,4S)—N-(3,4-dichlorophenyl)-3-(pyrimidin-4-yl)-7-oxabicyclo[2.2.1]heptane-2-carboxamide; (1R,2R,3S,4S)—N-(3,4-dichlorophenyl)-3-(2-(dimethylamino)pyrimidin-5-yl)-7-oxabicyclo[2.2.1]heptane-2-carboxamide; methyl 5-chloro-2-((1R,2S,3R,4S)-3-(pyridin-4-yl)-7-oxabicyclo[2.2.1]heptane-2-carboxamido)benzoate; (1R,2S,3S,4S)-3-(4-carbamoylphenyl)-N-(3,4-dichlorophenyl)-7-oxabicyclo

[2.2.1]heptane-2-carboxamide; (1R,2S,3R,4S)—N-(2'-chloro-2-fluoro-[1,1'-biphenyl]-4-yl)-3-(pyridin-4-yl)-7-oxabicyclo[2.2.1]heptane-2-carboxamide; (1R,2R,3S,4S)—N-(2-chloro-2'-fluoro-[1,1'-biphenyl]-4-yl)-3-(6-(trifluoromethyl)pyridin-2-yl)-7-oxabicyclo[2.2.1]heptane-2-carboxamide; (1S,4S)—N-(2,2'-difluoro-[1,1'-biphenyl]-4-yl)-3-(1H-pyrazol-5-yl)-7-oxabicyclo[2.2.1]hept-2-ene-2-carboxamide; (1R,2R,3S,4S)—N-(3,4-dichlorophenyl)-3-(4-(3,5-dimethyl-1H-pyrazol-1-yl)phenyl)-7-oxabicyclo[2.2.1]heptane-2-carboxamide; (1R,2R,3S,4S)-3-(5-aminopyridin-3-yl)-N-(3,4-dichlorophenyl)-7-oxabicyclo[2.2.1]heptane-2-carboxamide; (1S,4S)—N-(2'-chloro-2-fluoro-[1,1'-biphenyl]-4-yl)-3-(1-(tetrahydro-2H-pyran-4-yl)-1H-pyrazol-5-yl)-7-oxabicyclo[2.2.1]hept-2-ene-2-carboxamide; (1S,4S)—N-(2,2'-difluoro-[1,1'-biphenyl]-4-yl)-3-(2-methylpyridin-4-yl)-7-oxabicyclo[2.2.1]hept-2-ene-2-carboxamide; (1R,2S,3R,4S)—N-(4-chloro-3-fluorophenyl)-3-(pyridin-4-yl)-7-oxabicyclo[2.2.1]heptane-2-carboxamide; (1R,2S,3S,4S)—N-(3,4-dichlorophenyl)-3-(2-(dimethylamino)pyrimidin-5-yl)-7-oxabicyclo[2.2.1]heptane-2-carboxamide; (1R,2R,3S,4S)-3-(4-carbamoylphenyl)-N-(3,4-dichlorophenyl)-7-oxabicyclo[2.2.1]heptane-2-carboxamide; (3aR,6R,7S,7aS)-2-([1,1'-biphenyl]-4-yl)-7-(pyridin-4-yl)-2,3,7,7a-tetrahydro-3a,6-epoxyisoindol-1(6H)-one; (1R,2R,3S,4S)-3-(2-aminopyrimidin-5-yl)-N-(3,4-dichlorophenyl)-7-oxabicyclo[2.2.1]heptane-2-carboxamide; (1S,4R)—N-(2-phenylpyrimidin-5-yl)-3-(pyridin-4-yl)-7-oxabicyclo[2.2.1]hept-2-ene-2-carboxamide; (1R,2S,3R,4S)—N-(2-chloro-[1,1'-biphenyl]-4-yl)-3-(pyridin-4-yl)-7-oxabicyclo[2.2.1]heptane-2-carboxamide; (1R,2R,3S,4S)-3-(6-aminopyridin-3-yl)-N-(3,4-dichlorophenyl)-7-oxabicyclo[2.2.1]heptane-2-carboxamide; (1R,2S,3R,4S)—N-(3-chloro-2-fluorophenyl)-3-(pyridin-4-yl)-7-oxabicyclo[2.2.1]heptane-2-carboxamide; (1R,2R,3S,4S)-3-(2-cyanopyridin-4-yl)-N-(3,4-dichlorophenyl)-7-oxabicyclo[2.2.1]heptane-2-carboxamide; ethyl 2-fluoro-4-(3-(6-(trifluoromethyl)pyridin-2-yl)-7-oxabicyclo[2.2.1]hept-2-ene-2-carboxamido)benzoate; (1S,4S)-3-(2-chloropyridin-4-yl)-N-(2,2'-difluoro-[1,1'-biphenyl]-4-yl)-7-oxabicyclo[2.2.1]hept-2-ene-2-carboxamide; ethyl 5-((1S,2S,3S,4R)-3-((3,4-dichlorophenyl)carbamoyl)-7-oxabicyclo[2.2.1]heptan-2-yl)nicotinate; (1S,4S)-3-cyano-N-(2,2'-difluoro-[1,1'-biphenyl]-4-yl)-7-oxabicyclo[2.2.1]hept-2-ene-2-carboxamide; (1R,4S)—N-(2-chloro-[1,1'-biphenyl]-4-yl)-3-(1H-pyrazol-5-yl)-7-oxabicyclo[2.2.1]hept-2-ene-2-carboxamide; ethyl 5-((1S,2S,3R,4R)-3-((3,4-dichlorophenyl)carbamoyl)-7-oxabicyclo[2.2.1]heptan-2-yl)nicotinate; (1S,4S)-3-(2-aminopyridin-4-yl)-N-(2,2'-difluoro-[1,1'-biphenyl]-4-yl)-7-oxabicyclo[2.2.1]hept-2-ene-2-carboxamide; (1S,4S)—N-(2-chloro-[1,1'-biphenyl]-4-yl)-3-(1-(tetrahydro-2H-pyran-4-yl)-1H-pyrazol-5-yl)-7-oxabicyclo[2.2.1]hept-2-ene-2-carboxamide; (1S,4S)—N-(2-fluoro-3-(trifluoromethoxy)phenyl)-3-(pyridin-4-yl)-7-oxabicyclo[2.2.1]hept-2-ene-2-carboxamide; (1R,2S,3R,4S)—N-(2,2'-difluoro-[1,1'-biphenyl]-4-yl)-3-(pyridin-4-yl)-7-oxabicyclo[2.2.1]heptane-2-carboxamide; (1R,2S,3S,4S)—N-(3,4-dichlorophenyl)-3-(pyrimidin-4-yl)-7-oxabicyclo[2.2.1]heptane-2-carboxamide; methyl 5-chloro-2-((1S,4S)-3-(pyridin-4-yl)-7-oxabicyclo[2.2.1]hept-2-ene-2-carboxamido)benzoate; (1R,2S,3S,4S)—N-([1,1'-biphenyl]-4-yl)-3-(pyridin-3-yl)-7-oxabicyclo[2.2.1]heptane-2-carboxamide; (1S,4S)-3-(2-cyanopyridin-4-yl)-N-(2,2'-difluoro-[1,1'-biphenyl]-4-yl)-7-oxabicyclo[2.2.1]hept-2-ene-2-carboxamide; (1R,2R,3S,4S)—N-([1,1'-biphenyl]-4-yl)-3-(pyridin-3-yl)-7-oxabicyclo[2.2.1]heptane-2-carboxamide; ethyl 2-morpholino-4-((1R,2S,3R,4S)-3-(pyridin-4-yl)-7-oxabicyclo[2.2.1]heptane-2-carboxamido)benzoate; (1R,2S,3S,4S)-3-(2-cyanopyridin-4-yl)-N-(3,4-dichlorophenyl)-7-oxabicyclo[2.2.1]heptane-2-carboxamide; (1R,2R,3R,4S)-3-cyano-N-(2,2'-difluoro-[1,1'-biphenyl]-4-yl)-7-oxabicyclo[2.2.1]heptane-2-carboxamide; (1S,4S)—N-(5-methyl-1-phenyl-1H-pyrazol-3-yl)-3-(pyridin-4-yl)-7-oxabicyclo[2.2.1]hept-2-ene-2-carboxamide; (1S,4R)—N-(2,2'-difluoro-[1,1'-biphenyl]-4-yl)-3-(1-(tetrahydro-2H-pyran-4-yl)-1H-pyrazol-5-yl)-7-oxabicyclo[2.2.1]hept-2-ene-2-carboxamide; (1R,2S,3S,4S)-3-(2-aminopyrimidin-5-yl)-N-(3,4-dichlorophenyl)-7-oxabicyclo[2.2.1]heptane-2-carboxamide; (1R,2R,3R,4S)-3-(2-aminopyridin-4-yl)-N-(2,2'-difluoro-[1,1'-biphenyl]-4-yl)-7-oxabicyclo[2.2.1]heptane-2-carboxamide; (1R,2R,3R,4S)—N-(2,2'-difluoro-[1,1'-biphenyl]-4-yl)-3-(2-methyl-2H-indazol-5-yl)-7-oxabicyclo[2.2.1]heptane-2-carboxamide; (1R,2S,3S,4S)-3-(6-aminopyridin-3-yl)-N-(3,4-dichlorophenyl)-7-oxabicyclo[2.2.1]heptane-2-carboxamide; ethyl 2-fluoro-4-((1S,4R)-3-(pyridin-4-yl)-7-oxabicyclo[2.2.1]hept-2-ene-2-carboxamido)benzoate; (1R,2R,3S,4S)-3-(6-acetamidopyridin-3-yl)-N-(3,4-dichlorophenyl)-7-oxabicyclo[2.2.1]heptane-2-carboxamide; (1R,2R,3S,4S)—N-(3,4-dichlorophenyl)-3-(2-methylpyridin-4-yl)-7-oxabicyclo[2.2.1]heptane-2-carboxamide; (1R,2S,3R,4S)-3-(pyridin-4-yl)-N-(2,2',4'-trifluoro-[1,1'-biphenyl]-4-yl)-7-oxabicyclo[2.2.1]heptane-2-carboxamide; (1R,2R,3S,4S)—N-(3,4-dichlorophenyl)-3-(pyridin-4-yl)-7-oxabicyclo[2.2.1]heptane-2-carboxamide; (1R,2R,3S,4S)—N-(2,2'-difluoro-[1,1'-biphenyl]-4-yl)-3-(pyridin-4-yl)-7-oxabicyclo[2.2.1]heptane-2-carboxamide; tert-butyl 4-((1S,2S,3S,4R)-3-((3,4-dichlorophenyl)carbamoyl)-7-oxabicyclo[2.2.1]heptan-2-yl)-5,6-dihydropyridine-1(2H)-carboxylate; (1R,2R,3R,4S)—N-([1,1'-biphenyl]-4-yl)-3-(pyridin-4-yl)-7-oxabicyclo[2.2.1]heptane-2-carboxamide; (1R,2R,4S,5S)—N-(4'-chloro-2'-cyano-2-fluoro-[1,1'-biphenyl]-4-yl)-4-(pyridin-4-yl)-8-oxatricyclo[3.2.1.02,4]octane-2-carboxamide; (1R,2R,3S,4S)—N-(2'-chloro-2-fluoro-[1,1'-biphenyl]-4-yl)-3-(pyridin-4-yl)-7-oxabicyclo[2.2.1]heptane-2-carboxamide; (1S,2S,3R,4R)-3-cyano-N-(3,4-dichlorophenyl)-7-oxabicyclo[2.2.1]heptane-2-carboxamide; (1R,2R,3R,4S)—N-(2,2'-difluoro-[1,1'-biphenyl]-4-yl)-3-(2-(dimethylamino)pyrimidin-5-yl)-7-oxabicyclo[2.2.1]heptane-2-carboxamide; (1R,2R,4S,5S)—N-([1,1'-biphenyl]-4-yl)-4-(pyridin-4-yl)-8-oxatricyclo[3.2.1.02,4]octane-2-carboxamide; (1R,2R,3S,4S)—N-(2,2'-difluoro-[1,1'-biphenyl]-4-yl)-3-(pyridin-2-yl)-7-oxabicyclo[2.2.1]heptane-2-carboxamide; (1R,2S,3S,4S)—N-(3,4-dichlorophenyl)-3-(3,6-dihydro-2H-pyran-4-yl)-7-oxabicyclo[2.2.1]heptane-2-carboxamide; (1R,2R,3S,4S)—N-(2,2'-difluoro-[1,1'-biphenyl]-4-yl)-3-(1-methyl-3-(trifluoromethyl)-1H-pyrazol-5-yl)-7-oxabicyclo[2.2.1]heptane-2-carboxamide; (1R,2R,3S,4S)—N-(2-chloro-[1,1'-biphenyl]-4-yl)-3-(6-(trifluoromethyl)pyridin-2-yl)-7-oxabicyclo[2.2.1]heptane-2-carboxamide; (1R,2S,3S,4S)—N-(2,2'-difluoro-[1,1'-biphenyl]-4-yl)-3-(1-methyl-3-(trifluoromethyl)-1H-pyrazol-5-yl)-7-oxabicyclo[2.2.1]heptane-2-carboxamide; (1R,2R,4S,5S)—N-(2'-chloro-2-fluoro-[1,1'-biphenyl]-4-yl)-4-(pyridin-4-yl)-8-oxatricyclo[3.2.1.02,4]octane-2-carboxamide; (1R,2R,3S,4S)—N-(2,2'-difluoro-[1,1'-biphenyl]-4-yl)-3-(6-(trifluoromethyl)pyridin-2-yl)-7-oxabicyclo[2.2.1]heptane-2-carboxamide; (1R,2R,3R,4S)-3-(2,6-dichloropyridin-4-yl)-N-(2,2'-difluoro-[1,1'-biphenyl]-4-yl)-7-oxabicyclo[2.2.1]heptane-2-carboxamide; tert-butyl 4-((1S,2S,3R,4R)-3-((3,4-dichlorophenyl)carbamoyl)-7-oxabicyclo[2.2.1]heptan-2-yl)-5,6-dihydropyridine-1(2H)-carboxylate; (1R,2R,3S,4S)—N-(3,4-dichlorophenyl)-3-(1-methyl-3-(trifluoromethyl)-1H- pyrazol-5-yl)-7-oxabicyclo[2.2.1]heptane-2-carboxamide; (1R,2R,4S,5S)—N-(2-chloro-[1,1'-biphenyl]-4-yl)-4-(pyridin-4-yl)-8-oxatricyclo[3.2.1.02,4]octane-2-carboxamide; (1R,2R,3S,4S)-3-(2-aminopyridin-4-yl)-N-(2,2'-difluoro-[1,1'-biphenyl]-4-yl)-7-oxabicyclo[2.2.1]heptane-2-carboxamide; (1R,2R,3S,4S)—N-(3,4-dichlorophenyl)-3-(6-(trifluoromethyl)pyridin-2-yl)-7-oxabicyclo[2.2.1]heptane-2-carboxamide; (1R,2R,3R,4S)—N-(2,2'-difluoro-[1,1'-biphenyl]-4-yl)-1,4-dimethyl-3-(pyridin-4-yl)-7-oxabicyclo[2.2.1]heptane-2-carboxamide; (1R,2R,3S,4S)—N-(3,4-dichlorophenyl)-3-(1,2,3,6-tetrahydropyridin-4-yl)-7-oxabicyclo[2.2.1]heptane-2-carboxamide; (1R,2R,3R,4S)-3-(3-chloro-2-fluoropyridin-4-yl)-N-(2,2'-difluoro-[1,1'-biphenyl]-4-yl)-7-oxabicyclo[2.2.1]heptane-2-carboxamide; (1R,2R,4S,5S)—N-(2-chloro-2'-fluoro-[1,1'-biphenyl]-4-yl)-4-(pyridin-4-yl)-8-oxatricyclo[3.2.1.02,4]octane-2-carboxamide; (1S,4S)-3-(3-chloro-2-fluoropyridin-4-yl)-N-(2,2'-difluoro-[1,1'-biphenyl]-4-yl)-7-oxabicyclo[2.2.1]hept-2-ene-2-carboxamide; (1R,2R,3S,4S)—N-(2-chloro-[1,1'-biphenyl]-4-yl)-3-(pyridin-4-yl)-7-oxabicyclo[2.2.1]heptane-2-carboxamide; (1R,2R,3S,4S)-3-(2-chloropyridin-4-yl)-N-(3,4-dichlorophenyl)-7-oxabicyclo[2.2.1]heptane-2-carboxamide; (1R,2R,3S,4S)—N-(2-chloro-[1,1'-biphenyl]-4-yl)-3-(1-methyl-3-(trifluoromethyl)-1H-pyrazol-5-yl)-7-oxabicyclo[2.2.1]heptane-2-carboxamide; (1S,2R,3R,4R)-3-cyano-N-(2,2'-difluoro-[1,1'-biphenyl]-4-yl)-7-oxabicyclo[2.2.1]heptane-2-carboxamide; (1R,2S,3S,4S)-3-(pyridin-4-yl)-N-(2,2',4'-trifluoro-[1,1'-biphenyl]-4-yl)-7-oxabicyclo[2.2.1]heptane-2-carboxamide; (1S,2S,3R,4R)—N-(3,4-dichlorophenyl)-3-(pyridin-4-yl)-7-oxabicyclo[2.2.1]heptane-2-carboxamide; 1R,2S,3S,4S)—N-(2-chloro-[1,1'-biphenyl]-4-yl)-3-(pyridin-4-yl)-7-oxabicyclo[2.2.1]heptane-2-carboxamide; ethyl 4-((1R,2R,3S,4S)-3-(pyridin-4-yl)-7-oxabicyclo[2.2.1]heptane-2-carboxamido)benzoate; (1R,2R,3S,4S)-3-(2-aminopyridin-4-yl)-N-(2-chloro-[1,1'-biphenyl]-4-yl)-7-oxabicyclo[2.2.1]heptane-2-carboxamide; (1R,2R,3S,4S)-3-(2-aminopyridin-4-yl)-N-(3,4-dichlorophenyl)-7-oxabicyclo[2.2.1]heptane-2-carboxamide; (1R,2R,4S,5S)—N-(3,4-dichlorophenyl)-4-(pyridin-4-yl)-8-oxatricyclo[3.2.1.02,4]octane-2-carboxamide; (1S,4S)—N-(2,2'-difluoro-[1,1'-biphenyl]-4-yl)-3-(3-fluoropyridin-4-yl)-7-oxabicyclo[2.2.1]hept-2-ene-2-carboxamide; (1R,2S,3S,4S)-3-(2-aminopyridin-4-yl)-N-(2-chloro-[1,1'-biphenyl]-4-yl)-7-oxabicyclo[2.2.1]heptane-2-carboxamide; (1R,2R,3S,4S)-3-(pyridin-4-yl)-N-(2,2',4'-trifluoro-[1,1'-biphenyl]-4-yl)-7-oxabicyclo[2.2.1]heptane-2-carboxamide; (1S,2R,3S,4R)—N2-(2,2'-difluoro-[1,1'-biphenyl]-4-yl)-7-oxabicyclo[2.2.1]heptane-2,3-dicarboxamide; (1R,2R,4S,5S)—N-(2,2'-difluoro-[1,1'-biphenyl]-4-yl)-4-(pyridin-4-yl)-8-oxatricyclo[3.2.1.02,4]octane-2-carboxamide; (1R,2R,4S,5S)—N-(2'-chloro-2-cyano-[1,1'-biphenyl]-4-yl)-4-(pyridin-4-yl)-8-oxatricyclo[3.2.1.02,4]octane-2-carboxamide; (1R,2S,3S,4S)-3-(2-aminopyridin-4-yl)-N-(3,4-dichlorophenyl)-7-oxabicyclo[2.2.1]heptane-2-carboxamide; (1R,4S)-3-(2,6-dichloropyridin-4-yl)-N-(2,2'-difluoro-[1,1'-biphenyl]-4-yl)-7-oxabicyclo[2.2.1]hept-2-ene-2-carboxamide; (1R,2R,3S,4S)—N-(3,4-dichlorophenyl)-3-(3,6-dihydro-2H-pyran-4-yl)-7-oxabicyclo[2.2.1]heptane-2-carboxamide; ethyl 4-((1R,2S,3S,4S)-3-(2-aminopyridin-4-yl)-7-oxabicyclo[2.2.1]heptane-2-carboxamido)benzoate; (1R,2R,3S,4S)—N-([1,1'-biphenyl]-4-yl)-3-(pyridin-4-yl)-7-oxabicyclo[2.2.1]heptane-2-carboxamide; (1S,2S,3S,4R)—N-([1,1'-biphenyl]-4-yl)-3-(pyridin-3-yl)-7-oxabicyclo[2.2.1]heptane-2-carboxamide; (1S,2S,3S,4R)—N-([1,1'-biphenyl]-4-yl)-3-(1-methyl-1H-pyrazol-3-yl)-7-oxabicyclo[2.2.1]heptane-2-carboxamide; (1S,2S,3S,4R)—N-(2'-chloro-2-fluoro-[1,1'-biphenyl]-4-yl)-3-(6-(trifluoromethyl)pyridin-2-yl)-7-oxabicyclo[2.2.1]heptane-2-carboxamide; (1R,2S,3R,4S)—N-(1-methylpiperidin-4-yl)-3-(pyridin-4-yl)-7-oxabicyclo[2.2.1]heptane-2-carboxamide; (1R,2R,3R,4S)—N-(2-fluoro-3-(trifluoromethyl)phenyl)-3-((2R)-6-(trifluoromethyl)piperidin-2-yl)-7-oxabicyclo[2.2.1]heptane-2-carboxamide; ethyl 4-((1S,2S,3R,4S)-3-(1-methyl-3-(trifluoromethyl)-1H-pyrazol-5-yl)-7-oxabicyclo[2.2.1]heptane-2-carboxamido)benzoate; ethyl 3-((1R,2S,3R,4S)-3-(pyridin-4-yl)-7-oxabicyclo[2.2.1]heptane-2-carboxamido)benzoate; (1R,2S,3R,4S)—N-(2-fluoro-3-(trifluoromethoxy)phenyl)-3-(4-methylpyridin-2-yl)-7-oxabicyclo[2.2.1]heptane-2-carboxamide; ethyl 4-((1S,4S)-3-(6-(trifluoromethyl)pyridin-2-yl)-7-oxabicyclo[2.2.1]hept-2-ene-2-carboxamido)benzoate; (1S,4S)—N-(2-fluoro-3-(trifluoromethyl)phenyl)-3-(1-methyl-3-(trifluoromethyl)-1H-pyrazol-5-yl)-7-oxabicyclo[2.2.1]hept-2-ene-2-carboxamide; (1S,2S,3R,4S)—N-(1-(methylsulfonyl)piperidin-4-yl)-3-(pyridin-4-yl)-7-oxabicyclo[2.2.1]heptane-2-carboxamide; methyl 5-chloro-2-((1S,2S,3R,4S)-3-(pyridin-4-yl)-7-oxabicyclo[2.2.1]heptane-2-carboxamido)benzoate; (1S,2S,3R,4S)-3-(pyridin-4-yl)-N-(3-(trifluoromethoxy)phenyl)-7-oxabicyclo[2.2.1]heptane-2-carboxamide; (1R,2S,3R,4S)—N-(3,4-dichlorophenyl)-3-(1-methyl-3-(trifluoromethyl)-1H-pyrazol-5-yl)-7-oxabicyclo[2.2.1]heptane-2-carboxamide; (1R,2R,3R,4S)—N-(3,4-dichlorophenyl)-3-(pyridin-4-yl)-7-oxabicyclo[2.2.1]heptane-2-carboxamide; (1R,4S)—N-(3,4-dichlorophenyl)-3-(6-(trifluoromethyl)pyridin-2-yl)-7-oxabicyclo[2.2.1]hept-2-ene-2-carboxamide; (1S,4S)—N-(2,2'-difluoro-[1,1'-biphenyl]-4-yl)-3-(1-methyl-3-(trifluoromethyl)-1H-pyrazol-5-yl)-7-oxabicyclo[2.2.1]hept-2-ene-2-carboxamide; methyl 4-fluoro-3-((1S,2S,3R,4S)-3-(pyridin-4-yl)-7-oxabicyclo[2.2.1]heptane-2-carboxamido)benzoate; (1S,2S,3R,4S)-3-(pyridin-4-yl)-N-(4-(trifluoromethoxy)phenyl)-7-oxabicyclo[2.2.1]heptane-2-carboxamide; (1S,2R,3R,4S)—N-(3,4-dichlorophenyl)-3-(pyrazin-2-yl)-7-oxabicyclo[2.2.1]heptane-2-carboxamide; (1R,4S)—N-(3,4-dichlorophenyl)-3-(1-methyl-3-(trifluoromethyl)-1H-pyrazol-5-yl)-7-oxabicyclo[2.2.1]hept-2-ene-2-carboxamide; ethyl 4-((1R,4S)-3-(1-methyl-3-(trifluoromethyl)-1H-pyrazol-5-yl)-7-oxabicyclo[2.2.1]hept-2-ene-2-carboxamido)benzoate; (1R,2R,3R,4S)—N-(2,2'-difluoro-[1,1'-biphenyl]-4-yl)-3-(6-(trifluoromethyl)pyridin-2-yl)-7-oxabicyclo[2.2.1]heptane-2-carboxamide; (1R,4S)—N-(3,4-dichlorophenyl)-3-(pyrazin-2-yl)-7-oxabicyclo[2.2.1]hept-2-ene-2-carboxamide; (1R,2S,3R,4S)—N-(5-chloro-2-fluorophenyl)-3-(pyridin-4-yl)-7-oxabicyclo[2.2.1]heptane-2-carboxamide; (1R,2S,3R,4S)—N-(1-acetylpiperidin-4-yl)-3-(pyridin-4-yl)-7-oxabicyclo[2.2.1]heptane-2-carboxamide; (1R,2S,3R,4S)—N-(4-chloro-3-fluorophenyl)-3-(pyridin-4-yl)-7-oxabicyclo[2.2.1]heptane-2-carboxamide; (1R,2S,3R,4S)—N-(4-chloro-2-cyanophenyl)-3-(pyridin-4-yl)-7-oxabicyclo[2.2.1]heptane-2-carboxamide; ethyl 4-((1R,2S,3R,4S)-3-(pyridin-4-yl)-7-oxabicyclo[2.2.1]heptane-2-carboxamido)benzoate; (1R,4S)—N-(2,2'-difluoro-[1,1'-biphenyl]-4-yl)-3-(6-(trifluoromethyl)pyridin-2-yl)-7-oxabicyclo[2.2.1]hept-2-ene-2-carboxamide; ethyl 4-((1R,2S,3R,4S)-3-(5-methoxypyridin-2-yl)-7-oxabicyclo[2.2.1]heptane-2-carboxamido)benzoate; (1R,2R,3R,4S)—N-(2-chloro-[1,1'-biphenyl]-4-yl)-3-(1-methyl-3-(trifluoromethyl)-1H-pyrazol-5-yl)-7-oxabicyclo[2.2.1]heptane-2-carboxamide; (1R,2R,3R,4S)—N-(2-fluoro-3-(trifluoromethyl)phenyl)-3-(1-methyl-3-(trifluoromethyl)-1H-pyrazol-5-yl)-7-oxabicyclo[2.2.1]heptane-2-carboxamide; (1R,2R,3R,4S)—N-(2- fluoro-3-(trifluoromethoxy)phenyl)-3-(4-methylpyridin-2-yl)-7-oxabicyclo[2.2.1]heptane-2-carboxamide; (1R,2R,3R,4S)—N-(3,4-dichlorophenyl)-3-(6-(trifluoromethyl)pyridin-2-yl)-7-oxabicyclo[2.2.1]heptane-2-carboxamide; (1R,2R,3R,4S)—N-(3,4-dichlorophenyl)-3-(1-methyl-3-(trifluoromethyl)-1H-pyrazol-5-yl)-7-oxabicyclo[2.2.1]heptane-2-carboxamide; (1R,4S)—N-(2-fluoro-3-(trifluoromethyl)phenyl)-3-(6-(trifluoromethyl)pyridin-2-yl)-7-oxabicyclo[2.2.1]hept-2-ene-2-carboxamide; ethyl 4-((1R,2R,3R,4S)-3-(1-methyl-3-(trifluoromethyl)-1H-pyrazol-5-yl)-7-oxabicyclo[2.2.1]heptane-2-carboxamido)benzoate; (1R,2S,3R,4S)—N-cyclohexyl-3-(pyridin-4-yl)-7-oxabicyclo[2.2.1]heptane-2-carboxamide; (1R,4S)—N-(2-chloro-[1,1'-biphenyl]-4-yl)-3-(6-(trifluoromethyl)pyridin-2-yl)-7-oxabicyclo[2.2.1]hept-2-ene-2-carboxamide; (1R,2S,3R,4S)—N-(5-chloro-4-methylpyridin-2-yl)-3-(pyridin-4-yl)-7-oxabicyclo[2.2.1]heptane-2-carboxamide; (1R,2S,3R,4S)—N-(3,4-dichlorophenyl)-3-(pyridin-4-yl)-7-oxabicyclo[2.2.1]heptane-2-carboxamide; (1R,2S,3R,4S)—N-(2,3-dihydrobenzo[b][1,4]dioxin-5-yl)-3-(pyridin-4-yl)-7-oxabicyclo[2.2.1]heptane-2-carboxamide; (1R,4S)—N-(2,2'-difluoro-[1,1'-biphenyl]-4-yl)-3-(pyrazin-2-yl)-7-oxabicyclo[2.2.1]hept-2-ene-2-carboxamide, (1R,2S,3R,4S)—N-(3-chloro-2-fluorophenyl)-3-(pyridin-4-yl)-7-oxabicyclo[2.2.1]heptane-2-carboxamide; (1R,2R,3R,4S)—N-(2,2'-difluoro-[1,1'-biphenyl]-4-yl)-3-(4-methylpyridin-2-yl)-7-oxabicyclo[2.2.1]heptane-2-carboxamide; (1R,4S)—N-(2,2'-difluoro-[1,1'-biphenyl]-4-yl)-3-(2-((S)-3-hydroxypyrrolidin-1-yl)pyridin-4-yl)-7-oxabicyclo[2.2.1]hept-2-ene-2-carboxamide; (1R,2R,3R,4S)—N-(2-fluoro-3-(trifluoromethyl)phenyl)-3-(pyrazin-2-yl)-7-oxabicyclo[2.2.1]heptane-2-carboxamide; (1R,2S,3R,4S)—N-(3-fluoro-4-(trifluoromethoxy)phenyl)-3-(pyridin-4-yl)-7-oxabicyclo[2.2.1]heptane-2-carboxamide; (1R,2R,3R,4S)—N-(5-chloropyridin-2-yl)-3-(pyridin-4-yl)-7-oxabicyclo[2.2.1]heptane-2-carboxamide; (1R,2S,3R,4S)—N-(2,2'-difluoro-[1,1'-biphenyl]-4-yl)-3-(4-methylpyridin-2-yl)-7-oxabicyclo[2.2.1]heptane-2-carboxamide; (1R,2S,3R,4S)—N-(2-fluoro-3-(trifluoromethoxy)phenyl)-3-(pyridin-4-yl)-7-oxabicyclo[2.2.1]heptane-2-carboxamide; (1R,2R,3R,4S)—N-(2,2'-difluoro-[1,1'-biphenyl]-4-yl)-3-(1-methyl-3-(trifluoromethyl)-1H-pyrazol-5-yl)-7-oxabicyclo[2.2.1]heptane-2-carboxamide; (1R,2S,3R,4S)—N-(4-chloropyridin-2-yl)-3-(pyridin-4-yl)-7-oxabicyclo[2.2.1]heptane-2-carboxamide; ethyl 4-((1R,2R,3R,4S)-3-(pyrazin-2-yl)-7-oxabicyclo[2.2.1]heptane-2-carboxamido)benzoate; and (1R,2S,3R,4S)—N-(4-cyanophenyl)-3-(pyridin-4-yl)-7-oxabicyclo[2.2.1]heptane-2-carboxamide.

It is noted that the compounds of the present invention may be in the form of a pharmaceutically acceptable salt. It is further note that the compound of the present invention may comprise a single enantiomer, or a mixture of the corresponding enantioments.

Further compounds of the invention are detailed in the Examples, infra.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or mixture of the corresponding enantiomers, and racemates of the compound. "Enantiomers" are a pair of stereoisomers that are non-superimposable mirror images of each other. Generally, a 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including diasteriomeric mixtures enantiomers mixture, and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Methods for the determination of stereochemistry and the separation of stereoisomers are well known in the art (e.g., see "Advanced Organic Chemistry", 4th edition, March, Jerry, John Wiley & Sons, New York, 1992). Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}F$, $^{32}F$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

II. Preparation of the Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Synthesis", John Wiley and Sons, 1991.

Typically, the compounds of formula (I) can be prepared according to synthetic routes 1-6 provided infra., where $R^1$ and $R^3$ and the formulae are as defined in the Detailed Description of the Invention. The following reaction schemes are given to be illustrative, not limiting, descriptions of the synthesis of compounds of the invention. Detailed descriptions of the synthesis of compounds of the invention are given in the Examples, infra.

General Synthetic Route 1

Reaction Conditions:

a. Intermediate I-1 can be prepared from methyl propiolate by bromination, followed by Diels-Alder reaction with furan. Methods for the bromination are known, using N-bromosuccinimide or similar brominating agents in the presence of a silver catalyst, such as silver nitrate in a polar solvent such as acetone or MEK. The Diels-Alder cycloaddition occurs with mild heating (ca. 80° C.) in excess furan.
b. Compound I-2 can be prepared by hydrogenation of I-1 using a palladium catalyst under a low hydrogen pressure in a non-protic solvent such as ethyl acetate.
c. Compound I-3 can be prepared from I-2 by hydrolysis of the methyl ester under conventional conditions, followed by formation of the t-butyl ester. Hydrolysis occurs under mild conditions using aqueous base (e.g., lithium hydroxide, room temperature) in a solvent mixture typically containing an alcohol and a water-miscible co-solvent such as THF. Formation of the t-butyl ester can be accomplished under known conditions such as mild heating (e.g., 40-80° C.) with excess DMF di-t-butyl acetal in toluene.
d. Compound I-3 is conveniently debrominated to compound I-4 using a dissolving metal reduction, such as reaction with zinc in mildly acidic aqueous mixture. A suitable co-solvent such as THF is used, and a mild acid such as formic or acetic acid. The reaction can be conducted at 0° C. to room temperature.
e. The t-butyl ester of compound I-4 can be hydrolyzed under acidic conditions, using a strong acid such as hydrochloric, sulfuric or phosphoric acid in a suitable polar aprotic solvent such as dioxane, to produce the free carboxylic acid. Conventional amide formation conditions can be used to make the amide I-5. For example, the carboxylic acid can be treated with a desired aniline and a dehydrating agent such as a carbodiimide (DCC, EDCI) and catalytic DMAP in pyridine.
f. Arylation of compound I-5 with an aryl boronate ester can be achieved with a rhodium dimer catalyst and BINAP with aqueous base in dioxane, with microwave heating at about 100° C. Arylation provides a mixture of cis and trans isomers that can be separated; the trans

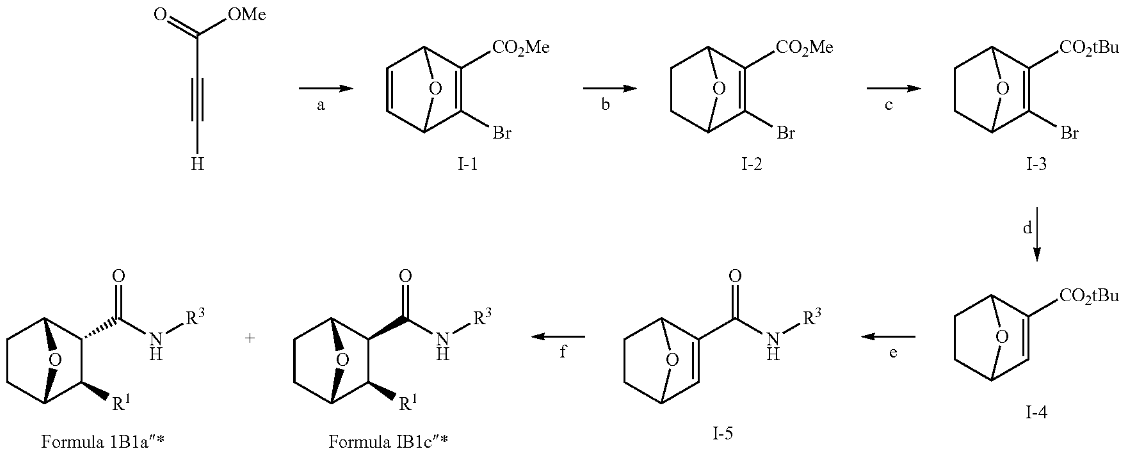

I-1 I-2 I-3 I-4 I-5

Formula 1B1a"* + Formula IB1c"*

* The product includes a mixture of the formulae as shown and their corresponding enantiomers.

isomer is typically the major product, with the aryl group added syn to the ether bridge of the product.

General Synthetic Route 2

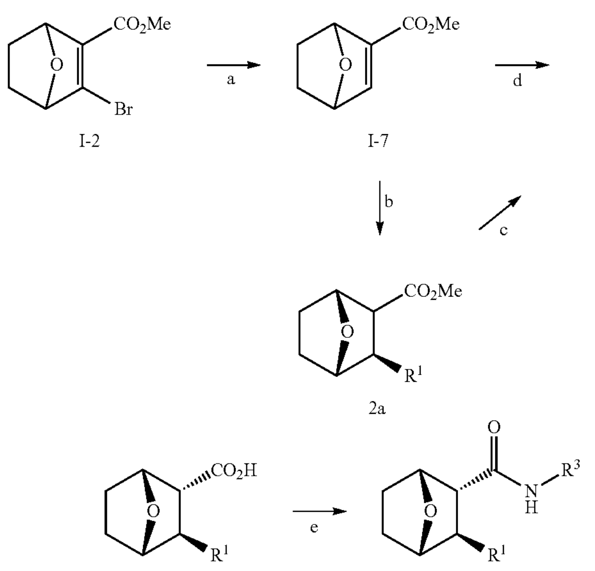

I-2

I-7

2a

2b

Formula IB1a″*

*The product is a mixture of Formula IB1a″ and the corresponding enantiomer.

Reaction Conditions:

a. Compound I-2, made in General Synthetic Route 1, can be de-brominated with zinc in aqueous acetic acid under mild conditions, e.g., 0° C. to room temperature.

b-c or d. The arylation of compound I-7 with an aryl boronate ester is conducted with a dimeric rhodium catalyst plus BINAP and an aqueous base in dioxane, with microwave heating at about 100° C. Arylation provides a mixture of cis and trans isomers that can be separated; the trans isomer is typically the major product, with the aryl group added syn to the ether bridge of the product. Hydrolysis to the free carboxylic acid can be achieved with aqueous base and an organic co-solvent either in the same pot as the arylation, or the ester can be isolated and then hydrolyzed in a separate step.

e. Formation of the amide product can be accomplished using known amide formation conditions, such as treating the acid plus the desired aniline or amine with T3P (propyl phosphonic anhydride) and an amine base (diisopropyl ethylamine, triethylamine) in organic solvent such as ethyl acetate plus DMF, at room temperature or at elevated temperature up to about 100° C.

General Synthetic Route 3

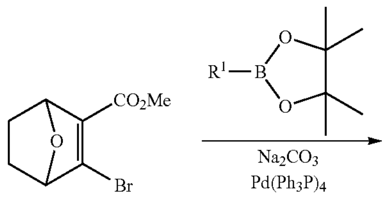

I-2

-continued

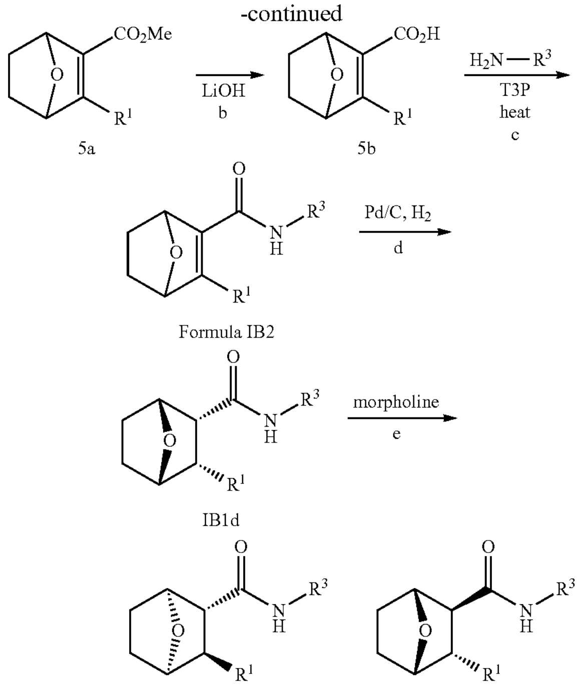

5a

5b

Formula IB2

IB1d

Formula IB1b′

Formula IB1b″

Reaction Conditions:

a. Intermediate 5a can be prepared from intermediate I-2 using standard Suzuki coupling conditions. Typically a mixture or bromide, boronic ester, base, and tetrakis in 3:1 1,4-dioxane:water was warmed (ca. 100° C.) for 30 minutes in a microwave reactor.

b. Compound 5b can be prepared from 5a by hydrolysis of the methyl ester under conventional conditions. Hydrolysis occurs under mild conditions using aqueous base (e.g., lithium hydroxide, room temperature) in a solvent mixture typically containing an alcohol and a water-miscible co-solvent such as THF.

c. Formation of the amide product can be accomplished using known amide formation conditions, such as treating the acid plus the desired aniline or amine with T3P (propyl phosphonic anhydride) and an amine base (diisopropyl ethylamine, triethylamine) in organic solvent such as ethyl acetate at room temperature or at elevated temperature up to about 80° C.

d. Compound IB1d can be prepared by hydrogenation of IB2 using a palladium catalyst under a low hydrogen pressure in a solvent such as ethyl acetate.

e. Compound IB1b (enantiomers IB1b' and IB1b") can be prepared by warming (ca. 80° C.) a solution of IB1d in morpholine.

General Synthetic Route 4

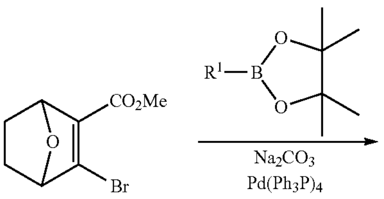

I-2

-continued

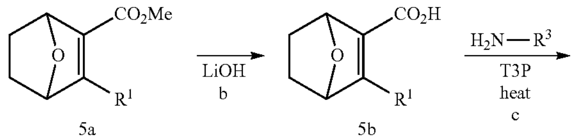

5a 5b

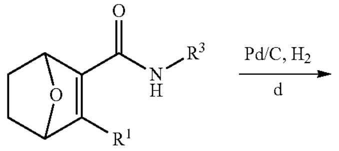

Formula IB2

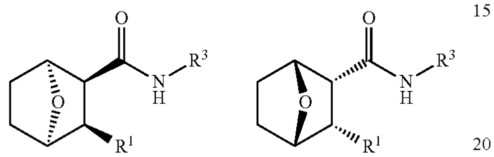

Formula IB1d' Formula IB1d"

Reaction Conditions:

a. Intermediate 5a can be prepared from intermediate I-2 using standard Suzuki coupling conditions. Typically a mixture or bromide, boronic ester, base, and tetrakis in 3:1 1,4-dioxane:water was warmed (ca. 100° C.) for 30 minutes in a microwave reactor.

b. Compound 5b can be prepared from 5a by hydrolysis of the methyl ester under conventional conditions. Hydrolysis occurs under mild conditions using aqueous base (e.g., lithium hydroxide, room temperature) in a solvent mixture typically containing an alcohol and a water-miscible co-solvent such as THF.

c. Formation of the amide product can be accomplished using known amide formation conditions, such as treating the acid plus the desired aniline or amine with T3P (propyl phosphonic anhydride) and an amine base (diisopropyl ethylamine, triethylamine) in organic solvent such as ethyl acetate at room temperature or at elevated temperature up to about 80° C.

d. Compound IB1d (enantiomers IB1d' and IB1d") can be prepared by hydrogenation of IB2 using a palladium catalyst under a low hydrogen pressure in a solvent such as ethyl acetate.

General Synthetic Route 5

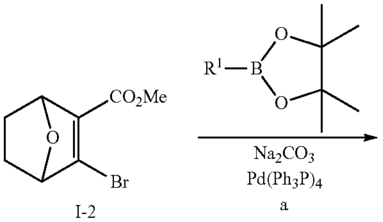

I-2

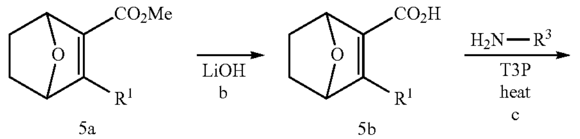

5a 5b

-continued

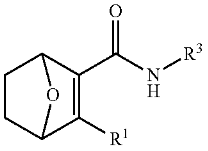

Formula IB2

Reaction Conditions:

a. Intermediate 5a can be prepared from intermediate I-2 using standard Suzuki coupling conditions. Typically a mixture or bromide, boronic ester, base, and tetrakis in 3:1 1,4-dioxane:water was warmed (ca. 100° C.) for 30 minutes in a microwave reactor.

b. Compound 5b can be prepared from 5a by hydrolysis of the methyl ester under conventional conditions. Hydrolysis occurs under mild conditions using aqueous base (e.g., lithium hydroxide, room temperature) in a solvent mixture typically containing an alcohol and a water-miscible co-solvent such as THF.

c. Formation of the amide product can be accomplished using known amide formation conditions, such as treating the acid plus the desired aniline or amine with T3P (propyl phosphonic anhydride) and an amine base (diisopropyl ethylamine, triethylamine) in organic solvent such as ethyl acetate at room temperature or at elevated temperature up to about 80° C.

General Synthetic Route 6

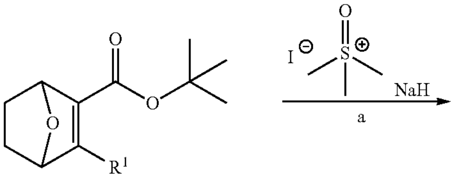

6a

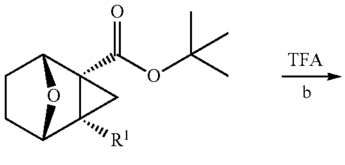

6b

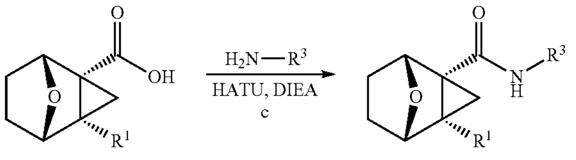

6c Formula IB3b

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Reaction Conditions:

a. Intermediate 6b can be prepared from intermediate 6a using known cyclopropanation conditions. Typically a mixture of trimethylsulfoxonium iodide in a solvent such as DMSO was treated with NaH followed by 6a and gently warmed (ca. 50° C.) overnight.

b. Compound 6c can be prepared from 6b by conventional deprotection conditions. Typically a solution of 6b in a solvent such as DCM was treated with TFA and stirred at room temperature.

c. Formation of IB3b can be accomplished using known amide formation conditions, such as treating the acid plus the desired aniline or amine with HATU (1-[Bis (dimethylamino)methylene]-1H-1,2,3-triazolo[4,5-b] pyridinium 3-oxid hexafluorophosphate) and an amine base (diisopropyl ethylamine, triethylamine) in organic solvent such as EtOAc at room temperature or at elevated temperature up to about 80° C.

Compounds of the invention and intermediates can also be converted into each other according to methods generally known to those skilled in the art.

III. Methods of Therapeutic Use of the Compounds and Composition of the Invention, and Indications The present invention provides a method of treating, ameliorating or preventing arthrist of joint injury in a mammal in need thereof, the method including administering to the mammal a therapeutically effective amount of a compound of the invention, wherein the subject has or is at risk of joint damage or arthritis. The invention also provides a method of treating, ameliorating or preventing arthritis or joint injury in a human patient, the method comprising: administering to a joint of the patient a composition comprising an effective amount of a compound of the invention, thereby treating, ameliorating or preventing arthritis or joint injury in the patient. In some embodiments, the patient has arthritis or joint injury. In some embodiments, the individual does not have, but is at risk for, arthritis or joint injury. In some embodiments, the arthritis is osteoarthritis, trauma arthritis, or autoimmune arthritis. In some embodiments, the composition administered to the further comprises hyaluronic acid.

The compounds of the present invention are also useful for inducing differentiation of mesenchymal stem cells (MSCs) into chondrocytes. In some embodiment, the present invention provides a method of inducing differentiation of mesenchymal stem cells into chondrocytes, the method including contacting mesenchymal stem cells with a sufficient amount of a compound of the invention, thereby inducing differentiation of the stem cells into chondrocytes.

MSCs are multipotent stem cells that can differentiate into several different types of cells including, but not limited to, osteoblasts, chondrocytes and adipocytes. Differentiation is the process by which a specialized cell type is formed from a less specialized cell type, for example, a chondrocyte from a MSC. In some embodiments, the method is performed in vitro. In some embodiments, the method is performed in vivo in a mammal and the stem cells are present in the mammal.

In some embodiment, the contacting occurs in a matrix or biocompatible scaffold. In some embodiment, contacting the compound occurs in conjunction with one or more additional chondrogenic factors. In other embodiment, contacting the compound occurs in conjunction with an agent selected from angiopoietin-like 3 protein (ANGPTL3), oral salmon calcitonin, SD-6010 (iNOS inhibitor), vitamin D3 (choliecalciferol), collagen hydrolyzate, FGF18, BMP7, rusalatide acetate, avocado soy unsaponifiables (ASU), a steroid, and a non-steroidal anti-inflammatory agent (NSAID) and hyaluronic acid.

Inducing differentiation of MSCs into chondrocytes can be accomplished using any suitable amount of a compound of the present invention. In some embodiment, the compound of the present invention can be present in an amount form about 0.1 mg to about 10000 mg, e.g., 1.0 mg to 1000 mg, e.g., 10 mg to 500 mg, according to the particular application and potency of the active component. In some embodiments, the compound of the present invention can be present in a concentration of 0.1 μM to to about 100 μM, in an intraarticular injection to the knee.

It is contemplated that compounds, compositions, and methods of the present invention may be used to treat, ameliorate or prevent any type of articular cartilage damage (e.g., joint damage or injury) including, for example, damage arising from a traumatic event or tendon or ligament tear. In some embodiments, the compounds or compositions of the invention are administered to prevent or ameliorate arthritis or joint damage, for example where there is a genetic or family history of arthritis or joint damage or joint injury or prior or during joint surgery. In some embodiments, compounds, compositions and methods are used to treat joint damage. In particular embodiments, the joint damage is traumatic joint injury. In other embodiments, the joint damage is damage arising from age or inactivity. In yet other embodiments, the joint damage is damage arising from an autoimmune disorder. In some embodiments of the invention, compounds, compositions, and methods of the present invention may be used to treat, ameliorate or prevent osteoarthritis. In some embodiments, the compounds, compositions and methods are used to ameliorate or prevent arthritis in a subject at risk of having or acquiring arthritis. In some embodiments, the compounds, compositions and methods are used to ameliorate or prevent joint damage in a subject at risk of having or acquiring joint damage.

In some embodiments, compounds, compositions, and methods of the present invention provide a method for stimulating chondrocyte proliferation and cartilage production in cartilagenous tissues that have been damaged, e.g., due to traumatic injury or chondropathy. In particular embodiments compounds, compositions, and methods of the present invention are useful for treatment of cartilage damage in joints, e.g., at articulated surfaces, e.g., spine, shoulder, elbow, wrist, joints of the fingers, hip, knee, ankle, and joints of the feet. Examples of diseases or disorders that may benefit from treatment include osteoarthritis, rheumatoid arthritis, other autoimmune diseases, or osteochondritis dessicans. In addition, cartilage damage or disruption occurs as a result of certain genetic or metabolic disorders, cartilage malformation is often seen in forms of dwarfism in humans, and/or cartilage damage or disruption is often a result of reconstructive surgery; thus compounds, compositions, and methods would be useful therapy in these patients, whether alone or in connection with other approaches.

It is further contemplated that compounds, compositions, and methods of the present invention may be used to treat, ameliorate or prevent various cartilagenous disorders and/or associated symptoms or effects of such conditions. Exemplary conditions or disorders for treatment, amelioration and/or prevention with compounds, compositions, and methods of the invention, include, but are not limited to systemic lupus erythematosis, rheumatoid arthritis, juvenile chronic arthritis, osteoarthritis, degenerative disc disease, spondyloarthropathies, Ehlers Danlos syndrome, systemic sclerosis (scleroderma) or tendon disease. Other conditions or disorders that may benefit from treatment with compounds for amelioration of associated effects include idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barr syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

In some embodiments, compounds and compositions of the present invention are applied by direct injection into the synovial fluid of a joint, systemic administration (oral or intravenously) or directly into a cartilage defect, either alone or complexed with a suitable carrier for extended release of protein. In some embodiments, compounds or compositions are administered in a biocompatible matrix or scaffold. Compounds, compositions, and methods of the present invention can also be used in conjunction with a surgical procedure at an affected joint. Administration of a compounds or composition of the invention may occur prior to, during or in conjunction with, and/or after a surgical procedure. For example, compounds, compositions and methods of the invention can be used to expand chondrocyte populations in culture for autologous or allogenic chondrocyte implantation (ACI). Chondrocytes can be optionally implanted with concurrent treatment consisting of administration of compounds and compositions of the present invention. In these procedures, for example, chondrocytes can be harvested arthroscopically from an uninjured minor load-bearing area of a damaged joint, and can be cultured in vitro, optionally in the presence of compounds and compositions of the present invention and/or other growth factors to increase the number of cells prior to transplantation. Expanded cultures are then optionally admixed with compounds and compositions of the present invention and/or placed in the joint space or directly into the defect. In certain embodiments, expanded cultures (optionally with compounds of the present invention) are placed in the joint space suspended in a matrix or membrane. In other embodiments, compounds and compositions of the present invention can be used in combination with one or more periosteal or perichondrial grafts that contain cartilage forming cells and/or help to hold the transplanted chondrocytes or chondrocyte precursor cells in place. In some embodiments, compounds and compositions of the present invention are used to repair cartilage damage in conjunction with other procedures, including but not limited to lavage of a joint, stimulation of bone marrow, abrasion arthroplasty, subchondral drilling, or microfracture of proximal subchondral bone. Optionally, following administration of compounds and compositions of the present invention and growth of cartilage, additional surgical treatment may be beneficial to suitably contour newly formed cartilage surface(s).

Collagen is the major structural component of the dermi. Collagen is vital for skin health and has been widely used in dermal treatment of wrinkles and skin aging, and as a healing aid for burn patients. Collagen is produced in fibroblast, and both human and bovine collagen is widely used. It is contemplated that compounds and/or compositions of the present invention can promote expression of collagen in human dermal fibroblast. The invention therefore provides a method of increasing production of collagen in fibroblast by contacting the fibroblasts with a compound or compostion of the invention, thereby increasing the production of collagen in the fibroblast. The contacting may be in vivo by direct injection of the compound in the areas to be treated. The contacting may be in vitro into a population of fibroblasts.

A "patient" as used herein refers to any subject that is administered a therapeutic compounds of the invention. It is contemplated that the compounds, compositions, and methods of the present invention may be used to treat a mammal. As used herein a "subject" refers to any mammal, including humans, domestic and farm animals, and zoo, sports or pet animals, such as cattle (e.g. cows), horses, dogs, sheep, pigs, rabbits, goats, cats, etc. In some embodiments of the invention, the subject is a human. In certain embodiments, the subject is a horse. In other embodiments the subject is a dog.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease. In another non-limiting embodiment, the term "a therapeutically effective amount" refers to the amount of the compound of the present invention that, when administered to a cell, or a tissue, or a non-cellular biological material, or a medium, is effective to promote chondrgenesis.

As used herein, the terms "treat", "treating", "treatment" plus "ameliorate" and "ameliorating" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, a subject is "in need of" a treatment if such subject would benefit biologically, medically or in quality of life from such treatment.

"At increased risk for" refers to a patient having an above average risk for a particular disease or condition, wherein the increased risk is a result of existing health conditions, genetic or family history, existing or prior injuries, repetitive motion actions or conditions.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, "administering" refers to administration to a specific joint.

IV. Pharmaceutical Compositions, Medicaments, Kits

Therapeutic compositions comprising compounds of the invention are within the scope of the present invention. Thus, in one embodiment, the invention provides a pharmaceutical composition comprising a therapeutically effective amount of a compound, a salt thereof, or a stereoisomer thereof, of the invention, and a pharmaceutically acceptable excipient or carrier.

In another embodiment, the invention provides a pharmaceutical composition formulated for intra-articular delivery, the composition comprising a pharmaceutically effective amount of a compound, a salt or a stereoisomer thereof, and a pharmaceutically acceptable excipient.

In some embodiment, the pharmaceutical composition can also include angiopoietin-like 3 protein (ANGPTL3), oral salmon calcitonin, SD-6010 (iNOS inhibitor), vitamin D3 (choliecalciferol), collagen hydrolyzate, FGF18, BMP7, avocado soy unsaponifiables (ASU) or hyaluronic acid. ANGPTL3 is described in more detail in WO/2011/008773 (incorporated herein in its entirety).

In some embodiments, a pharmaceutical composition further comprises a hyaluronic acid or a derivative thereof.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329 and subsequent editions of the same). Except insofar as any conventional carrier is incompatible with the active ingredient, its use in the therapeutic or pharmaceutical compositions is contemplated.

Formulations suitable for administration include excipients, including but not limited to, aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In certain embodiments pharmaceutical compositions comprise a therapeutically effective amount of a compound of the invention in admixture with a pharmaceutically acceptable formulation agent selected for suitability with the mode of administration, delivery format, and desired dosage. See, e.g., Remington's. The primary vehicle or carrier in a pharmaceutical composition can be aqueous or non-aqueous in nature. For example, a suitable vehicle or carrier for injection can be water, physiological saline solution or artificial cerebrospinal fluid, optionally supplemented with other materials common in compositions for parenteral administration. For example, buffers may be used, e.g., to maintain the composition at physiological pH or at a slightly lower pH, typically within a range of from about pH 5 to about pH 8, and may optionally include sorbitol, serum albumin or other additional component. In certain embodiments pharmaceutical compositions comprising compounds of the invention can be prepared for storage in a lyophilized form using appropriate excipients (e.g., sucrose).

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Liquid form preparations include solutions, suspensions, and emulsions, for example, water or water/propylene glycol solutions. For injection, liquid preparations can be formulated in solution in aqueous polyethylene glycol solution.

Aqueous solutions suitable for use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In one embodiment, the compound of the invention may be formulate with an agent, such as injectable microshperes, bio-erodable particles, polymeric compounds, beads, or liposomes or other biocompatible matrix that provides for controlled or sustained release of the compound of the invention can then be delivered via a depot injection. For example, compounds of the invention may be encapsulated in liposomes, or formulated as microparticles or microcapsules or may be incorporated into other vehicles, such as biodegradable polymers, hydrogels, cyclodextrins (see for example Gonzalez et al., 1999, Bioconjugate Chem., 10, 1068-1074; Wang et al., International PCT publication Nos. WO 03/47518 and WO 03/46185), poly(lactic-co-glycolic) acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722) or by the use of conjugates. Still other suitable delivery mechanisms include implantable delivery devices.

In another aspect of the present invention, provided compounds or pharmaceutical composition for use as a medicament for treatment of joint damage is contemplated.

In certain embodiments compounds of the invention for use as a medicament for amelioration of arthritis or joint damage are provided. In some embodiments arthritis is osteoarthritis, trauma arthritis or autoimmune arthritis. In some embodiments joint damage is traumatic joint injury, autoimmune damage, age related damage, or damage related to inactivity.

The medicament, in addition to the compound of the invention, may further include a second agent. The second agent may be one or more additional chondrogenic factors (e.g., oral salmon calcitonin, SD-6010 (iNOS inhibitor), vitamin D3 (choliecalciferol), collagen hydrolyzate, rusalatide acetate, avocado soy unsaponifiables (ASU), a compound described in WO2012/129562, kartogenin), a steroid, a non-steroidal anti-inflammatory agent (NSAID), etc.). In some embodiment, the medicament may include an agent selected angiopoietin-like 3 protein (ANGPTL3), oral salmon calcitonin, SD-6010 (iNOS inhibitor), vitamin D3 (choliecalciferol), collagen hydrolyzate, FGF18, BMP7, rusalatide acetate, avocado soy unsaponifiables (ASU), a steroid, and a non-steroidal anti-inflammatory agent (NSAID) and hyaluronic acid.

Also provided are kits comprising the compound of the invention. In one embodiment provided are kits for producing a single dose administration unit. The kit comprises a first container comprising a compound of the invention as a dried solid and a second container having an aqueous reconstitution formula. In certain embodiments one container comprises a single chamber pre-filled syringe. In other embodiments the containers are encompassed as a multi-chambered pre-filled syringe V. Method of Administration and Dosage In general, compounds of the invention will be administered in therapeutically effective amounts via any of the usual and acceptable modes known in the art, either singly or in combination with one or more therapeutic agents.

The compounds and compositions of the present invention can be applied by direct by direct injection into the synovial fluid of a joint, systemic administration (oral or intravenously) or directly into a cartilage defect, either alone or complexed with a suitable carrier for extended release of protein. In some embodiments, compounds or compositions are administered in a biocompatible matrix or scaffold. Compounds, compositions, and methods of the present invention can also be used in conjunction with a surgical procedure at an affected joint. Administration of a compounds of the invention may occur prior to, during or in conjunction with, and/or after a surgical procedure. For example, compounds, compositions and methods of the invention can be used to expand chondrocyte populations in culture for autologous or allogenic chondrocyte implantation (ACI). Chondrocytes can be optionally implanted with concurrent treatment consisting of administration of polypeptides and compositions of the present invention. In these procedures, for example, chondrocytes can be harvested arthroscopically from an uninjured minor load-bearing area of a damaged joint, and can be cultured in vitro, optionally in the presence of compounds and compositions of the present invention and/or other growth factors to increase the number of cells prior to transplantation. Expanded cultures are then optionally admixed with compounds and compositions of the present invention and/or placed in the joint space or directly into the defect. In certain embodiments, expanded cultures (optionally with compounds of the present invention) are placed in the joint space suspended in a matrix or membrane. In other embodiments, compounds and compositions of the present invention can be used in combination with one or more periosteal or perichondrial grafts that contain cartilage forming cells and/or help to hold the transplanted chondrocytes or chondrocyte precursor cells in place. In some embodiments, compounds and compositions of the present invention are used to repair cartilage damage in conjunction with other procedures, including but not limited to lavage of a joint, stimulation of bone marrow, abrasion arthroplasty, subchondral drilling, or microfracture of proximal subchondral bone. Optionally, following administration of compound and compositions of the present invention and growth of cartilage, additional surgical treatment may be beneficial to suitably contour newly formed cartilage surface(s).

Any method for delivering the compound of the invention of the invention to an affected joint can be used. In the practice of this invention, compositions can be parenterally administered, for example injected, e.g., intra-articularly (i.e., into a joint), intravenously, intramuscularly, subcutaneously; infused, or implanted, e.g., in a membrane, matrix, device, etc. When injected, infused or implanted, delivery can be directed into the suitable tissue or joint, and delivery may be direct bolus delivery or continuous delivery. In some embodiments delivery can be in a suitable tissue located in close proximity to an affected joint. In some embodiments delivery may be via diffusion, or via timed release bolus. In some embodiments, a controlled release system (e.g., a pump) can be placed in proximity of the therapeutic target, e.g., the joint to which the polypeptide is administered. In other embodiments, compositions can be selected for ingestion, e.g., inhalation or oral delivery.

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Formulations of compounds can be stored in sterile vials as a solution, suspension, gel, emulsion, solid, or as a dehydrated or lyophilized powder. Formulations can be presented in unit-dose or multi-dose sealed containers, such as ampules and vials. In some embodiments formulations can be presented in single or multi-chambered pre-filled syringes (e.g., liquid syringes, lysosyringes). Solutions and suspensions can be prepared from sterile powders, granules, and tablets of the kind previously described.

The dose of a compound of the present invention for treating the above-mentioned diseases or disorders varies depending upon the manner of administration, the age and/or the body weight of the subject, and the condition of the subject to be treated, and ultimately will be decided by the attending physician or veterinarian. The dose administered to a subject, in the context of the present invention should be sufficient to effect a beneficial response in the subject over time. Such a dose is a “therapeutically effective amount”. Accordingly, an appropriate dose may be determined by the efficacy of the particular compound employed and the condition of the subject, as well as the body weight or surface area of the area to be treated. The size of the dose also will be determined by the existence, nature, and extent of any adverse side-effects that accompany the administration of a particular compound in a particular subject. Administration can be accomplished via single or divided doses, or as a continuous infusion via an implantation device or catheter. Frequency of dosing will depend upon the pharmacokinetic parameters of the compound of the invention in the formulation used. A clinician may titer dosage and/or modify administration to achieve the desired therapeutic effects.

A typical dosage for intra-articular injection to the knee may range from about 0.1 μM to to about 100 μM, depending on the factors discussed above.

The compounds and compositions of the invention of the present invention can also be used effectively in combination with one or more therapeutic agents.

Non-limiting examples of compounds which can be used in combination with compounds of the invention includes hyaluronic acid or a derivative or salt thereof, growth factors (e.g., FGF18, BMP7), chondrogenic agents (e.g., oral salmon calcitonin, SD-6010 (iNOS inhibitor), vitamin D3 (choliecalciferol), collagen hydrolyzate, rusalatide acetate, avocado soy unsaponifiables (ASU), other chondrogenesis promoters (e.g., a compound described in WO2012/129562, kartogenin), a steroid, a non-steroidal anti-inflammatory agent (NSAID), etc.). In some embodiments, the composition can also include angiopoietin-like 3 protein (ANGPTL3). ANGPTL3 is described in more detail in WO/2011/008773 (incorporated herein in its entirety). The selection of the second agent would dependon the desired therapy or effect to improve or enhance the therapeutic effect of either.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of the invention and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

Enumerated Embodiments

Various enumerated embodiments of the invention are described herein. It will be recognized that features specified in each embodiment may be combined with other specified features to provide further embodiments of the present invention.

In a first embodiment, the invention provides a compound of the formula (I), or a pharmaceutical acceptable salt, tautomer or stereoisomer thereof:

I

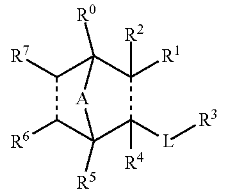

wherein

"- - - - -" represents a single or double bond;

A is $CR^{8a}R^{8b}$, $NR^9$, or O; wherein $R^{8a}$, $R^{8b}$ and $R^9$ are each independently hydrogen or $C_{1-6}$alkyl;

L is *—C(O)$NR^{10}$— or *—C(O)O—, wherein "*" represents the point of attachment of L to the bicyclic ring containing A, and $R^{10}$ is hydrogen or $C_{1-6}$alkyl;

$R^0$ is selected from hydrogen and $C_{1-6}$alkyl;

$R^1$ is selected from halo, cyano, —C(O)$R^{11}$, —C(O)$NR^{12a}R^{12b}$, —C(O)O$NR^{12a}R^{12b}$, 5- and 6-membered heterocycloalkyl, 5- and 6-membered heterocyclyl, phenyl, and 5- to 9-membered heteroaryl, wherein $R^{11}$ is hydrogen or $C_{1-6}$alkyl;

$R^{12a}$ and $R^{12b}$ are each independently hydrogen or $C_{1-6}$alkyl;

the heterocycloalkyl, heterocyclyl, phenyl, or heteroaryl of $R^1$ is unsubstituted or substituted by 1 to 2 substituents independently selected from halo, cyano, $C_{1-6}$alkyl, $C_{1-6}$haloalkyl, —C(O)$R^{13}$, —C(O)O$R^{13}$, —$NR^{14a}R^{14b}$, 5- and 6-membered heterocycloalkyl, phenyl, and 5- and 6-membered heteroaryl; wherein $R^{13}$ is selected from hydrogen, $C_{1-6}$alkyl, $C_{1-6}$haloalkyl, amino, and $C_{1-6}$alkylamino;

$R^{14a}$ and $R^{14b}$ are each independently selected from hydrogen, $C_{1-6}$alkyl, —C(O)$R^{15}$, —C(O)O$R^{15}$, and —$S(O)_2R^{15}$, wherein $R^{15}$ is hydrogen or $C_{1-6}$alkyl; and the heterocycloalkyl, phenyl or heteroaryl substituent of $R^1$ is further substituted by 1 to 2 substituents independently selected from halo, $C_{1-6}$alkyl, $C_{1-6}$haloalkyl, and hydroxy;

$R^3$ is selected from $C_{1-6}$alkyl, $C_{1-6}$haloalkyl, 3- to 6-membered cycloalkyl, (159), 4- to 7-membered heterocycloalkyl, 5- to 10-membered heterocyclyl, phenyl, and 5- to 9-membered heteroaryl, wherein the cycloalkyl, heterocycloalkyl, heterocyclyl, phenyl, or heteroaryl of $R^3$ is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, —$S(O)_2R^{16}$, 5 and 6 membered heterocycloalkyl, and pheny; wherein $R^{16}$ is hydrogen or $C_{1-6}$alkyl;

the phenyl or heterocycloalkyl substituent or $R^3$ is unsubstituted or further substituted by 1 to 2 substituents independently selected from halo, cyano, $C_{1-6}$alkyl, and $C_{1-6}$haloalkyl; and $R^2$ and $R^4$ are each hydrogen or $C_{1-6}$alkyl; or $R^2$ and $R^4$ taken together form a cyclopropyl ring fused to the bicyclic ring containing A; or $R^2$ and $R^4$ taken together form a bond producing a double bond between the two carbons to which $R^2$ and $R^4$ are attached; and $R^5$ is hydrogen or $C_{1-6}$alkyl, or $R^5$ and $R^{10}$ taken with the atoms to which they are linked form a 5- or 6-membered ring fused to the bicyclic ring containing A; and $R^6$ and $R^7$ are each hydrogen or $C_{1-6}$alkyl; or $R^6$ and $R^7$ taken together form a bond producing a double bond between the two carbons to which $R^6$ and $R^7$ are attached.

Embodiment 2

A compound according to Embodiment 1 or salt, tautomer or stereoisomer thereof, wherein the compound is of Formula IA:

IA

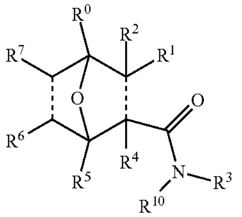

"- - - - -" represents a single or double bond;

$R^0$ is selected from hydrogen and $C_{1-6}$alkyl;

$R^1$ is selected from cyano, —C(O)N$R^{12a}R^{12b}$, 6-membered heterocycloalkyl, 6-membered heterocyclyl, phenyl, and 5- to 9-membered heteroaryl, wherein
- $R^{12a}$ and $R^{12b}$ are each independently hydrogen or $C_{1-6}$alkyl;
- the heterocycloalkyl, heterocyclyl, phenyl, or heteroaryl of $R^1$ is unsubstituted or substituted by 1 to 2 substituents independently selected from halo, cyano, $C_{1-6}$alkyl, $C_{1-6}$haloalkyl, —C(O)$R^{13}$, —C(O)O$R^{13}$, —N$R^{14a}R^{14b}$, 5- and 6-membered heterocycloalkyl, phenyl, and 5- and 6-membered heteroaryl; wherein
  - $R^{13}$ is selected from $C_{1-6}$alkyl, amino, and $C_{1-6}$alkylamino;
  - $R^{14a}$ and $R^{14b}$ are each independently selected from hydrogen, $C_{1-6}$alkyl, —C(O)$R^{15}$, —C(O)O$R^{15}$, and —S$(O)_2R^{15}$, wherein $R^{15}$ is hydrogen or $C_{1-6}$alkyl; and
  - the heterocycloalkyl, phenyl or heteroaryl substituent of $R^1$ is unsubstituted or further substituted by 1 to 2 substituents independently selected from halo, hydroxy, $C_{1-6}$alkyl, and $C_{1-6}$haloalkyl, $R^3$ is selected from $C_{1-6}$alkyl, $C_{1-6}$haloalkyl, 5- and 6-membered cycloalkyl, (159), 5- and 6-membered heterocycloalkyl, 6- and 10-membered heterocyclyl, phenyl, and 5- and 6-membered heteroaryl, wherein
- the cycloalkyl, heterocycloalkyl, heterocyclyl, phenyl, or heteroaryl of $R^3$ is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, —S$(O)_2R^{16}$, 5- and 6-membered heterocycloalkyl, and phenyl; wherein
  - $R^{16}$ is hydrogen or $C_{1-6}$alkyl;
  - the phenyl or heterocycloalkyl substituent of $R^3$ is unsubstituted or further substituted by 1 to 2 substituents independently selected from halo, and cyano; and $R^2$ and $R^4$ are each hydrogen or $C_{1-6}$alkyl; or $R^2$ and $R^4$ taken together form a cyclopropyl ring fused to the bicyclic ring; or $R^2$ and $R^4$ taken together form a bond producing a double bond between the two carbons to which $R^2$ and $R^4$ are attached; and $R^5$ is hydrogen or $C_{1-6}$alkyl, or $R^5$ and $R^{10}$ taken with the atoms to which they are linked form a 5- or 6-membered ring fused to the bicyclic ring, and $R^6$ and $R^7$ are each hydrogen or $C_{1-6}$alkyl; or $R^6$ and $R^7$ taken together form a bond producing a double bond between the two carbons to which $R^6$ and $R^7$ are attached.

Embodiment 3

A compound according to Embodiment 1 or 2, or salt, tautomer or stereoisomer thereof, wherein the compound is of a formula selected from:

IA1

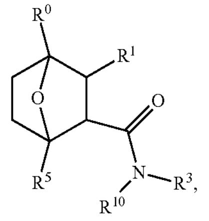

IA2

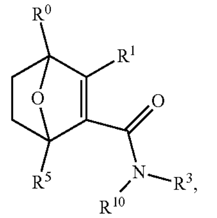

IA3

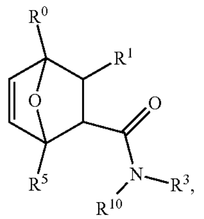

and

IA4

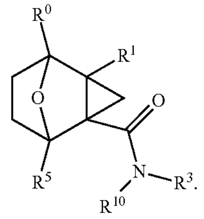

Embodiment 4

A compound according to any one of Embodiments 1 to 3, or salt, tautomer or stereoisomer thereof, wherein $R^1$ is phenyl, 5- or 6-membered heteroaryl, wherein the phenyl or heteroaryl is unsubstituted or substituted by 1 to 2 substituents independently selected from halo, cyano, $C_{1-6}$alkyl, $C_{1-6}$haloalkyl, —C(O)$R^{13}$, —C(O)O$R^{13}$, —N$R^{14a}R^{14b}$, 5- and 6-membered heterocycloalkyl, phenyl, and 5- and 6-membered heteroaryl, wherein
- $R^{13}$ is selected from $C_{1-6}$alkyl, amino, and $C_{1-6}$alkylamino;
- $R^{14a}$ and $R^{14b}$ are each independently selected from hydrogen, $C_{1-6}$alkyl, —C(O)$R^{15}$, and —C(O)O$R^{15}$, wherein $R^{15}$ is $C_{1-6}$alkyl; and
- the heterocycloalkyl, phenyl or heteroaryl substituent of $R^1$ is unsubstituted or further substituted by 1 to 2 substituents independently selected from hydroxy, halo, $C_{1-6}$alkyl, and $C_{1-6}$haloalkyl.
- $R^{13}$ is selected from $C_{1-6}$alkyl, amino, and $C_{1-6}$alkylamino;
- $R^{14a}$ and $R^{14b}$ are each independently selected from hydrogen, $C_{1-6}$alkyl, —C(O)$R^{15}$, and —C(O)O$R^{15}$, wherein $R^{15}$ is $C_{1-6}$alkyl; and
- the heterocycloalkyl or phenyl substituent of $R^1$ is unsubstituted or further substituted by 1 to 2 substituents independently selected from hydroxy, halo, $C_{1-6}$alkyl, and $C_{1-6}$haloalkyl.

Embodiment 5

A compound according to any one of Embodiments 1 to 3, or salt, tautomer or stereoisomer thereof, wherein $R^1$ is selected from

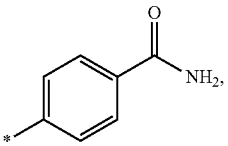
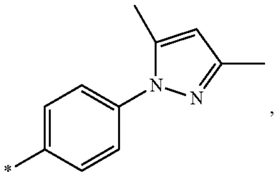
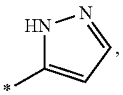
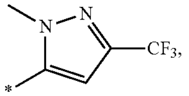
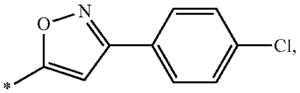
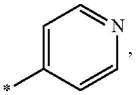
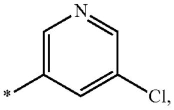
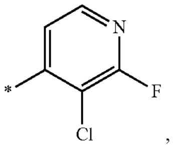
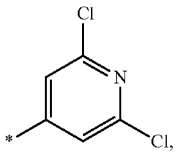
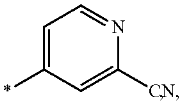
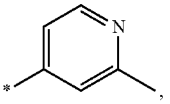
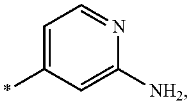
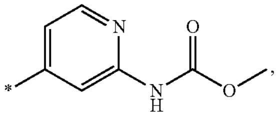
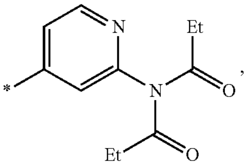
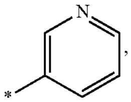
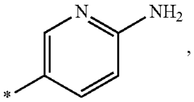
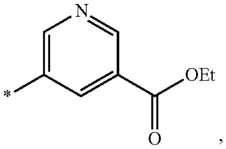
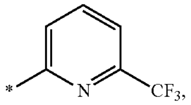
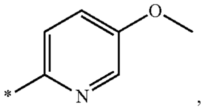
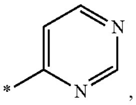
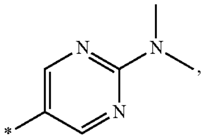
and
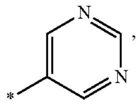

wherein "*" represents the point of attachment of $R^1$ to the bicyclic core ring.

Embodiment 6

A compound according to any one of Embodiments 1 to 5, or salt, tautomer or stereoisomer thereof, wherein $R^3$ is phenyl, 5- or 6-membered heteroaryl, wherein the phenyl, or heteroaryl of $R^3$ is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, —S(O)$_2$ $R^{16}$, 5- and 6-membered heterocycloalkyl, and pheny; wherein $R^{16}$ is $C_{1-6}$alkyl; and the phenyl or heterocycloalkyl substituent or $R^3$ is unsubstituted or further substituted by 1 to 2 substituents independently selected from halo or cyano.

Embodiment 7

A compound according to any one of Embodiments 1 to 5, or salt, tautomer or stereoisomer thereof, wherein $R^3$ is selected from:

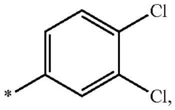
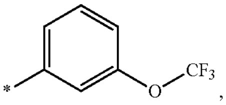
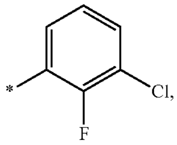
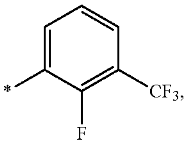
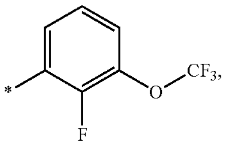
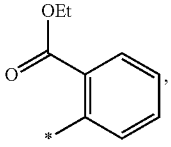
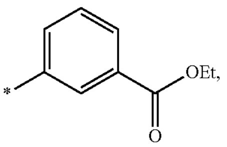
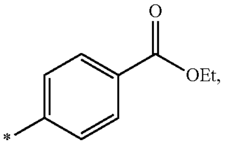
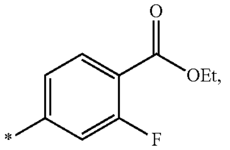
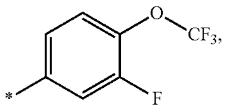
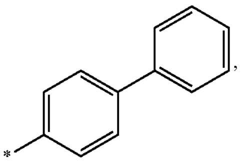
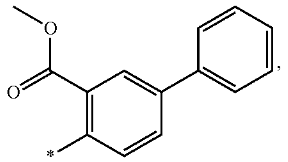
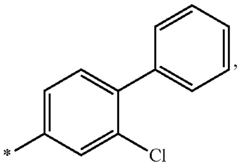
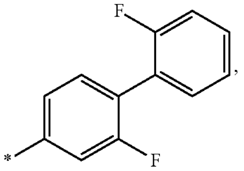
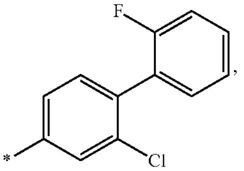
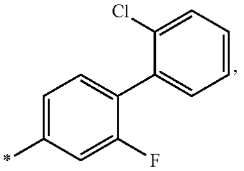

-continued

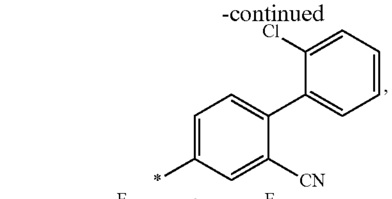

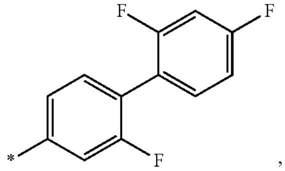

, and

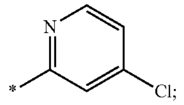

wherein "*" represents the point of attachment of $R^3$ to the bicyclic ring.

Embodiment 8

A compound according to Embodiment 1, or salt, tautomer or stereoisomer thereof, wherein the compound is of Formula 1B:

IB

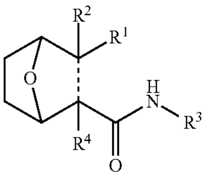

or a pharmaceutically acceptable salt, or a stereoisomer thereof, wherein

"- - - - -" represents a single or double bond;

$R^1$ is phenyl, 5- or 6-membered heteroaryl, wherein
- the phenyl or heteroaryl of $R^1$ is unsubstituted or substituted by 1 to 2 substituents independently selected from halo, cyano, $C_{1-6}$alkyl, $C_{1-4}$haloalkyl, —C(O)$R^{13}$, —C(O)O$R^{13}$, —N$R^{14a}R^{14b}$, 5- and 6-membered heterocycloalkyl, phenyl, and 5- and 6-membered heteroaryl, wherein
  - $R^{13}$ is $C_{1-6}$alkyl or amino;
  - $R^{14a}$ and $R^{14b}$ are independently is selected from hydrogen, $C_{1-6}$alkyl, —C(O)$R^{15}$, and —C(O)O$R^{15}$, wherein $R^{15}$ is $C_{1-4}$alkyl; and
  - the heterocycloalkyl, phenyl, or heteroaryl substituent of $R^1$ is unsubstituted or substituted by 1 to 2 substituents independently selected from halo, hydroxy, and $C_{1-6}$alkyl;

$R^3$ is phenyl, 5- or 6-membered heteroaryl, wherein the phenyl or heteroaryl is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, 5- and 6-membered heterocycloalkyl, and phenyl, wherein
- $R^{16}$ is $C_{1-6}$alkyl; and
- the heterocycloalkyl or phenyl is unsubstituted or substituted by 1 to 2 substituents selected from halo and cyano;

$R^2$ and $R^4$ are independently hydrogen or $C_{1-6}$alkyl, or $R^2$ and $R^4$ taken together form a cyclopropyl fused to the bicyclic ring, or $R^2$ and $R^4$ taken together form a bond, producing a double bond between the two carbons to which $R^2$ and $R^4$ are attached.

Embodiment 9

A compound according to Embodiment 8, or salt, tautomer or stereoisomer thereof, wherein the compound is of a formula selected from

IB1

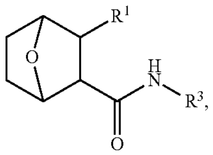

IB2

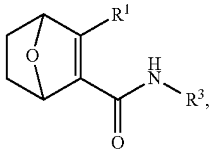

and

IB3

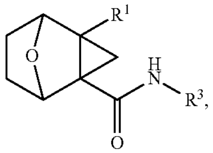

Embodiment 10

A compound according to Embodiment 8 or 9, or salt, tautomer or stereoisomer thereof, wherein the compound is of a formula selected from the formulae:

IB1a

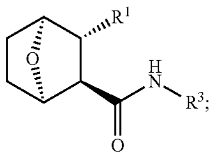

IB1c

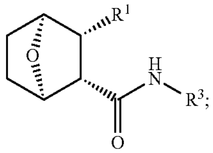

IB1b

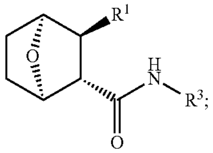

IB1b'

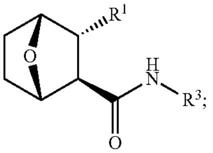

-continued

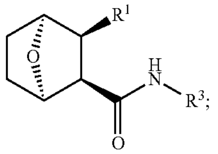

IB1d

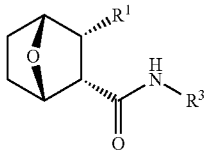

IB1d'

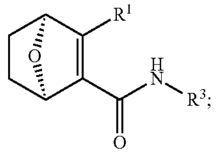

IB2

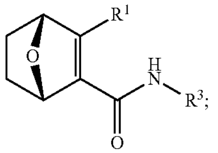

IB2'

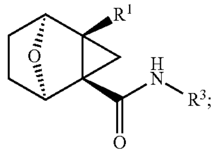

IB3b and

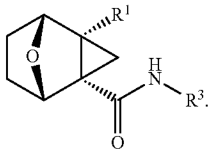

IB3b'

Embodiment 11

A compound according to any one of Embodiments 8 to 10, or salt, tautomer or stereoisomer thereof, wherein $R^1$ is a 5 or 6 membered heteroaryl, unsubstituted or substituted by 1 to 2 substituents independently selected from halo, $C_{1-4}$alkyl, $C_{1-4}$haloalkyl, and $NHR^{14b}$, wherein $R^{14b}$ is hydrogen or $C_{1-4}$alkyl.

Embodiment 12

A compound according to any one of Embodiments 8 to 10, or salt, tautomer or stereoisomer thereof, wherein $R^1$ is selected from pyrazolyl, oxadiazolyl, pyridinyl, pyrimidinyl and pyrazinyl, wherein the pyrazolyl, pyridinyl, pyrimidinyl or pyrazinyl is unsubstituted or substituted by —$NH_2$, —$NHC(O)OCH_3$ or trifluoromethyl.

Embodiment 13

A compound according to any one of Embodiments 8 to 10, or salt, tautomer or stereoisomer thereof, wherein $R^1$ is selected from:

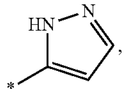 , 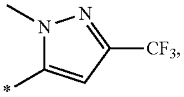 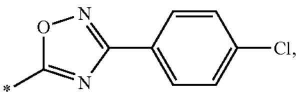 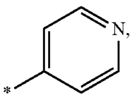 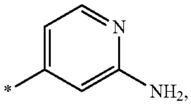 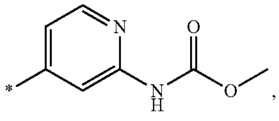 , 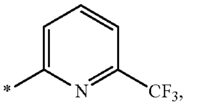 and 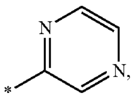

wherein "*" represents the point of attachment of $R^1$ to the bicyclic core ring.

Embodiment 14

A compound according to any one of Embodiments 8 to 13, or salt, tautomer or stereoisomer thereof, wherein $R^3$ is phenyl substituted by 1 to 2 substituents independently selected from halo, cyano, $C_{1-6}$alkyl, $C_{1-6}$haloalkyl, $C_{1-6}$alkoxy, $C_{1-6}$haloalkoxy, and phenyl, $C_{1-6}$alkyl, $C_{1-6}$haloalkyl, $C_{1-6}$alkoxy, $C_{1-6}$haloalkoxy, —$C(O)R^{16}$, —$C(O)OR^{16}$, wherein $R^{16}$ is $C_{1-6}$alkyl, and the phenyl substituent of $R^3$ is unsubstituted or further substituted by 1 to 2 substituents independently selected from halo and cyano.

Embodiment 15

A compound according to any one of Embodiments 8 to 13, or salt, tautomer or stereoisomer thereof, wherein $R^3$ is selected from:

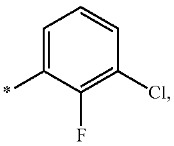 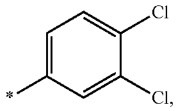 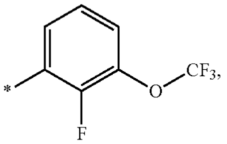 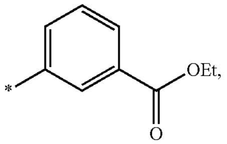 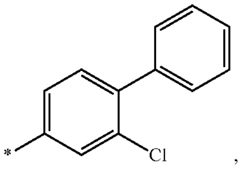 , 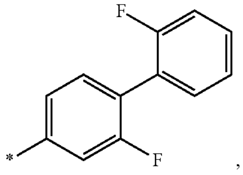 , 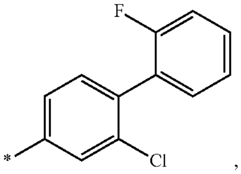 , and 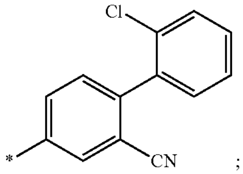 ;

wherein "*" represents the point of attachment of $R^1$ to the bicyclic core ring.

Embodiment 16

A compound according to Embodiment 1 or salt, tautomer or stereoisomer thereof, wherein the compound is selected from the list of compounds set forth in Table 3 and listed on pages 31 to 38 of the specification.

Embodiment 17

A pharmaceutical composition comprising a compound according to any one of Embodiments 1 to 16, or a salt or a stereoisomer thereof, and a pharmaceutically acceptable excipient.

Embodiment 18

A pharmaceutical composition formulated for intra-articular delivery, the composition comprising a pharmaceutically effective amount of a compound, according to any one of Embodiments 1 to 16, or a salt or a stereoisomer thereof, and a pharmaceutically acceptable excipient.

Embodiment 19

A pharmaceutical composition according to Embodiment 17 or 18, composition comprising an agent selected from angiopoietin-like 3 protein (ANGPTL3), oral salmon calcitonin, SD-6010 (iNOS inhibitor), vitamin D3 (choliecalciferol), collagen hydrolyzate, FGF18, BMP7, rusalatide acetate, avocado soy unsaponifiables (ASU), a steroid, and a non-steroidal anti-inflammatory agent (NSAID) and hyaluronic acid.

Embodiment 20

A method of treating, ameliorating or preventing arthritis or joint injury in a mammal in need thereof, the method comprising administering to a joint of the mammal a therapeutically effective amount of a compound according to any one of Embodiments 1 to 16, or a pharmaceutical composition according to any one of Embodiments 16 to 18, thereby treating, ameliorating or preventing arthritis or joint damage in the mammal.

Embodiment 21

A method of treating, ameliorating or preventing arthritis or joint injury in a mammal in need thereof, according to Embodiment 20, wherein the arthritis is osteoarthritis, trauma arthritis, or autoimmune arthritis.

Embodiment 22

A method of treating, ameliorating or preventing arthritis or joint injury according to Embodiment 20 or 21, wherein administering the compound or pharmaceutical composition occurs in a matrix or biocompatible scaffold.

Embodiment 23

A method of inducing differentiation of mesenchymal stem cells into chondrocytes, wherein the method comprising contacting mesenchymal stem cells with a sufficient amount of a compound, according to any one of Embodiments 1 to 16, or a salt or a stereoisomer thereof, or a pharmaceutical composition according to any one of Embodiments 17 to 19, thereby inducing differentiation of the stem cells into chondrocytes.

Embodiment 24

A method of inducing differentiation of mesenchymal stem cells into chondrocytes according to Embodiment 23, wherein the contacting is performed in vitro or in vivo in a mammal, and when in vivo, the stem cells are present in the mammal.

Embodiment 25

A method of inducing differentiation of mesenchymal stem cells into chondrocytes according to Embodiment 23 or 24, wherein the contacting compound occurs in a matrix or biocompatible scaffold.

Embodiment 26

A method of inducing differentiation of mesenchymal stem cells into chondrocytes according to any one of Embodiments 23 to 25, wherein contacting the compound occurs in conjunction with one or more additional chondrogenic factors.

Embodiment 27

A method of inducing differentiation of mesenchymal stem cells into chondrocytes according to any one of Embodiments 23 to 25, wherein contacting the compound occurs in conjunction with an agent selected from angiopoietin-like 3 protein (ANGPTL3), oral salmon calcitonin, SD-6010 (iNOS inhibitor), vitamin D3 (choliecalciferol), collagen hydrolyzate, FGF18, BMP7, rusalatide acetate, avocado soy unsaponifiables (ASU), a steroid, and a non-steroidal anti-inflammatory agent (NSAID) and hyaluronic acid.

Biological Assays

The compounds of the present invention were evaluated in two functional assays to assess their chondrogenesis activities (Type II Collagen Expression) and chondrocyte protective activities (NO release assay).

Type II Collagen Expression Assay

Cell-based 2D chondrogenesis was induced in vitro and assessed as described previously in Johnson, K., et al., (2012) *Science* 336, 717. The assay measures type II collagen, a chondrocytes specific protein. Briefly, primary human bone marrow derived mesenchymal stem cells (hMSCs) were plated in growth media then subsequently changed to a chondrogenic stimulation media with and without constructs, and cultured for 7 or 14 days. Cells were then fixed with formaldehyde, washed and then stained using standard immuno-cytochemical techniques to detect Type II collagen. a primary cartilage proteins.

Cell Culture and Differentiation

Primary human bone marrow derived mesenchymal stem cells (hMSCs) were purchased from Lonza (Walkersville, Md.). The cells were FACS sorted and proven to be >98% positive for CD29, CD44, CD166 and CD105 and <0.1% positive for CD45. The hMSCs were grown in Mesenchymal Stem Cell Growth Medium (MSCGM) (Lonza, Walkersville, Md.) and used from passages 2-8 for all of the experiments. Human cartilage resident MSCs (hCR-MSCs) were derived from human primary articular chondrocytes (Lonza, Walkersville, Md.) which were separated into single cells, clonally grown in MSCGM and validated as MSCs through chondrogenic, osteogenic and adipogenic differentiation. The cells were FACS sorted and proven to be >98% positive for CD166 and CD105. hCR-MSCs were cultured up to 20 passages with no alteration in the cell profile, growth or differentiation rates identified.

To initiate chondrogenesis in primary hMSCs or CR-MSCs, 5000 cells were plated/well in a Griener 384 well plate in MSCGM. After 24 hours the MSCGM was removed and replaced with 25 μl of DMEM containing 1% FBS. The test compound was then added to each well at the indicated dose. The cultures were grown at 37° C. for 18 days. A media supplement of an additional 25 μl of DMEM containing 1% FBS was given 10 days after chondrogenic induction.

Immunocytochemical Staining and Quantitation

To detect the presence of chondrogenic proteins, cells were fixed with 10% formalin for 15 minutes, permeablized with PBS containing 0.1% triton X-100, 0.25 g/ml of Collagenase 2 for 10 minutes, blocked with PBS containing 5% BSA for 1 hr at room temperature, followed by incubation with primary antibody (anti-type II collagen antibody) in PBS containing 1% BSA overnight at 4° C. Cells were washed 3 times with PBS and incubated with fluorophore-conjugated secondary antibody and DAPI or TO-PRO3 for 1 hour at room temperature, followed by washing with PBS for 3 times.

The total intensity of staining was imaged by fluoresecent microscopy and/or quantified by high content imagining with the ImageXpress Ultra (Molecular Devices, Sunnyvale, Calif.). Data analyses were performed with the customized multiwavelength cell-scoring application. The result is reported as the maximum efficacy observed at 40 μM concentration of the test compound in Table 2 below Reagents

TABLE 1

Reagents used for experimentation

| Description | Company | Catalog number | Dilution/ Concentration |
|---|---|---|---|
| Anti-type II collagen | Abcam | 3092 | 1:500 |
| Anti-mouse 488 | Life Technologies | A-11099 | 1:1000 |
| Anti-Rabbit 594 | Life Technologies | A-11005 | 1:1000 |
| Anti-aggrecan | Millipore | AB1031 | 1:500 |
| Anti-Sox9 | Abcam | AB26414 | 1:250 |
| TO-PRO3 | Life Technologies | T-3065 | 1:1000 |
| DAPI | Sigma | D8417 | 2 μg/ml |
| Anti-Type X collagen | Abcam | Ab58632 | 1:1000 |

NO Release Assay in Bovine Chondrocytes

The assay was described in Johnson, K., et al., (2012) *Science* 336, 717-721. Chondrocytes release NO during OA pathogenesis. This assay measures the inhibition of nitric oxide release by the treated compound (an indicator of chondro-protection) Primary articular chondrocytes from normal bovine knees (Animal Technologies, Tyler, Tex.) were isolated after dissection and collagenase digestion (Worthington Biochemical) of the tibial plateau and femoral condyle articular cartilage. The cells were initially plated at 80-90% confluency after isolation. Primary chondrocytes were cultured in high-glucose Dulbecco's modified Eagle's medium (DMEM) supplemented with 10% fetal bovine serum (FBS), 1% L-glutamine, 100 units/ml of penicillin, and 50 μg/ml of streptomycin (Life Technologies, Carlsbad, Calif.) and maintained at 37° C. in the presence of 5% CO2 for 7 days prior to initiation of each experiment. During the 7-day culture period, the cells adhered and established a chondrocyte-like appearance that was maintained throughout the experimental period. Functional studies on chondrocytes were performed in high-glucose DMEM with no FBS unless indicated otherwise.

After one week of culture, 8500 cells were plated per well in Greiner 384 well white clear bottom plates in growth media. Following 24 hours of culture, the media was removed and replaced with serum free DMEM containing 20 ng/ml TNFα and 10 ng/ml human oncostatin M (inflammatory mediators). The cells were treated for 48 hours with and without the test compound (where indicated) to assess the inhibition of the cytokine induced-NO release. 20 μl of the supernatant was mixed with 20 μl of the Greiss reagent (Promega # G2930) and quantitated at 540 nm. The Greiss reagent part A (1% Sulfanilamide in 5% phosphoric acid) was mixed at a 1:1 ration with Greiss reagent part B (0.1% N-1-napthylethylenediamine dihydrochloride in water) immediately prior to added to the culture supernatant. The μM concentration of the test compound at IC50 is reported in Table 2 below.

TABLE 2

Activity of the Compounds of the Invention in Inducing Chondrogenesis and in Inhibiting NO Release

| Ex. No. | Collagen Type II Max Eff observed μM (Eff) | NO Inh. $IC_{50}$ (μM) |
|---|---|---|
| 1 | 40 (102) | ND |
| 2 | 40 (1372) | >30 |
| 3 | 40 (188) | ND |
| 4 | 40 (234) | ND |
| 5 | 40 (2759) | 16 |
| 6 | 40 (304) | ND |
| 7 | 40 (350) | ND |
| 8 | 40 (367) | >33 |
| 9 | 40 (3901) | >11.1 |
| 10 | 40 (393) | 22 |
| 11 | 40 (435) | >33 |
| 12 | 40 (443) | ND |
| 13 | 40 (65) | ND |
| 14 | 40 (8224) | ND |
| 15 | 40 (853) | ND |
| 16 | 40 (90) | ND |
| 17 | 40 (955) | >11.1 |
| 18 | 40 (109) | >33 |
| 19 | 40 (1147) | ND |
| 20 | 40 (1160) | >33 |
| 21 | 40 (1329) | ND |
| 22 | 40 (1378) | ND |
| 23 | 40 (1447) | ND |
| 24 | 40 (155) | >33 |
| 25 | 40 (157) | ND |
| 26 | 40 (1660) | >3.4 |
| 27 | 40 (1676) | >33 |
| 28 | 40 (172) | ND |
| 29 | 40 (1890) | ND |
| 30 | 40 (191) | ND |
| 31 | 40 (199) | >33 |
| 32 | 40 (2165) | >27 |
| 33 | 40 (235) | >33 |
| 34 | 40 (254) | ND |
| 35 | 40 (3145) | ND |
| 36 | 40 (334) | ND |
| 37 | 40 (347) | ND |
| 38 | 40 (357) | >33 |
| 39 | 40 (3601) | >33 |
| 40 | 40 (36305) | ND |

TABLE 2-continued

Activity of the Compounds of the Invention in Inducing Chondrogenesis and in Inhibiting NO Release

| Ex. No. | Collagen Type II Max Eff observed μM (Eff) | NO Inh. $IC_{50}$ (μM) |
|---|---|---|
| 41 | 40 (371) | >33 |
| 42 | 40 (392) | ND |
| 43 | 40 (4523) | >33 |
| 44 | 40 (4578) | 28 |
| 45 | 40 (460) | ND |
| 46 | 40 (4960) | ND |
| 47 | 40 (5160) | 18 |
| 48 | 40 (5231) | ND |
| 49 | 40 (5500) | >33 |
| 50 | 40 (565) | 14 |
| 51 | 40 (58) | 26 |
| 52 | 40 (612) | >33 |
| 53 | 40 (623) | ND |
| 54 | 40 (63) | >33 |
| 55 | 40 (64) | ND |
| 56 | 40 (6656) | >33 |
| 57 | 40 (6833) | ND |
| 58 | 40 (69) | ND |
| 59 | 40 (700) | ND |
| 60 | 40 (71) | ND |
| 61 | 40 (74) | >33 |
| 62 | 40 (76) | 15 |
| 63 | 40 (814) | ND |
| 64 | 40 (8429) | >33 |
| 65 | 40 (88) | >33 |
| 66 | 40 (883) | ND |
| 67 | 40 (94) | >33 |
| 68 | 40 (943) | ND |
| 69 | 40 (953) | 21 |
| 70 | 40 (954) | >33 |
| 71 | 40 (1286) | >29 |
| 72 | 20 (102) | ND |
| 73 | 40 (1035) | ND |
| 74 | 40 (107) | >33 |
| 75 | 40 (117) | ND |
| 76 | 40 (1194) | >33 |
| 77 | 40 (125) | ND |
| 78 | 40 (135) | 0.24 |
| 79 | 40 (139) | ND |
| 80 | 40 (145) | >17 |
| 81 | 40 (149) | ND |
| 82 | 40 (1546) | ND |
| 83 | 40 (1610) | >33 |
| 84 | 40 (1637) | ND |
| 85 | 40 (1669) | ND |
| 86 | 40 (1673) | >33 |
| 87 | 40 (1750) | >33 |
| 88 | 40 (1800) | ND |
| 89 | 40 (2087) | >33 |
| 90 | 40 (2440) | ND |
| 91 | 40 (2555) | ND |
| 92 | 40 (2603) | >33 |
| 93 | 40 (268) | >33 |
| 94 | 40 (2741) | ND |
| 95 | 40 (2907) | 0.18 |
| 96 | 40 (3222) | ND |
| 97 | 40 (3620) | 22.6 |
| 98 | 40 (3645) | >33 |
| 99 | 40 (3747) | ND |
| 100 | 40 (458) | ND |
| 101 | 40 (51) | ND |
| 102 | 40 (52) | ND |
| 103 | 40 (546) | >29 |
| 104 | 40 (56) | >33 |
| 105 | 40 (57) | ND |
| 106 | 40 (571) | ND |
| 107 | 40 (5766) | >33 |
| 108 | 40 (589) | ND |
| 109 | 40 (66) | >33 |
| 110 | 40 (681) | ND |
| 111 | 40 (708) | >33 |
| 112 | 40 (709) | ND |
| 113 | 40 (72) | ND |
| 114 | 40 (7238) | ND |
| 115 | 40 (74) | 26 |
| 116 | 40 (750) | 0.12 |
| 117 | 40 (810) | ND |
| 118 | 40 (825) | >33 |
| 119 | 40 (86) | ND |
| 120 | 40 (86) | ND |
| 121 | 40 (105) | >23 |
| 122 | 40 (186) | >33 |
| 123 | 40 (918) | >11 |
| 124 | 40 (104) | ND |
| 125 | 40 (111) | ND |
| 126 | 40 (119) | ND |
| 127 | 40 (1269) | ND |
| 128 | 40 (134) | ND |
| 129 | 40 (1377) | >33 |
| 130 | 40 (153) | ND |
| 131 | 40 (170) | ND |
| 132 | 40 (172) | ND |
| 133 | 40 (1765) | ND |
| 134 | 40 (189) | ND |
| 135 | 40 (191) | >33 |
| 136 | 40 (1937) | 0.14 |
| 137 | 40 (1987) | 8.2 |
| 138 | 40 (205) | ND |
| 139 | 40 (227) | ND |
| 140 | 40 (238) | >33 |
| 141 | 40 (2508) | 17 |
| 142 | 40 (268) | >33 |
| 143 | 40 (2703) | ND |
| 144 | 40 (288) | >33 |
| 145 | 40 (291) | ND |
| 146 | 40 (295) | ND |
| 147 | 40 (315) | ND |
| 148 | 40 (324) | ND |
| 149 | 40 (336) | ND |
| 150 | 40 (34502) | ND |
| 151 | 40 (3753) | >33 |
| 152 | 40 (4144) | ND |
| 153 | 40 (444) | ND |
| 154 | 40 (445) | ND |
| 155 | 40 (4599) | >33 |
| 156 | 40 (4730) | ND |
| 157 | 40 (4735) | 25 |
| 158 | 40 (481) | ND |
| 159 | 40 (485) | ND |
| 160 | 40 (5050) | 5.4 |
| 161 | 40 (513) | ND |
| 162 | 40 (549) | >33 |
| 163 | 40 (55) | ND |
| 164 | 40 (60) | >33 |
| 165 | 40 (6280) | ND |
| 166 | 40 (631) | >33 |
| 167 | 40 (644) | >33 |
| 168 | 40 (67) | ND |
| 169 | 40 (695) | ND |
| 170 | 40 (73) | ND |
| 171 | 40 (77) | ND |
| 172 | 40 (824) | ND |
| 173 | 40 (849) | ND |
| 174 | 40 (904) | ND |
| 175 | 40 (96) | ND |
| 176 | 40 (55) | ND |

ND means no data

EXAMPLES

The present invention is further exemplified, but not to be limited, by the following examples and intermediates that illustrate the preparation of compounds of Formula I according to the invention. It is understood that if there appears to be a discrepancy between the name and structure of a particular compound, the structure is to be considered correct as the compound names were generated from the structures.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

LC-MS Method

Method A: (2.0 min) (C18, 10-100% ACN (0.035% TFA) in water (0.05% TFA) over 2 min).

Example 1: Synthesis of (1R,2R,3S,4S)-3-(2-aminopyridin-4-yl)-N-(3,4-dichlorophenyl)-7-oxabicyclo[2.2.1]heptane-2-carboxamide (Compound 107) and (1R,2S,3S,4S)-3-(2-aminopyridin-4-yl)-N-(3,4-dichlorophenyl)-7-oxabicyclo[2.2.1]heptane-2-carboxamide (Compound 115)

Step 1: Preparation of methyl 3-bromo-7-oxabicyclo[2.2.1]hepta-2,5-diene-2-carboxylate, (Intermediate I-1)

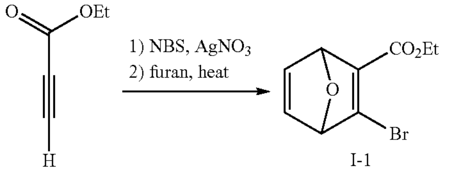 [SMILES: C#CC(=O)OCC ; CCOC(=O)C1=C(Br)C2C=CC1O2 ; [I-]]

I-1

A solution of ethyl propiolate (2.03 mL, 20.0 mmoL) in acetone (40 mL) at RT was treated with silver nitrate (340 mg, 2.00 mmol). After 5 minutes, NBS (3.92 g, 22.0 mmol) was added and the reaction was stirred at RT for 3 hours. The reaction mixture was filtered through a pad of celite, which was washed with acetone (3×20 mL). Concentration of the acetone solution provided crude brominated alkyne, which was used directly in the next step without purification. (Note: the alkyne is volatile and must not be placed on a high vac line).

A solution of alkyne (50.8 mmol) in furan (22 mL, 305 mmol) was transferred into 4-40 mL thick vials with caps. The reaction vials were warmed at 80° C. for 20 h. The reaction was cooled to RT and the solvent removed under reduced pressure. The crude compound was taken up in DCM and purified by FCC (hexanes/ethyl acetate) to afford the desired product Intermediate I-1 (8.1 g, 65%). LCMS m/z (M+1, 245, 247). This compound is known in the art and has been described in the literature.

An alternate procedure for the bromination using methyl propiolate is described in a 2003 US patent publication US2003/236270 A1. Methyl propiolate (52 ml, 0.583 mol) is combined with recrystallized N-bromo-succinimide (120 g, 0.674 mol) in 1,700 ml acetone under nitrogen. The solution is treated with silver nitrate (9.9 g, 0.0583 mol) neat in a single lot and the reaction is stirred 6 h at RT. The acetone is removed under reduced pressure (25° C., bath temperature) to provide a gray slurry. The slurry is washed with 2×200 ml hexane, the gray solid is removed by filtration, and the filtrate is concentrated in vacuo to provide 95 g of a pale yellow oily residue. The crude material was distilled via short path under reduced pressure (65° C., about 25 mm Hg) into a dry ice/acetone cooled receiver to give 83.7 g (88%) of methyl-3-bromo-propiolate as a pale yellow oil.

ADDITIONAL LITERATURE

1. Poulsen, Thomas B.; Bernardi, Luca; Aleman, Jose; Overgaard, Jacob; Joergensen, Karl Anker *Journal of the American Chemical Society* 2007, 129, 441-449.
2. Andersen, Neil G.; Maddaford, Shawn P.; Keay, Brian A. *Journal of Organic* Chemistry 1996, 61, 2885-2887.
3. Leroy, Jacques *Tetrahedron Letters* 1992, 33, 2969-2972.
4. Christensen, Helena S.; Boye, Soeren V.; Thinggaard, Jacob; Sinning, Steffen; Wiborg, Ove; Schioett, Birgit; Bols, Mikael *Bioorganic and Medicinal Chemistry* 2007, 15, 5262-5274,
5. Rainier, Jon D.; Xu, Qing *Organic Letters* 1999, 1, 27-29.

Step 2. Preparation of methyl 3-bromo-7-oxabicyclo[2.2.1]hept-2-ene-2-carboxylate (Intermediate I-2)

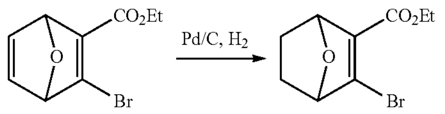

I-1 I-2

To a stirring solution of I-1 (5 g, 20.40 mmol) in EtOAc (50 mL) was added 10% palladium on carbon (2.5 g, wet basis). The reaction mixture was hydrogenated at 1 atm for 3 h. LCMS showed the reaction to be complete. The reaction was filtered over celite and washed with EtOAc. The solvent was concentrated and the crude compound was purified by FCC (hexanes/EtOAc) to afford the desired product Intermediate I-2 (3.2 g, 56%). LCMS m/z (M+1, 247, 249); $^1H$ NMR (400 MHz, DMSO) δ 5.18 (d, J=4.0 Hz, 1H), 5.07 (d, J=4.0 Hz, 1H), 4.21-4.13 (M, 2H), 1.85-1.75 (m, 2H), 1.38-1.32 (m, 2H), 1.24 (t, J=8.0 Hz, 3H). This compound is known in the art and has been described in the literature.

LITERATURE

1. Christensen, Helena S.; Boye, Soeren V.; Thinggaard, Jacob; Sinning, Steffen; Wiborg, Ove; Schioett, Birgit; Bols, Mikael *Bioorganic and Medicinal Chemistry* 2007, 15, 5262-5274.
2. *Bull. Korean Chem. Soc.* 2007, 28, 307.

Step 3. Preparation of tert-butyl 3-bromo-7-oxabicyclo[2.2.1]hept-2-ene-2-carboxylate (Intermediate I-3)

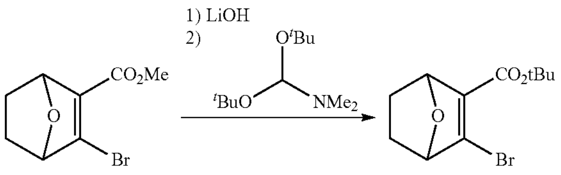

I-2 I-3

A solution of I-2 (4.00 g, 17.2 mmol) in 2:1:1 THF:MeOH:water (100 mL) was treated with LiOH (1.23 g, 51.5 mmol) and stirred at RT for 2 hours. LCMS showed the reaction to be complete. The reaction was quenched with sat. aq. $NH_4Cl$, diluted with EtOAc, washed with water and brine, dried ($Na_2SO_4$), and concentrated. The resulting oil (3.33 g, 15.2 mmol) was dissolved in toluene (20 mL) was treated with DMF di-t-butyl acetal (18.2 mL, 76.0 mmol) and stirred at 60° C. for 16 hours. LCMS showed formation of a new product. The solvent was removed under reduced pressure and the resulting oil was purified by FCC (EtOAc/hexanes) to afford Intermediate I-3 (2.07 g, 47%). LCMS m/z (M+H-tBu, 219.0, 221.0); $^1H$ NMR (400 MHz, DMSO) δ 5.16-5.09 (m, 1H), 5.06-4.99 (m, 1H), 1.85-1.73 (m, 2H), 1.46 (s, 9H), 1.38-1.27 (m, 2H).

Step 4. Preparation of tert-butyl 7-oxabicyclo[2.2.1]hept-2-ene-2-carboxylate (Intermediate I-4)

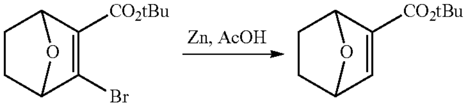

I-3 I-4

To a stirring solution of I-3 (10 g, 36.3 mmol) in THF (24 mL) and water (24 mL) at 0° C. was added acetic acid (10.4 mL) and portion-wise Zn powder (7.1 g, 109 mmol). The reaction slurry was stirred to room temperature for 30 minutes. Additional Zn powder (~10 g) was added as needed to get the reaction to go to completion. The reaction was filtered through a plug of celite and the solid was washed with EtOAc. The filtrate was neutralized with saturated sodium bicarbonate (pH ~8-10), further diluted with EtOAc, washed with water and brine, dried ($Na_2SO_4$), filtered, and concentrated. The resulting yellow oil, Intermediate I-4, (7.0 grams, 98%) was used in the next step without further purification. LCMS m/z (M+H-tBu, 141.1); $^1H$ NMR (400 MHz, $CDCl_3$) δ 6.90 (d, J=1.8 Hz, 1H), 5.19-5.15 (m, 1H), 5.08-5.06 (m, 1H), 1.94-1.81 (m, 2H), 1.49 (s, 9H), 1.33-1.25 (m, 2H).

Step 5. Preparation of N-(3,4-dichlorophenyl)-7-oxabicyclo[2.2.1]hept-2-ene-2-carboxamide (Intermediate I-5)

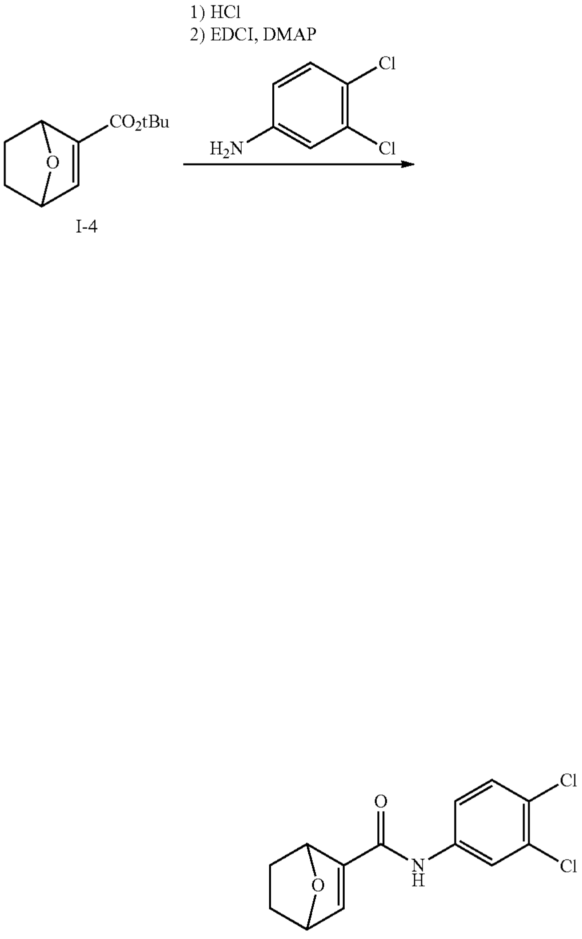

I-4

I-5

To a stirring solution of I-4 (3.50 g, 17.8 mmol) in 1,4-dioxane (6 mL) was added HCl (37%, 6 mL). The reaction was stirred at room temperature for 2 h. LCMS showed the reaction was complete. The solvent was removed under reduced pressure and the compound was diluted with water and extracted with ethyl acetate. The organic layer was washed with water and brine, dried ($Na_2SO_4$), filtered, and concentrated. The crude carboxylic acid product (2.4 g) was dissolved in anhydrous pyridine (12 mL) with 3,4-dichloroaniline (2.30 g, 14.3 mmol), EDCI (4.00 g, 21.4 mmol) and DMAP (872 mg, 7.14 mmol). The reaction was stirred at room temperature for 4 h. The solvent was removed under reduced pressure and the resulting residue was taken up in ethyl acetate and 1M HCl. The organic layer was washed with 1M HCl and brine, dried ($Na_2SO_4$), filtered, and concentrated. The resulting residue was purified by FCC to afford Intermediate I-5 as a tan solid (1.5 g, 30% overall). LCMS m/z (M+H, 283.1); $^1H$ NMR (400 MHz, DMSO) δ 10.11 (s, 1H), 8.04 (d, J=2.3 Hz, 1H), 7.63 (dd, J=8.9, 2.4 Hz, 1H), 7.58 (d, J=8.8 Hz, 1H), 7.10 (d, J=1.8 Hz, 1H), 5.22 (d, J=4.0 Hz, 1H), 5.18-5.15 (m, 1H), 1.80-1.74 (m, 2H), 1.28-1.20 (m, 2H).

Step 6. Preparation of Compound 107 and Compound 115

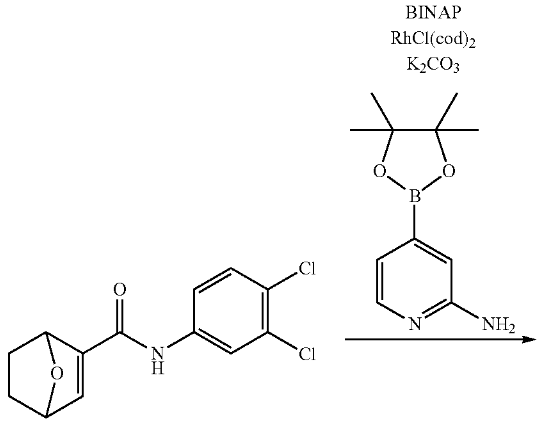

I-5

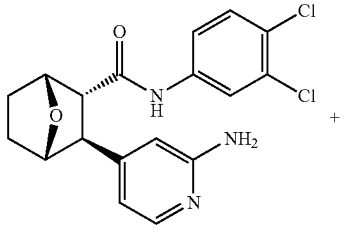

107

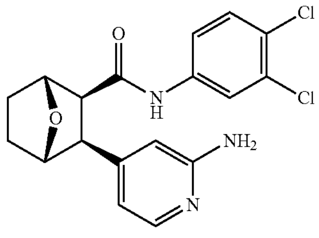

115

A mixture I-5 (500 mg, 1.76 mmol), 4-(4,4,5,5-tetramethyl-1,3,2-dioxaborolan-2-yl)pyridin-2-amine (581 mg, 2.64 mmol), 2,2-bis(diphenylphosphino)-1,1-binapthalene (110 mg, 0.176 mmol), chloro(1,5-cyclooctadiene)rhodium (I) dimer (43 mg, 0.088 mol) and potassium carbonate (121 mg, 0.88 mmol) in dioxane (10 mL) and water (2 mL) was heated in the microwave at 100° C. for 1 h. LCMS shows two peaks with mass M+1, 378, 380; one minor and major. The crude reaction was filtered and the crude compound was purified by HPLC (10 to 70% 0.05% TFA in acetonitrile). The fractions containing the second peak to elute were concentrated under reduced pressure. The resulting residue was taken up in ethyl acetate, washed with 10% aq. sodium bicarbonate, water and brine, dried ($Na_2SO_4$), filtered, and concentrated. The resulting residue was taken up in 1:1 water/acetonitrile and was lyophilized to afford Compound 107 (324 mg, 46%) as a white solid. The same was process was performed for the first peak to elute off the HPLC to afford Compound 115 (95 mg, 14%).

Compound 107:

LCMS m/z (M+H, 378.1); $^1$H NMR (400 MHz, DMSO) δ 10.34 (s, 1H), 8.01 (d, J=2.4 Hz, 1H), 7.79 (d, J=5.2 Hz, 1H), 7.57 (d, J=9.0 Hz, 1H), 7.44 (dd, J=8.9, 2.4 Hz, 1H), 6.39 (dd, J=5.2, 1.5 Hz, 1H), 6.33 (d, J=1.4 Hz, 1H), 5.85 (s, 2H), 4.86 (t, J=5.1 Hz, 1H), 4.54 (d, J=4.6 Hz, 1H), 3.17 (d, J=5.1 Hz, 1H), 2.99 (td, J=5.2, 1.5 Hz, 1H), 1.78-1.46 (m, 4H).

Compound 115

LCMS (M+H, 378.0); $^1$H NMR (400 MHz, DMSO) δ 9.51 (s, 1H), 7.50 (d, J=5.3 Hz, 1H), 7.45 (d, J=2.3 Hz, 1H), 7.32 (d, J=8.8 Hz, 1H), 7.00 (dd, J=8.8, 2.4 Hz, 1H), 6.32 (d, J=5.5 Hz, 2H), 5.56 (s, 2H), 4.78 (d, J=3.5 Hz, 1H), 4.38 (d, J=3.9 Hz, 1H), 3.14 (d, J=9.8 Hz, 1H), 3.05 (d, J=9.6 Hz, 1H), 1.57 (ddq, J=17.7, 6.8, 4.1, 3.1 Hz, 4H).

Example 2: Synthesis of (1R,2R,3S,4S)—N-(3,4-dichlorophenyl)-3-(pyridin-4-yl)-7-oxabicyclo[2.2.1]heptane-2-carboxamide (Compound 118) and Isolation of Enantiomers Step 1. Preparation of methyl 7-oxabicyclo[2.2.1]hept-2-ene-2-carboxylate (Intermediate I7)

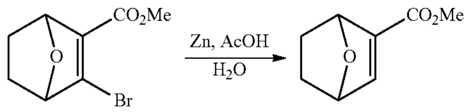

I-2

I-7

A solution of I-2 (1.00 g, 4.29 mmol) in water (10 mL) was cooled to 0° C. and was treated with acetic acid (1.23 mL). Zinc dust (421 mg, 6.44 mmol) was added over the course of 2 minutes and the mixture was allowed to warm to RT over 10 min. LCMS indicated the reaction to be complete. The reaction was diluted with EtOAc, washed with sat. aq. $NaHCO_3$ and brine, dried ($MgSO_4$), filtered, and concentrated. The resulting residue was taken up in DCM and purified by FCC (80 g, 0-80% EtOAc, 30 min) to afford the desired I7 (1.18 g, 85% yield). LCMS m/z (M+1, 155.2); $^1$H NMR (400 MHz, DMSO) δ 7.11 (s, 1H), 5.10 (d, J=4.4 Hz, 2H), 3.69 (s, 3H), 1.82-1.69 (m, 2H), 1.24-1.13 (m, 2H).

Step 2. Preparation of 1R,2R,3S,4S)-methyl 3-(pyridin-4-yl)-7-oxabicyclo[2.2.1]heptane-2-carboxylate (Intermediate I-8)

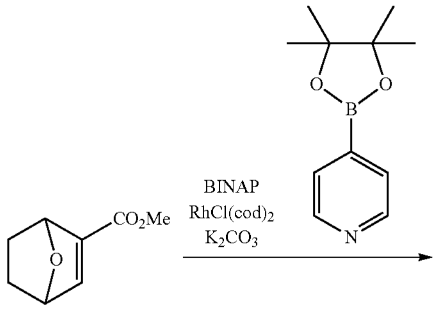

I-7

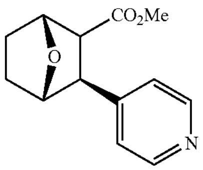

I-8

A solution of I-7 (200 mg, 1.297 mmol), BINAP (72.7 mg, 0.117 mmol), 4-(4,4,5,5-tetramethyl-1,3,2-dioxaborolan-2-yl)pyridine (559 mg, 2.72 mmol), $K_2CO_3$ (90 mg, 0.649 mmol), and $RhCl(cod)_2$ (12 mg, 1.297 mmol) in dioxane (12 mL)/water (4 mL) was evacuated and purged with argon twice and then warmed at 100° C. for 60 min in a microwave reactor. LCMS showed mostly product mass with small amounts of 1-9 near the solvent front. The reaction was diluted with EtOAc, washed with water and brine, dried ($Na_2SO_4$), filtered, and concentrated. The resulting residue was taken up in DCM and purified by FCC (DCM/EtOAc) to afford the desired product Intermediate I-8 as a 4:1 mixture of trans:cis (261 mg, 82%). LCMS m/z (M+1, 234.2). $^1H$ NMR of 4:1 mixture (400 MHz, DMSO) δ 8.47 (d, J=6.1 Hz, 2H), 8.41 (d, J=6.1 Hz, 0.5H), 7.29 (d, J=6.1 Hz, 2H), 7.20 (d, J=6.1 Hz, 0.5H), 4.89-4.81 (m, 1.3H), 4.53 (d, J=4.7 Hz, 1H), 4.50 (d, J=4.1 Hz, 0.3H), 3.65 (s, 3.8H), 3.44 (d, J=9.8 Hz, 0.3H), 3.30-3.27 (m, 1.3H), 3.12-3.05 (m, 1H), 1.78-1.52 (m, 5H).

Step 3: Preparation of (1R,2R,3S,4S)-3-(pyridin-4-yl)-7-oxabicyclo[2.2.1]heptane-2-carboxylic acid (Intermediate I-9)

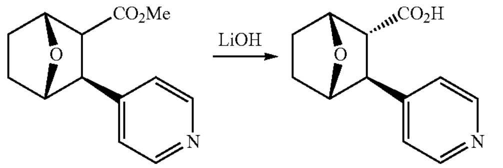

I-8 I-9

A solution of a I-8 (4:1 mixture of trans:cis, 168 mg, 0.720 mmol) in THF (3 mL), MeOH (2 mL) and water (1 mL) was treated with LiOH (103 mg, 4.32 mmol) and stirred at 80° C. for 2 hours. LCMS showed the reaction to be complete. The solution was taken to pH 3 with HCl and was concentrated under reduced pressure. The resulting residue, Intermediate I-9, was dried under vacuum overnight and was used directly in the next step without purification assuming quantitative yield. LCMS m/z (M+1, 220.2).

Alternatively, I-9 may be synthesis from I-7 in a one pot reaction:

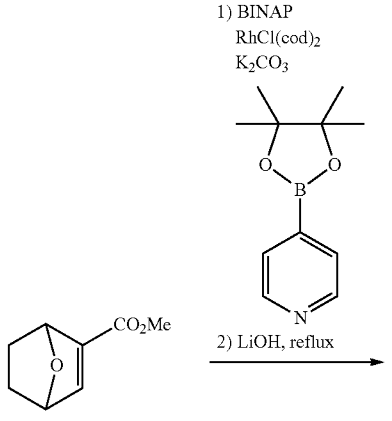

I-7

-continued

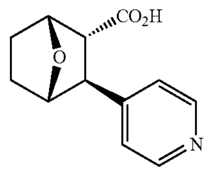

I-9

A solution of I-7 (200 mg, 1.297 mmol), BINAP (72.7 mg, 0.117 mmol), 4-(4,4,5,5-tetramethyl-1,3,2-dioxaborolan-2-yl)pyridine (559 mg, 2.72 mmol), $K_2CO_3$ (90 mg, 0.649 mmol), and $RhCl(cod)_2$ (12 mg, 1.297 mmol) in dioxane (12 mL)/water (4 mL) was evacuated and purged with argon twice and then warmed at 100° C. for 60 min in a microwave reactor. LCMS showed mostly I-8 was present with small amounts of I-9. The reaction was repeated 7 times on the same scale to the same result (total of 1.6 grams of I-7 used, 10.38 mmol). The reactions were combined, diluted with MeOH (200 mL) and THF (200 mL), and treated with LiOH (746 mg, 31.1 mmol). The reaction was stirred at RT for 2 hours. LCMS showed no change in the ratio of I-9:I-8. Another 746 mg LiOH (31.1 mmol) was added and the reaction was warmed at 80° C. for 1 h. LCMS showed an approximate 1:2 ratio of I-9:I-8. Another 746 mg LiOH (31.1 mmol) was added and the reaction was stirred for 1 hour at 80° C. LCMS showed the reaction was complete. The resulting solution was concentrated under reduced pressure and dried under vacuum overnight. The resulting residue containing product and inorganic solids was taken up in 300 mL of 1:1 DCM:MeOH, celite was added, and the solution was concentrated. The celite mixture was loaded onto a column and the product was eluted (80 g column, 0-90% MeOH/DCM, 35 min) to afford the desired acid product with a large amount of silica gel (7.8 grams crude mass; 2.28 grams was theoretical). The product mixture was used in the next step as is assuming only 25% of the mass corresponded to the desired acid product. (Note: I-9 is water soluble under basic, neutral, and acidic workup conditions and therefore no workup was performed). LCMS m/z (M+1, 220.2).

Step 4. Preparation of Compound 118

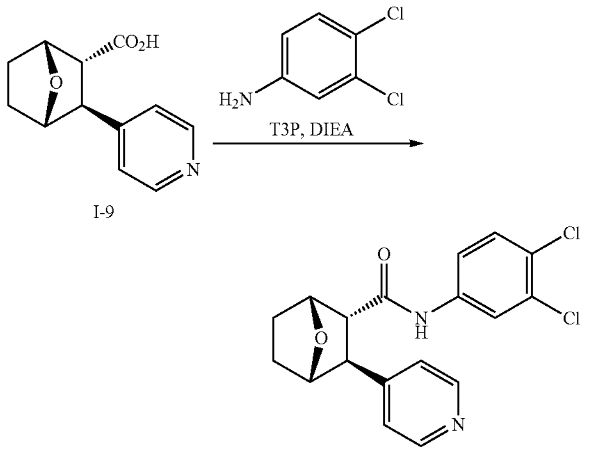

I-9

118

A suspension of I-9 (90 mg, 0.411 mmol) (360 mg including $SiO_2$), 3,4-dichloroaniline (100 mg, 0.616 mmol), and T3P (0.489 mL, 0.821 mmol) in ethyl acetate (8 mL) was treated with DIEA (0.215 mL, 1.232 mmol). After 5 minutes of stirring at 23° C., the solution remained a suspension. DMF (3 mL) was added and only a slight precipitate remained. The reaction was stirred for 30 minutes at RT, after which LCMS showed 1:1 SM:product. The reaction was warmed at 80° C. for 20 minutes and LCMS showed the same ratio of SM to product. Additional T3P (0.489 mL, 0.821 mmol) and DIEA (0.43 mL, 6 equiv) were added and the reaction was continued at 80° C. for 40 additional minutes.

LCMS showed the reaction to be at ~90% conversion. The reaction was stirred for another 1 hour at 80° C. then was cooled to room temperature. An identical reaction was run on 1.0 grams of I-9 (4.0 grams including mass of $SiO_2$), 10.8 mL of T3P (4 equiv), 7.17 mL DIEA (9 equiv), in 100 mL of EtOAc and 30 mL of DMF. The reaction was warmed at 80° C. for 45 minutes and was judged to be complete by LCMS. After cooling to RT, the two reactions were combined and diluted with EtOAc, washed with water and brine, dried ($Na_2SO_4$), filtered, and concentrated. The residue was purified by chromatography (80 g gold column, 0-70% EtOAc/DCM for 20 minutes, then 0-40% MeOH/DCM for 20 minutes) to afford the desired product Compound 118 (1.34 g, 3.50 mmol, 74% yield) as a white solid.

Compound 118 was purified by recrystallization. The solid was dissolved in ~150 mL of MeCN and was heated to reflux until the solid completely dissolved. The solution was placed in a −20° C. freezer overnight. The crystals were filtered off and washed with cold MeCN to obtain 1.05 grams of an off-white crystallized solid. The mother liquor was concentrated and recrystallized from MeCN in identical fashion to afford 0.155 g additional Compound 118 (~93% recovery overall). Both batches of material were pure by $^1H$ NMR and were dried under high vacuum. Melting point was determined to be 228-230° C. (10° C./min, uncorrected).

Chiral separation of 155 mg of Compound 118 afforded 66.9 mg of (1R,2R,3S,4S)—N-(3,4-dichlorophenyl)-3-(pyridin-4-yl)-7-oxabicyclo[2.2.1]heptane-2-carboxamide (Compound 71) (peak 1) and 62.9 mg of (1S,2S,3R,4R)—N-(3,4-dichlorophenyl)-3-(pyridin-4-yl)-7-oxabicyclo[2.2.1]heptane-2-carboxamide (Compound 103) (peak 2) after recrystallization of both enantiomers from MeCN. LCMS m/z (M+1, 363.1); $^1H$ NMR (400 MHz, DMSO) δ 10.35 (s, 1H), 8.48 (dd, J=4.4, 1.6 Hz, 2H), 8.01 (d, J=2.4 Hz, 1H), 7.57 (d, J=8.8 Hz, 1H), 7.43 (dd, J=8.8, 2.4 Hz, 1H), 7.27 (dd, J=4.5, 1.7 Hz, 2H), 4.93 (t, J=5.1 Hz, 1H), 4.59 (d, J=4.3 Hz, 1H), 3.39 (d, J=5.0 Hz, 1H), 3.07 (td, J=5.1, 1.5 Hz, 1H), 1.80-1.49 (m, 4H).

Example 3. Synthesis of (1R,4S)—N-(2-chloro-[1,1'-biphenyl]-4-yl)-3-(6-(trifluoromethyl)pyridin-2-yl)-7-oxabicyclo[2.2.1]hept-2-ene-2-carboxamide (Compound 160)

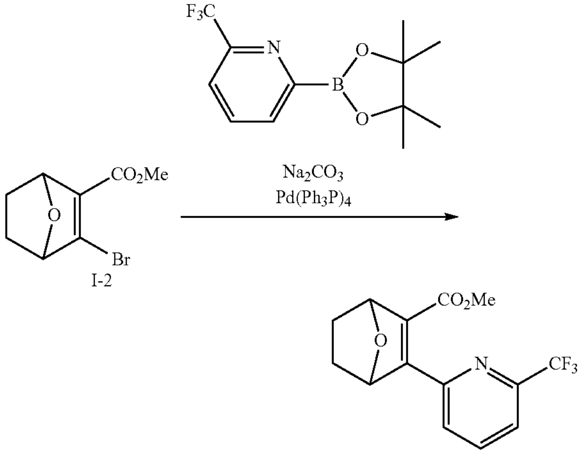

I-2

I-10

Step 1. Preparation of methyl 3-(6-(trifluoromethyl)pyridin-2-yl)-7-oxabicyclo[2.2.1]hept-2-ene-2-carboxylate (Intermediate I-10)

A dioxane (10 mL) suspension of methyl 3-bromo-7-oxabicyclo[2.2.1]hept-2-ene-2-carboxylate I-2 (356 mg, 1.526 mmol), 2-(4,4,5,5-tetramethyl-1,3,2-dioxaborolan-2-yl)-6-(trifluoromethyl)pyridine (500 mg, 1.831 mmol) and tetrakis (176 mg, 0.153 mmol) was treated with sodium carbonate (1.144 mL, 2.289 mmol, 2M solution). The reaction mixture was purged with nitrogen and heated in microwave reactor for 45 min at 120° C. AcOEt was added and washed with water. The organic phase was concentrated and purified by FCC (0 to 40% EtOAc/hex) to give a yellow syrup as the desired product Intermediate I-10 (295 mg, 61%). LCMS m/z (M+1, 300.0).

Step 2. Preparation of 3-(6-(trifluoromethyl)pyridin-2-yl)-7-oxabicyclo[2.2.1]hept-2-ene-2-carboxylic acid (Intermediate I-11)

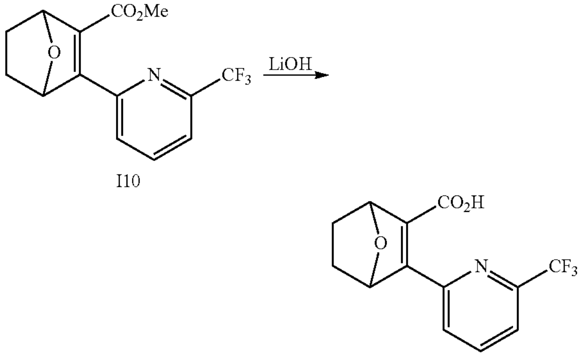

I10

I11

A solution of I-10 (290 mg, 0.969 mmol) in MeOH (5 mL) was treated with lithium hydroxide (1.938 mL, 1.938 mmol, 1N solution) and stirred at RT for 6 hr. The reaction mixture was acidified with AcOH to pH 5-6. A white solid was precipitated. Filtration followed by washed with water gave a white solid as the desired product Intermediate I-11 (220 mg, 76%). LCMS m/z (M+1, 286.0).

Step 3. Preparation of Compound 160

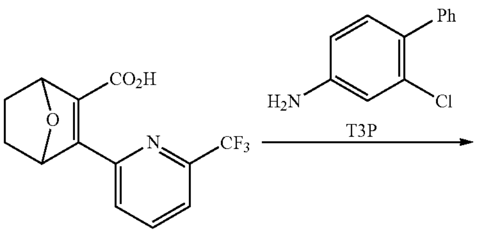

I11

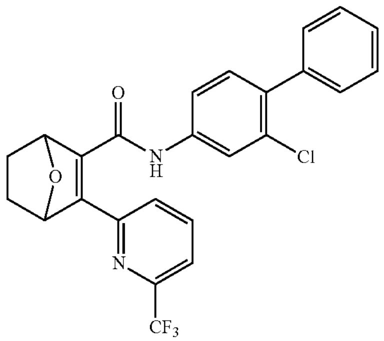

160

A EtOAc (3 mL) solution of I11 (40 mg, 0.140 mmol) and 2-chloro-[1,1'-biphenyl]-4-amine (28.6 mg, 0.140 mmol) was treated with propanephosphonic anhydride (0.427 mL, 0.701 mmol). After addition, the solution was heated to 80° C. overnight. The reaction was diluted with EtOAc, washed with sat. aq. $NaHCO_3$, dried ($Na_2SO_4$), filtered, and concentrated. The resulting residue was purified by FCC (0 to 60% AcOEt/hex) to give a solid as the desired product Compound 160 (42 mg, 57% yield). $^1$H NMR (400 MHz, $CDCl_3$) δ 11.70 (s, 1H), 8.09 (d, J=8.0, 1 H), 7.89 (d, J=2.1, 1 H), 7.82-7.73 (m, 1H), 7.67-7.53 (m, 2H), 7.51-7.39 (m, 5H), 7.35 (d, J=8.4, 1 H), 5.76-5.59 (m, 1H), 5.59-5.44 (m, 1H), 2.28-2.11 (m, 2H), 1.76 (t, J=8.4, 1 H), 1.65 (d, J=8.8, 1 H); LCMS m/z (M+1, 471.1).

Example 4: (1R,2R,3R,4S)—N-(3,4-dichlorophenyl)-3-(6-(trifluoromethyl)pyridin-2-yl)-7-oxabicyclo[2.2.1]heptane-2-carboxamide (Compound 155)

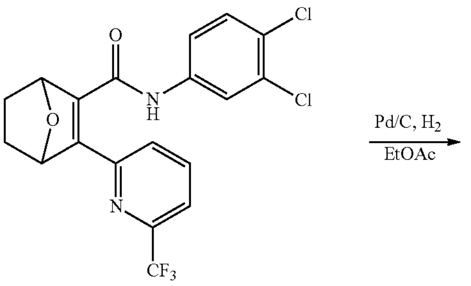

I-19

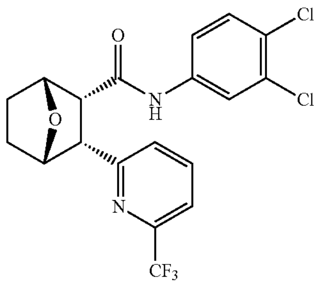

155

A solution of N-(3,4-dichlorophenyl)-3-(6-(trifluoromethyl)pyridin-2-yl)-7-oxabicyclo[2.2.1]hept-2-ene-2-carboxamide (22 mg, 0.051 mmol) and 5% palladium on carbon (20 mg) was hydrogenated at 1 atm for 16 h. The reaction was filtered over celite and washed with EtOAc. The solvent was concentrated and the crude compound was purified by HPLC (10-90% ACN/water) to afford the desired product Compound 155 (20 mg, 86%). $^1$H NMR (400 MHz, $CDCl_3$) δ 7.80 (t, J=7.8, 1H), 7.51 (t, J=9.7, 2H), 7.35-7.27 (m, 3H), 7.11 (dd, J=2.3, 8.7, 1 H), 4.98-4.86 (m, 2H), 3.92 (dd, J=4.5, 11.3, 1 H), 3.52 (dd, J=5.1, 11.4, 1H), 2.39 (t, J=8.6, 1H), 1.99 (t, J=8.4, 1H), 1.78 (dd, J=4.6, 8.0, 2H); LCMS m/z (M+1, 431.1).

Example 5. Synthesis of (1R,2S,3R,4S)—N-(3,4-dichlorophenyl)-3-(1-methyl-3-(trifluoromethyl)-1H-pyrazol-5-yl)-7-oxabicyclo[2.2.1]heptane-2-carboxamide (Compound 134)

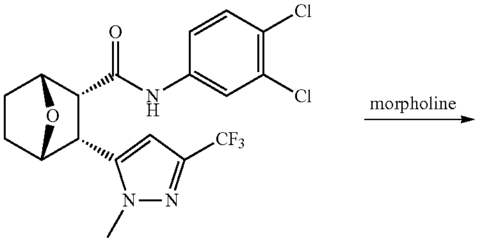

156

-continued

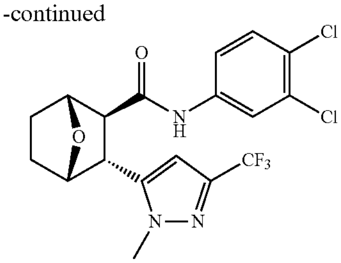

134

To (1R,2R,3R,4S)—N-(3,4-dichlorophenyl)-3-(1-methyl-3-(trifluoromethyl)-1H-pyrazol-5-yl)-7-oxabicyclo[2.2.1]heptane-2-carboxamide 156 (5 mg, 0.012 mmol) was added morpholine (1 mL) and the reaction was heated to 80° C. overnight. The reaction mixture was purified directly with HPLC (20 to 90% ACN/water) to afford the desired product Compound 134 (3.0 mg, 54%). $^1$H NMR (400 MHz, $CDCl_3$) δ 8.01 (s, 1H), 7.78 (t, J=1.3, 1H), 7.40 (d, J=1.4, 2H), 6.49 (s, 1H), 4.91 (dd, J=5.2, 10.9, 2H), 3.93 (s, 3H), 3.78-3.65 (m, 1H), 2.83 (d, J=5.2, 1 H), 2.06-1.91 (m, 1H), 1.74-1.61 (m, 3H); LCMS m/z (M+1, 438.1).

Example 6. Synthesis of (1R,2R,4S,5S)—N-(2'-chloro-2-fluoro-[1,1'-biphenyl]-4-yl)-4-(pyridin-4-yl)-8-oxatricyclo[3.2.1.02,4]octane-2-carboxamide (Compound 85)

Step 1. Preparation of (1R,2R,4S,5S)-tert-butyl 4-(pyridin-4-yl)-8-oxatricyclo[3.2.1.02,4]octane-2-carboxylate (Intermediate I-13)

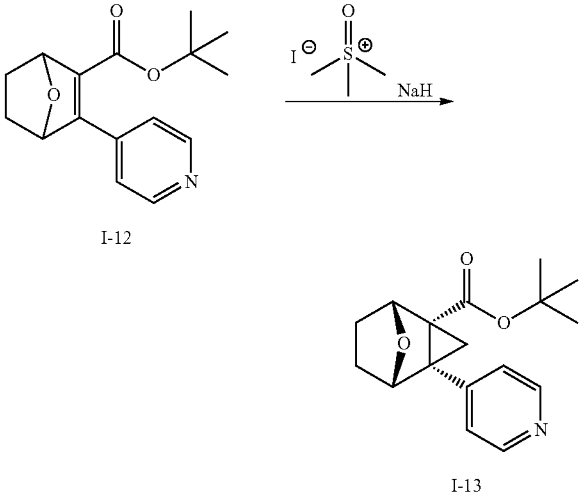

I-12

I-13

A solution of trimethylsulfoxonium iodide (483 mg, 2.195 mmol) in DMSO (7.3 mL) was treated with 60% NaH in mineral oil (88 mg, 2.195 mmol) and was stirred at room temperature for 30 min (gas evolution had ceased). Intermediate I-12 (200 mg, 0.732 mmol) in 7.0 mL DMSO was added dropwise and the resulting mixture was warmed at 50° C. for 16 hr. The reaction was diluted with EtOAc, washed with water and brine, dried (Na2SO4), filtered, and concentrated to afford the desired product, Intermediate I-13, (200 mg, 90%). LCMS m/z (M+1, 288.3).

Step 2. Preparation of (1R,2R,4S,5S)-4-(pyridin-4-yl)-8-oxatricyclo[3.2.1.02,4]octane-2-carboxylic acid (Intermediate I-14)

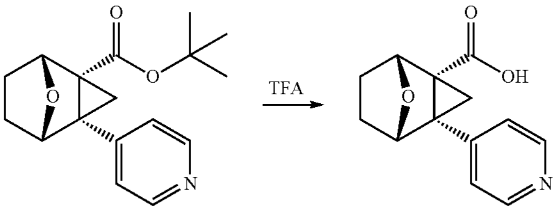

I-13

I-14

A solution of I-13 (195 mg, 0.679 mmol) in DCM (Volume: 5 mL) at 23° C. was treated with TFA (5 mL, 64.9 mmol) and stirred for 2 h. The volatiles were removed under a stream of nitrogen, and the resulting residue was azetroped with toluene twice to afford the desired product Intermediate I-14 as the TFA salt (234 mg, 95%). LCMS m/z (M+1, 232.1).

Step 3. Preparation of Compound 85

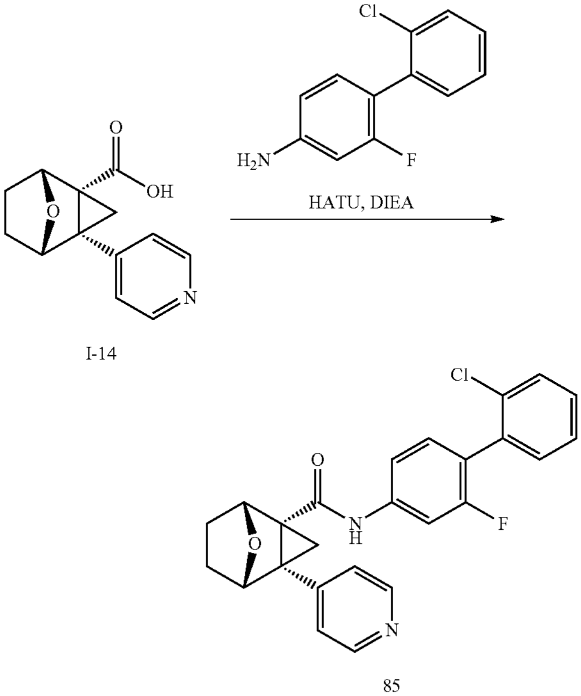

I-14

85

A solution of I-14 (15 mg, 0.065 mmol), amine (21.6 mg, 0.097 mmol) and HATU (49 mg, 0.130 mmol) in EtOAc (1 mL) was treated with DIEA (0.034 ml, 0.195 mmol) and the reaction mixture was stirred at 70° C. for 5 h. The reaction was diluted with EtOAc, washed with water and brine, dried (Na2SO4), filtered, and concentrated. The residue was purified by FCC to afford the desired product Compound 85 (9.7 mg, 31%). $^1$H NMR (400 MHz, MeOD) δ 8.47-8.43 (m, 2H), 7.70-7.17 (m, 9H), 4.79 (d, J=4.7 Hz, 1H), 4.65 (d, J=4.8 Hz, 1H), 2.45 (ddd, J=11.5, 9.1, 4.0 Hz, 1H), 2.04-1.96

(m, 1H), 1.88 (d, J=4.9 Hz, 1H), 1.83 (dt, J=11.3, 4.4 Hz, 1H), 1.79-1.69 (m, 1H), 1.26 (d, J=4.8 Hz, 1H); LCMS m/z (M+1, 435.2).

Example 7. Synthesis of (1S,2S,3R,4R)-3-cyano-N-(3,4-dichlorophenyl)-7-oxabicyclo[2.2.1]heptane-2-carboxamide (Compound 77)

Step 1. Preparation of (1R,2S,3R,4S)-3-((3,4-dichlorophenyl)carbamoyl)-7-oxabicyclo[2.2.1]heptane-2-carboxylic acid (Intermediate I-16)

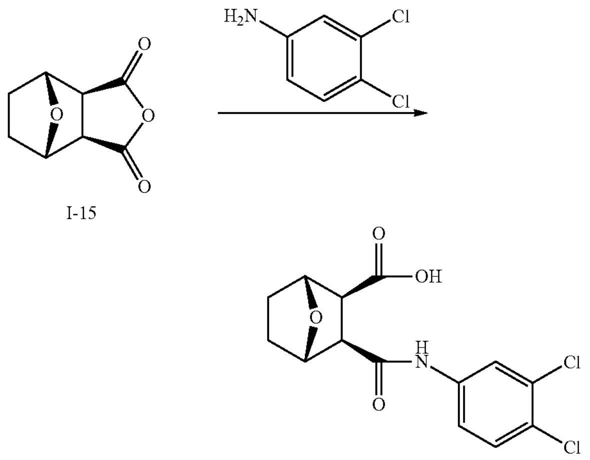

I-15

I-16

A solution of I-15 from Alfa Aesar (500 mg, 2.97 mmol) and 3,4-dichloroaniline (482 mg, 2.97 mmol) in THF (Volume: 25 mL) was stirred at 23° C. for 16 hr. A precipitate had formed. The reaction was filtered to afford 1-16 (368 mg, 35%). LCMS m/z (M+1, 330.0).

Step 2. Preparation of (1R,2S,3S,4S)-3-((3,4-dichlorophenyl)carbamoyl)-7-oxabicyclo[2.2.1]heptane-2-carboxylic acid (Intermediate I-17)

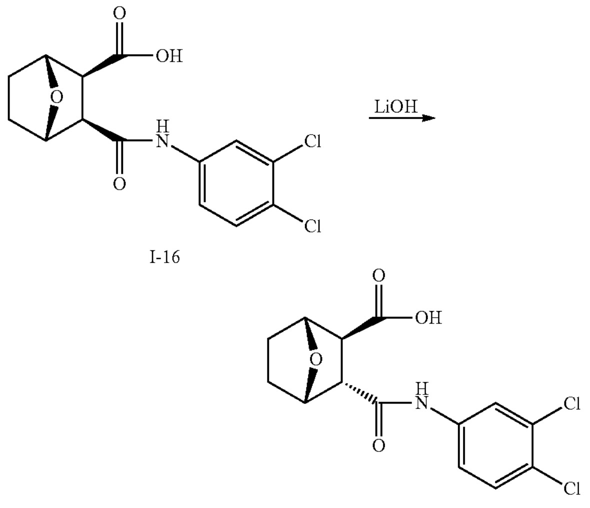

I-16

I-17

A solution of I-16 (300 mg, 0.909 mmol) in THF (6 mL) and water (6 mL) was treated with LiOH (218 mg, 9.09 mmol) and the solution was warmed at 80° C. for 16 hr. LCMS indicated complete product formation. The reaction mixture was acidified with 1 N HCl, diluted with EtOAc, washed with water and brine, dried (Na2SO4), filtered, and concentrated to afford 1-17 (300 mg, 95%). LCMS m/z (M+1, 330.1).

Step 3. Preparation of (1R,2S,3S,4S)-3-((3,4-dichlorophenyl)carbamoyl)-7-oxabicyclo[2.2.1]heptane-2-carboxylic acid (Intermediate I-18)

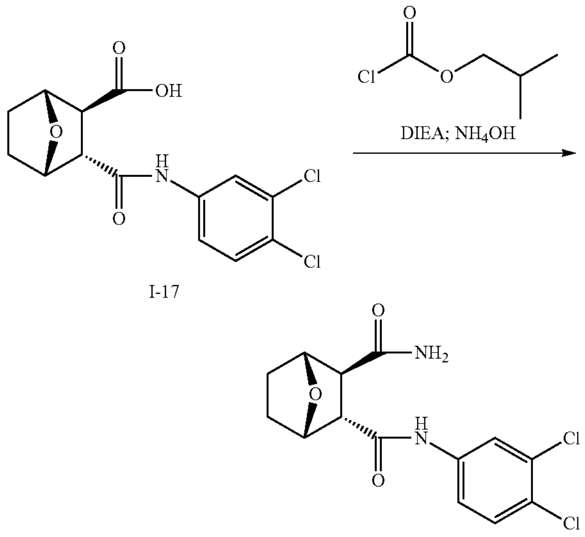

I-17

I-18

A solution of I-17 (100 mg, 0.303 mmol) in tetrahydrofuran (1212 μl) was treated with DIEA (58.2 μl, 0.333 mmol) and isobutyl chloroformate (43.6 μl, 0.333 mmol) and was stirred at RT for 30 minutes. Ammonium hydroxide (126 μl, 0.909 mmol) was added and the reaction was stirred for 30 minutes. LCMS showed the desired product in approximately an equal ratio to starting material. The reaction repeated with 200 mg 1-17 to the same result. The two batches were combined, washed with water and brine, dried (Na2SO4), filtered, and concentrated. The resulting residue was attempted to be purified by FCC; however, the intended product Intermediate I-18 could not be separated from unreacted starting material. The product containing fractions were combined, concentrated, and carried forward to the next reaction as is.

Step 4. Preparation of Compound 77

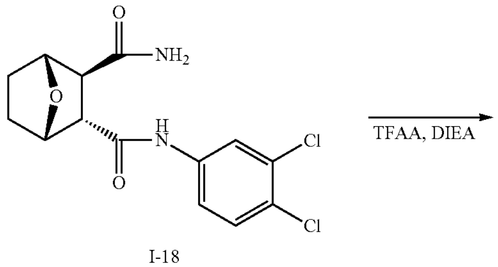

I-18

-continued

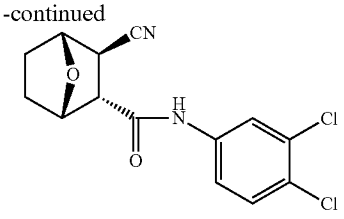

77

A solution of I-18 (100 mg, 0.304 mmol) in DCM (Volume: 2 mL) was treated with TFAA (0.064 mL, 0.456 mmol) and DIEA (0.106 mL, 0.608 mmol) and was stirred at 23° C. for 4 hr. LCMS showed product formation along with SM carboxylic acid from the previous reaction. The volatiles were removed under a stream of nitrogen and the residue was purified by FCC to afford the desired product nitrile, Compound 77, (58 mg, 58%). LCMS m/z (M+1, 311.1).

By repeating the procedures described in the general procedures and the above examples, using appropriate starting materials, the following compounds of Formula I, as identified in Table 3 below, were obtained.

It is understood that if there appears to be a discrepancy between the name and structure of a particular compound, the structure is to be considered correct as the compound names were generated from the structures.

It is further understood that, unless specifically identified, the structure depicted in Table represents a mixture of the enantiomers.

TABLE 3

Exemplified Compounds of Formula I of the Invention

| Ex. No. | Structure | Physical Data MS (m/z), Elemental Analysis, $^1H$ NMR, Melting Point, HPLC RT |
|---|---|---|
| 1 | 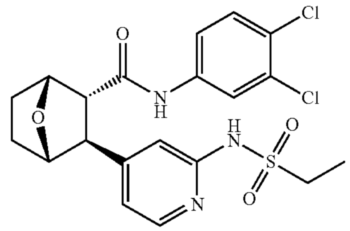 [SMILES: CCS(=O)(=O)Nc1cc([C@@H]2[C@@H](C(=O)Nc3ccc(Cl)c(Cl)c3)[C@H]3CC[C@@H]2O3)ccn1] | $^1H$ NMR (400 MHz, MeOD) δ 7.88 (d, J = 5.4 Hz, 1H), 7.83-7.81 (m, 2H), 7.33 (d, J = 1.8 Hz, 1H), 6.97 (s, 1H), 6.83 (d, J = 5.7 Hz, 1H), 4.82 (t, J = 5.2 Hz, 1H), 4.52 (d, J = 4.7 Hz, 1H), 3.36 (d, J = 5.0 Hz, 1H), 2.97 (td, J = 5.2, 1.5 Hz, 1H), 1.78-1.60 (m, 4H), 1.22 (t, J = 7.4 Hz, 3H). LCMS m/z 472.2. RT 2.17 min. (5 min) (C18, 20-90%, water (0.05% TFA)/ACN) |
| 2 | 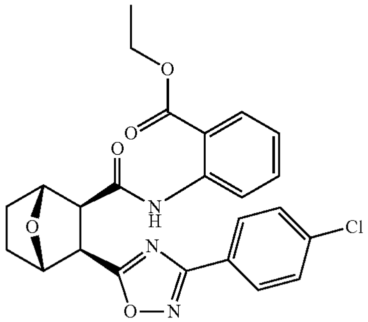 [SMILES: CCOC(=O)c1ccccc1NC(=O)[C@H]1[C@@H](c2nc(-c3ccc(Cl)cc3)no2)[C@@H]2CC[C@H]1O2] | $^1H$ NMR (400 MHz, DMSO) δ 10.63 (s, 1H), 8.01 (dd, J = 1.0, 8.4 Hz, 1H), 7.83 (d, J = 1.6, 8.0 Hz, 1H), 7.79 (d, J = 8.0 Hz, 2H), 7.54 (d, J = 8.0 Hz, 2H), 7.47-7.40 (m, 1H), 7.11-7.05 (m, 1H), 5.11 (s, 1H), 4.98 (s, 1H), 4.30 (q, J = 7.1 Hz, 2H), 4.04 (d, J = 9.6 Hz, 1H), 3.44 (d, J = 9.6 Hz, 1H), 1.78-1.71 (m, 4H). 1.30 (t, J = 7.1 Hz, 3H). LCMS m/z (M + 1, 468.12). RT 1.66 min. (3.5 min) (C18, 20-100%, water (0.05% TFA)/ACN) |
| 3 | 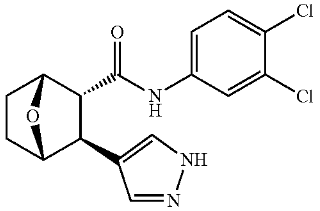 [SMILES: O=C(Nc1ccc(Cl)c(Cl)c1)[C@@H]1[C@@H](c2cn[nH]c2)[C@@H]2CC[C@H]1O2] | $^1H$ NMR (400 MHz, DMSO) δ 10.33 (s, 1H), 10.10 (s, 2H), 8.01 (d, J = 2.4 Hz, 1H), 7.57 (d, J = 8.8 Hz, 1H), 7.45 (dd, J = 2.4, 8.9 Hz, 1H), 7.43 (s, 1H), 4.84 (t, J = 5.1 Hz, 1H), 4.38 (d, J = 4.5 Hz, 1H), 3.29 (d, J = 4.7 Hz, 1H), 3.00 (t, J = 4.5 Hz, 1H), 1.69-1.48 (m, 4H). LCMS m/z (M + 1), 352.05). RT 2.22 min. (5 min) (C18, 10-90%, water (0.05% TFA)/ACN) |
| 4 | 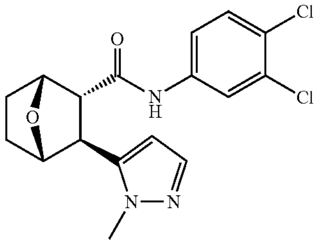 [SMILES: Cn1nccc1[C@@H]1[C@@H](C(=O)Nc2ccc(Cl)c(Cl)c2)[C@H]2CC[C@@H]1O2] | $^1H$ NMR (600 MHz, DMSO) δ = 10.37 (s, 1H), 8.00 (d, J = 2.4 Hz, 1H), 7.58 (d, J = 8.8 Hz, 1H), 7.45 (dd, J = 2.5, 8.8 Hz, 1H), 7.29 (d, J = 1.8 Hz, 1H), 6.07 (d, J = 1.8 Hz, 1H), 4.90 (t, J = 5.2 Hz, 1H), 4.60-4.55 (m, 1H), 3.50 (d, J = 5.0 Hz, 1H), 3.05 (td, J = 1.4, 5.2 Hz, 1H), 1.73-1.52 (m, 4H). LCMS m/z (M + 1, 366.07). RT 1.61 min. (3.5 min) (C18, 10-90%, water (0.05% TFA)/ACN) |

TABLE 3-continued

Exemplified Compounds of Formula I of the Invention

| Ex. No. | Structure | Physical Data MS (m/z), Elemental Analysis, $^1$H NMR, Melting Point, HPLC RT |
|---|---|---|
| 5 | 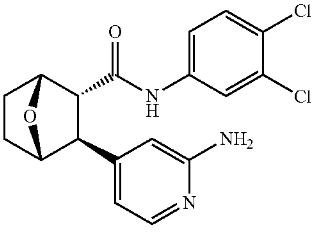 Single enantiomer | $^1$H NMR (400 MHz, DMSO) δ 10.26 (s, 1H), 7.93 (d, J = 2.4 Hz, 1H), 7.72 (d, J = 5.3 Hz, 1H), 7.50 (d, J = 8.8 Hz, 1H), 7.37 (dd, J = 8.8, 2.4 Hz, 1H), 6.31 (dd, J = 5.3, 1.4 Hz, 1H), 6.25 (s, 1H), 5.78 (s, 2H), 4.79 (t, J = 5.0 Hz, 1H), 4.46 (d, J = 4.7 Hz, 1H), 3.09 (d, J = 5.1 Hz, 1H), 2.92 (t, J = 4.7 Hz, 1H), 1.65-1.47 (m, 4H). LCMS m/z (M + 1, 378.07). RT 1.54 min. (3.5 min) (C18, 10-100%, water (0.05% TFA)/ACN) |
| 6 | 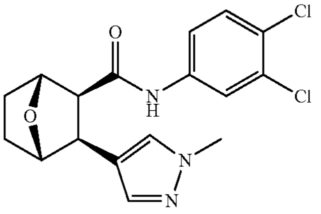 [SMILES: Cn1cc([C@@H]2[C@H](C(=O)Nc3ccc(Cl)c(Cl)c3)[C@H]3CC[C@@H]2O3)cn1] | $^1$H NMR (400 MHz, DMSO) δ 9.66 (s, 1H), 7.50 (d, J = 2.4 Hz, 1H), 7.44 (d, J = 8.8 Hz, 1H), 7.32 (s, 1H), 7.12 (s, 1H), 7.10 (dd, J = 2.4, 8.8 Hz, 1H), 4.82 (d, J = 3.2 Hz, 1H), 4.32 (d, J = 4.8 Hz, 1H), 3.59 (s, 3H), 3.37 (d, J = 9.4 Hz, 1H), 2.99 (d, J = 9.4 Hz, 1H), 1.71-1.55 (m, 4H). LCMS m/z (M + 1, 366.07). RT 1.46 min. (5 min) (C18, 10-90%, water (0.05% TFA)/ACN) |
| 7 | 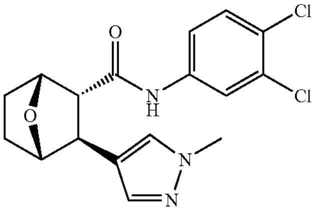 [SMILES: Cn1cc([C@@H]2[C@@H](C(=O)Nc3ccc(Cl)c(Cl)c3)[C@H]3CC[C@@H]2O3)cn1] | LCMS m/z (M + 1, 366.07). RT 2.23 min. (5 min) (C18, 10-90%, water (0.05% TFA)/ACN) |
| 8 | 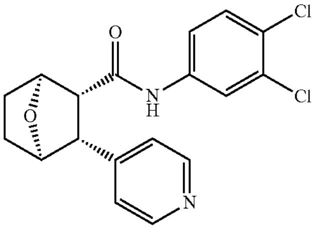 single enantiomer | $^1$H NMR (400 MHz, DMSO) δ 9.70 (s, 1H), 8.28 (d, J = 6.0 Hz, 2H), 7.41 (d, J = 2.4 Hz, 1H), 7.38 (d, J = 8.8 Hz, 1H), 7.26 (d, J = 6.1 Hz, 2H), 6.99 (dd, J = 8.8, 2.4 Hz, 1H), 4.89 (d, J = 3.4 Hz, 1H), 4.53 (d, J = 4.2 Hz, 1H), 3.44 (d, J = 9.7 Hz, 1H), 3.21 (d, J = 9.8 Hz, 1H), 1.75-1.63 (m, 4H). Calc. C, 59.52; H, 4.44; Cl, 19.52; N, 7.71; O, 8.81. Found C, 59.66; H, 4.46; N, 7.75. LCMS m/z (M + 1, 363.06). RT 1.26 min. (2 min) (C18, 10-100%, water (0.05% TFA)/ACN) |
| 9 | 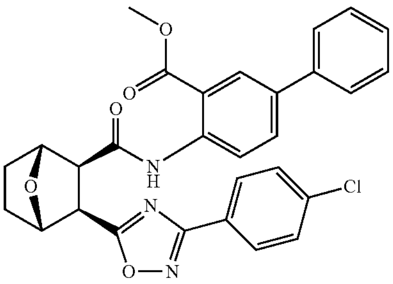 [SMILES: COC(=O)c1cc(-c2ccccc2)ccc1NC(=O)[C@H]1[C@@H](c2nc(-c3ccc(Cl)cc3)no2)[C@@H]2CC[C@H]1O2] | $^1$H NMR (400 MHz, DMSO) δ 10.63 (s, 1H), 8.12 (d, J = 8.7 Hz, 1H), 8.04 (d, J = 2.3 Hz, 1H), 7.80-7.73 (m, 3H), 7.59-7.54 (m, 2H), 7.51 (d, J = 8.7 Hz, 2H), 7.46-7.42 (m, 2H), 7.38-7.33 (m, 1H), 5.14 (s, 1H), 5.01 (s, 1H), 4.06 (t, J = 9.2 Hz, 1H), 3.89 (s, 3H), 3.47 (d, J = 9.7 Hz, 1H), 1.78-1.74 (m, 4H). LCMS m/z (M + 1, 530.14). RT 3.11 min. (5 min) (C18, 20-90%, water (0.05% TFA)/ACN) |

TABLE 3-continued

Exemplified Compounds of Formula I of the Invention

| Ex. No. | Structure | Physical Data MS (m/z), Elemental Analysis, $^1$H NMR, Melting Point, HPLC RT |
|---|---|---|
| 10 | 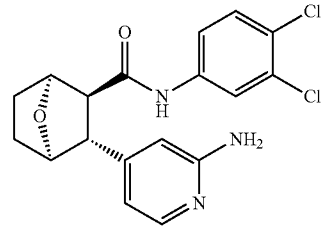 Single enantiomer | $^1$H NMR (400 MHz, DMSO) δ 10.34 (s, 1H), 8.01 (d, J = 2.4 Hz, 1H), 7.79 (d, J = 5.3 Hz, 1H), 7.57 (d, J = 8.8 Hz, 1H), 7.44 (dd, J = 8.8, 2.4 Hz, 1H), 6.39 (dd, J = 5.3, 1.4 Hz, 1H), 6.33 (s, 2H), 5.85 (s, 1H), 4.86 (s, 1H), 4.54 (d, J = 4.7 Hz, 1H), 3.17 (d, J = 5.2 Hz, 1H), 2.99 (t, J = 4.7 Hz, 1H), 1.70-1.53 (m, 4H). Calc. C, 57.16; H, 4.53; Cl, 18.75; N, 11.11; O, 8.46. Found C, 57.29; H, 5.03; N, 10.42. LCMS m/z (M + 1, 378.07). RT 1.51 min. (3.5 min) (C18, 10-100%, water (0.05% TFA)/ACN) |
| 11 | 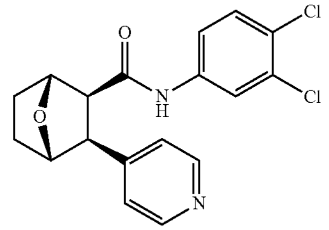 Single enantiomer | $^1$H NMR (400 MHz, DMSO) δ 9.70 (s, 1H), 8.28 (d, J = 6.0 Hz, 2H), 7.41 (d, J = 2.4 Hz, 1H), 7.38 (d, J = 8.7 Hz, 1H), 7.26 (d, J = 6.1 Hz, 2H), 6.99 (dd, J = 8.8, 2.5 Hz, 1H), 4.89 (d, J = 3.4 Hz, 1H), 4.53 (d, J = 4.1 Hz, 1H), 3.44 (d, J = 9.7 Hz, 1H), 3.21 (d, J = 9.7 Hz, 1H), 1.74-1.62 (m, 4H). Calc. C, 59.52; H, 4.44; Cl, 19.52; N, 7.71; O, 8.81. Found C, 59.64; H, 4.52; N, 7.67. LCMS m/z (M + 1, 363.06). RT 1.27 min. (3.5 min) (C18, 10-100%, water (0.05% TFA)/ACN) |
| 12 | 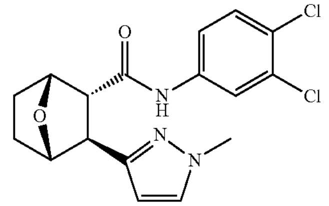 [SMILES: Cn1ccc([C@@H]2[C@@H](C(=O)Nc3ccc(Cl)c(Cl)c3)[C@H]3CC[C@@H]2O3)n1] | $^1$H NMR (600 MHz, DMSO) δ 10.38 (s, 1H), 8.00 (d, J = 2.4 Hz, 1H), 7.56 (dd, J = 3.3, 5.5 Hz, 2H), 7.47 (dd, J = 2.5, 8.8 Hz, 1H), 6.07 (d, J = 2.2 Hz, 1H), 4.81 (t, J = 5.2 Hz, 1H), 4.50 (d, J = 4.8 Hz, 1H), 3.74 (s, 3H), 3.41-3.38 (m, 1H), 3.36 (d, J = 4.9 Hz, 1H), 1.69-1.57 (m, 4H). LCMS m/z (M + 1, 366.07). RT 2.39 min. (5 min) (C18, 10-100%, water (0.05% TFA)/ACN) |
| 13 | 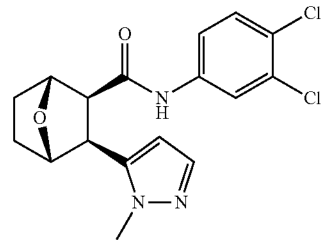 [SMILES: Cn1nccc1[C@@H]1[C@H](C(=O)Nc2ccc(Cl)c(Cl)c2)[C@H]2CC[C@@H]1O2] | $^1$H NMR (600 MHz, DMSO) δ 9.59 (s, 1H), 7.50 (d, J = 2.4 Hz, 1H), 7.43 (d, J = 8.8 Hz, 1H), 7.12-7.06 (m, 2H), 6.02 (d, J = 1.9 Hz, 1H), 4.87 (d, J = 4.3 Hz, 1H), 4.46 (s, 1H), 3.63 (d, J = 9.5 Hz, 1H), 3.13 (d, J = 9.6 Hz, 1H), 1.72-1.58 (m, 4H). LCMS m/z (M + 1), 366.07). RT 1.50 min. (3.5min) (C18, 10-90%, water (0.05% TFA)/ACN) |
| 14 | 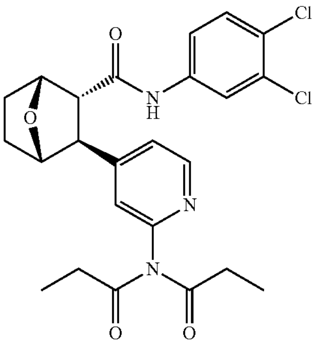 [SMILES: CCC(=O)N(C(=O)CC)c1cc([C@@H]2[C@@H](C(=O)Nc3ccc(Cl)c(Cl)c3)[C@H]3CC[C@@H]2O3)ccn1] | $^1$H NMR (400 MHz, MeOD) δ 8.47 (d, J = 5.2 Hz, 1H), 7.93 (d, J = 1.7 Hz, 1H), 7.47 (dd, J = 5.3, 1.5 Hz, 1H), 7.43 (d, J = 2.5 Hz, 2H), 7.38 (s, 1H), 4.95 (t, J = 5.2 Hz, 1H), 4.66 (d, J = 4.6 Hz, 1H), 3.60 (d, J = 4.9 Hz, 1H), 3.11 (td, J = 5.2, 1.4 Hz, 1H), 2.55 (q, J = 7.3 Hz, 4H), 1.89-1.70 (m, 4H), 1.08 (t, J = 7.3 Hz, 6H). LCMS m/z (M + 1, 490.12). RT 2.66 min. (5 min) (C18, 20-90%, water (0.05% TFA)/ACN) |

TABLE 3-continued

Exemplified Compounds of Formula I of the Invention

| Ex. No. | Structure | Physical Data MS (m/z), Elemental Analysis, $^{1}$H NMR, Melting Point, HPLC RT |
|---|---|---|
| 15 | 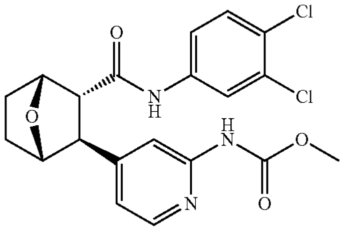 | $^{1}$H NMR (400 MHz, DMSO) δ 10.29 (s, 1H), 10.07 (s, 1H), 8.08 (d, J = 5.2 Hz, 1H), 7.93 (d, J = 2.4 Hz, 1H), 7.75 (s, 1H), 7.50 (d, J = 8.8 Hz, 1H), 7.37 (dd, J = 8.8, 2.4 Hz, 1H), 3.30-3.28 (m, 1H), 6.88 (dd, J = 5.2, 1.4 Hz, 1H), 4.85 (t, J = 5.0 Hz, 1H), 4.48 (d, J = 4.3 Hz, 1H), 3.59 (s, 3H), 3.01 (t, J = 4.7 Hz, 1H), 1.66-1.50 (m, 4H). LCMS m/z (M + 1, 436.08). RT 1.51 min. (3.5 min) (C18, 10-100%, water (0.05% TFA)/ACN) |
| 16 | 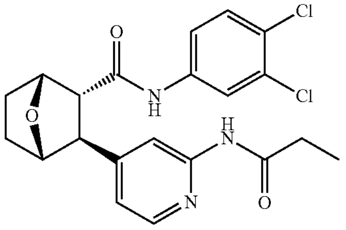 [SMILES: CCC(=O)Nc1cc([C@@H]2[C@@H](C(=O)Nc3ccc(Cl)c(Cl)c3)[C@H]3CC[C@@H]2O3)ccn1] | $^{1}$H NMR (400 MHz, DMSO) δ 10.31 (s, 1H), 10.29 (s, 1H), 8.12 (d, J = 5.2 Hz, 1H), 8.01 (s, 1H), 7.93 (d, J = 2.4 Hz, 1H), 7.50 (d, J = 8.8 Hz, 1H), 7.37 (dd, J = 8.8, 2.4 Hz, 1H), 6.91 (dd, J = 5.2, 1.5 Hz, 1H), 4.85 (t, J = 5.1 Hz, 1H), 4.47 (d, J = 4.3 Hz, 1H), 3.29 (s, 1H), 3.01 (t, J = 4.6 Hz, 1H), 2.30 (q, J = 7.5 Hz, 2H), 1.66-1.48 (m, 4H), 0.98 (t, J = 7.5 Hz, 3H). LCMS m/z (M + 1, 434.10). RT 1.80 min. (5 min) (C18, 20-90%, water (0.05% TFA)/ACN) |
| 17 | 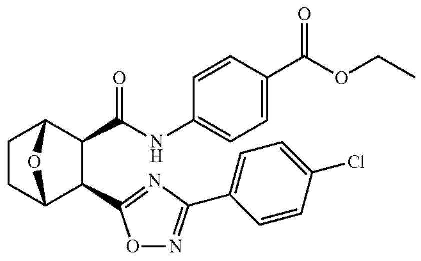 [SMILES: CCOC(=O)c1ccc(NC(=O)[C@H]2[C@@H](c3nc(-c4ccc(Cl)cc4)no3)[C@@H]3CC[C@H]2O3)cc1] | $^{1}$H NMR (400 MHz, DMSO) δ 10.30 (s, 1H), 7.86 (d, J = 8.0 Hz, 2H), 7.80 (d, J 8.0 Hz, 2H), 7.55 (d, J = 8.0 Hz, 2H), 7.49 (d, J = 8.0 Hz, 2H), 5.10 (s, 1H), 4.88 (d, J = 2.8 Hz, 1H), 4.25 (q, J = 7.1 Hz, 2H), 3.90 (d, J = 9.4 Hz, 1H), 3.41 (d, J = 9.4 Hz, 1H), 1.76-1.65 (m, 4H), 1.28 (t, J = 7.2 Hz, 3H). LCMS m/z (M + 1, 468.12). RT 2.50 min. (5 min) (C18, 20-90%, water (0.05% TFA)/ACN) |
| 18 | 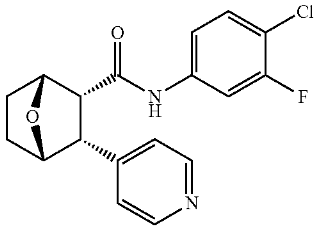 [SMILES: O=C(Nc1ccc(Cl)c(F)c1)[C@@H]1[C@H](c2ccncc2)[C@@H]2CC[C@H]1O2] | LCMS m/z (M + 1, 347.0) |
| 19 | 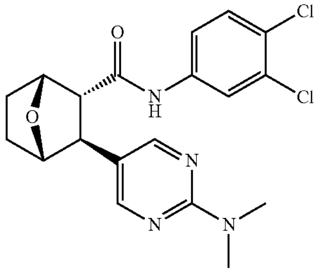 [SMILES: CN(C)c1ncc([C@@H]2[C@@H](C(=O)Nc3ccc(Cl)c(Cl)c3)[C@H]3CC[C@@H]2O3)cn1] | $^{1}$H NMR (400 MHz, DMSO) δ 10.24 (s, 1H), 8.25 (s, 2H), 7.99 (d, J = 2.4 Hz, 1H), 7.55 (d, J = 8.8 Hz, 1H), 7.45 (dd, J = 8.8, 2.4 Hz, 1H), 4.91 (t, J = 5.1 Hz, 1H), 4.45 (d, J = 4.2 Hz, 1H), 3.24 (d, J = 4.9 Hz, 1H), 3.10 (s, 6H), 3.08-2.97 (m, 1H), 1.82-1.44 (m, 4H). LCMS m/z (M + 1, 407.1) |

TABLE 3-continued

| Exemplified Compounds of Formula I of the Invention | | |
|---|---|---|
| Ex. No. | Structure | Physical Data MS (m/z), Elemental Analysis, $^1$H NMR, Melting Point, HPLC RT |
| 20 | 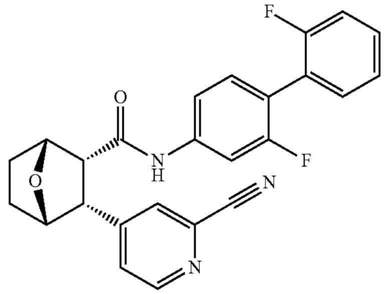 [SMILES: N#Cc1cc([C@H]2[C@@H](C(=O)Nc3ccc(-c4ccccc4F)c(F)c3)[C@H]3CC[C@@H]2O3)ccn1] | $^1$H NMR (400 MHz, DMSO) δ 10.25 (s, 1H), 8.52 (dd, J = 5.2, 0.8 Hz, 1H), 7.76-7.60 (m, 1H), 7.50-7.02 (m, 8H), 4.88 (t, J = 4.8 Hz, 1H), 4.78 (t, J = 4.9 Hz, 1H), 3.68-3.46 (m, 2H), 1.94 (ddd, J = 11.9, 8.9, 3.2 Hz, 1H), 1.77 (ddd, J = 12.0, 8.8, 5.2 Hz, 1H), 1.70-1.41 (m, 2H). LCMS m/z (M + 1, 432.1) |
| 21 | 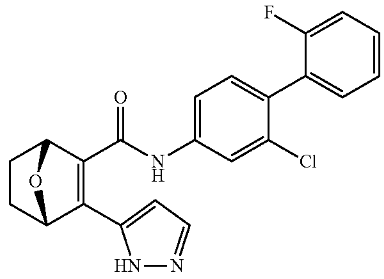 | LCMS m/z (M + 1, 410.1) |
| 22 | 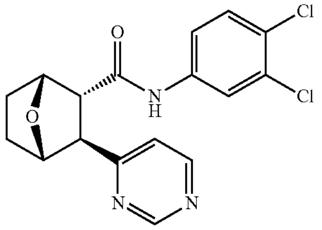 [SMILES: O=C(Nc1ccc(Cl)c(Cl)c1)[C@@H]1[C@@H](c2ccncn2)[C@@H]2CC[C@H]1O2] | $^1$H NMR (400 MHz, DMSO) δ 10.25 (s, 1H), 9.06 (s, 1H), 8.70 (s, 2H), 7.99 (d, J = 2.4 Hz, 1H), 7.56 (d, J = 8.8 Hz, 1H), 7.45 (dd, J = 8.8, 2.5 Hz, 1H), 4.99 (t, J = 5.1 Hz, 1H), 4.60 (d, J = 4.0 Hz, 1H), 3.47 (d, J = 4.8 Hz, 1H), 3.16 (td, J = 5.2, 1.6 Hz, 1H), 1.80~1.52 (m, , 4H). LCMS m/z (M + 1, 364.0) |
| 23 | 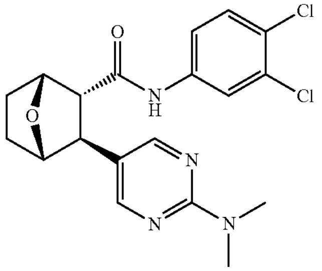 [SMILES: CN(C)c1ncc([C@@H]2[C@@H](C(=O)Nc3ccc(Cl)c(Cl)c3)[C@H]3CC[C@@H]2O3)cn1] | LCMS m/z (M + 1, 407.1) |
| 24 | 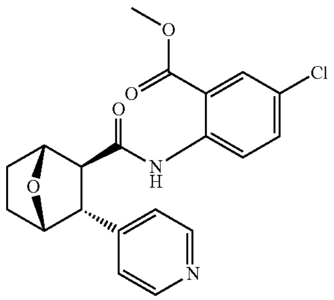 [SMILES: COC(=O)c1cc(Cl)ccc1NC(=O)[C@H]1[C@H](c2ccncc2)[C@@H]2CC[C@H]1O2] | LCMS m/z (M + 1, 387.0) |

TABLE 3-continued
Exemplified Compounds of Formula I of the Invention
| Ex. No. | Structure | Physical Data MS (m/z), Elemental Analysis, $^1H$ NMR, Melting Point, HPLC RT |
|---|---|---|
| 25 | 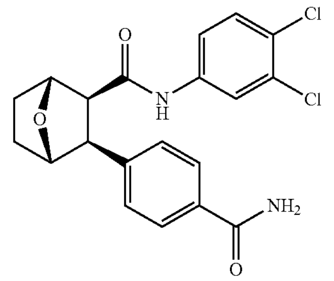 [SMILES: NC(=O)c1ccc([C@@H]2[C@H](C(=O)Nc3ccc(Cl)c(Cl)c3)[C@H]3CC[C@@H]2O3)cc1] | LCMS m/z (M + 1, 405.1) |
| 26 | 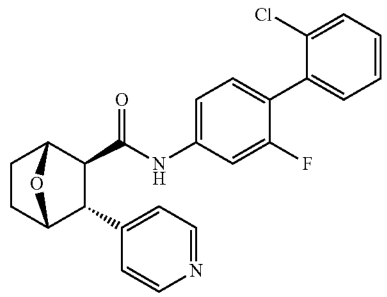 | $^1H$ NMR (400 MHz, DMSO) δ 8.40 (d, J = 5.6 Hz, 2H), 7.7 (s, 1H), 7.54 (dd, J = 12.0 2.0 Hz, 1H), 7.43~7.38 (m, 1H), 7.28~7.16 (m, 7H), 4.83 (dd, J = 5.2 5.2 Hz, 1H), 4.58 (d, J = 4.8 Hz, 1H), 3.40 (d, J = 4.8 Hz, 1H), 2.90 (ddd, J = 5.2, 5.2, 1.2 Hz, 1H), 2.01~1.94 (m, 1H), 1.86~1.64 (m, 3H). LCMS m/z (M + 1, 423.0) |
| 27 | 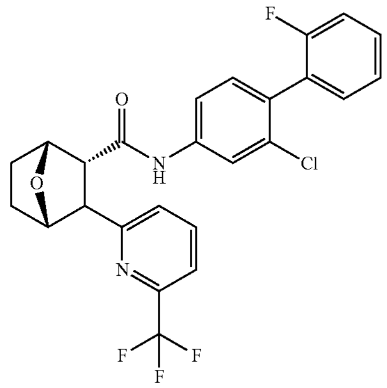 [SMILES: O=C(Nc1ccc(-c2ccccc2F)c(Cl)c1)[C@@H]1C(c2cccc(C(F)(F)F)n2)[C@@H]2CC[C@H]1O2] | LCMS m/z (M + 1, 491.1) |
| 28 | 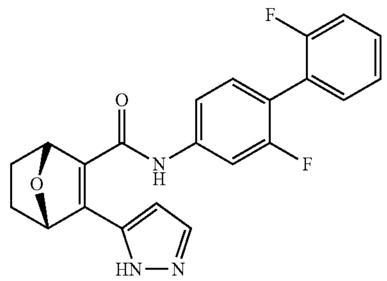 | $^1H$ NMR (400 MHz, DMSO) δ 12.79 (s, 1H), 8.07-7.99 (m, 1H), 7.83 (dd, J = 12.6, 2.0 Hz, 1H), 7.64 (dd, J = 8.4, 2.0 Hz, 1H), 7.39-7.25 (m, 2H), 6.81 (d, J = 2.0 Hz, 1H), 5.61 (d, J = 3.9 Hz, 1H), 5.44 (d, J = 2.7 Hz, 1H), 1.96-1.87 (m, 1H), 1.51-1.27 (m, 2H). LCMS m/z (M + 1, 394.1) |

TABLE 3-continued

Exemplified Compounds of Formula I of the Invention

| Ex. No. | Structure | Physical Data MS (m/z), Elemental Analysis, $^1$H NMR, Melting Point, HPLC RT |
|---|---|---|
| 29 | 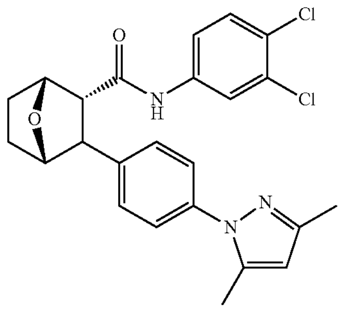 [SMILES: Cc1cc(C)n(-c2ccc(C3[C@@H]4CC[C@@H](O4)[C@@H]3C(=O)Nc3ccc(Cl)c(Cl)c3)cc2)n1] | $^1$H NMR (400 MHz, DMSO) δ 10.28 (s, 1H), 8.00 (d, J = 2.4 Hz, 1H), 7.55 (d, J = 8.8 Hz, 1H), 7.50-7.34 (m, 5H), 6.04 (s, 1H), 4.93 (t, J = 5.1 Hz, 1H), 4.58 (d, J = 3.9 Hz, 1H), 3.45 (d, J = 5.0 Hz, 1H), 3.15-3.08 (m, 1H), 2.51 (p, J = 1.9 Hz, 2H), 2.27 (d, J = 0.8 Hz, 3H), 2.17 (s, 3H), 1.80~1.51 (m, 4H). LCMS m/z (M + 1, 456.1) |
| 30 | 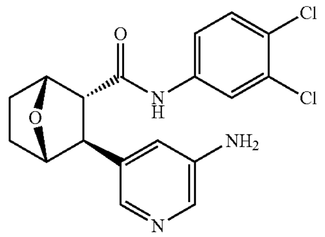 [SMILES: Nc1cncc([C@@H]2[C@@H](C(=O)Nc3ccc(Cl)c(Cl)c3)[C@H]3CC[C@@H]2O3)c1] | $^1$H NMR (400 MHz, DMSO) δ 10.19 (s, 1H), 7.91 (d, J = 2.4 Hz, 1H), 7.70 (d, J = 2.6 Hz, 1H), 7.55 (d, J = 1.9 Hz, 1H), 7.47 (d, J = 8.8 Hz, 1H), 7.37 (dd, J = 8.8, 2.4 Hz, 1H), 6.79 (t, J = 2.3 Hz, 1H), 5.16 (s, 2H), 4.81 (t, J = 5.1 Hz, 1H), 4.43 (d, J = 4.3 Hz, 1H), 3.25~3.15 (m, 1H), 2.95 (td, J = 5.2, 1.6 Hz, 1H), 1.70~1.43 (m, 4H). LCMS m/z (M + 1, 378.0) |
| 31 | 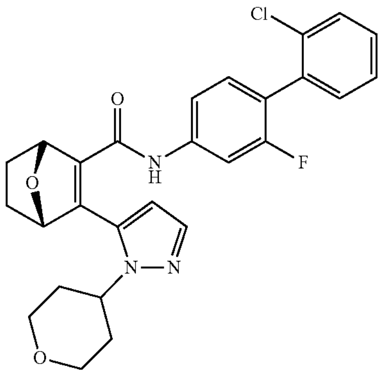 | LCMS m/z (M + 1, 494.1) |
| 32 | 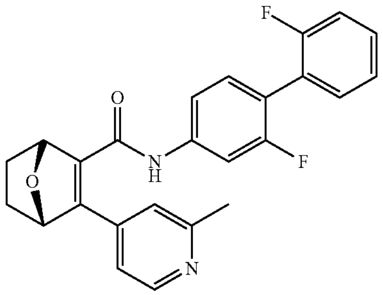 | LCMS m/z (M + 1, 419.1) |
| 33 | 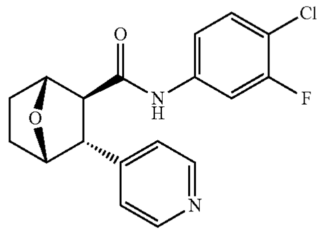 [SMILES: O=C(Nc1ccc(Cl)c(F)c1)[C@H]1[C@H](c2ccncc2)[C@@H]2CC[C@H]1O2] | $^1$H NMR (400 MHz, DMSO) δ 10.24 (s, 1H), 8.48 (d, J = 3.6 Hz. 2H), 7.69 (dd, J = 11.9, 2.4 Hz, 1H), 7.42 (t, J = 8.6 Hz, 1H), 7.23 (ddd, J = 8.8, 2.4, 1.1 Hz, 1H), 7.19 (d, J = 6.1 Hz, 2H), 4.86 (t, J = 5.1 Hz, 1H), 4.51 (d, J = 4.3 Hz, 1H), 3.33 (d, J = 5.0 Hz, 1H), 3.01 (td, J = 5.2, 1.6 Hz, 1H), 1.78-1.36 (m, 4H). LCMS m/z (M + 1, 347.0) |

TABLE 3-continued
| Ex. No. | Structure | Physical Data MS (m/z), Elemental Analysis, $^1$H NMR, Melting Point, HPLC RT |
|---|---|---|
| | Exemplified Compounds of Formula I of the Invention | |
| 34 | 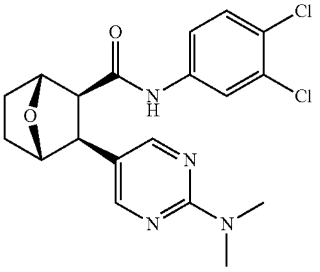 [SMILES: CN(C)c1ncc([C@@H]2[C@H](C(=O)Nc3ccc(Cl)c(Cl)c3)[C@H]3CC[C@@H]2O3)cn1] | LCMS m/z (M + 1, 407.1) |
| 35 | 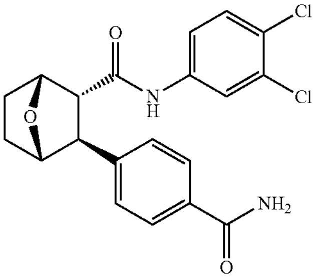 [SMILES: NC(=O)c1ccc([C@@H]2[C@@H](C(=O)Nc3ccc(Cl)c(Cl)c3)[C@H]3CC[C@@H]2O3)cc1] | LCMS m/z (M + 1, 405.0) |
| 36 | 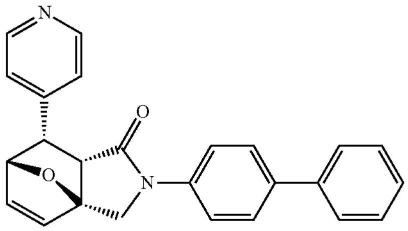 | $^1$H NMR (400 MHz, DMSO) δ 8.42 (d, J = 5.2 Hz, 2H), 7.77 (d, J = 8.8 Hz, 2H), 7.70-7.54 (m, 3H), 7.39 (dd, J = 8.4, 6.9 Hz, 2H), 7.29 (tt, J = 8.0, 1.2 Hz, 1H), 7.19 (d, J = 6.3 Hz, 2H), 6.72 (d, J = 5.8 Hz, 1H), 6.22 (dd, J = 5.8, 1.7 Hz, 1H), 5.30 (dd, J = 4.6, 1.7 Hz, 1H), 4.61 (d, J = 11.8 Hz, 1H), 4.11 (d, J = 11.8 Hz, 1H), 3.69 (t, J = 4.3 Hz, 1H), 3.11 (d, J = 4.2 Hz, 1H). LCMS m/z (M + 1, 381.1) |
| 37 | 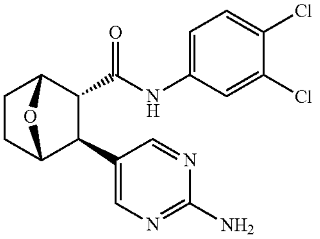 [SMILES: Nc1ncc([C@@H]2[C@@H](C(=O)Nc3ccc(Cl)c(Cl)c3)[C@H]3CC[C@@H]2O3)cn1] | LCMS m/z (M + 1, 379.0) |
| 38 | 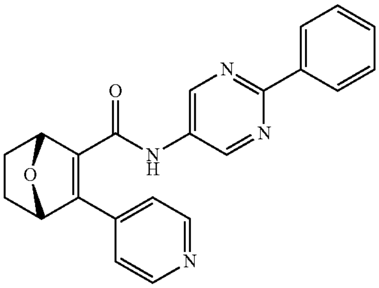 | LCMS m/z (M + 1, 371.1) |

TABLE 3-continued

Exemplified Compounds of Formula I of the Invention

| Ex. No. | Structure | Physical Data MS (m/z), Elemental Analysis, $^1$H NMR, Melting Point, HPLC RT |
|---|---|---|
| 39 | 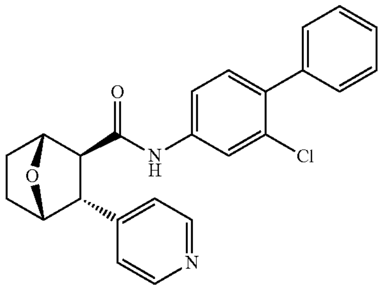 [SMILES: O=C(Nc1ccc(-c2ccccc2)c(Cl)c1)[C@H]1[C@H](c2ccncc2)[C@@H]2CC[C@H]1O2] | $^1$H NMR (400 MHz, DMSO) δ 8.55 (d, J = 5.6 Hz, 2H), 8.00 (d, J = 2.0 Hz, 1H), 7.60~7. 40 (m, 8H), 7.37~7.33 (m, 2H), 5.01 (dd, J = 4.8, 4.8 Hz, 1H), 4.66 (d, J = 4.4 Hz, 1H), 3.48 (d, J = 5.2 Hz, 1H), 3.15 (brt, J = 5.2 Hz, 1H), 1.85~1.74 (m, 3H), 1.71~1.60 (m, 1H). LCMS m/z (M + 1, 405.1) |
| 40 | 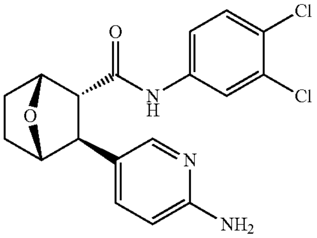 [SMILES: Nc1ccc([C@@H]2[C@@H](C(=O)Nc3ccc(Cl)c(Cl)c3)[C@H]3CC[C@@H]2O3)cn1] | $^1$H NMR (400 MHz, DMSO) δ 10.18 (brs, 1H), 7.91 (d, J = 2.4 Hz, 1H), 7.69 (d, J = 2.5 Hz, 1H), 7.47 (d, J = 8.8 Hz, 1H), 7.38 (dd, J = 8.8, 2.4 Hz, 1H), 7.22 (dd, J = 8.5, 2.5 Hz, 1H), 6.34 (brd, J + 8.4 Hz, 1H), 5.59 (s, 2H), 4.79 (t, J = 5.1 Hz, 1H), 4.32 (d, J = 4.2 Hz, 1H), 3.11 (d, J = 5.0 Hz, 1H), 2.92 (td, J = 5.2, 1.5 Hz, 1H), 1.70-1.36 (m, 4H). LCMS m/z (M + 1, 378.0) |
| 41 | 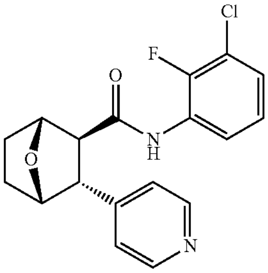 [SMILES: O=C(Nc1cccc(Cl)c1F)[C@H]1[C@H](c2ccncc2)[C@@H]2CC[C@H]1O2] | LCMS m/z (M + 1, 347.1) |
| 42 | 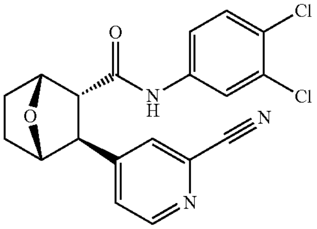 [SMILES: N#Cc1cc([C@@H]2[C@@H](C(=O)Nc3ccc(Cl)c(Cl)c3)[C@H]3CC[C@@H]2O3)ccn1] | $^1$H NMR (400 MHz, DMSO) δ 10.25 (s, 1H), 8.67 (dd, J = 5.1, 0.8 Hz, 1H), 7.99 (d, J = 2.5 Hz, 1H), 7.87 (d, J = 1.4 Hz, 1H), 7.62 (dd, J = 5.1, 1.8 Hz, 1H), 7.56 (d, J = 8.8 Hz, 1H), 7.45 (dd, J = 8.8, 2.5 Hz, 1H), 4.98 (t, J = 5.1 Hz, 1H), 4.64 (d, J = 4.6 Hz, 1H), 3.53 (d, J = 4.9 Hz, 1H), 3.12 (td, J = 5.2, 1.6 Hz, 1H), 1.85-1.46 (m, 4H). LCMS m/z (M + 1, 388.1) |
| 43 | 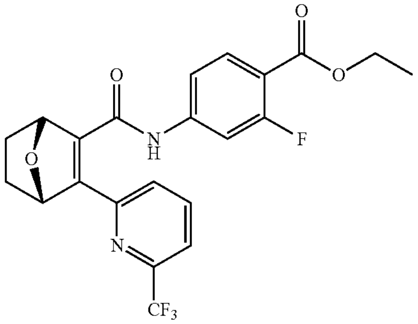 | LCMS m/z (M + 1, 451.1) |

TABLE 3-continued

| Ex. No. | Structure | Physical Data MS (m/z), Elemental Analysis, $^1$H NMR, Melting Point, HPLC RT |
|---|---|---|
| | Exemplified Compounds of Formula I of the Invention | |
| 44 | 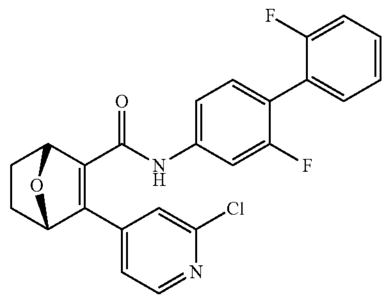 | LCMS m/z (M + 1, 439.1) |
| 45 | 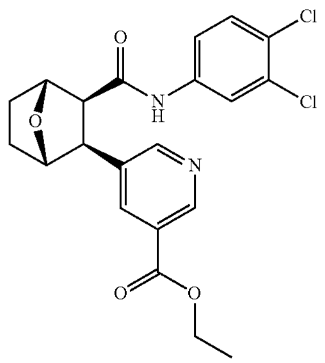 [SMILES: CCOC(=O)c1cncc([C@@H]2[C@H](C(=O)Nc3ccc(Cl)c(Cl)c3)[C@H]3CC[C@@H]2O3)c1] | $^1$H NMR (400 MHz, DMSO) δ 9.68 (s, 1H), 8.61 (dd, J = 13.9, 2.1 Hz, 2H), 8.15 (t, J = 2.4 H, 1H), 7.26 (d, J = 8.8 Hz, 1H), 7.22 (d, J = 2.4 Hz, 1H), 6.88 (dd, J = 8.8, 2.4 Hz, 1H), 4.83 (d, J = 3.4 Hz, 1H), 4.53 (d, J = 4.5 Hz, 1H), 4.22 (q, J = 7.1 Hz, 2H), 3.52 (d, J = 9.6 Hz, 1H), 3.20~3.12 (m, 1H), 1.87-1.40 (m, 4H), 1.22 (t, J = 7.1 Hz, 3H). LCMS m/z (M + 1, 435.1) |
| 46 | 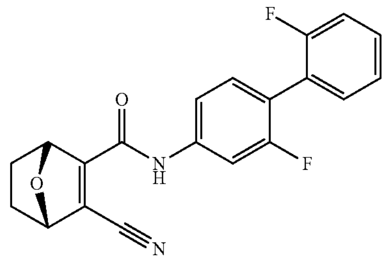 | $^1$H NMR (400 MHz, DMSO) δ 10.6 (s, 1H), 7.77 (dd, J = 12.4, 2.0 Hz, 1H), 7.58 (dd, J = 8.4, 2.0 Hz, 1H), 7.52~7.44 (m, 3H), 7.37~7.29 (m, 2H), 5.69 (d, J = 4.4 Hz, 1H), 5.49 (d, J = 4.0 Hz, 1H), 2.24~1.86 (m, 2H), 1.54~1.42 (m, 2H). LCMS m/z (M + 1, 353.1) |
| 47 | 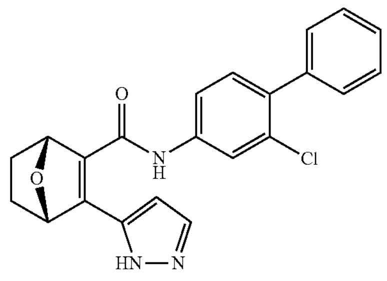 [SMILES: O=C(Nc1ccc(-c2ccccc2)c(Cl)c1)C1=C(c2ccn[nH]2)[C@@H]2CC[C@H]1O2] | LCMS m/z (M + 1, 392.1) |

TABLE 3-continued
| Exemplified Compounds of Formula I of the Invention | | |
|---|---|---|
| Ex. No. | Structure | Physical Data MS (m/z), Elemental Analysis, $^1$H NMR, Melting Point, HPLC RT |
| 48 | 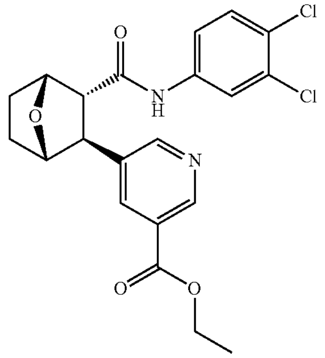 [SMILES: CCOC(=O)c1cncc([C@@H]2[C@@H](C(=O)Nc3ccc(Cl)c(Cl)c3)[C@H]3CC[C@@H]2O3)c1] | $^1$H NMR (400 MHz, DMSO) δ 10.20 (s, 1H), 8.88 (d, J = 2.1 Hz, 1H), 8.62 (d, J = 2.2 Hz, 1H), 8.11 (t, J = 2.0 Hz, 1H), 7.91 (d, J = 2.4 Hz, 1H), 7.47 (d, J = 8.8 Hz, 1H), 7.36 (dd, J = 8.8, 2.5 Hz, 1H), 4.91 (t, J = 5.1 Hz, 1H), 4.48 (dd, J = 3.3, 1.6 Hz, 1H), 4.29 (q, J = 7.1 Hz, 2H), 3.47 (d, J = 4.8 Hz, 1H), 3.06 (td, J = 5.2, 1.6 Hz, 1H), 1.77-1.33 (m, 4H), 1.27 (t, J = 7.1 Hz, 2H). LCMS m/z (M + 1, 435.0) |
| 49 | 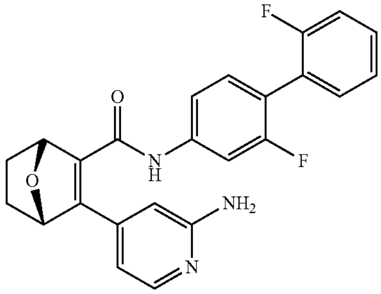 | LCMS m/z (M + 1, 420.1) |
| 50 | 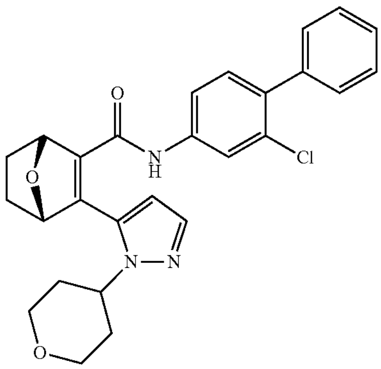 | LCMS m/z (M + 1, 476.1) |
| 51 | 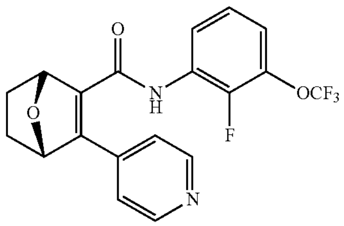 | LCMS m/z (M + 1, 395.1) |

TABLE 3-continued
| Ex. No. | Structure | Physical Data MS (m/z), Elemental Analysis, $^1$H NMR, Melting Point, HPLC RT |
|---|---|---|
| | Exemplified Compounds of Formula I of the Invention | |
| 52 | 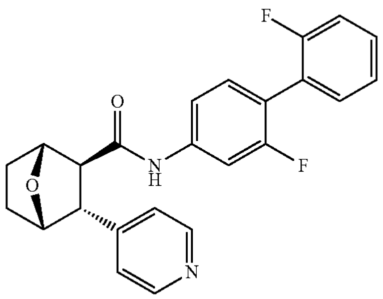 [SMILES: O=C(Nc1ccc(-c2ccccc2F)c(F)c1)[C@H]1[C@H](c2ccncc2)[C@@H]2CC[C@H]1O2] | LCMS m/z (M + 1, 407.1) |
| 53 | 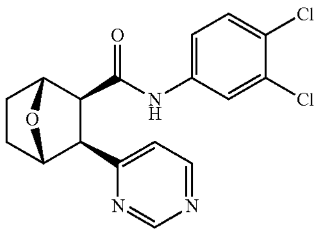 [SMILES: O=C(Nc1ccc(Cl)c(Cl)c1)[C@H]1[C@@H](c2ccncn2)[C@@H]2CC[C@H]1O2] | LCMS m/z (M + 1, 364.0) |
| 54 | 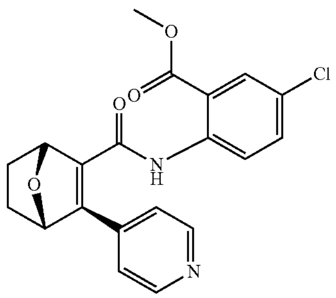 | LCMS m/z (M + 1, 385.0) |
| 55 | 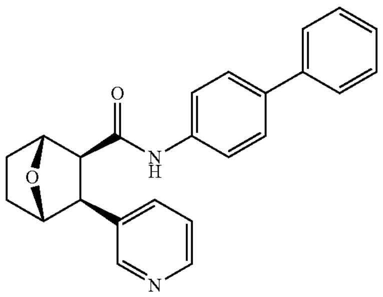 [SMILES: O=C(Nc1ccc(-c2ccccc2)cc1)[C@H]1[C@@H](c2cccnc2)[C@@H]2CC[C@H]1O2] | LCMS m/z (M + 1, 371.1) |
| 56 | 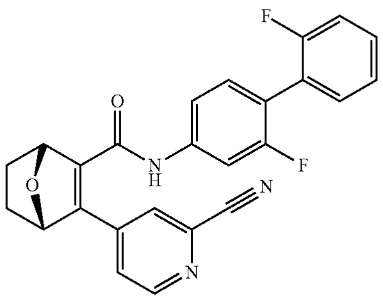 | LCMS m/z (M + 1, 430.1) |

TABLE 3-continued
| Ex. No. | Structure | Physical Data MS (m/z), Elemental Analysis, $^1$H NMR, Melting Point, HPLC RT |
|---|---|---|
| | Exemplified Compounds of Formula I of the Invention | |
| 57 | 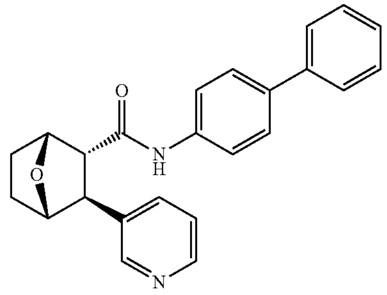 [SMILES: O=C(Nc1ccc(-c2ccccc2)cc1)[C@@H]1[C@@H](c2cccnc2)[C@@H]2CC[C@H]1O2] | LCMS m/z (M + 1, 371.1) |
| 58 | 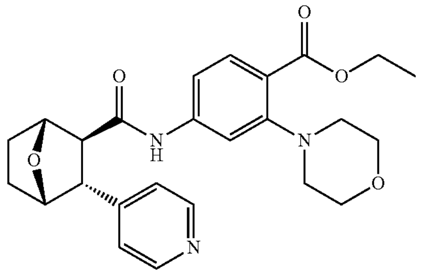 [SMILES: CCOC(=O)c1ccc(NC(=O)[C@H]2[C@H](c3ccncc3)[C@@H]3CC[C@H]2O3)cc1N1CCOCC1] | $^1$H NMR (400 MHz, DMSO) δ 10.12 (s, 1H), 8.41 (dd, J = 4.4, 1.6 Hz, 2H), 7.57 (d, J = 8.5 Hz, 1H), 7.32 (d, J = 2.0 Hz, 1H), 7.25-6.94 (m, 3H), 4.87 (t, J = 5.1 Hz, 1H), 4.51 (d, J = 4.0 Hz, 1H), 4.16 (q, J = 7.1 Hz, 2H), 3.71-3.55 (m, 4H), 3.34 (d, J = 5.0 Hz, 1H), 3.05-3.00 (m, 1H), 2.92-2.80 (m, 4H), 1.75-1.46 (m, 4H), 1.22 (t, J = 7.1 Hz, 3H). LCMS m/z (M + 1, 452.1) |
| 59 | 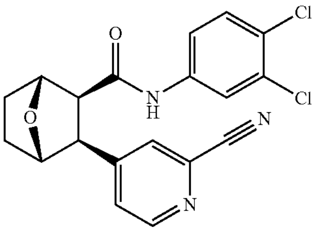 [SMILES: N#Cc1cc([C@@H]2[C@H](C(=O)Nc3ccc(Cl)c(Cl)c3)[C@H]3CC[C@@H]2O3)ccn1] | LCMS m/z (M + 1, 388.0) |
| 60 | 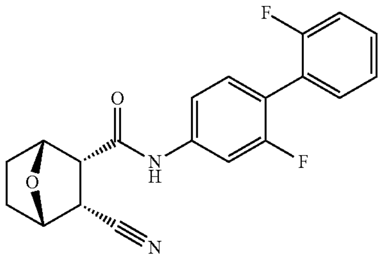 [SMILES: N#C[C@H]1[C@@H](C(=O)Nc2ccc(-c3ccccc3F)c(F)c2)[C@H]2CC[C@@H]1O2] | LCMS m/z (M + 1, 355.1) |
| 61 | 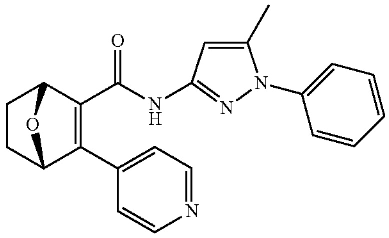 | LCMS m/z (M + 1, 373.1) |

TABLE 3-continued
| Exemplified Compounds of Formula I of the Invention | | |
|---|---|---|
| Ex. No. | Structure | Physical Data MS (m/z), Elemental Analysis, $^{1}$H NMR, Melting Point, HPLC RT |
| 62 | 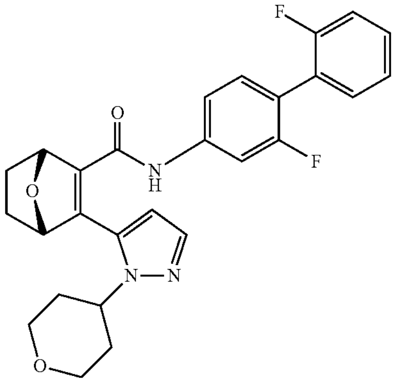 | LCMS m/z (M + 1, 478.1) |
| 63 | 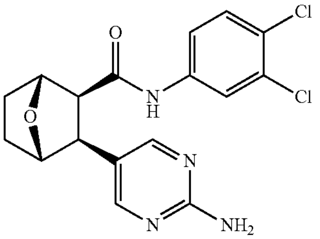 [SMILES: Nc1ncc([C@@H]2[C@H](C(=O)Nc3ccc(Cl)c(Cl)c3)[C@H]3CC[C@@H]2O3)cn1] | LCMS m/z (M + 1, 379.0) |
| 64 | 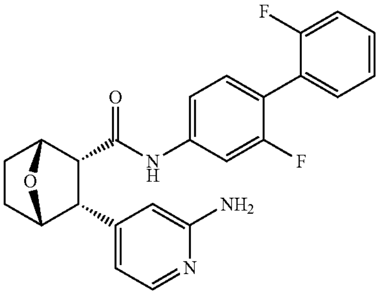 [SMILES: Nc1cc([C@H]2[C@@H](C(=O)Nc3ccc(-c4ccccc4F)c(F)c3)[C@H]3CC[C@@H]2O3)ccn1] | LCMS m/z (M + 1, 422.1) |
| 65 | 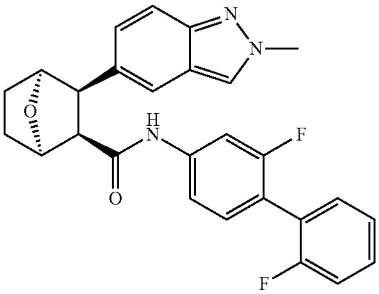 [SMILES: Cn1cc2cc([C@H]3[C@@H](C(=O)Nc4ccc(-c5ccccc5F)c(F)c4)[C@H]4CC[C@@H]3O4)ccc2n1] | LCMS m/z (M + 1, 460.1) |
| 66 | 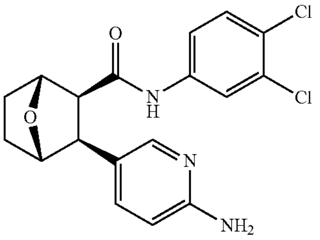 [SMILES: Nc1ccc([C@@H]2[C@H](C(=O)Nc3ccc(Cl)c(Cl)c3)[C@H]3CC[C@@H]2O3)cn1] | LCMS m/z (M + 1, 378.0) |

TABLE 3-continued

Exemplified Compounds of Formula I of the Invention

| Ex. No. | Structure | Physical Data MS (m/z), Elemental Analysis, $^1$H NMR, Melting Point, HPLC RT |
| --- | --- | --- |
| 67 | 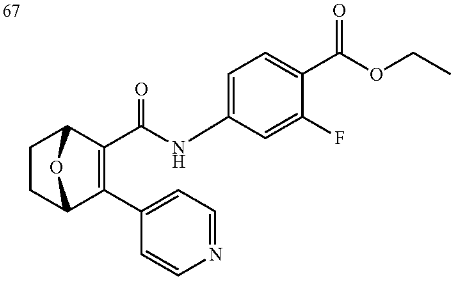 | LCMS m/z (M + 1, 383.1) |
| 68 | 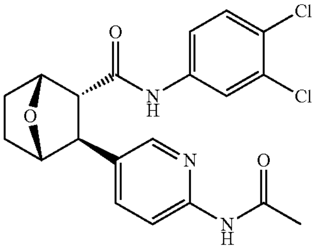 [SMILES: CC(=O)Nc1ccc([C@@H]2[C@@H](C(=O)Nc3ccc(Cl)c(Cl)c3)[C@H]3CC[C@@H]2O3)cn1] | $^1$H NMR (400 MHz, DMSO) δ 10.40 (s, 1H), 10.26 (s, 1H), 8.09 (brd, J = 2.0 Hz, 1H), 7.96 (brs, 1H), 7.94 (d, J = 2.3 Hz, 1H), 7.59 (dd, J = 8.6, 2.4 Hz, 1H), 7.49 (d, J = 8.8 Hz, 1H), 7.37 (dd, J = 8.8, 2.4 Hz, 1H), 4.86 (t, J = 5.1 Hz, 1H), 4.44 (d, J = 3.9 Hz, 1H), 3.30 (d, J = 5.0 Hz, 1H), 3.12-2.96 (m, 1H), 1.99 (s, 3H), 1.76-1.44 (m, 4H). LCMS m/z (M + 1, 420.0) |
| 69 | 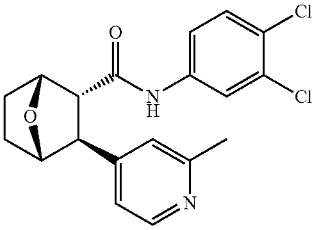 [SMILES: Cc1cc([C@@H]2[C@@H](C(=O)Nc3ccc(Cl)c(Cl)c3)[C@H]3CC[C@@H]2O3)ccn1] | LCMS m/z (M + 1, 377.1) |
| 70 | 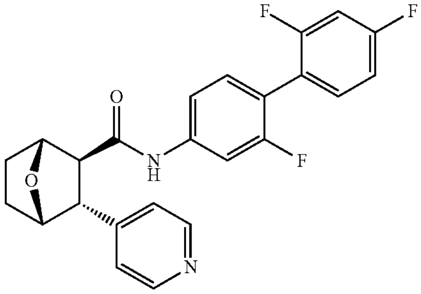 [SMILES: O=C(Nc1ccc(-c2ccc(F)cc2F)c(F)c1)[C@H]1[C@H](c2ccncc2)[C@@H]2CC[C@H]1O2] | $^1$H NMR (400 MHz, DMSO) δ 10.35 (s, 1H), 8.46 (d, J = 6.0 Hz, 2H), 7.60~7.50 (m, 2H), 7.46~7.35 (m, 2H), 7.29~7.24 (m, 2H), 7.15 (d, J = 6.0 Hz, 2H), 4.93 (dd, J = 4.4, 4.4 Hz, 1H), 4.88 (dd, J = 4.4, 4.4 Hz, 1H), 3.73 (dd, J = 11.6, 4.8 Hz, 1H), 3.59 (dd, J = 11.6, 5.2 Hz, 1H), 2.34~2.27 (m, 1H), 1.71~1.63 (m, 2H). LCMS m/z (M + 1, 425.1) |
| 71 | 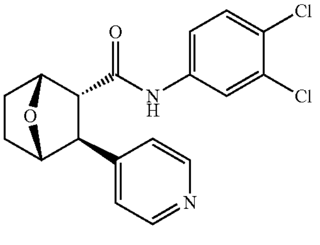 Single enantiomer | $^1$H NMR (400 MHz, DMSO) δ 10.34 (s, 1H), 8.53-8.41 (m, 2H), 8.01 (d, J = 2.4 Hz, 1H), 7.57 (d, J = 8.8 Hz, 1H), 7.44 (dd, J = 8.8, 2.4 Hz, 1H), 7.32-7.21 (m, 2H), 4.93 (t, J = 5.1 Hz, 1H), 4.59 (d, J = 4.4 Hz, 1H), 3.40 (d, J = 5.0 Hz, 1H), 3.07 (td, J = 5.2, 1.5 Hz, 1H), 1.79-1.50 (m, 4H), LCMS m/z (M + 1, 363.1) |

TABLE 3-continued

Exemplified Compounds of Formula I of the Invention

| Ex. No. | Structure | Physical Data MS (m/z), Elemental Analysis, $^1$H NMR, Melting Point, HPLC RT |
|---|---|---|
| 72 | 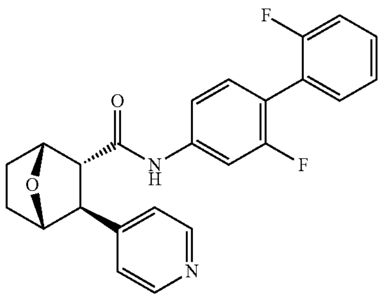 [SMILES: O=C(Nc1ccc(-c2ccccc2F)c(F)c1)[C@@H]1[C@@H](c2ccncc2)[C@@H]2CC[C@H]1O2] | $^1$H NMR (400 MHz, MeOD) δ 8.50-8.44 (m, 2H), 7.66-7.60 (m, 1H), 7.57-7.52 (m, 2H), 7.41-7.29 (m, 4H), 7.25-7.19 (m, 1H), 7.15 (ddd, J = 9.9, 8.5, 1.3 Hz, 1H), 4.98 (t, J = 5.2 Hz, 1H), 4.63 (d, J = 4.5 Hz, 1H), 3.64 (d, J = 5.0 Hz, 1H), 3.12 (td, J = 5.2, 1.7 Hz, 1H), 1.86 (m, 3H), 1.72 (m, 1H). LCMS m/z (M + 1, 407.1); |
| 73 | 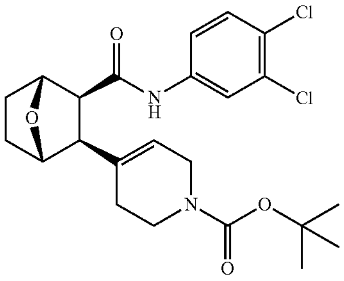 [SMILES: CC(C)(C)OC(=O)N1CC=C([C@@H]2[C@H](C(=O)Nc3ccc(Cl)c(Cl)c3)[C@H]3CC[C@@H]2O3)CC1] | $^1$H NMR (400 MHz, Acetonitrile-d$_3$) δ 8.24 (s, 1H), 7.83 (d, J = 2.4 Hz, 1H), 7.42 (d, J = 8.7 Hz, 1H), 7.36 (s, 1H), 5.65 (s, 1H), 4.88-4.84 (m, 1H), 4.60-4.54 (m, 1H), 3.66 (dt, J = 5.7, 3.0 Hz, 2H), 3.16 (t, J = 6.0 Hz, 2H), 2.99-2.89 (m, 2H), 2.01 (dddd, J = 7.5, 6.0, 3.9, 2.1 Hz, 2H), 1.75-1.69 (m, 2H), 1.61-1.56 (m, 2H), 1.34 (s, 9H). LCMS m/z (M + 1 − Boc, 367.2); |
| 74 | 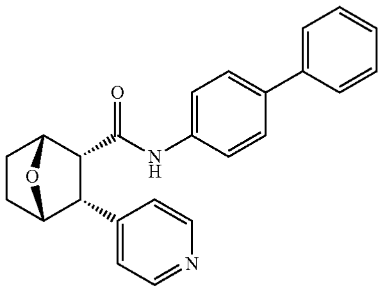 [SMILES: O=C(Nc1ccc(-c2ccccc2)cc1)[C@@H]1[C@H](c2ccncc2)[C@@H]2CC[C@H]1O2] | $^1$H NMR (400 MHz, DMSO) δ 10.09 (s, 1H), 8.46 (d, J = 6.3 Hz, 2H), 7.65-7.20 (m, 11H), 4.86 (m, 1H), 4.78 (m, 1H), 3.66 (dd, J = 11.5, 4.3 Hz, 1H), 3.57 (dd, J = 11.4, 5.2 Hz, 1H), 2.04 (t, J = 8.4 Hz, 1H), 1.83-1.73 (m, 1H), 1.66-1.49 (m, 2H). LCMS m/z (M + 1, 371.2); |
| 75 | 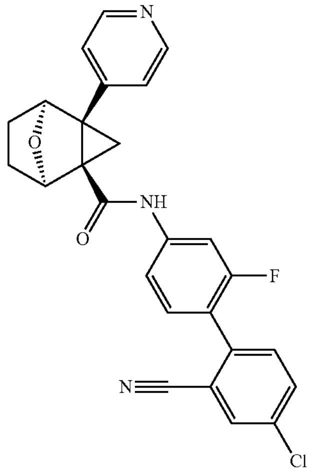 [SMILES: N#Cc1cc(Cl)ccc1-c1ccc(NC(=O)[C@]23C[C@@]2(c2ccncc2)[C@@H]2CC[C@H]3O2)cc1F] | $^1$H NMR (400 MHz, MeOD) δ 8.61 (dd, J = 4.5, 1.4 Hz, 1H), 8.36-8.32 (m, 2H), 7.82 (d, J = 2.3 Hz, 1H), 7.67 (dd, J = 8.5, 2.3 Hz, 1H), 7.62-7.50 (m, 1H), 7.49-7.41 (m, 1H), 7.36 (dd, J = 8.5, 2.0 Hz, 1H), 7.24-7.20 (m, 2H), 4.70 (d, J = 4.6 Hz, 1H), 4.55 (d, J = 4.7 Hz, 1H), 2.33 (ddd, J = 11.6, 9.0, 4.0 Hz, 1H), 1.94-1.86 (m, 1H), 1.79 (d, J = 4.9 Hz, 1H), 1.76-1.70 (m, 1H), 1.67-1.58 (m, 1H), 1.17 (d, J = 4.8 Hz, 1H). LCMS m/z (M + 1, 460.1); |

TABLE 3-continued

| Ex. No. | Structure | Physical Data MS (m/z), Elemental Analysis, $^1H$ NMR, Melting Point, HPLC RT |
|---|---|---|
| | Exemplified Compounds of Formula I of the Invention | |
| 76 | 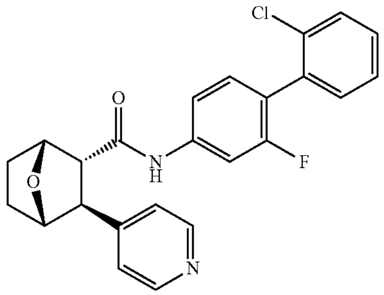 | $^1H$ NMR (400 MHz, Methylene Chloride-$d_2$) δ 8.51 (s, 2H), 7.64 (dd, J = 12.0, 2.0 Hz, 1H), 7.59 (s, 2H), 7.53-7.46 (m, 1H), 7.38-7.30 (m, 4H), 7.25 (t, J = 8.3 Hz, 1H), 4.99 (t, J = 5.2 Hz, 1H), 4.64 (d, J = 4.6 Hz, 1H), 3.66 (d, J = 4.9 Hz, 1H), 3.13 (td, J = 5.2, 1.7 Hz, 1H), 1.95-1.81 (m, 3H), 1.75 (dtd, J = 10.2, 5.0, 1.9 Hz, 1H). LCMS m/z (M + 1, 423.1); |
| 77 | 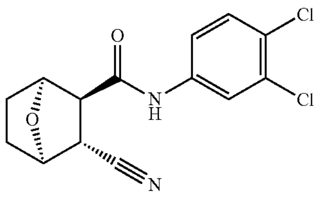 [SMILES: N#C[C@H]1[C@H](C(=O)Nc2ccc(Cl)c(Cl)c2)[C@@H]2CC[C@H]1O2] | LCMS m/z (M + 1, 311.1); RT 1.55 min. (Method A) |
| 78 | 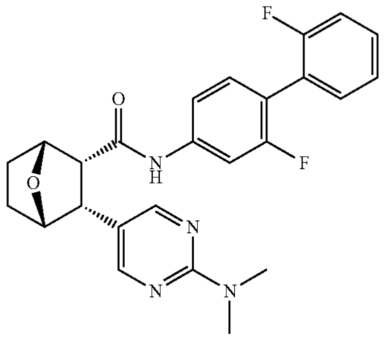 [SMILES: CN(C)c1ncc([C@H]2[C@@H](C(=O)Nc3ccc(-c4ccccc4F)c(F)c3)[C@H]3CC[C@@H]2O3)cn1] | $^1H$ NMR (400 MHz, Chloroform-d) δ 8.14 (s, 2H), 7.38-7.23 (m, 4H), 7.21-7.02 (m, 4H), 4.80 (dd, J = 6.0, 3.6 Hz, 1H), 4.68 (dd, J = 5.8, 3.9 Hz, 1H), 3.49 (m, 1H), 3.37 (dd, J = 12.2, 5.0 Hz, 1H), 3.11 (s, 6H), 2.51 (ddd, J = 11.8, 8.5, 3.7 Hz, 1H), 1.87 (ddd, J = 12.5, 8.8, 3.5 Hz, 1H), 1.72 (dq, J = 29.5, 9.0, 5.7 Hz, 2H). LCMS m/z (M + 1, 451.2); |
| 79 | 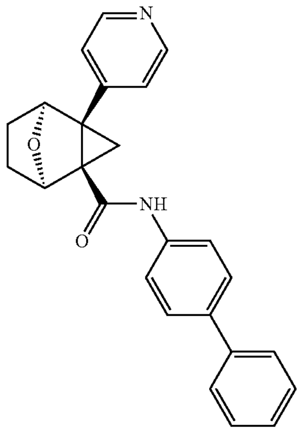 [SMILES: O=C(Nc1ccc(-c2ccccc2)cc1)[C@]12C[C@@]1(c1ccncc1)[C@@H]1CC[C@H]2O1] | $^1H$ NMR (600 MHz, MeOD) δ 8.46-8.43 (m, 2H), 7.62-7.57 (m, 6H), 7.45-7.40 (m, 2H), 7.33-7.30 (m, 3H), 4.79 (d, J = 4.7 Hz, 1H), 4.65 (d, J = 4.9 Hz, 1H), 2.48 (ddd, J = 11.8, 9.1, 4.2 Hz, 1H), 2.03-1.98 (m, 1H), 1.88 (d, J = 4.8 Hz, 1H), 1.87-1.81 (m, 1H), 1.73 (tt, J = 11.7, 4.5 Hz, 1H), 1.27-1.25 (m, 1H). LCMS m/z (M + 1, 383.3); |

TABLE 3-continued

Exemplified Compounds of Formula I of the Invention

| Ex. No. | Structure | Physical Data MS (m/z), Elemental Analysis, $^1$H NMR, Melting Point, HPLC RT |
|---|---|---|
| 80 | 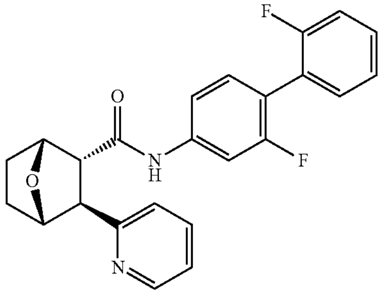 [SMILES: O=C(Nc1ccc(-c2ccccc2F)c(F)c1)[C@@H]1[C@@H](c2ccccn2)[C@@H]2CC[C@H]1O2] | LCMS m/z (M + 1, 407.1); RT 1.40 min. (Method A) |
| 81 | 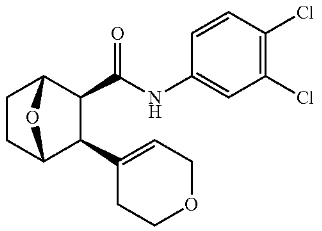 [SMILES: O=C(Nc1ccc(Cl)c(Cl)c1)[C@H]1[C@@H](C2=CCOCC2)[C@@H]2CC[C@H]1O2] | $^1$H NMR (400 MHz, Acetonitrile-$d_3$) δ 8.27 (s, 1H), 7.85 (d, J = 2.5 Hz, 1H), 7.44 (d, J = 8.8 Hz, 1H), 7.38 (s, 1H), 5.69 (dq, J = 2.8, 1.2 Hz, 1H), 4.90-4.83 (m, 1H), 4.62-4.57 (m, 1H), 3.95-3.81 (m, 2H), 3.41 (td, J = 5.5, 3.0 Hz, 2H), 2.97 (d, J = 9.6 Hz, 1H), 2.89 (d, J = 9.6 Hz, 1H), 2.01 (dq, J = 5.5, 2.6 Hz, 2H), 1.75-1.69 (m, 2H), 1.62-1.56 (m, 2H). LCMS m/z (M + 1, 368.1); |
| 82 | 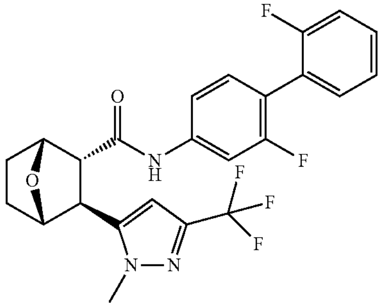 [SMILES: Cn1nc(C(F)(F)F)cc1[C@@H]1[C@@H](C(=O)Nc2ccc(-c3ccccc3F)c(F)c2)[C@H]2CC[C@@H]1O2] | $^1$H NMR (400 MHz, Methylene Chloride-$d_2$) δ 7.64 (dd, J = 12.0, 1.9 Hz, 1H), 7.45 (s, 1H), 7.42-7.32 (m, 3H), 7.24 (ddd, J = 8.7, 6.7, 1.3 Hz, 2H), 7.21-7.14 (m, 1H), 6.48 (s, 1H), 4.91 (t, J = 5.0 Hz, 1H), 4.63 (d, J = 4.9 Hz, 1H), 3.85 (s, 3H), 3.68 (d, J = 4.4 Hz, 1H), 3.03-2.96 (m, 1H), 1.92-1.64 (m, 4H). LCMS m/z (M + 1, 478.2); |
| 83 | 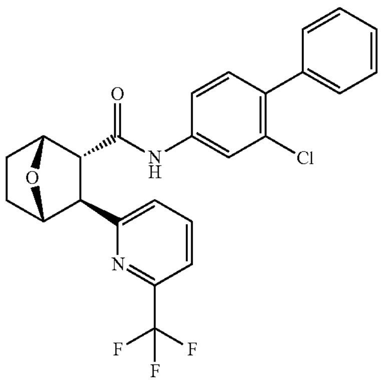 [SMILES: O=C(Nc1ccc(-c2ccccc2)c(Cl)c1)[C@@H]1[C@@H](c2cccc(C(F)(F)F)n2)[C@@H]2CC[C@H]1O2] | $^1$H NMR (400 MHz, MeOD) δ 10.13 (s, 1H), 7.95 (t, J = 7.9 Hz, 1H), 7.88 (t, J = 1.8 Hz, 1H), 7.65 (d, J = 8.0 Hz, 1H), 7.62 (d, J = 7.8 Hz, 1H), 7.53 (dt, J = 8.5, 1.7 Hz, 1H), 7.43 (s, 1H), 7.42-7.40 (m, 3H), 7.40-7.34 (m, 1H), 7.30 (d, J = 8.4 Hz, 1H), 4.98 (t, J = 5.2 Hz, 1H), 4.81 (t, J = 2.7 Hz, 1H), 3.81 (d, J = 5.1 Hz, 1H), 3.72-3.67 (m, 1H), 2.00-1.86 (m, 3H), 1.74 (tdd, J = 9.2, 4.6, 1.7 Hz, 1H). LCMS m/z (M + 1, 473.1); |

TABLE 3-continued

Exemplified Compounds of Formula I of the Invention

| Ex. No. | Structure | Physical Data MS (m/z), Elemental Analysis, $^{1}$H NMR, Melting Point, HPLC RT |
|---|---|---|
| 84 | 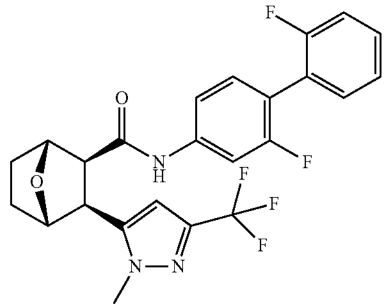 [SMILES: Cn1nc(C(F)(F)F)cc1[C@@H]1[C@H](C(=O)Nc2ccc(-c3ccccc3F)c(F)c2)[C@H]2CC[C@@H]1O2] | $^{1}$H NMR (400 MHz, Methylene Chloride-$d_2$) δ 7.88 (s, 1H), 7.40-7.30 (m, 2H), 7.25-7.11 (m, 4H), 6.88 (dd, J = 8.3, 2.1 Hz, 1H), 6.54 (s, 1H), 5.02 (d, J = 4.2 Hz, 1H), 4.97-4.94 (m, 1H), 3.83 (s, 3H), 3.53 (d, J = 9.1 Hz, 1H), 3.21 (d, J = 9.2 Hz, 1H), 1.96 (dtd, J = 8.0, 4.5, 3.7, 1.9 Hz, 2H), 1.80-1.70 (m, 2H). LCMS m/z (M + 1, 478.2); |
| 85 | 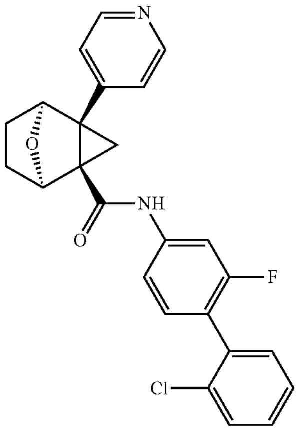 [SMILES: O=C(Nc1ccc(-c2ccccc2Cl)c(F)c1)[C@]12C[C@@]1(c1ccncc1)[C@@H]1CC[C@H]2O1] | $^{1}$H NMR (400 MHz, MeOD) δ 8.47-8.43 (m, 2H), 7.70-7.17 (m, 9H), 4.79 (d, J = 4.7 Hz, 1H), 4.65 (d, J = 4.8 Hz, 1H), 2.45 (ddd, J = 11.5, 9.1, 4.0 Hz, 1H), 2.04-1.96 (m, 1H), 1.88 (d, J = 4.9 Hz, 1H), 1.83 (dt, J = 11.3, 4.4 Hz, 1H), 1.79-1.69 (m, 1H), 1.26 (d, J = 4.8 Hz, 1H). LCMS m/z (M + 1, 435.2); |
| 86 | 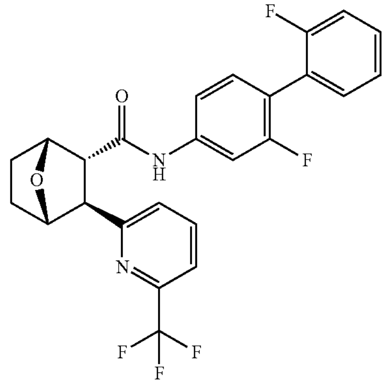 [SMILES: O=C(Nc1ccc(-c2ccccc2F)c(F)c1)[C@@H]1[C@@H](c2cccc(C(F)(F)F)n2)[C@@H]2CC[C@H]1O2] | $^{1}$H NMR (400 MHz, MeOD) δ 10.07 (s, 1H), 7.93 (t, J = 7.9 Hz, 1H), 7.70-7.59 (m, 3H), 7.43-7.31 (m, 4H), 7.24 (td, J = 7.5, 1.3 Hz, 1H), 7.20-7.13 (m, 1H), 4.97 (t, J = 5.2 Hz, 1H), 4.83 (d, J = 4.0 Hz, 1H), 3.78 (d, J = 5.3 Hz, 1H), 3.65 (td, J = 5.3, 1.6 Hz, 1H), 2.04-1.95 (m, 1H), 1.92-1.84 (m, 2H), 1.79-1.70 (m, 1H). LCMS m/z (M + 1, 475.1); |
| 87 | 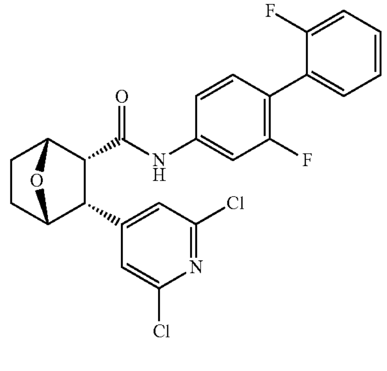 [SMILES: O=C(Nc1ccc(-c2ccccc2F)c(F)c1)[C@@H]1[C@H](c2cc(Cl)nc(Cl)c2)[C@@H]2CC[C@H]1O2] | $^{1}$H NMR (400 MHz, Chloroform-d) δ 7.58-7.01 (m, 8H), 6.97 (d, J = 3.3 Hz, 2H), 4.80 (q, J = 5.2 Hz, 2H), 3.49 (qd, J = 11.3, 4.6 Hz, 2H), 2.18 (ddd, J = 12.1, 8.7, 3.0 Hz, 1H), 1.99 (ddd, J = 16.5, 7.9, 4.2 Hz, 1H), 1.84-1.62 (m, 2H). LCMS m/z (M + 1, 475.0); |

TABLE 3-continued

| Ex. No. | Structure | Physical Data MS (m/z), Elemental Analysis, $^1$H NMR, Melting Point, HPLC RT |
|---|---|---|
| | Exemplified Compounds of Formula I of the Invention | |
| 88 | 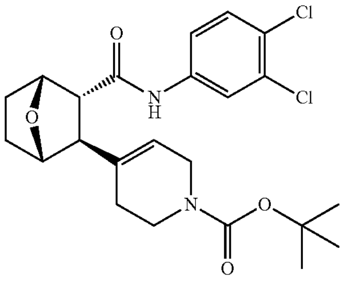 [SMILES: CC(C)(C)OC(=O)N1CC=C([C@@H]2[C@@H](C(=O)Nc3ccc(Cl)c(Cl)c3)[C@H]3CC[C@@H]2O3)CC1] | $^1$H NMR (400 MHz, Acetonitrile-$d_3$) δ 8.57 (s, 1H), 7.97-7.90 (m, 1H), 7.47-7.43 (m, 2H), 5.49 (s, 1H), 4.76 (t, J = 5.0 Hz, 1H), 4.47 (d, J = 4.9 Hz, 1H), 3.83 (dd, J = 5.5, 3.0 Hz, 2H), 3.51 (dt, J = 13.1, 5.6 Hz, 1H), 3.45-3.35 (m, 1H), 2.93-2.83 (m, 2H), 2.08 (ddt, J = 5.8, 4.0, 2.2 Hz, 2H), 1.77-1.66 (m, 2H), 1.63-1.52 (m, 2H), 1.44 (s, 9H). LCMS m/z (M + 1 − Boc, 367.2); |
| 89 | 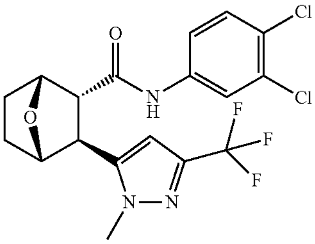 [SMILES: Cn1nc(C(F)(F)F)cc1[C@@H]1[C@@H](C(=O)Nc2ccc(Cl)c(Cl)c2)[C@H]2CC[C@@H]1O2] | $^1$H NMR (400 MHz, Methylene Chloride-$d_2$) δ 7.84 (d, J = 2.4 Hz, 1H), 7.40 (d, J = 8.7 Hz, 1H), 7.38 (s, 1H), 7.29 (dd, J = 8.8, 2.5 Hz, 1H), 6.46 (s, 1H), 4.88 (t, J = 5.1 Hz, 1H), 4.62 (d, J = 4.9 Hz, 1H), 3.83 (s, 3H), 3.65 (d, J = 4.4 Hz, 1H), 2.96 (td, J = 5.1, 1.6 Hz, 1H), 1.92-1.66 (m, 4H). LCMS m/z (M + 1, 434.1); |
| 90 | 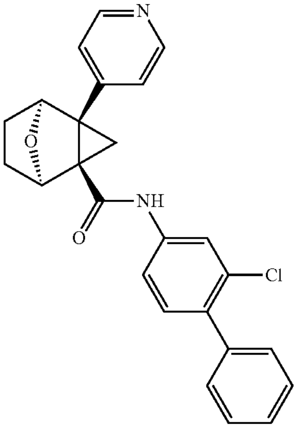 [SMILES: O=C(Nc1ccc(-c2ccccc2)c(Cl)c1)[C@]12C[C@@]1(c1ccncc1)[C@@H]1CC[C@H]2O1] | $^1$H NMR (400 MHz, MeOD) δ 8.47-8.43 (m, 2H), 7.81 (d, J = 2.1 Hz, 1H), 7.69-7.16 (m, 9H), 4.79 (d, J = 4.6 Hz, 1H), 4.64 (d, J = 4.7 Hz, 1H), 2.45 (ddd, J = 11.5, 9.3, 4.2 Hz, 1H), 2.03-1.96 (m, 1H), 1.88 (d, J = 4.8 Hz, 1H), 1.83 (dt, J = 11.5, 4.4 Hz, 1H), 1.77-1.70 (m, 1H), 1.26 (d, J = 4.9 Hz, 1H). LCMS m/z (M + 1, 417.2); |
| 91 | 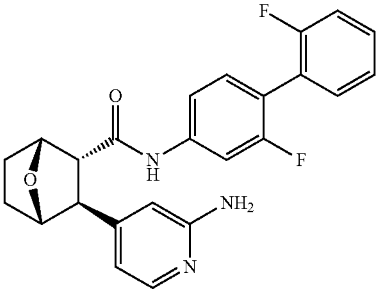 [SMILES: Nc1cc([C@@H]2[C@@H](C(=O)Nc3ccc(-c4ccccc4F)c(F)c3)[C@H]3CC[C@@H]2O3)ccn1] | $^1$H NMR (400 MHz, Methylene Chloride-$d_2$) δ 9.51 (s, 1H), 7.81 (d, J = 5.7 Hz, 1H), 7.67-7.62 (m, 1H), 7.42-7.30 (m, 4H), 7.26-7.21 (m, 1H), 7.17 (ddd, J = 10.0, 8.7, 1.2 Hz, 1H), 6.68 (dd, J = 5.7, 1.5 Hz, 1H), 6.57 (d, J = 1.3 Hz, 1H), 5.40 (br s, 2H), 4.89 (t, J = 5.2 Hz, 1H), 4.60 (d, J = 4.7 Hz, 1H), 3.41 (d, J = 5.1 Hz, 1H), 3.05 (td, J = 5.2, 1.6 Hz, 1H), 1.92-1.64 (m, 4H). LCMS m/z (M + 1, 422.2); |

TABLE 3-continued

Exemplified Compounds of Formula I of the Invention

| Ex. No. | Structure | Physical Data MS (m/z), Elemental Analysis, $^1$H NMR, Melting Point, HPLC RT |
|---|---|---|
| 92 | 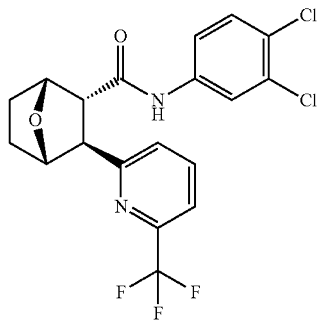 [SMILES: O=C(Nc1ccc(Cl)c(Cl)c1)[C@@H]1[C@@H](c2cccc(C(F)(F)F)n2)[C@@H]2CC[C@H]1O2] | $^1$H NMR (400 MHz, MeOD) δ 10.15 (s, 1H), 7.97-7.91 (m, 2H), 7.62 (t, J = 8.4 Hz, 2H), 7.47-7.38 (m, 2H), 4.95 (t, J = 5.2 Hz, 1H), 4.81-4.77 (m, 1H), 3.78 (d, J = 5.2 Hz, 1H), 3.70-3.64 (m, 1H), 1.94-1.84 (m, 3H), 1.72 (ddd, J = 10.1, 5.1, 1.8 Hz, 1H). LCMS m/z (M + 1, 431.1); |
| 93 | 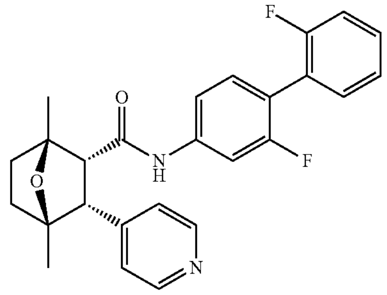 [SMILES: C[C@]12CC[C@](C)(O1)[C@@H](c1ccncc1)[C@H]2C(=O)Nc1ccc(-c2ccccc2F)c(F)c1] | $^1$H NMR (400 MHz, DMSO) δ 10.00 (s, 1H), 8.51-8.47 (m, 2H), 8.47-8.40 (m, 1H), 7.51-7.04 (m, 8H), 3.52 (dd, J = 12.7, 1.8 Hz, 1H), 3.25 (ddd, J = 12.6, 5.8, 2.2 Hz, 1H), 1.83 (ddd, J = 13.1, 9.2, 4.3 Hz, 1H), 1.73 (ddd, J = 12.8, 9.2, 4.1 Hz, 1H), 1.65-1.53 (m, 2H), 1.46 (s, 3H), 1.29 (s, 3H). LCMS m/z (M + 1, 435.2); |
| 94 | 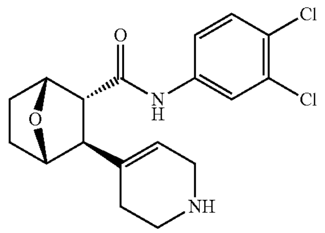 [SMILES: O=C(Nc1ccc(Cl)c(Cl)c1)[C@@H]1[C@@H](C2=CCNCC2)[C@@H]2CC[C@H]1O2] | LCMS m/z (M + 1, 367.1); RT 1.27 min. (Method A) |
| 95 | 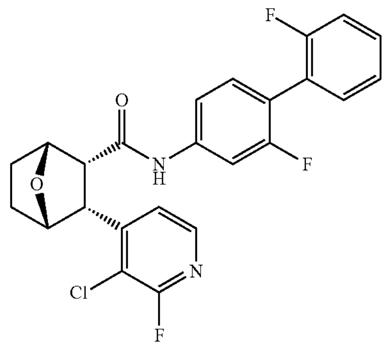 [SMILES: O=C(Nc1ccc(-c2ccccc2F)c(F)c1)[C@@H]1[C@H](c2ccnc(F)c2Cl)[C@@H]2CC[C@H]1O2] | $^1$H NMR (400 MHz, Chloroform-d) δ 7.95 (d, J = 5.3 Hz, 1H), 7.32 (dd, J = 11.7, 1.9 Hz, 1H), 7.29-7.02 (m, 8H), 4.85 (t, J = 5.1 Hz, 2H), 3.73 (dd, J = 10.7, 5.9 Hz, 1H), 3.58-3.52 (m, 1H), 2.24-2.15 (m, 1H), 1.88 (td, J = 10.8, 3.2 Hz, 2H), 1.67 (dq, J = 12.5, 6.8, 6.0 Hz, 1H). LCMS m/z (M + 1, 459.1); |

TABLE 3-continued

Exemplified Compounds of Formula I of the Invention

| Ex. No. | Structure | Physical Data MS (m/z), Elemental Analysis, $^{1}$H NMR, Melting Point, HPLC RT |
|---|---|---|
| 96 | 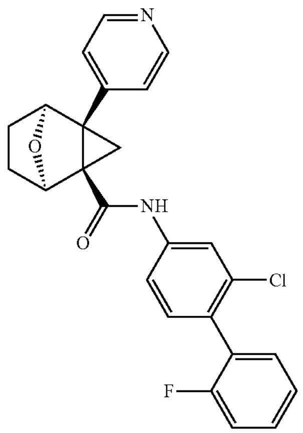 [SMILES: O=C(Nc1ccc(-c2ccccc2F)c(Cl)c1)[C@]12C[C@@]1(c1ccncc1)[C@@H]1CC[C@H]2O1] | $^{1}$H NMR (400 MHz, MeOD) δ 8.47-8.42 (m, 2H), 7.84 (d, J = 2.2 Hz, 1H), 7.71-6.96 (m, 8H), 4.79 (d, J = 4.7 Hz, 1H), 4.65 (d, J = 4.9 Hz, 1H), 2.45 (ddd, J = 11.6, 9.1, 4.1 Hz, 1H), 2.06-1.97 (m, 1H), 1.88 (d, J = 4.8 Hz, 1H), 1.84 (td, J = 7.6, 3.9 Hz, 1H), 1.72 (tt, J = 11.8, 4.6 Hz, 1H), 1.26 (d, J = 4.8 Hz, 1H). LCMS m/z (M + 1, 435.2); |
| 97 | 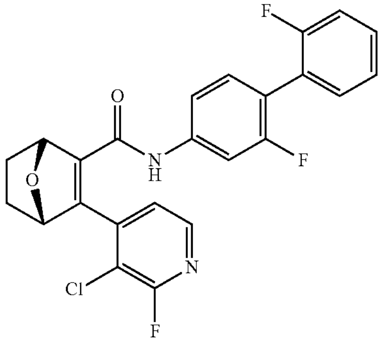 | $^{1}$H NMR (400 MHz, MeOD) δ 8.11 (d, J = 5.1 Hz, 1H), 7.54 (d, J = 12.4 Hz, 1H), 7.43-7.12 (m, 7H), 5.50 (dd, J = 4.4, 0.9 Hz, 1H), 5.39-5.37 (m, 1H), 2.14-1.97 (m, 2H), 1.76 (ddd, J = 10.9, 8.8, 3.0 Hz, 1H), 1.56 (ddd, J = 11.8, 8.7, 3.1 Hz, 1H). LCMS m/z (M + 1, 457.0); |
| 98 | 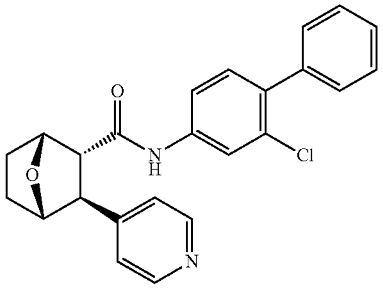 [SMILES: O=C(Nc1ccc(-c2ccccc2)c(Cl)c1)[C@@H]1[C@@H](c2ccncc2)[C@@H]2CC[C@H]1O2] | $^{1}$H NMR (400 MHz, MeOD) δ 10.45 (s, 1H), 9.12-9.04 (m, 2H), 8.48 (t, J = 1.9 Hz, 1H), 8.14-8.04 (m, 6H), 8.04-7.97 (m, 1H), 7.92 (d, J = 8.4 Hz, 1H), 5.59 (t, J = 5.2 Hz, 1H), 5.26 (d, J = 4.6 Hz, 1H), 4.22 (d, J = 4.9 Hz, 1H), 3.74 (td, J = 5.2, 1.6 Hz, 1H), 2.58-2.30 (m, 4H). LCMS m/z (M + 1, 405.1); |
| 99 | 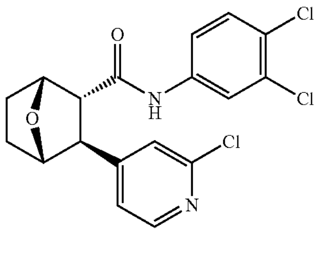 [SMILES: O=C(Nc1ccc(Cl)c(Cl)c1)[C@@H]1[C@@H](c2ccnc(Cl)c2)[C@@H]2CC[C@H]1O2] | $^{1}$H NMR (400 MHz, Acetonitrile-$d_3$) δ 8.55 (s, 1H), 8.29 (d, J = 5.3 Hz, 1H), 7.92 (d, J = 2.3 Hz, 1H), 7.49-7.40 (m, 2H), 7.35 (d, J = 1.6 Hz, 1H), 7.31-7.24 (m, 1H), 4.94 (t, J = 5.1 Hz, 1H), 4.59 (d, J = 4.9 Hz, 1H), 3.51 (d, J = 4.9 Hz, 1H), 3.05 (td, J = 5.2, 1.7 Hz, 1H), 1.84-1.62 (m, 4H). LCMS m/z (M + 1, 397.1); |

TABLE 3-continued

Exemplified Compounds of Formula I of the Invention

| Ex. No. | Structure | Physical Data MS (m/z), Elemental Analysis, $^1$H NMR, Melting Point, HPLC RT |
|---|---|---|
| 100 | 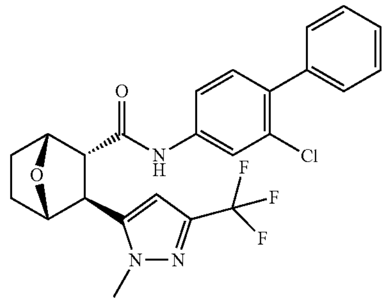 [SMILES: Cn1nc(C(F)(F)F)cc1[C@@H]1[C@@H](C(=O)Nc2ccc(-c3ccccc3)c(Cl)c2)[C@H]2CC[C@@H]1O2] | $^1$H NMR (400 MHz, Methylene Chloride-$d_2$) δ 7.80 (d, J = 2.1 Hz, 1H), 7.46-7.35 (m, 7H), 7.31 (d, J = 8.2 Hz, 1H), 6.48 (s, 1H), 4.91 (t, J = 5.1 Hz, 1H), 4.63 (d, J = 4.9 Hz, 1H), 3.84 (s, 3H), 3.68 (d, J = 4.5 Hz, 1H), 3.00 (td, J = 5.2, 1.6 Hz, 1H), 1.93-1.68 (m, 4H). LCMS m/z (M + 1, 476.2); |
| 101 | 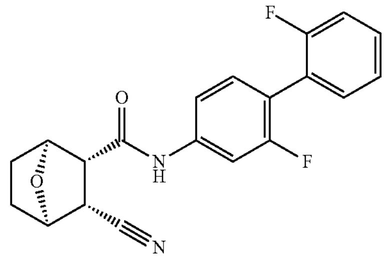 [SMILES: N#C[C@H]1[C@@H](C(=O)Nc2ccc(-c3ccccc3F)c(F)c2)[C@@H]2CC[C@H]1O2] | $^1$H NMR (400 MHz, Acetonitrile-$d_3$) δ 8.62 (s, 1H), 7.70-7.62 (m, 1H), 7.51-7.36 (m, 4H), 7.34-7.21 (m, 2H), 5.01 (d, J = 4.5 Hz, 1H), 4.88-4.83 (m, 1H), 3.40 (d, J = 9.4 Hz, 1H), 3.07 (d, J = 9.4 Hz, 1H), 1.84-1.56 (m, 4H). LCMS m/z (M + 1, 355.2); |
| 102 | 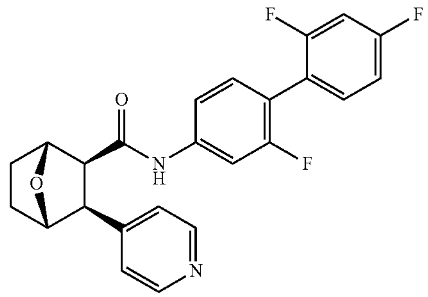 [SMILES: O=C(Nc1ccc(-c2ccc(F)cc2F)c(F)c1)[C@H]1[C@@H](c2ccncc2)[C@@H]2CC[C@H]1O2] | $^1$H NMR (400 MHz, MeOD) δ 8.68 (d, J = 4.9 Hz, 2H), 7.80-7.73 (m, 2H), 7.67 (td, J = 8.4, 6.3 Hz, 1H), 7.50 (t, J = 8.3 Hz, 1H), 7.45 (dd, J = 12.2, 2.1 Hz, 1H), 7.38-7.26 (m, 2H), 7.24 (dd, J = 8.4, 2.1 Hz, 1H), 5.41 (d, J = 4.3 Hz, 1H), 5.08 (d, J = 4.3 Hz, 1H), 3.88 (d, J = 9.7 Hz, 1H), 3.61 (d, J = 9.7 Hz, 1H), 2.33-2.20 (m, 2H), 2.15-2.03 (m, 2H). LCMS m/z (M + 1, 425.1); |
| 103 | 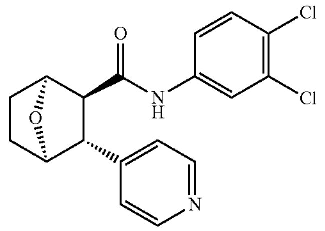 Single enantiomer | $^1$H NMR (400 MHz, DMSO) δ 10.35 (s, 1H), 8.48 (dd, J = 4.4, 1.6 Hz, 2H), 8.01 (d, J = 2.4 Hz, 1H), 7.57 (d, J = 8.8 Hz, 1H), 7.43 (dd, J = 8.8, 2.4 Hz, 1H), 7.27 (dd, J = 4.5, 1.7 Hz, 2H), 4.93 (t, J = 5.1 Hz, 1H), 4.59 (d, J = 4.3 Hz, 1H), 3.39 (d, J = 5.0 Hz, 1H), 3.07 (td, J = 5.1, 1.5 Hz, 1H), 1.80-1.49 (m, 4H). LCMS m/z (M + 1, 363.1); |
| 104 | 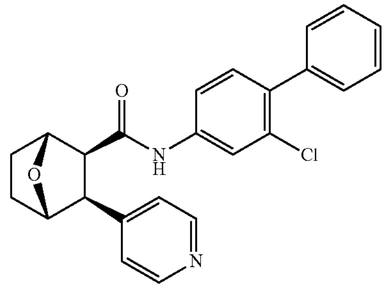 [SMILES: O=C(Nc1ccc(-c2ccccc2)c(Cl)c1)[C@H]1[C@@H](c2ccncc2)[C@@H]2CC[C@H]1O2] | $^1$H NMR (400 MHz, MeOD) δ 8.71 (d, J = 5.3 Hz, 2H), 7.84 (d, J = 5.3 Hz, 2H), 7.78-7.67 (m, 5H), 7.64 (d, J = 2.2 Hz, 1H), 7.49 (d, J = 8.4 Hz, 1H), 7.36 (dd, J = 8.3, 2.2 Hz, 1H), 5.41 (d, J = 4.3 Hz, 1H), 5.08 (d, J = 4.3 Hz, 1H), 3.90 (d, J = 9.7 Hz, 1H). 3.62 (d, J = 9.7 Hz, 1H), 2.29-2.22 (m, 2H), 2.16-2.03 (m, 2H). LCMS m/z (M + 1, 405.1); |

TABLE 3-continued

Exemplified Compounds of Formula I of the Invention

| Ex. No. | Structure | Physical Data MS (m/z), Elemental Analysis, $^1$H NMR, Melting Point, HPLC RT |
|---|---|---|
| 105 | 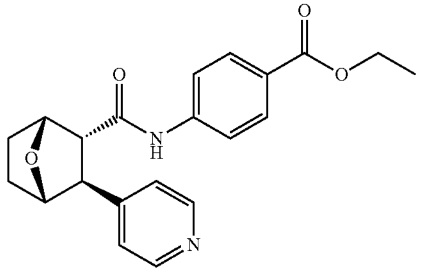 [SMILES: CCOC(=O)c1ccc(NC(=O)[C@@H]2[C@@H](c3ccncc3)[C@@H]3CC[C@H]2O3)cc1] | $^1$H NMR (400 MHz, MeOD) δ 8.45 (s, 2H), 7.99-7.94 (m, 2H), 7.73-7.65 (m, 2H), 7.42 (d, J = 5.1 Hz, 2H), 4.96 (t, J = 5.2 Hz, 1H), 4.64 (d, J = 4.5 Hz, 1H), 4.34 (q, J = 7.1 Hz, 2H), 3.55 (d, J = 5.0 Hz, 1H), 3.14 (td, J = 5.3, 1.6 Hz, 1H), 1.92-1.78 (m, 3H), 1.70 (dtd, J = 13.7, 5.0, 2.9 Hz, 1H), 1.38 (t, J = 7.1 Hz, 3H). LCMS m/z (M + 1, 367.2); |
| 106 | 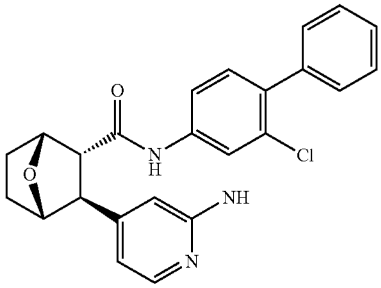 [SMILES: Nc1cc([C@@H]2[C@@H](C(=O)Nc3ccc(-c4ccccc4)c(Cl)c3)[C@H]3CC[C@@H]2O3)ccn1] | $^1$H NMR (400 MHz, Methylene Chloride-$d_2$) δ 8.14 (s, 1H), 7.83 (d, J = 2.2 Hz, 1H), 7.77 (d, J = 5.7 Hz, 1H), 7.46-7.35 (m, 6H), 7.29 (d, J = 8.3 Hz, 1H), 6.66 (dd, J = 5.8, 1.5 Hz, 1H), 6.58-6.54 (m, 1H), 5.73-5.36 (br s, 2H). 4.84 (t, J = 5.1 Hz, 1H), 4.60 (d, J = 5.0 Hz, 1H), 3.38 (d, J = 5.0 Hz, 1H), 2.96 (td, J = 5.1, 1.6 Hz, 1H), 1.99-1.65 (m, 4H). LCMS m/z (M + 1, 420.2); |
| 107 | 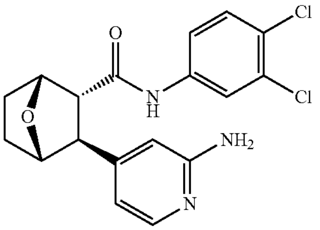 [SMILES: Nc1cc([C@@H]2[C@@H](C(=O)Nc3ccc(Cl)c(Cl)c3)[C@H]3CC[C@@H]2O3)ccn1] | $^1$H NMR (400 MHz, Methylene Chloride-$d_2$) δ 8.11 (s, 1H), 7.90-7.83 (m, 2H), 7.39-7.33 (m, 2H), 6.59 (dd, J = 5.4, 1.5 Hz, 1H), 6.45 (d, J = 1.4 Hz, 1H), 4.76 (t, J = 5.1 Hz, 1H), 4.59 (d, J = 5.0 Hz, 1H), 4.55 (br s, 2H), 3.29 (d, J = 5.0 Hz, 1H), 2.88 (td, J = 5.2, 1.7 Hz, 1H), 1.97-1.49 (m, 4H). LCMS m/z (M + 1, 378.1); |
| 108 | 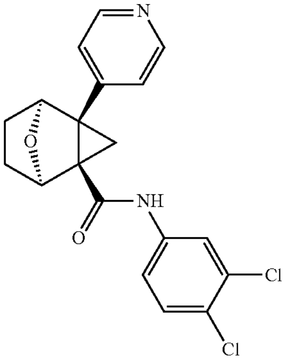 [SMILES: O=C(Nc1ccc(Cl)c(Cl)c1)[C@]12C[C@@]1(c1ccncc1)[C@@H]1CC[C@H]2O1] | $^1$H NMR (400 MHz, MeOD) δ 8.48-8.40 (m, 2H), 7.86 (d, J = 1.9 Hz, 1H), 7.45 (d, J = 2.3 Hz, 2H), 7.32-7.27 (m, 2H), 4.76 (d, J = 4.7 Hz, 1H), 4.63 (d, J = 4.8 Hz, 1H), 2.41 (ddd, J = 11.5, 9.1, 4.1 Hz, 1H), 2.02-1.95 (m, 1H), 1.85 (s, 1H), 1.81 (dt, J = 11.5, 4.3 Hz, 1H), 1.77-1.66 (m, 1H), 1.22 (d, J = 4.8 Hz, 1H). LCMS m/z (M + 1, 375.1); |
| 109 | 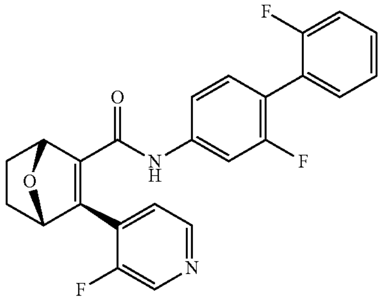 | $^1$H NMR (400 MHz, MeOD) δ 8.53 (d, J = 3.1 Hz, 1H), 8.40 (d, J = 5.8 Hz, 1H), 7.59 (d, J = 11.6 Hz, 1H), 7.52-7.45 (m, 1H), 7.42-7.29 (m, 4H), 7.24 (t, J = 7.5 Hz, 1H), 7.21-7.12 (m, 1H), 5.47 (d, J = 4.2 Hz, 1H), 5.40 (d, J = 5.4 Hz, 1H), 2.05 (td, J = 13.8, 11.0, 6.7 Hz, 2H), 1.73-1.63 (m, 1H), 1.60 (t, J = 8.4 Hz, 1H). LCMS m/z (M + 1, 423.0); |

TABLE 3-continued

| Exemplified Compounds of Formula I of the Invention | | |
|---|---|---|
| Ex. No. | Structure | Physical Data MS (m/z), Elemental Analysis, $^1$H NMR, Melting Point, HPLC RT |
| 110 | 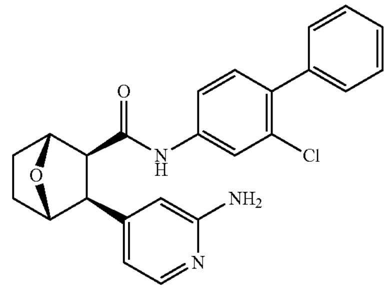 [SMILES: Nc1cc([C@@H]2[C@H](C(=O)Nc3ccc(-c4ccccc4)c(Cl)c3)[C@H]3CC[C@@H]2O3)ccn1] | $^1$H NMR (400 MHz, Methylene Chloride-$d_2$) δ 9.32 (s, 1H), 7.53 (t, J = 1.8 Hz, 1H), 7.50-7.30 (m, 6H), 7.23-7.16 (m, 2H), 7.10 (s, 1H), 6.93 (s, 1H), 5.04 (d, J = 4.0 Hz, 1H), 4.63 (d, J = 4.0 Hz, 1H), 3.56 (d, J = 9.5 Hz, 1H), 3.33 (d, J = 8.8 Hz, 1H), 1.94-1.66 (m, 4H). LCMS m/z (M + 1, 420.2); |
| 111 | 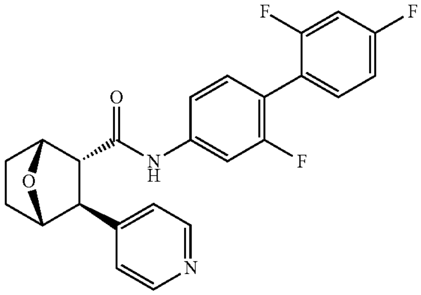 [SMILES: O=C(Nc1ccc(-c2ccc(F)cc2F)c(F)c1)[C@@H]1[C@@H](c2ccncc2)[C@@H]2CC[C@H]1O2] | $^1$H NMR (400 MHz, MeOD) δ 10.35 (s, 1H), 8.83-8.73 (m, 2H), 7.99 (dt, J = 12.4, 1.7 Hz, 1H), 7.79-7.75 (m, 2H), 7.75-7.61 (m, 3H), 7.38-7.26 (m, 2H), 5.31 (t, J = 5.2 Hz, 1H), 4.97 (d, J = 4.6 Hz, 1H), 3.92 (d, J = 5.0 Hz, 1H), 3.47 (td, J = 5.3, 1.6 Hz, 1H), 2.27-2.14 (m, 3H), 2.07 (tdd, J = 10.5, 5.1, 1.9 Hz, 1H). LCMS m/z (M + 1, 425.1); |
| 112 | 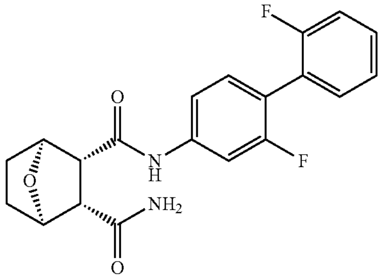 [SMILES: NC(=O)[C@H]1[C@@H](C(=O)Nc2ccc(-c3ccccc3F)c(F)c2)[C@@H]2CC[C@H]1O2] | $^1$H NMR (400 MHz, Chloroform-d) δ 8.98 (s, 1H), 7.50 (dd, J = 12.0, 2.0 Hz, 1H), 7.33-7.23 (m, 3H), 7.21-7.06 (m, 3H), 5.01-4.96 (m, 1H), 4.89-4.85 (m, 1H), 3.11-3.04 (m, 1H), 2.99 (d, J = 9.8 Hz, 1H), 1.91-1.76 (m, 2H), 1.62-1.49 (m, 2H). LCMS m/z (M + 23, 395.2); |
| 113 | 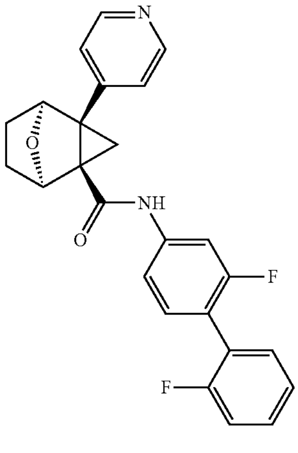 [SMILES: O=C(Nc1ccc(-c2ccccc2F)c(F)c1)[C@]12C[C@@]1(c1ccncc1)[C@@H]1CC[C@H]2O1] | $^1$H NMR (600 MHz, MeOD) δ 8.46-8.41 (m, 2H), 7.59 (dd, J = 12.3, 2.0 Hz, 1H), 7.46-7.36 (m, 5H), 7.35 (t, J = 8.2 Hz, 1H), 7.28-7.24 (m, 1H), 7.19 (ddd, J = 9.6, 8.3, 1.1 Hz, 1H), 4.79 (d, J = 4.7 Hz, 1H), 4.66 (d, J = 4.8 Hz, 1H), 2.45 (ddd, J = 11.8, 9.1, 4.1 Hz, 1H), 2.01 (ddd, J = 12.8, 9.1, 4.0 Hz, 1H, 1.88 (d, J = 4.8 Hz, 1H), 1.85 (ddd, J = 11.8, 7.4, 4.5 Hz, 1H), 1.77-1.71 (m, 1H), 1.27 (d, J = 4.8 Hz, 1H). LCMS m/z (M + 1, 419.2); |

TABLE 3-continued

Exemplified Compounds of Formula I of the Invention

| Ex. No. | Structure | Physical Data MS (m/z), Elemental Analysis, $^1$H NMR, Melting Point, HPLC RT |
|---|---|---|
| 114 | 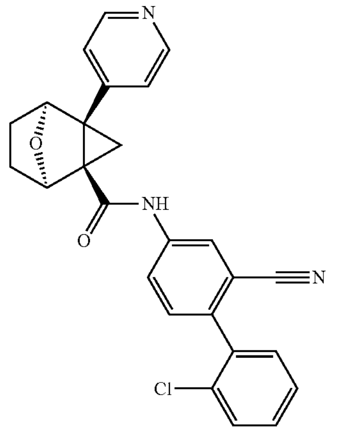 [SMILES: N#Cc1cc(NC(=O)[C@]23C[C@@]2(c2ccncc2)[C@@H]2CC[C@H]3O2)ccc1-c1ccccc1Cl] | $^1$H NMR (400 MHz, MeOD) δ 8.47-8.44 (m, 2H), 8.11 (d, J = 2.2 Hz, 1H), 7.88 (dd, J = 8.5, 2.3 Hz, 1H), 7.59-7.55 (m, 1H), 7.47-7.38 (m, 4H), 7.34-7.30 (m, 2H), 4.81 (d, J = 4.6 Hz, 1H), 4.65 (d, J = 4.7 Hz, 1H), 2.45 (ddd, J = 11.7, 9.1, 4.1 Hz, 1H), 2.01 (ddd, J = 12.7, 9.2, 4.0 Hz, 1H), 1.89 (d, J = 4.9 Hz, 1H), 1.88-1.81 (m, 1H), 1.78-1.69 (m, 1H), 1.28 (d, J = 5.0 Hz, 1H). LCMS m/z (M + 1, 442.2); |
| 115 | 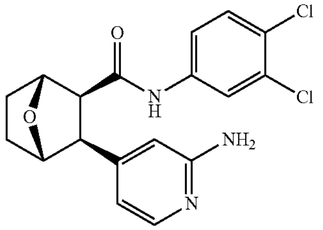 [SMILES: Nc1cc([C@@H]2[C@H](C(=O)Nc3ccc(Cl)c(Cl)c3)[C@H]3CC[C@@H]2O3)ccn1] | $^1$H NMR (400 MHz, Methylene Chloride-d$_2$) δ 7.62 (s, 1H), 7.49-7.04 (m, 5H), 6.93 (s, 1H), 5.02 (d, J = 3.4 Hz, 1H), 4.62 (d, J = 3.5 Hz, 1H), 3.58 (m, 1H), 3.34 (m, 1H), 1.92-1.82 (m, 2H), 1.72 (m, 2H). LCMS m/z (M + 1, 378.1); |
| 116 | 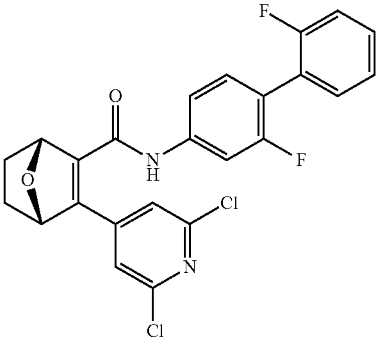 [SMILES: O=C(Nc1ccc(-c2ccccc2F)c(F)c1)C1=C(c2cc(Cl)nc(Cl)c2)[C@@H]2CC[C@H]1O2] | $^1$H NMR (400 MHz, MeOD) δ 7.64 (d, J = 12.0 Hz, 1H), 7.45-7.35 (m, 6H), 7.28-7.22 (m, 1H), 7.18 (dd, J = 10.3, 8.2 Hz, 1H), 5.45 (d, J = 3.8 Hz, 1H), 5.39-5.37 (m, 1H), 2.08 (dq, J = 9.5, 5.1, 4.0 Hz, 2H), 1.71 (t, J = 8.3 Hz, 1H), 1.51 (dd, J = 9.2, 7.7 Hz, 1H). LCMS m/z (M + 1, 473.0); |
| 117 | 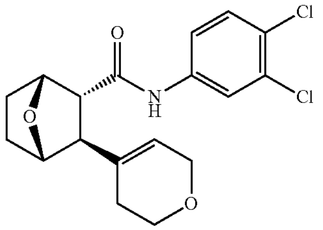 [SMILES: O=C(Nc1ccc(Cl)c(Cl)c1)[C@@H]1[C@@H](C2=CCOCC2)[C@@H]2CC[C@H]1O2] | $^1$H NMR (400 MHz, Acetonitrile-d$_3$) δ 8.60 (s, 1H), 7.94-7.90 (m, 1H), 7.45 (d, J = 1.8 Hz, 2H), 5.54 (tt, J = 2.7, 1.3 Hz, 1H), 4.76 (t, J = 5.0 Hz, 1H), 4.50 (d, J = 5.0 Hz, 1H), 4.05 (q, J = 2.6, 1.8 Hz, 2H), 3.78-3.66 (m, 2H), 2.92 (td, J = 5.2, 1.6 Hz, 1H), 2.83 (d, J = 5.2 Hz, 1H), 2.10-2.02 (m, 2H), 1.72 (dtt, J = 10.2, 7.6, 5.3 Hz, 2H), 1.63-1.50 (m, 2H). LCMS m/z (M + 1, 368.1); |
| 118 | 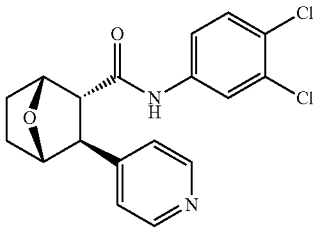 [SMILES: O=C(Nc1ccc(Cl)c(Cl)c1)[C@@H]1[C@@H](c2ccncc2)[C@@H]2CC[C@H]1O2] | $^1$H NMR (400 MHz, DMSO) δ 10.35 (s, 1H), 8.48 (dd, J = 4.4, 1.6 Hz, 2H), 8.01 (d, J = 2.4 Hz, 1H), 7.57 (d, J = 8.8 Hz, 1H), 7.43 (dd, J = 8.8, 2.4 Hz, 1H), 7.27 (dd, J = 4.5, 1.7 Hz, 2H), 4.93 (t, J = 5.1 Hz, 1H), 4.59 (d, J = 4.3 Hz, 1H), 3.39 (d, J = 5.0 Hz, 1H), 3.07 (td, J = 5.1, 1.5 Hz, 1H), 1.80-1.49 (m, 4H). LCMS m/z (M + 1, 363.1): |

TABLE 3-continued

| Ex. No. | Structure | Physical Data MS (m/z), Elemental Analysis, $^1H$ NMR, Melting Point, HPLC RT |
|---|---|---|
| Exemplified Compounds of Formula I of the Invention | | |
| 119 | 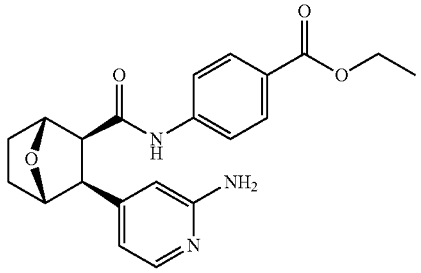 [SMILES: CCOC(=O)c1ccc(NC(=O)[C@H]2[C@@H](c3ccnc(N)c3)[C@@H]3CC[C@H]2O3)cc1] | $^1H$ NMR (400 MHz, Methylene Chloride-$d_2$) δ 7.87-7.82 (m, 2H), 7.41-7.37 (m, 3H), 7.10 (d, J = 1.5 Hz, 1H), 6.92-6.89 (m, 1H), 5.04 (d, J = 4.2 Hz, 1H), 4.62 (d, J = 4.2 Hz, 1H), 4.30 (q, J = 7.1 Hz, 2H), 3.55 (d, J = 1.4 Hz, 1H), 3.35-3.28 (m, 1H), 1.87 (td, J = 5.5, 4.7, 3.1 Hz, 2H), 1.77-1.67 (m, 2H), 1.34 (t, J = 7.1 Hz, 3H). LCMS m/z (M + 1, 382.2); |
| 120 | 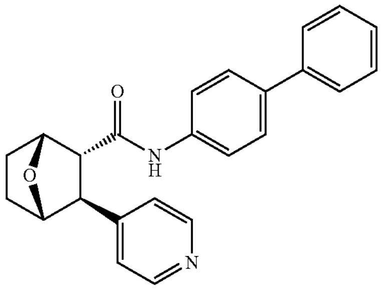 [SMILES: O=C(Nc1ccc(-c2ccccc2)cc1)[C@@H]1[C@@H](c2ccncc2)[C@@H]2CC[C@H]1O2] | $^1H$ NMR (400 MHz, DMSO) δ 10.15 (s, 1H), 8.53-8.42 (m, 2H), 7.69-7.60 (m, 6H), 7.44 (dd, J = 8.4, 7.0 Hz, 2H), 7.35-7.27 (m, 3H), 4.95 (t, J = 5.1 Hz, 1H), 4.59 (d, J = 3.9 Hz, 1H), 3.43 (d, J = 5.0 Hz, 1H), 3.10 (td, J = 5.2, 1.5 Hz, 1H), 1.77-1.67 (m, 3H), 1.63-1.54 (m, 1H). LCMS m/z (M + 1, 371.3); |
| 121 | 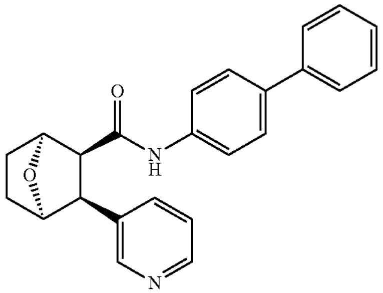 [SMILES: O=C(Nc1ccc(-c2ccccc2)cc1)[C@H]1[C@@H](c2cccnc2)[C@H]2CC[C@@H]1O2] | LCMS m/z (M + 1, 371.1); |
| 122 | 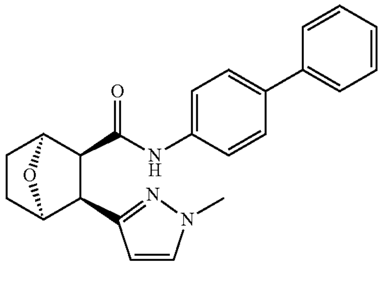 [SMILES: Cn1ccc([C@@H]2[C@H](C(=O)Nc3ccc(-c4ccccc4)cc3)[C@@H]3CC[C@H]2O3)n1] | LCMS m/z (M + 1, 374.1); |

TABLE 3-continued

Exemplified Compounds of Formula I of the Invention

| Ex. No. | Structure | Physical Data MS (m/z), Elemental Analysis, $^1$H NMR, Melting Point, HPLC RT |
|---|---|---|
| 123 | 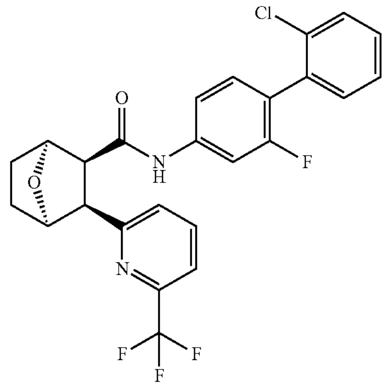 [SMILES: O=C(Nc1ccc(-c2ccccc2Cl)c(F)c1)[C@H]1[C@@H](c2cccc(C(F)(F)F)n2)[C@H]2CC[C@@H]1O2] | LCMS m/z (M + 1, 491.1); |
| 124 | 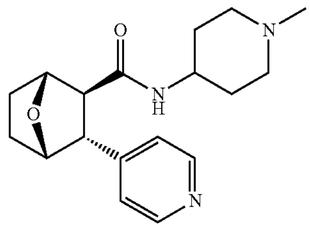 [SMILES: CN1CCC(NC(=O)[C@H]2[C@H](c3ccncc3)[C@@H]3CC[C@H]2O3)CC1] | LCMS m/z (M + 1, 316.1) |
| 125 | 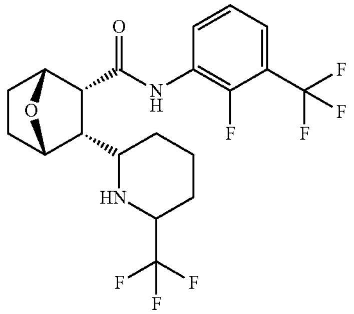 [SMILES: O=C(Nc1cccc(C(F)(F)F)c1F)[C@@H]1[C@H](C2CCCC(C(F)(F)F)N2)[C@@H]2CC[C@H]1O2] | $^1$H NMR (400 MHz, $CDCl_3$) δ 8.47 (t, J = 7.3, 1H), 7.69 (s, 1H), 7.36 (dd, J = 3.8, 10.6, 1H), 7.26 (dt, J = 4.2, 10.2, 1H), 4.76 (dt, J = 5.0, 16.1, 2H), 3.33 (t, J = 10.1, 1H), 3.20 (d, J = 6.9, 1H), 3.03 (dd, J = 5.1, 10.5, 1H), 2.25 (ddd, J = 6.4, 11.0, 12.2, 2H), 1.99 (ddd, J = 5.1, 9.2, 12.0, 1H), 1.87 (d, J = 9.7, 2H), 1.72-1.55 (m, 3H), 1.52-1.35 (m, 2H), 1.15 (d, J = 11.3, 1H). LCMS m/z (M + 1, 455.1) |
| 126 | 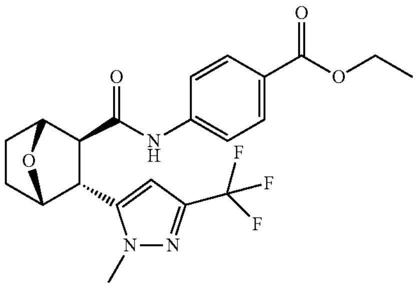 | $^1$H NMR (400 MHz, MeOD) δ 7.97 (d, J = 8.8, 2H), 7.80-7.63 (m, 2H), 6.64 (s, 1H), 4.93 (t, J = 4.8, 1H), 4.81 (d, J = 5.0, 1H), 4.34 (q, J = 7.1, 2H). 4.04 (t, J = 5.2, 1H), 3.96 (s, 3H), 2.99 (d, J = 5.7, 1H), 1.95-1.72 (m, 2H), 1.64-1.51 (m, 2H), 1.38 (t, J = 7.1, 3H). LCMS m/z (M + 1, 438.1) |
| 127 | 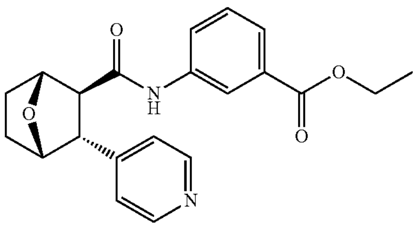 [SMILES: CCOC(=O)c1cccc(NC(=O)[C@H]2[C@H](c3ccncc3)[C@@H]3CC[C@H]2O3)c1] | LCMS m/z (M + 1, 367.1) |

TABLE 3-continued
| Exemplified Compounds of Formula I of the Invention | | |
|---|---|---|
| Ex. No. | Structure | Physical Data MS (m/z), Elemental Analysis, $^1$H NMR, Melting Point, HPLC RT |
| 128 | 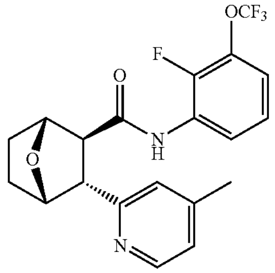 [SMILES: Cc1ccnc([C@H]2[C@H](C(=O)Nc3cccc(OC(F)(F)F)c3F)[C@H]3CC[C@@H]2O3)c1] | LCMS m/z (M + 1, 411.1) |
| 129 | 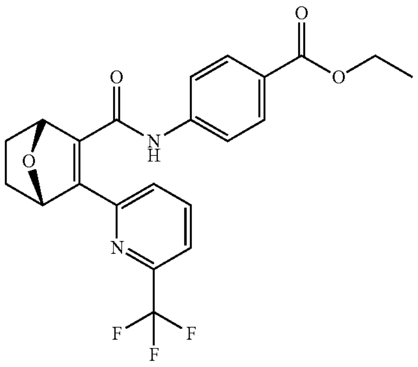 | $^1$H NMR (400 MHz, $CDCl_3$) δ 11.65 (s, 1H), 8.15-7.95 (m, 3H), 7.82-7.68 (m, 3H), 7.60 (d, J = 8.0, 1H), 5.68-5.63 (m, 1H), 5.50 (dd, J = 1.1, 4.3, 1H), 4.38 (dt, J = 5.5, 7.1, 2H), 2.22-2.14 (m, 2H), 1.75 (dd, J = 8.0, 8.8, 1H), 1.68-1.61 (m, 1H), 1.44-1.36 (m, 3H). LCMS m/z (M + 1, 433.1) |
| 130 | 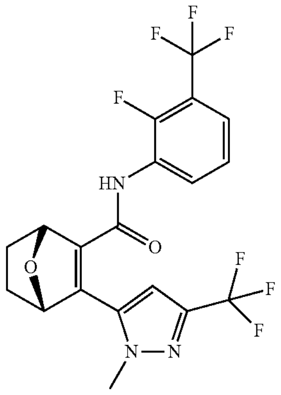 | $^1$H NMR (400 MHz, $CDCl_3$) δ 8.50 (s, 1H), 7.52-7.40 (m, 1H), 7.40-7.32 (m, 1H), 7.26-7.20 (m, 1H), 6.66 (s, 1H), 5.54 (d, J = 4.5, 1H), 5.28 (d, J = 4.0, 1H), 3.96 (s, 3H), 2.24-2.01 (m, 2H), 1.70-1.63 (m, 1H), 1.48 (ddd, J = 3.0, 8.8, 11.9, 1H). LCMS m/z (M + 1, 450.1) |
| 131 | 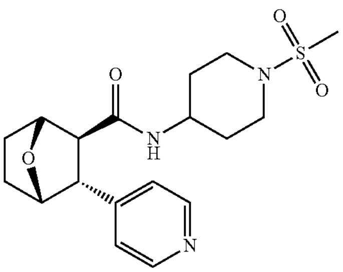 | LCMS m/z (M + 1, 380.1) |

TABLE 3-continued

| Ex. No. | Structure | Physical Data MS (m/z), Elemental Analysis, $^1$H NMR, Melting Point, HPLC RT |
|---|---|---|
| Exemplified Compounds of Formula I of the Invention | | |
| 132 | 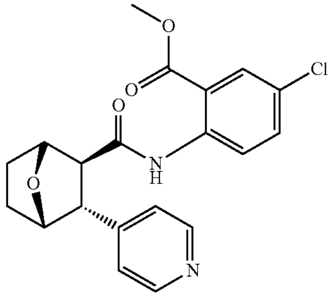 | LCMS m/z (M + 1, 387.1) |
| 133 | 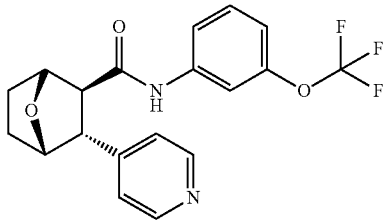 | LCMS m/z (M + 1, 379.1) |
| 134 | 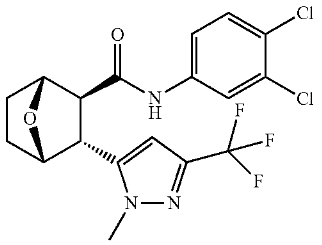 | $^1$H NMR (400 MHz, $CDCl_3$) δ 8.01 (s, 1H), 7.78 (t, J = 1.3, 1H), 7.40 (d, J = 1.4, 2H), 6.49 (s, 1H), 4.91 (dd, J = 5.2, 10.9, 2H), 3.93 (s, 3H), 3.78-3.65 (m, 1H), 2.83 (d, J = 5.2, 1H), 2.06-1.91 (m, 1H), 1.74-1.61 (m, 3H). LCMS m/z (M + 1, 438.1) |
| 135 | 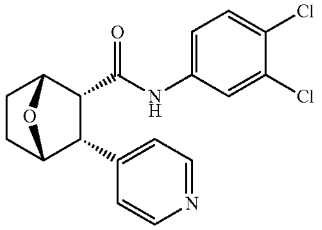 [SMILES: O=C(Nc1ccc(Cl)c(Cl)c1)[C@@H]1[C@H](c2ccncc2)[C@@H]2CC[C@H]1O2] | $^1$H NMR (400 MHz, $CDCl_3$) δ 8.47 (s, 1H), 8.22 (s, 1H), 7.61 (d, J = 2.3, 1H), 7.40-7.32 (m, 1H), 7.26 (s, 1H), 7.20-7.03 (m, 3H), 4.92 (t, J = 4.4, 1H), 4.86 (t, J = 4.8, 1H), 3.76-3.62 (m, 1H), 3.62-3.51 (m, 1H), 2.48-2.32 (m, 1H), 2.02-1.94 (m, 1H), 1.90-1.70 (m, 2H). LCMS m/z (M + 1, 363.0) |
| 136 | 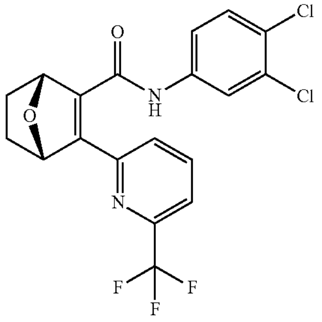 [SMILES: O=C(Nc1ccc(Cl)c(Cl)c1)C1=C(c2cccc(C(F)(F)F)n2)[C@@H]2CC[C@H]1O2] | $^1$H NMR (400 MHz, DMSO) δ 10.70 (s, 1H), 8.17 (t, J = 7.9, 1H), 8.02-7.90 (m, 2H), 7.87 (dd, J = 0.5, 7.8, 1H), 7.60 (d, J = 8.8, 1H), 7.54 (dd, J = 2.3, 8.8, 1H), 5.71 (d, J = 3.3, 1H), 5.41 (d, J = 3.2, 1H), 2.03-1.85 (m, 2H), 1.60 (t, J = 8.3, 1H), 1.43 (t, J = 8.3, 1H). LCMS m/z (M + 1, 429.0) |

TABLE 3-continued
| Ex. No. | Structure | Physical Data MS (m/z), Elemental Analysis, $^1H$ NMR, Melting Point, HPLC RT |
|---|---|---|
| | Exemplified Compounds of Formula I of the Invention | |
| 137 | 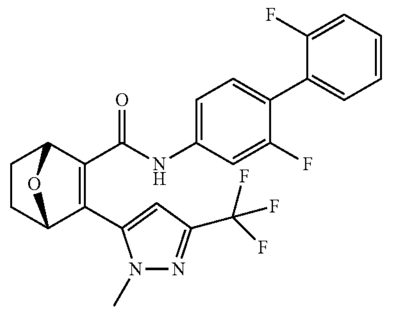 | $^1H$ NMR (400 MHz, $CDCl_3$) δ 7.61-7.47 (m, 1H), 7.43-7.30 (m, 3H), 7.25-7.11 (m, 3H), 7.00 (d, J = 7.6, 1H), 6.69 (s, 1H), 5.54 (d, J = 4.2, 1H), 5.30 (d, J = 4.4, 1H), 3.94 (s, 3H), 2.21-2.05 (m, 2H), 1.78-1.63 (m, 1H), 1.53-1.39 (m, 1H). LCMS m/z (M + 1, 476.1) |
| 138 | 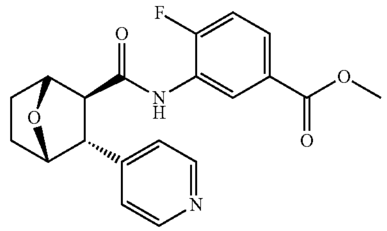 | LCMS m/z (M + 1, 371.1) |
| 139 | 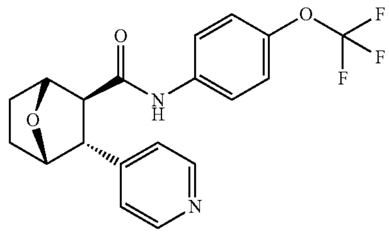 | LCMS m/z (M + 1, 379.1) |
| 140 | 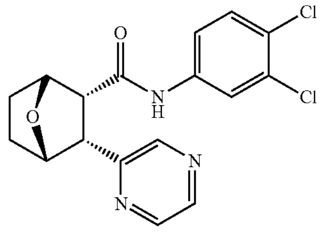 | LCMS m/z (M + 1, 364.0) |
| 141 | 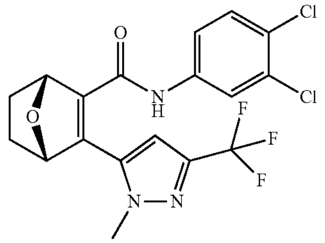 [SMILES: Cn1nc(C(F)(F)F)cc1C1=C(C(=O)Nc2ccc(Cl)c(Cl)c2)[C@H]2CC[C@@H]1O2] | $^1H$ NMR (400 MHz, $CDCl_3$) δ 7.69 (s, 1H), 7.38 (d, J = 8.7, 1H), 7.18-7.02 (m, 2H), 6.65 (s, 1H), 5.50 (d, J = 3.9, 1H), 5.28 (d, J = 4.4, 1H), 3.93 (s, 3H), 2.22-2.07 (m, 2H), 1.76-1.61 (m, 1H), 1.48-1.37 (m, 1H). LCMS m/z (M + 1, 432.0) |

TABLE 3-continued
| Exemplified Compounds of Formula I of the Invention | | |
|---|---|---|
| Ex. No. | Structure | Physical Data MS (m/z), Elemental Analysis, $^1$H NMR, Melting Point, HPLC RT |
| 142 | 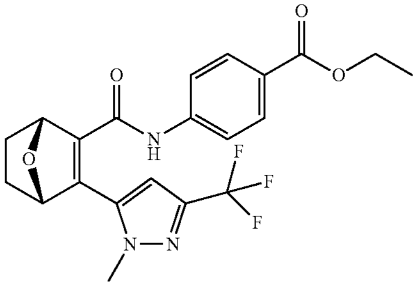 [SMILES: CCOC(=O)c1ccc(NC(=O)C2=C(c3cc(C(F)(F)F)nn3C)[C@@H]3CC[C@H]2O3)cc1] | LCMS m/z (M + 1, 436.1) |
| 143 | 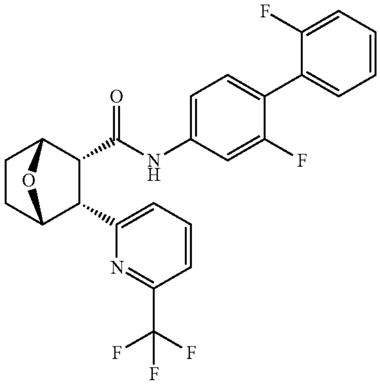 [SMILES: O=C(Nc1ccc(-c2ccccc2F)c(F)c1)[C@@H]1[C@H](c2cccc(C(F)(F)F)n2)[C@@H]2CC[C@H]1O2] | LCMS m/z (M + 1, 475.1) |
| 144 | 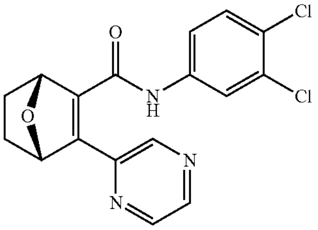 [SMILES: O=C(Nc1ccc(Cl)c(Cl)c1)C1=C(c2cnccn2)[C@@H]2CC[C@H]1O2] | $^1$H NMR (400 MHz, $CDCl_3$) δ 8.80 (d, J = 2.3, 1H), 8.74 (d, J = 2.4, 2H), 7.94 (d, J = 2.4, 1H), 7.52 (dd, J = 2.4, 8.7, 1H), 7.42 (d, J = 8.7, 1H), 5.68 (dd, J = 1.0, 4.3, 1H), 5.65-5.56 (m, 1H), 2.29-2.07 (m, 2H), 1.75-1.63 (m, 2H). LCMS m/z (M + 1, 362.0) |
| 145 | 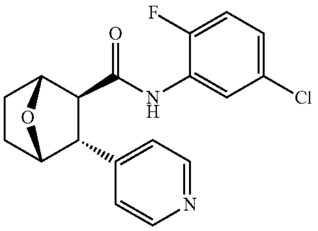 [SMILES: O=C(Nc1cc(Cl)ccc1F)[C@H]1[C@H](c2ccncc2)[C@@H]2CC[C@H]1O2] | $^1$H NMR (400 MHz, $CDCl_3$) δ 8.52 (dd, J = 1.6, 4.5, 2H), 8.46-8.34 (m, 1H), 7.32 (dddd, J = 0.7, 1.4, 2.0, 3.4, 1H), 7.30-7.27 (m, 2H), 7.08-6.97 (m, 2H), 4.91 (t, J = 5.0, 1H), 4.65 (d, J = 4.9, 1H), 3.47 (d, J = 5.0, 1H), 3.02 (td, J = 1.6, 5.2, 1H), 2.00-1.70 (m, 4H). LCMS m/z (M + 1, 347.1) |
| 146 | 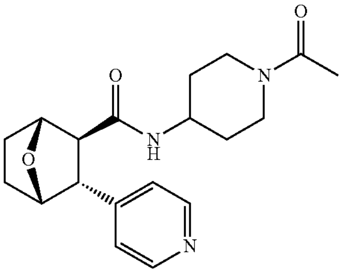 [SMILES: CC(=O)N1CCC(NC(=O)[C@H]2[C@H](c3ccncc3)[C@@H]3CC[C@H]2O3)CC1] | LCMS m/z (M + 1, 344.1) |

TABLE 3-continued
| Exemplified Compounds of Formula I of the Invention | | |
|---|---|---|
| Ex. No. | Structure | Physical Data MS (m/z), Elemental Analysis, $^1$H NMR, Melting Point, HPLC RT |
| 147 | 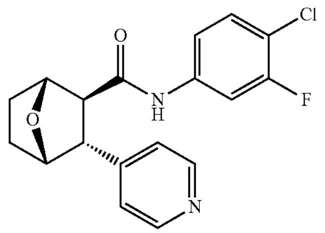 [SMILES: O=C(Nc1ccc(Cl)c(F)c1)[C@H]1[C@H](c2ccncc2)[C@@H]2CC[C@H]1O2] | LCMS m/z (M + 1, 347.1) |
| 148 | 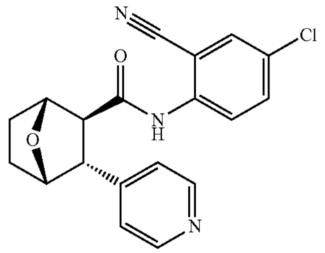 [SMILES: N#Cc1cc(Cl)ccc1NC(=O)[C@H]1[C@H](c2ccncc2)[C@@H]2CC[C@H]1O2] | LCMS m/z (M + 1, 354.1) |
| 149 | 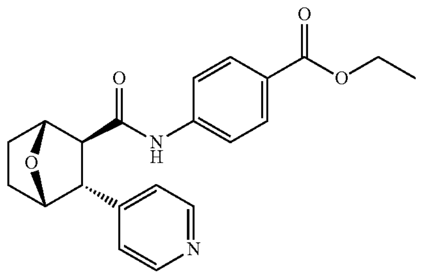 [SMILES: CCOC(=O)c1ccc(NC(=O)[C@H]2[C@H](c3ccncc3)[C@@H]3CC[C@H]2O3)cc1] | $^1$H NMR (400 MHz, $CDCl_3$) δ 9.03 (s, 1H), 8.62 (s, 2H), 7.96 (d, J = 8.8, 2H), 7.87 (dd, J = 7.2, 8.6, 3H), 7.64 (d, J = 8.7, 2H) 5.06 (t, J = 5.0, 1H), 4.66 (d, J = 4.7, 1H), 4.37 (q, J = 7.1, 2H), 3.83 (d, J = 4.6, 1H), 3.20 (t, J = 4.5, 1H), 2.04-1.74 (m, 4H), 1.41 (t, J = 7.1, 3H). LCMS m/z (M + 1, 367.1) |
| 150 | 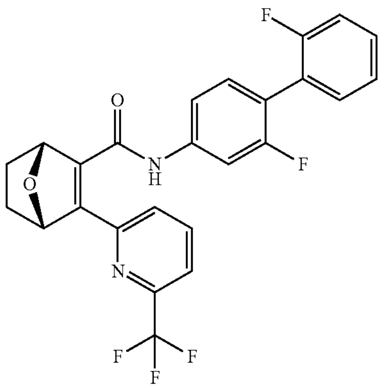 [SMILES: O=C(Nc1ccc(-c2ccccc2F)c(F)c1)C1=C(c2cccc(C(F)(F)F)n2)[C@@H]2CC[C@H]1O2] | LCMS m/z (M + 1, 473.1) |
| 151 | 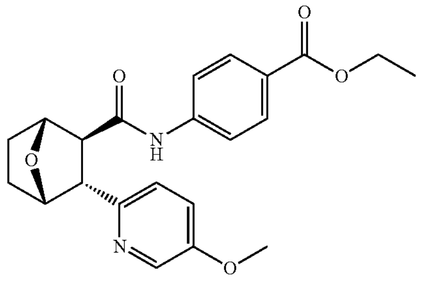 [SMILES: CCOC(=O)c1ccc(NC(=O)[C@H]2[C@H](c3ccc(OC)cn3)[C@@H]3CC[C@H]2O3)cc1] | LCMS m/z (M + 1, 397.2) |

TABLE 3-continued

| Ex. No. | Structure | Physical Data MS (m/z), Elemental Analysis, $^1$H NMR, Melting Point, HPLC RT |
|---|---|---|
| | Exemplified Compounds of Formula I of the Invention | |
| 152 | 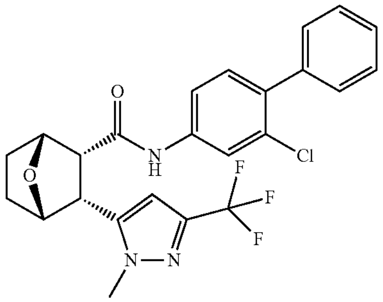 [SMILES: Cn1nc(C(F)(F)F)cc1[C@H]1[C@@H](C(=O)Nc2ccc(-c3ccccc3)c(Cl)c2)[C@H]2CC[C@@H]1O2] | $^1$H NMR (400 MHz, DMSO) δ 10.05 (s, 1H), 7.59 (d, J = 2.0 Hz, 1H), 7.56-7.45 (m, 1H), 7.44-7.19 (m, 6H), 6.34 (s, 1H), 4.78 (dt, J = 4.8, 10.0 Hz, 2H), 3.61 (dd, J = 4.8, 11.3 Hz, 1H), 3.45 (dd, J = 5.2, 11.4 Hz, 1H), 2.15-2.01 (m, 1H), 1.97-1.83 (m, 1H), 1.54 (dt, J = 6.8, 11.6 Hz, 2H). LCMS m/z (M + 1, 476.1) |
| 153 | 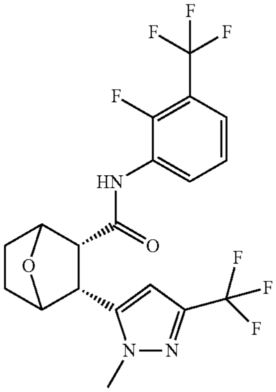 [SMILES: Cn1nc(C(F)(F)F)cc1[C@@H]1C2CCC(O2)[C@@H]1C(=O)Nc1cccc(C(F)(F)F)c1F] | $^1$H NMR (400 MHz, DMSO) δ 9.85 (s, 1H), 7.78 (t, J = 7.2 Hz, 1H), 7.42 (t, J = 6.8 Hz, 1H), 7.25 (t, J = 8.0 Hz, 1H), 6.29 (s, 1H), 4.77 (dt, J = 4.6, 11.8 Hz, 2H), 3.73 (s, 3H), 3.66 (dd, J = 4.7, 11.6 Hz, 1H), 3.55 (dd, J = 4.9, 11.6 Hz, 1H), 2.15 (t, J = 8.6 Hz, 1H), 1.84 (t, J = 8.3 Hz, 1H), 1.53 (dd, J = 4.9, 7.9 Hz, 2H). LCMS m/z (M + 1, 452.1) |
| 154 | 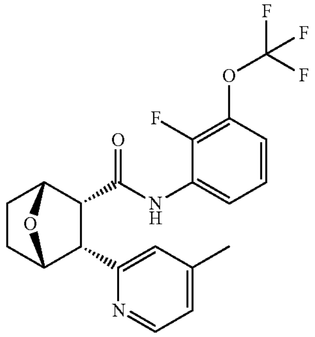 [SMILES: Cc1ccnc([C@H]2[C@@H](C(=O)Nc3cccc(OC(F)(F)F)c3F)[C@H]3CC[C@@H]2O3)c1] | LCMS m/z (M + 1, 411.1) |
| 155 | 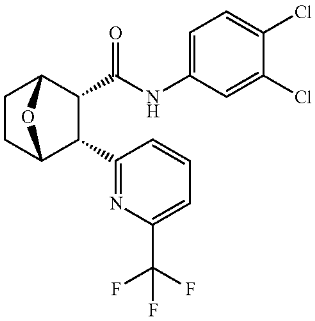 [SMILES: O=C(Nc1ccc(Cl)c(Cl)c1)[C@@H]1[C@H](c2cccc(C(F)(F)F)n2)[C@@H]2CC[C@H]1O2] | $^1$H NMR (400 MHz, $CDCl_3$) δ 7.80 (t, J = 7.8, 1H), 7.51 (t, J = 9.7, 2H), 7.35-7.27 (m, 3H), 7.11 (dd, J = 2.3, 8.7, 1H), 4.98-4.86 (m, 2H), 3.92 (dd, J = 4.5, 11.3, 1H), 3.52 (dd, J = 5.1, 11.4, 1H), 2.39 (t, J = 8.6, 1H), 1.99 (t, J = 8.4, 1H), 1.78 (dd, J = 4.6, 8.0, 2H). LCMS m/z (M + 1, 431.1) |

TABLE 3-continued

Exemplified Compounds of Formula I of the Invention

| Ex. No. | Structure | Physical Data MS (m/z), Elemental Analysis, $^1$H NMR, Melting Point, HPLC RT |
|---|---|---|
| 156 | 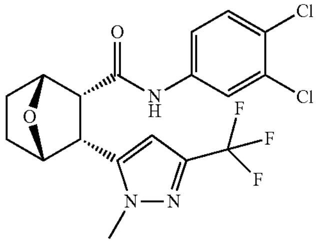 | $^1$H NMR (400 MHz, $CDCl_3$) δ 7.55 (d, J = 2.3, 1H), 7.36 (d, J = 8.7, 1H), 7.13 (dd, J = 2.3, 8.7, 1H), 6.97 (s, 1H), 6.49 (s, 1H), 4.95 (t, J = 4.5, 1H), 4.83 (t, J = 4.5, 1H), 3.83 (s, 3H), 3.63 (dd, J = 4.5, 11.3, 1H), 3.39 (dd, J = 4.9, 11.1, 1H), 2.35 (t, J = 8.9, 1H), 2.11 (t, J = 8.4, 1H), 1.92-1.68 (m, 2H). LCMS m/z (M + 1, 343.0) |
| 157 | 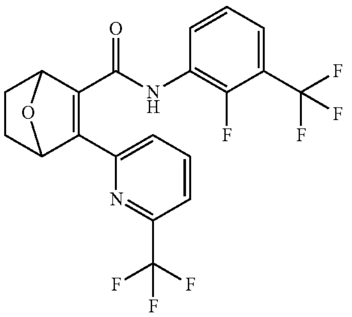 [SMILES: O=C(Nc1cccc(C(F)(F)F)c1F)C1=C(c2cccc(C(F)(F)F)n2)C2CCC1O2] | $^1$H NMR (400 MHz, $CDCl_3$) δ 11.91 (s, 1H), 8.10 (t, J = 7.8, 2H), 7.84-7.68 (m, 1H), 7.62 (d, J = 8.0, 1H), 7.43 (dd, J = 3.8, 10.2, 1H), 7.28-7.17 (m, 1H), 5.77-5.61 (m, 1H), 5.55 (dd, J = 1.5, 3.1, 1H), 2.26-2.08 (m, 2H), 1.72 (m, 1H), 1.62-1.54 (m, 1H). LCMS m/z (M + 1, 447.0) |
| 158 | 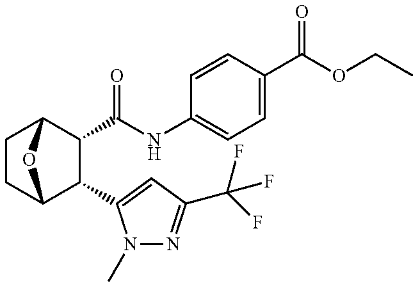 [SMILES: CCOC(=O)c1ccc(NC(=O)[C@@H]2[C@H](c3cc(C(F)(F)F)nn3C)[C@@H]3CC[C@H]2O3)cc1] | $^1$H NMR (400 MHz, $CDCl_3$) δ 7.89 (d, J = 8.7, 2H), 7.32 (d, J = 8.3, 2H), 7.13 (d, J = 0.6, 1H), 6.42 (s, 1H), 4.87 (t, 1H), 4.75 (t, 1H), 4.28 (q, J = 7.1, 2H), 3.72 (s, 3H), 3.60-3.48 (m, 1H), 3.41-3.28 (m, 1H), 2.29 (t, J = 8.9, 1H), 2.06-1.96 (m, 1H), 1.73 (m, 2H), 1.31 (t, J = 7.1, 3H). LCMS m/z (M + 1, 438.1) |
| 159 | 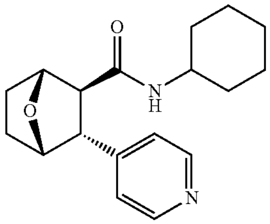 [SMILES: O=C(NC1CCCCC1)[C@H]1[C@H](c2ccncc2)[C@@H]2CC[C@H]1O2] | $^1$H NMR (400 MHz, MeOD) δ 8.31 (dd, J = 1.5, 4.7, 2H), 7.26 (dd, J = 1.5, 4.7, 2H), 4.69 (t, J = 5.2, 1H), 4.46 (d, J = 4.7, 1H), 3.60-3.47 (m, 1H), 3.34 (d, J = 5.0, 1H), 2.79 (td, J = 1.6, 5.2, 1H), 1.78-1.59 (m, 7H), 1.57-1.47 (m, J = 2.6, 4.9, 8.6, 2H), 1.34-1.16 (m, 2H), 1.16-0.98 (m, J = 2.9, 11.0, 11.9, 3H). LCMS m/z (M + 1, 301.1) |
| 160 | 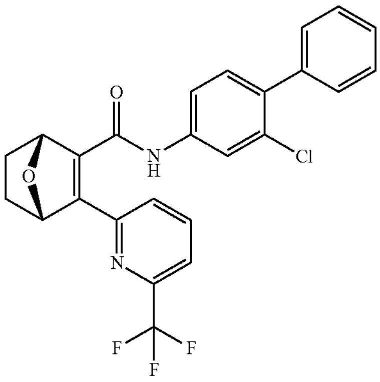 [SMILES: O=C(Nc1ccc(-c2ccccc2)c(Cl)c1)C1=C(c2cccc(C(F)(F)F)n2)[C@@H]2CC[C@H]1O2] | $^1$H NMR (400 MHz, $CDCl_3$) δ 11.70 (s, 1H), 8.09 (d, J = 8.0, 1H), 7.89 (d, J = 2.1, 1H), 7.82-7.73 (m, 1H), 7.67-7.53 (m, 2H), 7.51-7.39 (m, 5H), 7.35 (d, J = 8.4, 1H), 5.76-5.59 (m, 1H), 5.59-5.44 (m, 1H), 2.28-2.11 (m, 2H), 1.76 (t, J = 8.4, 1H), 1.65 (d, J = 8.8, 1H). LCMS m/z (M + 1, 471.1) |

TABLE 3-continued
| Ex. No. | Structure | Physical Data MS (m/z), Elemental Analysis, $^1$H NMR, Melting Point, HPLC RT |
|---|---|---|
| Exemplified Compounds of Formula I of the Invention | | |
| 161 | 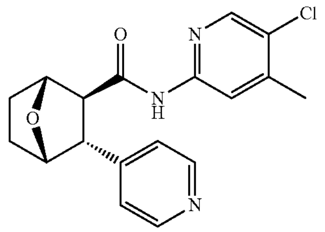 [SMILES: Cc1cc(NC(=O)[C@H]2[C@H](c3ccncc3)[C@@H]3CC[C@H]2O3)ncc1Cl] | $^1$H NMR (400 MHz, MeOD) δ 8.33 (d, J = 6.1, 2H), 8.08 (s, 1H), 8.02 (s, 1H), 7.35-7.24 (m, 2H), 4.87 (t, J = 5.2, 1H), 4.52 (d, J = 4.6, 1H), 3.46 (d, J = 4.9, 1H), 3.09 (t, J = 4.5, 1H), 2.30 (s, 3H), 1.80-1.65 (m, 3H), 1.65-1.50 (m, 1H). LCMS m/z (M + 1, 344.1) |
| 162 | 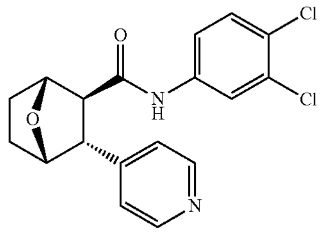 [SMILES: O=C(Nc1ccc(Cl)c(Cl)c1)[C@H]1[C@H](c2ccncc2)[C@@H]2CC[C@H]1O2] | LCMS m/z (M + 1, 363.0) |
| 163 | 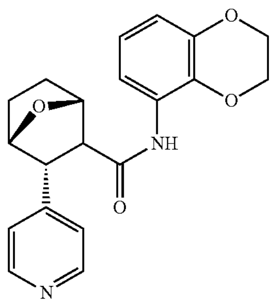 [SMILES: O=C(Nc1cccc2c1OCCO2)C1[C@H]2CC[C@H](O2)[C@H]1c1ccncc1] | $^1$H NMR (400 MHz, MeOD) δ 8.34 (d, J = 6.0, 2H), 7.40-7.27 (m, 2H), 7.24 (dd, J = 1.5, 8.0, 1H), 6.67 (t, J = 8.2, 1H), 6.56 (dd, J = 1.5, 8.3, 1H), 4.85 (d, J = 5.2, 1H), 4.51 (d, J = 4.8, 1H), 4.23-4.06 (m, 4H), 3.42 (d, J = 5.0, 1H), 3.13 (td, J = 1.4, 5.2, 1H), 1.88-1.79 (m, 1H), 1.79-1.50 (m, 3H). LCMS m/z (M + 1, 353.1) |
| 164 | 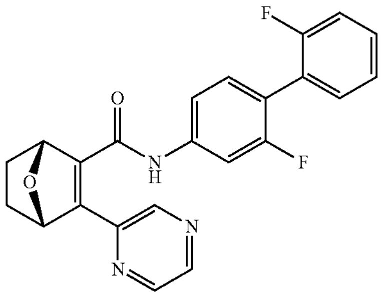 [SMILES: O=C(Nc1ccc(-c2ccccc2F)c(F)c1)C1=C(c2cnccn2)[C@@H]2CC[C@H]1O2] | LCMS m/z (M + 1, 406.1) |
| 165 | 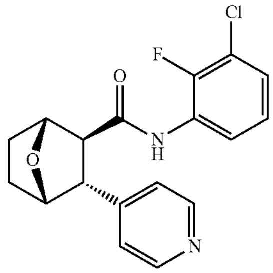 [SMILES: O=C(Nc1cccc(Cl)c1F)[C@H]1[C@H](c2ccncc2)[C@@H]2CC[C@H]1O2] | LCMS m/z (M + 1, 347.1) |

TABLE 3-continued
| Ex. No. | Structure | Physical Data MS (m/z), Elemental Analysis, $^1$H NMR, Melting Point, HPLC RT |
|---|---|---|
| Exemplified Compounds of Formula I of the Invention | | |
| 166 | 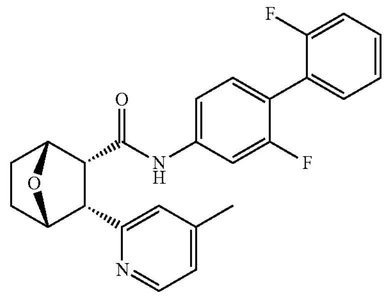 [SMILES: Cc1ccnc([C@H]2[C@@H](C(=O)Nc3ccc(-c4ccccc4F)c(F)c3)[C@H]3CC[C@@H]2O3)c1] | $^1$H NMR (400 MHz, DMSO) δ 9.83 (s, 1H), 8.15 (d, J = 4.8 Hz, 1H), 7.43-7.25 (m, 3H), 7.27-7.13 (m, 3H), 7.08 (dd, J = 1.9, 8.4 Hz, 1H), 6.91 (d, J = 21.3 Hz, 2H), 4.76 (t, J = 4.5 Hz, 1H), 4.69 (t, J = 4.0 Hz, 1H), 3.69 (dd, J = 4.9, 11.6 Hz, 1H), 3.38 (dd, J = 4.8, 11.4 Hz, 1H), 2.33-2.10 (m, 4H), 1.80 (t, J = 8.1 Hz, 1H), 1.55-1.35 (m, 2H). LCMS m/z (M + 1, 421.1) |
| 167 | 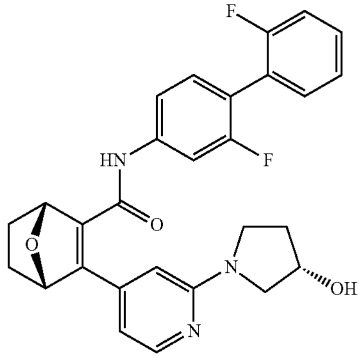 [SMILES: O=C(Nc1ccc(-c2ccccc2F)c(F)c1)C1=C(c2ccnc(N3CC[C@H](O)C3)c2)[C@@H]2CC[C@H]1O2] | LCMS m/z (M + 1, 490.2) |
| 168 | 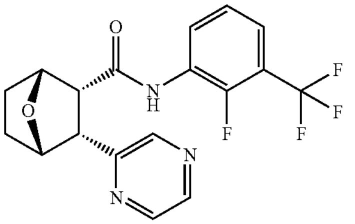 [SMILES: O=C(Nc1cccc(C(F)(F)F)c1F)[C@@H]1[C@H](c2cnccn2)[C@@H]2CC[C@H]1O2] | LCMS m/z (M + 1, 382.1) |
| 169 | 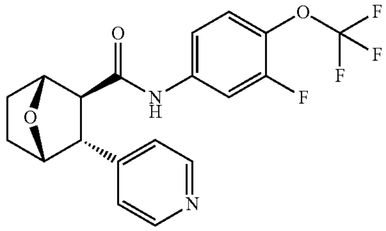 [SMILES: O=C(Nc1ccc(OC(F)(F)F)c(F)c1)[C@H]1[C@H](c2ccncc2)[C@@H]2CC[C@H]1O2] | LCMS m/z (M + 1, 397.1) |
| 170 | 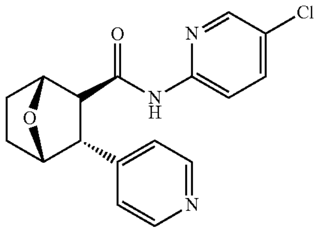 | LCMS m/z (M + 1, 330.1) |

TABLE 3-continued
| Exemplified Compounds of Formula I of the Invention | | |
|---|---|---|
| Ex. No. | Structure | Physical Data MS (m/z), Elemental Analysis, $^1$H NMR, Melting Point, HPLC RT |
| 171 | 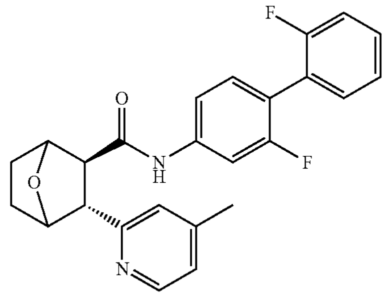 [SMILES: Cc1ccnc([C@@H]2C3CCC(O3)[C@H]2C(=O)Nc2ccc(-c3ccccc3F)c(F)c2)c1] | LCMS m/z (M + 1, 421.2) |
| 172 | 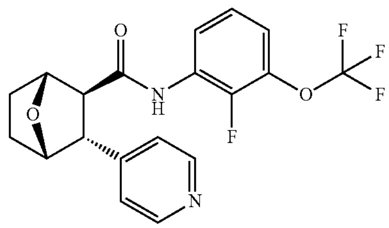 [SMILES: O=C(Nc1cccc(OC(F)(F)F)c1F)[C@H]1[C@H](c2ccncc2)[C@@H]2CC[C@H]1O2] | LCMS m/z (M + 1, 397.1) |
| 173 | 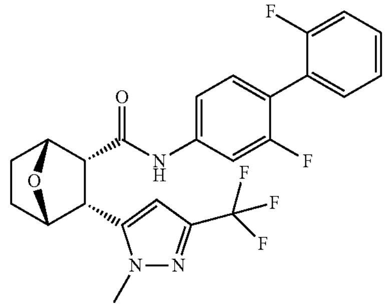 [SMILES: Cn1nc(C(F)(F)F)cc1[C@H]1[C@@H](C(=O)Nc2ccc(-c3ccccc3F)c(F)c2)[C@H]2CC[C@@H]1O2] | LCMS m/z (M + 1, 478.1) |
| 174 | 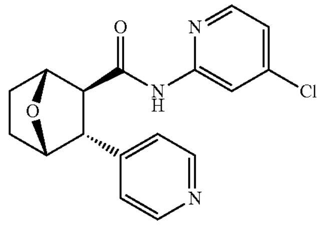 [SMILES: O=C(Nc1cc(Cl)ccn1)[C@H]1[C@H](c2ccncc2)[C@@H]2CC[C@H]1O2] | $^1$H NMR (400 MHz, MeOD) δ 8.34 (dd, J = 1.5, 4.7, 2H), 8.20-8.02 (m, 2H), 7.31 (dd, J = 1.3, 4.8, 2H), 7.11-6.95 (m, 1H), 4.88 (t, J = 5.2, 1H), 4.52 (d, J = 4.6, 1H), 3.47 (d, J = 4.9, 1H), 3.11 (dd, J = 3.1, 7.0, 1H), 1.82-1.67 (m, 3H), 1.64-1.52 (m, 1H). LCMS m/z (M + 1, 330.1) |
| 175 | 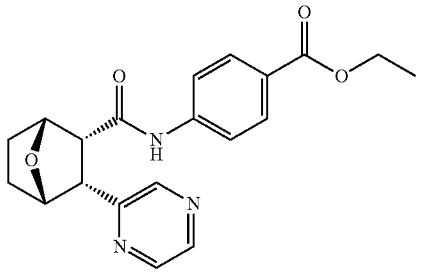 [SMILES: CCOC(=O)c1ccc(NC(=O)[C@@H]2[C@H](c3cnccn3)[C@@H]3CC[C@H]2O3)cc1] | LCMS m/z (M + 1, 368.1) |

TABLE 3-continued

| Ex. No. | Structure | Physical Data MS (m/z), Elemental Analysis, $^1$H NMR, Melting Point, HPLC RT |
|---|---|---|
| | Exemplified Compounds of Formula I of the Invention | |
| 176 | 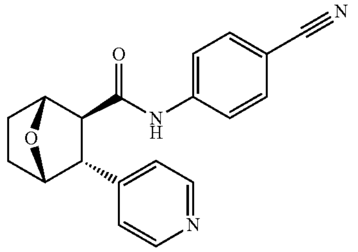 [SMILES: N#Cc1ccc(NC(=O)[C@H]2[C@H](c3ccncc3)[C@@H]3CC[C@H]2O3)cc1] | LCMS m/z (M + 1, 320.1) |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of formula (IA):

IA

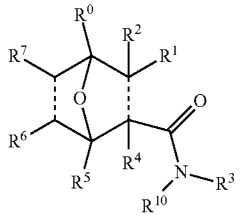

or a pharmaceutically acceptable salt, or stereoisomer thereof; wherein

"- - - - -" represents a single or double bond;

$R^0$ is selected from hydrogen and $C_{1-6}$alkyl;

$R^1$ is selected from cyano, 6-membered heterocycloalkyl, 6-membered heterocyclyl, phenyl, and 5- to 9-membered heteroaryl, wherein the heterocycloalkyl, heterocyclyl, phenyl, or heteroaryl of $R^1$ is unsubstituted or substituted by 1 to 2 substituents independently selected from halo, cyano, $C_{1-6}$alkyl, $C_{1-6}$haloalkyl, —C(O)$R^{13}$, —C(O)O$R^{13}$, —N$R^{14a}R^{14b}$, 5- and 6-membered heterocycloalkyl, phenyl, and 5- and 6-membered heteroaryl; wherein $R^{13}$ is selected from $C_{1-6}$alkyl, amino, and $C_{1-6}$alkylamino;

$R^{14a}$ and $R^{14b}$ are each independently selected from hydrogen, $C_{1-6}$alkyl, —C(O)$R^{15}$, —C(O)O$R^{15}$, and —S(O)$_2R^{15}$, wherein $R^{15}$ is hydrogen or $C_{1-6}$alkyl; and the heterocycloalkyl, phenyl or heteroaryl substituent of $R^1$ is unsubstituted or further substituted by 1 to 2 substituents independently selected from halo, hydroxy, $C_{1-6}$alkyl, and $C_{1-6}$haloalkyl, $R^3$ is selected from $C_{1-6}$alkyl, $C_{1-6}$haloalkyl, 5- and 6-membered cycloalkyl, 5- and 6-membered heterocycloalkyl, 6- and 10-membered heterocyclyl, phenyl, and 5- and 6-membered heteroaryl, wherein the cycloalkyl, heterocycloalkyl, heterocyclyl, phenyl, or heteroaryl of $R^3$ is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, —S(O)$_2R^{16}$, 5- and 6-membered heterocycloalkyl, and phenyl; wherein $R^{16}$ is hydrogen or $C_{1-6}$alkyl;

the phenyl or heterocycloalkyl substituent of $R^3$ is unsubstituted or further substituted by 1 to 2 substituents independently selected from halo, and cyano; and $R^2$ and $R^4$ are each hydrogen or $C_{1-6}$alkyl; or $R^2$ and $R^4$ taken together form a cyclopropyl ring fused to the bicyclic ring; or $R^2$ and $R^4$ taken together form a bond producing a double bond between the two carbons to which $R^2$ and $R^4$ are attached;

$R^5$ is hydrogen or $C_{1-6}$alkyl, or $R^5$ and $R^{10}$ taken with the atoms to which they are linked form a 5- or 6-membered ring fused to the bicyclic ring;

$R^6$ and $R^7$ are each hydrogen or $C_{1-6}$alkyl; or $R^6$ and $R^7$ taken together form a bond producing a double bond between the two carbons to which $R^6$ and $R^7$ are attached; and $R^{10}$ is hydrogen or $C_{1-6}$alkyl.

2. The compound according to claim 1, wherein the compound is of a formula selected from:

IA1

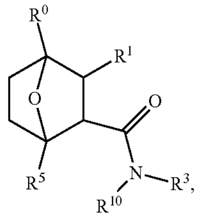

IA2

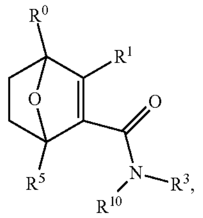

-continued

IA3

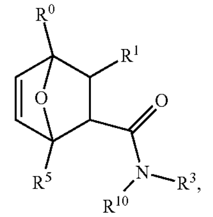

, and

IA4

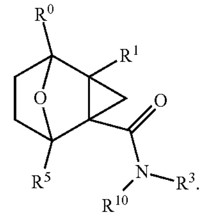

.

3. The compound according to claim 1, wherein $R^1$ is phenyl or 5- or 6-membered heteroaryl, wherein the phenyl or heteroaryl is unsubstituted or substituted by 1 to 2 substituents independently selected from halo, cyano, $C_{1-6}$alkyl, $C_{1-6}$haloalkyl, —C(O)$R^{13}$, —C(O)O$R^{13}$, —N$R^{14a}R^{14b}$, 5- and 6-membered heterocycloalkyl, phenyl, and 5- and 6-membered heteroaryl, wherein $R^{13}$ is selected from $C_{1-6}$alkyl, amino, and $C_{1-6}$alkylamino;

$R^{14a}$ and $R^{14b}$ are each independently selected from hydrogen, $C_{1-6}$alkyl, —C(O)$R^{15}$, and —C(O)O$R^{15}$, wherein $R^{15}$ is $C_{1-6}$alkyl; and the heterocycloalkyl, phenyl or heteroaryl substituent of $R^1$ is unsubstituted or further substituted by 1 to 2 substituents independently selected from hydroxy, halo, $C_{1-6}$alkyl, and $C_{1-6}$haloalkyl.

4. The compound according to claim 1, wherein $R^1$ is selected from

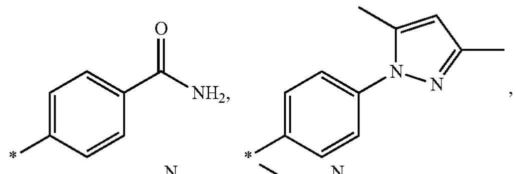

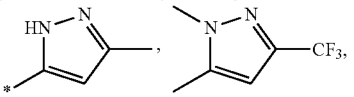

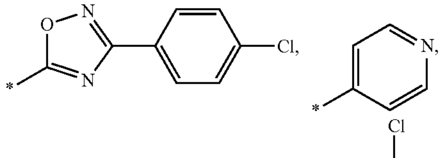

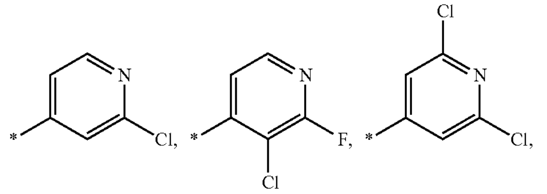

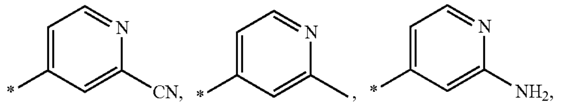

-continued

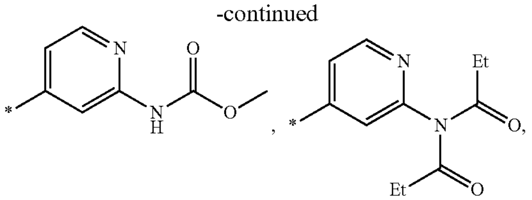

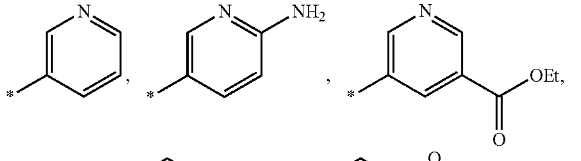

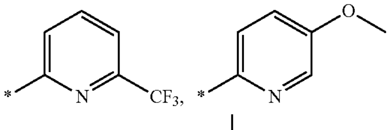

,

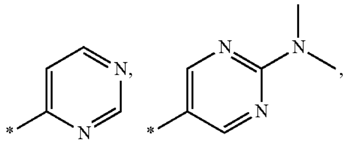

, and

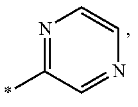

wherein "*" represents the point of attachment of $R^1$ to the bicyclic core ring.

5. The compound according to claim 1, wherein $R^3$ is phenyl or 5- or 6-membered heteroaryl, wherein the phenyl or heteroaryl of $R^3$ is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, —S(O)$_2$ $R^{16}$, 5- and 6-membered heterocycloalkyl, and phenyl; wherein $R^{16}$ is $C_{1-6}$alkyl; and the phenyl or heterocycloalkyl substituent of $R^3$ is unsubstituted or further substituted by 1 to 2 substituents independently selected from halo or cyano.

6. The compound according to claim 1, wherein $R^3$ is selected from:

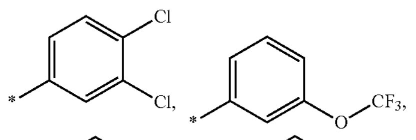

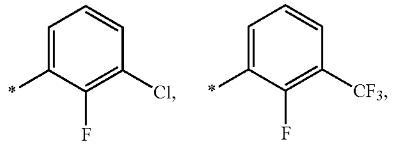

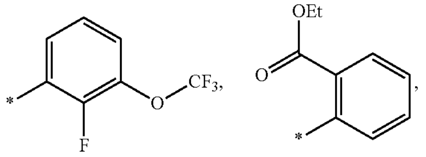

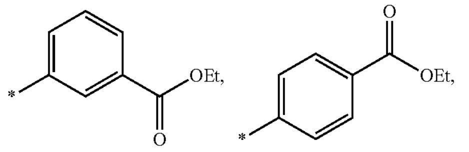

-continued

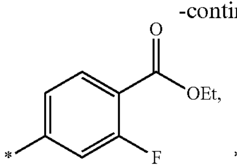
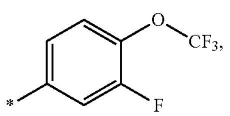
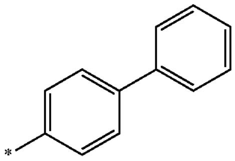
,
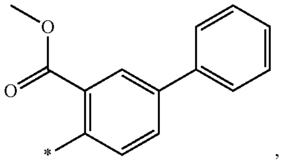
,
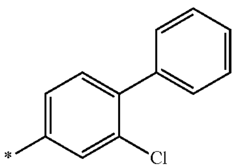
,
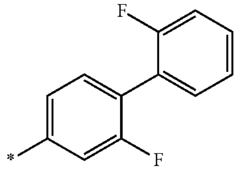
,
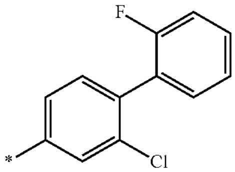
,
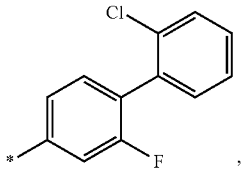
,
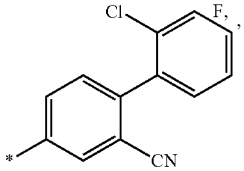
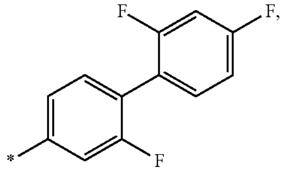
and
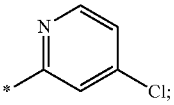

wherein "*" represents the point of attachment of $R^3$ to L.

7. The compound according to claim 1, wherein the compound is of Formula 1B:

IB

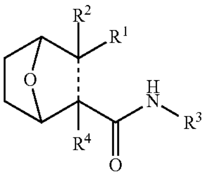

or a pharmaceutically acceptable salt, or a stereoisomer thereof, wherein

"- - - - -" represents a single or double bond;

$R^1$ is phenyl or 5- or 6-membered heteroaryl, wherein the phenyl or heteroaryl of $R^1$ is unsubstituted or substituted by 1 to 2 substituents independently selected from halo, cyano, $C_{1-6}$alkyl, $C_{1-4}$haloalkyl, —C(O)$R^{13}$, —C(O)O$R^{13}$, —N$R^{14a}R^{14b}$, 5- and 6-membered heterocycloalkyl, phenyl, and 5- and 6-membered heteroaryl, wherein $R^{13}$ is $C_{1-6}$alkyl or amino;

$R^{14a}$ and $R^{14b}$ are independently is selected from hydrogen, $C_{1-6}$alkyl, —C(O)$R^{15}$, and —C(O)O$R^{15}$, wherein $R^{15}$ is $C_{1-4}$alkyl; and the heterocycloalkyl, phenyl, or heteroaryl substituent of $R^1$ is unsubstituted or substituted by 1 to 2 substituents independently selected from halo, hydroxy, and $C_{1-6}$alkyl;

$R^3$ is phenyl or 5- or 6-membered heteroaryl, wherein the phenyl or heteroaryl is unsubstituted or substituted by 1 to 2 substituents independently selected from halo, cyano, $C_{1-6}$alkyl, $C_{1-6}$haloalkyl, $C_{1-6}$alkoxy, $C_{1-6}$haloalkoxy, —C(O)$R^{16}$, —C(O)O$R^{16}$, 5- and 6-membered heterocycloalkyl, and phenyl, wherein $R^{16}$ is $C_{1-6}$alkyl; and the heterocycloalkyl or phenyl is unsubstituted or substituted by 1 to 2 substituents selected from halo and cyano;

$R^2$ and $R^4$ are independently hydrogen or $C_{1-6}$alkyl, or $R^2$ and $R^4$ taken together form a cyclopropyl fused to the bicyclic ring, or $R^2$ and $R^4$ taken together form a bond, producing a double bond between the two carbons to which $R^2$ and $R^4$ are attached.

8. The compound of claim 7, wherein the compound is of a formula selected from

IB1

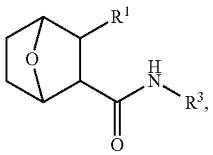

IB2

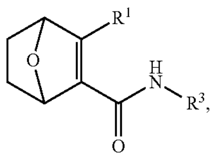
and

IB3

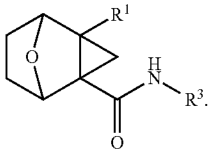

9. The compound according to claim 7, wherein the compound is of a formula selected from the formulae:

IB1a

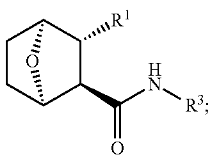

IB1b

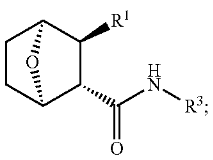

-continued

IB1b'

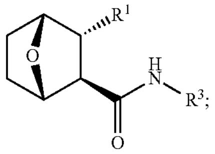

IB1c

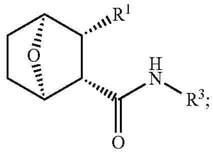

IB1d

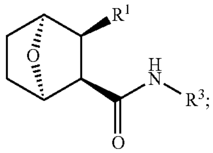

IB1d'

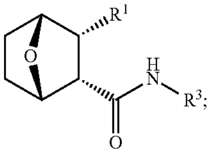

IB2

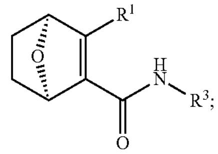

IB2'

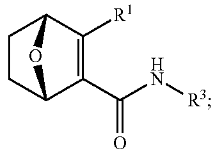

IB3b

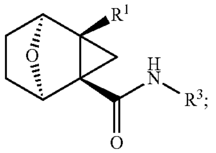

and

IB3b'

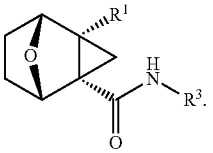

10. The compound according to claim 7, wherein $R^1$ is a 5 or 6 membered heteroaryl, unsubstituted or substituted by 1 to 2 substituents independently selected from halo, $C_{1-4}$alkyl, $C_{1-4}$haloalkyl, and $NHR^{14b}$, wherein $R^{14b}$ is hydrogen or $C_{1-4}$alkyl.

11. The compound according to claim 7, wherein $R^1$ is selected from pyrazolyl, oxadiazolyl, pyridinyl, pyrimidinyl and pyrazinyl, wherein the pyrazolyl, pyridinyl, pyrimidinyl or pyrazinyl is unsubstituted or substituted by —$NH_2$, —$NHC(O)OCH_3$ or trifluoromethyl.

12. The compound according to claim 7, wherein $R^1$ is selected from

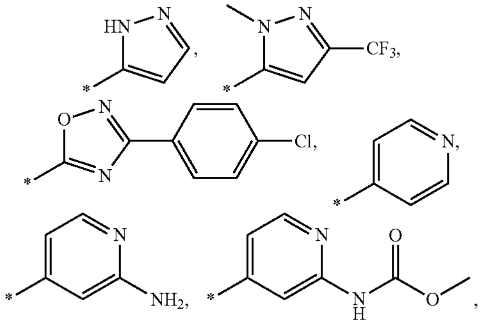

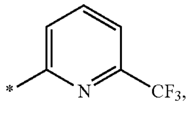

and

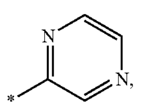

wherein "*" represents the point of attachment of $R^1$ to the bicyclic core ring.

13. The compound according to claim 7, wherein $R^3$ is phenyl substituted by 1 to 2 substituents independently selected from halo, cyano, $C_{1-6}$alkyl, $C_{1-6}$haloalkyl, $C_{1-6}$alkoxy, $C_{1-6}$haloalkoxy, and phenyl, —$C(O)R^{16}$, —$C(O)OR^{16}$, wherein $R^{16}$ is $C_{1-6}$alkyl, and the phenyl substituent of $R^3$ is unsubstituted or further substituted by 1 to 2 substituents independently selected from halo and cyano.

14. The compound according to claim 7, wherein $R^3$ is selected from

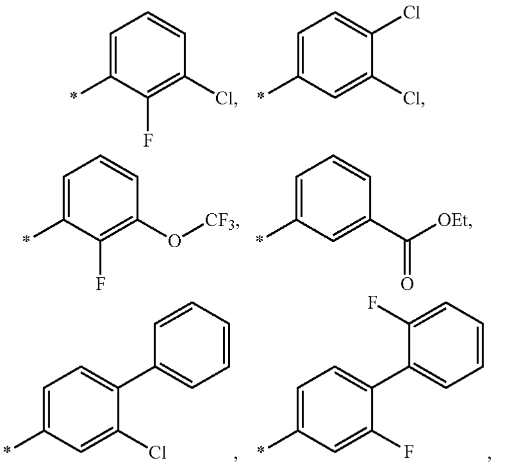

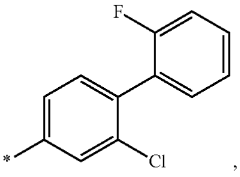

, and

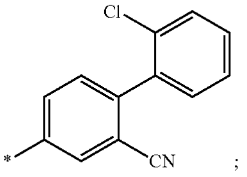

;

wherein "*" represents the point of attachment of $R^3$ to L.

15. The compound according to claim 1, or a pharmaceutically acceptable salt, or an enantiomer thereof, wherein the compound is selected from the list of compounds set forth in Table 3 and on pages 31 to 38 of the specification as follows:

(1R,2R,3S,4S)—N-(3,4-dichlorophenyl)-3-(2-(ethylsulfonamido)pyridin-4-yl)-7-oxabicyclo[2.2.1]heptane-2-carboxamide;

ethyl 2-((1R,2S,3R,4S)-3-(3-(4-chlorophenyl)-1,2,4-oxadiazol-5-yl)-7-oxabicyclo[2.2.1]heptane-2-carboxamido)benzoate;

(1R,2R,3S,4S)—N-(3,4-dichlorophenyl)-3-(1H-pyrazol-4-yl)-7-oxabicyclo[2.2.1]heptane-2-carboxamide;

(1R,2R,3S,4S)—N-(3,4-dichlorophenyl)-3-(1-methyl-1H-pyrazol-5-yl)-7-oxabicyclo[2.2.1]heptane-2-carboxamide;

(1R,2R,3S,4S)-3-(2-aminopyridin-4-yl)-N-(3,4-dichlorophenyl)-7-oxabicyclo[2.2.1]heptane-2-carboxamide;

(1R,2S,3S,4S)—N-(3,4-dichlorophenyl)-3-(1-methyl-1H-pyrazol-4-yl)-7-oxabicyclo[2.2.1]heptane-2-carboxamide;

(1R,2R,3S,4S)—N-(3,4-dichlorophenyl)-3-(1-methyl-1H-pyrazol-4-yl)-7-oxabicyclo[2.2.1]heptane-2-carboxamide;

(1S,2R,3R,4R)—N-(3,4-dichlorophenyl)-3-(pyridin-4-yl)-7-oxabicyclo[2.2.1]heptane-2-carboxamide;

methyl 4-((1R,2S,3R,4S)-3-(3-(4-chlorophenyl)-1,2,4-oxadiazol-5-yl)-7-oxabicyclo[2.2.1]heptane-2-carboxamido)-[1,1'-biphenyl]-3-carboxylate;

(1S,2S,3R,4R)-3-(2-aminopyridin-4-yl)-N-(3,4-dichlorophenyl)-7-oxabicyclo[2.2.1]heptane-2-carboxamide;

(1R,2S,3S,4S)—N-(3,4-dichlorophenyl)-3-(pyridin-4-yl)-7-oxabicyclo[2.2.1]heptane-2-carboxamide;

(1R,2R,3S,4S)—N-(3,4-dichlorophenyl)-3-(1-methyl-1H-pyrazol-3-yl)-7-oxabicyclo[2.2.1]heptane-2-carboxamide;

(1R,2S,3S,4S)—N-(3,4-dichlorophenyl)-3-(1-methyl-1H-pyrazol-5-yl)-7-oxabicyclo[2.2.1]heptane-2-carboxamide;

(1R,2R,3S,4S)—N-(3,4-dichlorophenyl)-3-(2-(N-propionylpropionamido)pyridin-4-yl)-7-oxabicyclo[2.2.1]heptane-2-carboxamide;

methyl (4-((1S,2S,3R,4R)-3-((3,4-dichlorophenyl)carbamoyl)-7-oxabicyclo[2.2.1]heptan-2-yl)pyridin-2-yl)carbamate;

(1R,2R,3S,4S)—N-(3,4-dichlorophenyl)-3-(2-propionamidopyridin-4-yl)-7-oxabicyclo[2.2.1]heptane-2-carboxamide;

ethyl 4-((1R,2S,3R,4S)-3-(3-(4-chlorophenyl)-1,2,4-oxadiazol-5-yl)-7-oxabicyclo[2.2.1]heptane-2-carboxamido)benzoate;

(1R,2R,3R,4S)—N-(4-chloro-3-fluorophenyl)-3-(pyridin-4-yl)-7-oxabicyclo[2.2.1]heptane-2-carboxamide;

(1R,2R,3S,4S)—N-(3,4-dichlorophenyl)-3-(2-(dimethylamino)pyrimidin-5-yl)-7-oxabicyclo[2.2.1]heptane-2-carboxamide;

(1R,2R,3R,4S)-3-(2-cyanopyridin-4-yl)-N-(2,2'-difluoro-[1,1'-biphenyl]-4-yl)-7-oxabicyclo[2.2.1]heptane-2-carboxamide;

(1S,4S)—N-(2-chloro-2'-fluoro-[1,1'-biphenyl]-4-yl)-3-(1H-pyrazol-5-yl)-7-oxabicyclo[2.2.1]hept-2-ene-2-carboxamide (1R,2R,3S,4S)—N-(3,4-dichlorophenyl)-3-(pyrimidin-4-yl)-7-oxabicyclo[2.2.1]heptane-2-carboxamide;

(1R,2R,3S,4S)—N-(3,4-dichlorophenyl)-3-(2-(dimethylamino)pyrimidin-5-yl)-7-oxabicyclo[2.2.1]heptane-2-carboxamide;

methyl 5-chloro-2-((1R,2S,3R,4S)-3-(pyridin-4-yl)-7-oxabicyclo[2.2.1]heptane-2-carboxamido)benzoate;

(1R,2S,3S,4S)-3-(4-carbamoylphenyl)-N-(3,4-dichlorophenyl)-7-oxabicyclo[2.2.1]heptane-2-carboxamide;

(1R,2S,3R,4S)—N-(2'-chloro-2-fluoro-[1,1'-biphenyl]-4-yl)-3-(pyridin-4-yl)-7-oxabicyclo[2.2.1]heptane-2-carboxamide;

(1R,2R,3S,4S)—N-(2-chloro-2'-fluoro-[1,1'-biphenyl]-4-yl)-3-(6-(trifluoromethyl)pyridin-2-yl)-7-oxabicyclo[2.2.1]heptane-2-carboxamide;

(1S,4S)—N-(2,2'-difluoro-[1,1'-biphenyl]-4-yl)-3-(1H-pyrazol-5-yl)-7-oxabicyclo[2.2.1]hept-2-ene-2-carboxamide;

(1R,2R,3S,4S)—N-(3,4-dichlorophenyl)-3-(4-(3,5-dimethyl-1H-pyrazol-1-yl)phenyl)-7-oxabicyclo[2.2.1]heptane-2-carboxamide;

(1R,2R,3S,4S)-3-(5-aminopyridin-3-yl)-N-(3,4-dichlorophenyl)-7-oxabicyclo[2.2.1]heptane-2-carboxamide;

(1S,4S)—N-(2'-chloro-2-fluoro-[1,1'-biphenyl]-4-yl)-3-(1-(tetrahydro-2H-pyran-4-yl)-1H-pyrazol-5-yl)-7-oxabicyclo[2.2.1]hept-2-ene-2-carboxamide;

(1S,4S)—N-(2,2'-difluoro-[1,1'-biphenyl]-4-yl)-3-(2-methylpyridin-4-yl)-7-oxabicyclo[2.2.1]hept-2-ene-2-carboxamide;

(1R,2S,3R,4S)—N-(4-chloro-3-fluorophenyl)-3-(pyridin-4-yl)-7-oxabicyclo[2.2.1]heptane-2-carboxamide;

(1R,2S,3S,4S)—N-(3,4-dichlorophenyl)-3-(2-(dimethylamino)pyrimidin-5-yl)-7-oxabicyclo[2.2.1]heptane-2-carboxamide;

(1R,2R,3S,4S)-3-(4-carbamoylphenyl)-N-(3,4-dichlorophenyl)-7-oxabicyclo[2.2.1]heptane-2-carboxamide;

(1R,2R,3S,4S)-3-(2-aminopyrimidin-5-yl)-N-(3,4-dichlorophenyl)-7-oxabicyclo[2.2.1]heptane-2-carboxamide;

(1S,4R)—N-(2-phenylpyrimidin-5-yl)-3-(pyridin-4-yl)-7-oxabicyclo[2.2.1]hept-2-ene-2-carboxamide;

(1R,2S,3R,4S)—N-(2-chloro-[1,1'-biphenyl]-4-yl)-3-(pyridin-4-yl)-7-oxabicyclo[2.2.1]heptane-2-carboxamide;

(1R,2R,3S,4S)-3-(6-aminopyridin-3-yl)-N-(3,4-dichlorophenyl)-7-oxabicyclo[2.2.1]heptane-2-carboxamide;

(1R,2S,3R,4S)—N-(3-chloro-2-fluorophenyl)-3-(pyridin-4-yl)-7-oxabicyclo[2.2.1]heptane-2-carboxamide;

(1R,2R,3S,4S)-3-(2-cyanopyridin-4-yl)-N-(3,4-dichlorophenyl)-7-oxabicyclo[2.2.1]heptane-2-carboxamide;

ethyl 2-fluoro-4-(3-(6-(trifluoromethyl)pyridin-2-yl)-7-oxabicyclo[2.2.1]hept-2-ene-2-carboxamido)benzoate;

(1S,4S)-3-(2-chloropyridin-4-yl)-N-(2,2'-difluoro-[1,1'-biphenyl]-4-yl)-7-oxabicyclo[2.2.1]hept-2-ene-2-carboxamide;

ethyl 5-((1S,2S,3S,4R)-3-((3,4-dichlorophenyl)carbamoyl)-7-oxabicyclo[2.2.1]heptan-2-yl)nicotinate;

(1S,4S)-3-cyano-N-(2,2'-difluoro-[1,1'-biphenyl]-4-yl)-7-oxabicyclo[2.2.1]hept-2-ene-2-carboxamide;

(1R,4S)—N-(2-chloro-[1,1'-biphenyl]-4-yl)-3-(1H-pyrazol-5-yl)-7-oxabicyclo[2.2.1]hept-2-ene-2-carboxamide;

ethyl 5-((1S,2S,3R,4R)-3-((3,4-dichlorophenyl)carbamoyl)-7-oxabicyclo[2.2.1]heptan-2-yl)nicotinate;

(1S,4S)-3-(2-aminopyridin-4-yl)-N-(2,2'-difluoro-[1,1'-biphenyl]-4-yl)-7-oxabicyclo[2.2.1]hept-2-ene-2-carboxamide;

(1S,4S)—N-(2-chloro-[1,1'-biphenyl]-4-yl)-3-(1-(tetrahydro-2H-pyran-4-yl)-1H-pyrazol-5-yl)-7-oxabicyclo[2.2.1]hept-2-ene-2-carboxamide;

(1S,4S)—N-(2-fluoro-3-(trifluoromethoxy)phenyl)-3-(pyridin-4-yl)-7-oxabicyclo[2.2.1]hept-2-ene-2-carboxamide;

(1R,2S,3R,4S)—N-(2,2'-difluoro-[1,1'-biphenyl]-4-yl)-3-(pyridin-4-yl)-7-oxabicyclo[2.2.1]heptane-2-carboxamide;

(1R,2S,3S,4S)—N-(3,4-dichlorophenyl)-3-(pyrimidin-4-yl)-7-oxabicyclo[2.2.1]heptane-2-carboxamide;

methyl 5-chloro-2-((1S,4S)-3-(pyridin-4-yl)-7-oxabicyclo[2.2.1]hept-2-ene-2-carboxamido)benzoate;

(1R,2S,3S,4S)—N-([1,1'-biphenyl]-4-yl)-3-(pyridin-3-yl)-7-oxabicyclo[2.2.1]heptane-2-carboxamide;

(1S,4S)-3-(2-cyanopyridin-4-yl)-N-(2,2'-difluoro-[1,1'-biphenyl]-4-yl)-7-oxabicyclo[2.2.1]hept-2-ene-2-carboxamide;

(1R,2R,3S,4S)—N-([1,1'-biphenyl]-4-yl)-3-(pyridin-3-yl)-7-oxabicyclo[2.2.1]heptane-2-carboxamide;

ethyl 2-morpholino-4-((1R,2S,3R,4S)-3-(pyridin-4-yl)-7-oxabicyclo[2.2.1]heptane-2-carboxamido)benzoate;

(1R,2S,3S,4S)-3-(2-cyanopyridin-4-yl)-N-(3,4-dichlorophenyl)-7-oxabicyclo[2.2.1]heptane-2-carboxamide;

(1R,2R,3R,4S)-3-cyano-N-(2,2'-difluoro-[1,1'-biphenyl]-4-yl)-7-oxabicyclo[2.2.1]heptane-2-carboxamide;

(1S,4S)—N-(5-methyl-1-phenyl-1H-pyrazol-3-yl)-3-(pyridin-4-yl)-7-oxabicyclo[2.2.1]hept-2-ene-2-carboxamide;

(1S,4R)—N-(2,2'-difluoro-[1,1'-biphenyl]-4-yl)-3-(1-(tetrahydro-2H-pyran-4-yl)-1H-pyrazol-5-yl)-7-oxabicyclo[2.2.1]hept-2-ene-2-carboxamide;

(1R,2S,3S,4S)-3-(2-aminopyrimidin-5-yl)-N-(3,4-dichlorophenyl)-7-oxabicyclo[2.2.1]heptane-2-carboxamide;

(1R,2R,3R,4S)-3-(2-aminopyridin-4-yl)-N-(2,2'-difluoro-[1,1'-biphenyl]-4-yl)-7-oxabicyclo[2.2.1]heptane-2-carboxamide;

(1R,2R,3R,4S)—N-(2,2'-difluoro-[1,1'-biphenyl]-4-yl)-3-(2-methyl-2H-indazol-5-yl)-7-oxabicyclo[2.2.1]heptane-2-carboxamide;

(1R,2S,3S,4S)-3-(6-aminopyridin-3-yl)-N-(3,4-dichlorophenyl)-7-oxabicyclo[2.2.1]heptane-2-carboxamide;

ethyl 2-fluoro-4-((1S,4R)-3-(pyridin-4-yl)-7-oxabicyclo[2.2.1]hept-2-ene-2-carboxamido)benzoate;

(1R,2R,3S,4S)-3-(6-acetamidopyridin-3-yl)-N-(3,4-dichlorophenyl)-7-oxabicyclo[2.2.1]heptane-2-carboxamide;

(1R,2R,3S,4S)—N-(3,4-dichlorophenyl)-3-(2-methylpyridin-4-yl)-7-oxabicyclo[2.2.1]heptane-2-carboxamide;

(1R,2S,3R,4S)-3-(pyridin-4-yl)-N-(2,2',4'-trifluoro-[1,1'-biphenyl]-4-yl)-7-oxabicyclo[2.2.1]heptane-2-carboxamide (1R,2R,3S,4S)—N-(3,4-dichlorophenyl)-3-(pyridin-4-yl)-7-oxabicyclo[2.2.1]heptane-2-carboxamide;

(1R,2R,3S,4S)—N-(2,2'-difluoro-[1,1'-biphenyl]-4-yl)-3-(pyridin-4-yl)-7-oxabicyclo[2.2.1]heptane-2-carboxamide;

tert-butyl 4-((1S,2S,3S,4R)-3-((3,4-dichlorophenyl)carbamoyl)-7-oxabicyclo[2.2.1]heptan-2-yl)-5,6-dihydropyridine-1 (2H)-carboxylate;

(1R,2R,3R,4S)—N-([1,1'-biphenyl]-4-yl)-3-(pyridin-4-yl)-7-oxabicyclo[2.2.1]heptane-2-carboxamide;

(1R,2R,4S,5S)—N-(4'-chloro-2'-cyano-2-fluoro-[1,1'-biphenyl]-4-yl)-4-(pyridin-4-yl)-8-oxatricyclo[3.2.1.02,4]octane-2-carboxamide;

(1R,2R,3S,4S)—N-(2'-chloro-2-fluoro-[1,1'-biphenyl]-4-yl)-3-(pyridin-4-yl)-7-oxabicyclo[2.2.1]heptane-2-carboxamide;

(1S,2S,3R,4R)-3-cyano-N-(3,4-dichlorophenyl)-7-oxabicyclo[2.2.1]heptane-2-carboxamide;

(1R,2R,3R,4S)—N-(2,2'-difluoro-[1,1'-biphenyl]-4-yl)-3-(2-(dimethylamino)pyrimidin-5-yl)-7-oxabicyclo[2.2.1]heptane-2-carboxamide;

(1R,2R,4S,5S)—N-([1,1'-biphenyl]-4-yl)-4-(pyridin-4-yl)-8-oxatricyclo[3.2.1.02,4]octane-2-carboxamide;

(1R,2R,3S,4S)—N-(2,2'-difluoro-[1,1'-biphenyl]-4-yl)-3-(pyridin-2-yl)-7-oxabicyclo[2.2.1]heptane-2-carboxamide;

(1R,2S,3S,4S)—N-(3,4-dichlorophenyl)-3-(3,6-dihydro-2H-pyran-4-yl)-7-oxabicyclo[2.2.1]heptane-2-carboxamide;

(1R,2R,3S,4S)—N-(2,2'-difluoro-[1,1'-biphenyl]-4-yl)-3-(1-methyl-3-(trifluoromethyl)-1H-pyrazol-5-yl)-7-oxabicyclo[2.2.1]heptane-2-carboxamide;

(1R,2R,3S,4S)—N-(2-chloro-[1,1'-biphenyl]-4-yl)-3-(6-(trifluoromethyl)pyridin-2-yl)-7-oxabicyclo[2.2.1]heptane-2-carboxamide;

(1R,2S,3S,4S)—N-(2,2'-difluoro-[1,1'-biphenyl]-4-yl)-3-(1-methyl-3-(trifluoromethyl)-1H-pyrazol-5-yl)-7-oxabicyclo[2.2.1]heptane-2-carboxamide;

(1R,2R,4S,5S)—N-(2'-chloro-2-fluoro-[1,1'-biphenyl]-4-yl)-4-(pyridin-4-yl)-8-oxatricyclo[3.2.1.02,4]octane-2-carboxamide;

(1R,2R,3S,4S)—N-(2,2'-difluoro-[1,1'-biphenyl]-4-yl)-3-(6-(trifluoromethyl)pyridin-2-yl)-7-oxabicyclo[2.2.1]heptane-2-carboxamide;

(1R,2R,3R,4S)-3-(2,6-dichloropyridin-4-yl)-N-(2,2'-difluoro-[1,1'-biphenyl]-4-yl)-7-oxabicyclo[2.2.1]heptane-2-carboxamide;

tert-butyl 4-((1S,2S,3R,4R)-3-((3,4-dichlorophenyl)carbamoyl)-7-oxabicyclo[2.2.1]heptan-2-yl)-5,6-dihydropyridine-1 (2H)-carboxylate;

(1R,2R,3S,4S)—N-(3,4-dichlorophenyl)-3-(1-methyl-3-(trifluoromethyl)-1H-pyrazol-5-yl)-7-oxabicyclo[2.2.1]heptane-2-carboxamide;

(1R,2R,4S,5S)—N-(2-chloro-[1,1'-biphenyl]-4-yl)-4-(pyridin-4-yl)-8-oxatricyclo[3.2.1.02,4]octane-2-carboxamide;

(1R,2R,3S,4S)-3-(2-aminopyridin-4-yl)-N-(2,2'-difluoro-[1,1'-biphenyl]-4-yl)-7-oxabicyclo[2.2.1]heptane-2-carboxamide;

(1R,2R,3S,4S)—N-(3,4-dichlorophenyl)-3-(6-(trifluoromethyl)pyridin-2-yl)-7-oxabicyclo[2.2.1]heptane-2-carboxamide;

(1R,2R,3R,4S)—N-(2,2'-difluoro-[1,1'-biphenyl]-4-yl)-1,4-dimethyl-3-(pyridin-4-yl)-7-oxabicyclo[2.2.1]heptane-2-carboxamide;

(1R,2R,3S,4S)—N-(3,4-dichlorophenyl)-3-(1,2,3,6-tetrahydropyridin-4-yl)-7-oxabicyclo[2.2.1]heptane-2-carboxamide;

(1R,2R,3R,4S)-3-(3-chloro-2-fluoropyridin-4-yl)-N-(2,2'-difluoro-[1,1'-biphenyl]-4-yl)-7-oxabicyclo[2.2.1]heptane-2-carboxamide;

(1R,2R,4S,5S)—N-(2-chloro-2'-fluoro-[1,1'-biphenyl]-4-yl)-4-(pyridin-4-yl)-8-oxatricyclo[3.2.1.02,4]octane-2-carboxamide;

(1S,4S)-3-(3-chloro-2-fluoropyridin-4-yl)-N-(2,2'-difluoro-[1,1'-biphenyl]-4-yl)-7-oxabicyclo[2.2.1]hept-2-ene-2-carboxamide;

(1R,2R,3S,4S)—N-(2-chloro-[1,1'-biphenyl]-4-yl)-3-(pyridin-4-yl)-7-oxabicyclo[2.2.1]heptane-2-carboxamide;

(1R,2R,3S,4S)-3-(2-chloropyridin-4-yl)-N-(3,4-dichlorophenyl)-7-oxabicyclo[2.2.1]heptane-2-carboxamide;

(1R,2R,3S,4S)—N-(2-chloro-[1,1'-biphenyl]-4-yl)-3-(1-methyl-3-(trifluoromethyl)-1H-pyrazol-5-yl)-7-oxabicyclo[2.2.1]heptane-2-carboxamide;

(1S,2R,3R,4R)-3-cyano-N-(2,2'-difluoro-[1,1'-biphenyl]-4-yl)-7-oxabicyclo[2.2.1]heptane-2-carboxamide;

(1R,2S,3S,4S)-3-(pyridin-4-yl)-N-(2,2',4'-trifluoro-[1,1'-biphenyl]-4-yl)-7-oxabicyclo[2.2.1]heptane-2-carboxamide;

(1S,2S,3R,4R)—N-(3,4-dichlorophenyl)-3-(pyridin-4-yl)-7-oxabicyclo[2.2.1]heptane-2-carboxamide;

(1R,2S,3S,4S)—N-(2-chloro-[1,1'-biphenyl]-4-yl)-3-(pyridin-4-yl)-7-oxabicyclo[2.2.1]heptane-2-carboxamide;

ethyl 4-((1R,2R,3S,4S)-3-(pyridin-4-yl)-7-oxabicyclo[2.2.1]heptane-2-carboxamido)benzoate;

(1R,2R,3S,4S)-3-(2-aminopyridin-4-yl)-N-(2-chloro-[1,1'-biphenyl]-4-yl)-7-oxabicyclo[2.2.1]heptane-2-carboxamide;

(1R,2R,3S,4S)-3-(2-aminopyridin-4-yl)-N-(3,4-dichlorophenyl)-7-oxabicyclo[2.2.1]heptane-2-carboxamide;

(1R,2R,4S,5S)—N-(3,4-dichlorophenyl)-4-(pyridin-4-yl)-8-oxatricyclo[3.2.1.02,4]octane-2-carboxamide;

(1S,4S)—N-(2,2'-difluoro-[1,1'-biphenyl]-4-yl)-3-(3-fluoropyridin-4-yl)-7-oxabicyclo[2.2.1]hept-2-ene-2-carboxamide;

(1R,2S,3S,4S)-3-(2-aminopyridin-4-yl)-N-(2-chloro-[1,1'-biphenyl]-4-yl)-7-oxabicyclo[2.2.1]heptane-2-carboxamide;

(1R,2R,3S,4S)-3-(pyridin-4-yl)-N-(2,2',4'-trifluoro-[1,1'-biphenyl]-4-yl)-7-oxabicyclo[2.2.1]heptane-2-carboxamide;

(1R,2R,4S,5S)—N-(2,2'-difluoro-[1,1'-biphenyl]-4-yl)-4-(pyridin-4-yl)-8-oxatricyclo[3.2.1.02,4]octane-2-carboxamide;

(1R,2R,4S,5S)—N-(2'-chloro-2-cyano-[1,1'-biphenyl]-4-yl)-4-(pyridin-4-yl)-8-oxatricyclo[3.2.1.02,4]octane-2-carboxamide;

(1R,2S,3S,4S)-3-(2-aminopyridin-4-yl)-N-(3,4-dichlorophenyl)-7-oxabicyclo[2.2.1]heptane-2-carboxamide;

(1R,4S)-3-(2,6-dichloropyridin-4-yl)-N-(2,2'-difluoro-[1,1'-biphenyl]-4-yl)-7-oxabicyclo[2.2.1]hept-2-ene-2-carboxamide;

(1R,2R,3S,4S)—N-(3,4-dichlorophenyl)-3-(3,6-dihydro-2H-pyran-4-yl)-7-oxabicyclo[2.2.1]heptane-2-carboxamide;

ethyl 4-((1R,2S,3S,4S)-3-(2-aminopyridin-4-yl)-7-oxabicyclo[2.2.1]heptane-2-carboxamido)benzoate;

(1R,2R,3S,4S)—N-([1,1'-biphenyl]-4-yl)-3-(pyridin-4-yl)-7-oxabicyclo[2.2.1]heptane-2-carboxamide;

(1S,2S,3S,4R)—N-([1,1'-biphenyl]-4-yl)-3-(pyridin-3-yl)-7-oxabicyclo[2.2.1]heptane-2-carboxamide;

(1S,2S,3S,4R)—N-([1,1'-biphenyl]-4-yl)-3-(1-methyl-1H-pyrazol-3-yl)-7-oxabicyclo[2.2.1]heptane-2-carboxamide;

(1S,2S,3S,4R)—N-(2'-chloro-2-fluoro-[1,1'-biphenyl]-4-yl)-3-(6-(trifluoromethyl)pyridin-2-yl)-7-oxabicyclo[2.2.1]heptane-2-carboxamide;

(1R,2S,3R,4S)—N-(1-methylpiperidin-4-yl)-3-(pyridin-4-yl)-7-oxabicyclo[2.2.1]heptane-2-carboxamide;

(1R,2R,3R,4S)—N-(2-fluoro-3-(trifluoromethyl)phenyl)-3-((2R)-6-(trifluoromethyl)piperidin-2-yl)-7-oxabicyclo[2.2.1]heptane-2-carboxamide;

ethyl 4-((1S,2S,3R,4S)-3-(1-methyl-3-(trifluoromethyl)-1H-pyrazol-5-yl)-7-oxabicyclo[2.2.1]heptane-2-carboxamido)benzoate;

ethyl 3-((1R,2S,3R,4S)-3-(pyridin-4-yl)-7-oxabicyclo[2.2.1]heptane-2-carboxamido)benzoate;

(1R,2S,3R,4S)—N-(2-fluoro-3-(trifluoromethoxy)phenyl)-3-(4-methylpyridin-2-yl)-7-oxabicyclo[2.2.1]heptane-2-carboxamide;

ethyl 4-((1S,4S)-3-(6-(trifluoromethyl)pyridin-2-yl)-7-oxabicyclo[2.2.1]hept-2-ene-2-carboxamido)benzoate;

(1S,4S)—N-(2-fluoro-3-(trifluoromethyl)phenyl)-3-(1-methyl-3-(trifluoromethyl)-1H-pyrazol-5-yl)-7-oxabicyclo[2.2.1]hept-2-ene-2-carboxamide;

(1S,2S,3R,4S)—N-(1-(methylsulfonyl)piperidin-4-yl)-3-(pyridin-4-yl)-7-oxabicyclo[2.2.1]heptane-2-carboxamide;

methyl 5-chloro-2-((1S,2S,3R,4S)-3-(pyridin-4-yl)-7-oxabicyclo[2.2.1]heptane-2-carboxamido)benzoate;

(1S,2S,3R,4S)-3-(pyridin-4-yl)-N-(3-(trifluoromethoxy)phenyl)-7-oxabicyclo[2.2.1]heptane-2-carboxamide;

(1R,2S,3R,4S)—N-(3,4-dichlorophenyl)-3-(1-methyl-3-(trifluoromethyl)-1H-pyrazol-5-yl)-7-oxabicyclo[2.2.1]heptane-2-carboxamide;

(1R,2R,3R,4S)—N-(3,4-dichlorophenyl)-3-(pyridin-4-yl)-7-oxabicyclo[2.2.1]heptane-2-carboxamide;

(1R,4S)—N-(3,4-dichlorophenyl)-3-(6-(trifluoromethyl)pyridin-2-yl)-7-oxabicyclo[2.2.1]hept-2-ene-2-carboxamide;

(1S,4S)—N-(2,2'-difluoro-[1,1'-biphenyl]-4-yl)-3-(1-methyl-3-(trifluoromethyl)-1H-pyrazol-5-yl)-7-oxabicyclo[2.2.1]hept-2-ene-2-carboxamide;

methyl 4-fluoro-3-((1S,2S,3R,4S)-3-(pyridin-4-yl)-7-oxabicyclo[2.2.1]heptane-2-carboxamido)benzoate;

(1S,2S,3R,4S)-3-(pyridin-4-yl)-N-(4-(trifluoromethoxy)phenyl)-7-oxabicyclo[2.2.1]heptane-2-carboxamide;

(1S,2R,3R,4S)—N-(3,4-dichlorophenyl)-3-(pyrazin-2-yl)-7-oxabicyclo[2.2.1]heptane-2-carboxamide;

(1R,4S)—N-(3,4-dichlorophenyl)-3-(1-methyl-3-(trifluoromethyl)-1H-pyrazol-5-yl)-7-oxabicyclo[2.2.1]hept-2-ene-2-carboxamide;

ethyl 4-((1R,4S)-3-(1-methyl-3-(trifluoromethyl)-1H-pyrazol-5-yl)-7-oxabicyclo[2.2.1]hept-2-ene-2-carboxamido)benzoate;

(1R,2R,3R,4S)—N-(2,2'-difluoro-[1,1'-biphenyl]-4-yl)-3-(6-(trifluoromethyl)pyridin-2-yl)-7-oxabicyclo[2.2.1]heptane-2-carboxamide;

(1R,4S)—N-(3,4-dichlorophenyl)-3-(pyrazin-2-yl)-7-oxabicyclo[2.2.1]hept-2-ene-2-carboxamide;

(1R,2S,3R,4S)—N-(5-chloro-2-fluorophenyl)-3-(pyridin-4-yl)-7-oxabicyclo[2.2.1]heptane-2-carboxamide;

(1R,2S,3R,4S)—N-(1-acetylpiperidin-4-yl)-3-(pyridin-4-yl)-7-oxabicyclo[2.2.1]heptane-2-carboxamide;

(1R,2S,3R,4S)—N-(4-chloro-3-fluorophenyl)-3-(pyridin-4-yl)-7-oxabicyclo[2.2.1]heptane-2-carboxamide;

(1R,2S,3R,4S)—N-(4-chloro-2-cyanophenyl)-3-(pyridin-4-yl)-7-oxabicyclo[2.2.1]heptane-2-carboxamide;

ethyl 4-((1R,2S,3R,4S)-3-(pyridin-4-yl)-7-oxabicyclo[2.2.1]heptane-2-carboxamido)benzoate;

(1R,4S)—N-(2,2'-difluoro-[1,1'-biphenyl]-4-yl)-3-(6-(trifluoromethyl)pyridin-2-yl)-7-oxabicyclo[2.2.1]hept-2-ene-2-carboxamide;

ethyl 4-((1R,2S,3R,4S)-3-(5-methoxypyridin-2-yl)-7-oxabicyclo[2.2.1]heptane-2-carboxamido)benzoate;

(1R,2R,3R,4S)—N-(2-chloro-[1,1'-biphenyl]-4-yl)-3-(1-methyl-3-(trifluoromethyl)-1H-pyrazol-5-yl)-7-oxabicyclo[2.2.1]heptane-2-carboxamide;

(1R,2R,3R,4S)—N-(2-fluoro-3-(trifluoromethyl)phenyl)-3-(1-methyl-3-(trifluoromethyl)-1H-pyrazol-5-yl)-7-oxabicyclo[2.2.1]heptane-2-carboxamide;

(1R,2R,3R,4S)—N-(2-fluoro-3-(trifluoromethoxy)phenyl)-3-(4-methylpyridin-2-yl)-7-oxabicyclo[2.2.1]heptane-2-carboxamide;

(1R,2R,3R,4S)—N-(3,4-dichlorophenyl)-3-(6-(trifluoromethyl)pyridin-2-yl)-7-oxabicyclo[2.2.1]heptane-2-carboxamide;

(1R,2R,3R,4S)—N-(3,4-dichlorophenyl)-3-(1-methyl-3-(trifluoromethyl)-1H-pyrazol-5-yl)-7-oxabicyclo[2.2.1]heptane-2-carboxamide;

(1R,4S)—N-(2-fluoro-3-(trifluoromethyl)phenyl)-3-(6-(trifluoromethyl)pyridin-2-yl)-7-oxabicyclo[2.2.1]hept-2-ene-2-carboxamide;

ethyl 4-((1R,2R,3R,4S)-3-(1-methyl-3-(trifluoromethyl)-1H-pyrazol-5-yl)-7-oxabicyclo[2.2.1]heptane-2-carboxamido)benzoate;

(1R,2S,3R,4S)—N-cyclohexyl-3-(pyridin-4-yl)-7-oxabicyclo[2.2.1]heptane-2-carboxamide;

(1R,4S)—N-(2-chloro-[1,1'-biphenyl]-4-yl)-3-(6-(trifluoromethyl)pyridin-2-yl)-7-oxabicyclo[2.2.1]hept-2-ene-2-carboxamide;

(1R,2S,3R,4S)—N-(5-chloro-4-methylpyridin-2-yl)-3-(pyridin-4-yl)-7-oxabicyclo[2.2.1]heptane-2-carboxamide;

(1R,2S,3R,4S)—N-(3,4-dichlorophenyl)-3-(pyridin-4-yl)-7-oxabicyclo[2.2.1]heptane-2-carboxamide;

(1R,2S,3R,4S)—N-(2,3-dihydrobenzo[b][1,4]dioxin-5-yl)-3-(pyridin-4-yl)-7-oxabicyclo[2.2.1]heptane-2-carboxamide;

(1R,4S)—N-(2,2'-difluoro-[1,1'-biphenyl]-4-yl)-3-(pyrazin-2-yl)-7-oxabicyclo[2.2.1]hept-2-ene-2-carboxamide, (1R,2S,3R,4S)—N-(3-chloro-2-fluorophenyl)-3-(pyridin-4-yl)-7-oxabicyclo[2.2.1]heptane-2-carboxamide;

(1R,2R,3R,4S)—N-(2,2'-difluoro-[1,1'-biphenyl]-4-yl)-3-(4-methylpyridin-2-yl)-7-oxabicyclo[2.2.1]heptane-2-carboxamide;

(1R,4S)—N-(2,2'-difluoro-[1,1'-biphenyl]-4-yl)-3-(2-((S)-3-hydroxypyrrolidin-1-yl)pyridin-4-yl)-7-oxabicyclo[2.2.1]hept-2-ene-2-carboxamide;

(1R,2R,3R,4S)—N-(2-fluoro-3-(trifluoromethyl)phenyl)-3-(pyrazin-2-yl)-7-oxabicyclo[2.2.1]heptane-2-carboxamide;

(1R,2S,3R,4S)—N-(3-fluoro-4-(trifluoromethoxy)phenyl)-3-(pyridin-4-yl)-7-oxabicyclo[2.2.1]heptane-2-carboxamide;

(1R,2R,3R,4S)—N-(5-chloropyridin-2-yl)-3-(pyridin-4-yl)-7-oxabicyclo[2.2.1]heptane-2-carboxamide;

(1R,2S,3R,4S)—N-(2,2'-difluoro-[1,1'-biphenyl]-4-yl)-3-(4-methylpyridin-2-yl)-7-oxabicyclo[2.2.1]heptane-2-carboxamide;

(1R,2S,3R,4S)—N-(2-fluoro-3-(trifluoromethoxy)phenyl)-3-(pyridin-4-yl)-7-oxabicyclo[2.2.1]heptane-2-carboxamide;

(1R,2R,3R,4S)—N-(2,2'-difluoro-[1,1'-biphenyl]-4-yl)-3-(1-methyl-3-(trifluoromethyl)-1H-pyrazol-5-yl)-7-oxabicyclo[2.2.1]heptane-2-carboxamide;

(1R,2S,3R,4S)—N-(4-chloropyridin-2-yl)-3-(pyridin-4-yl)-7-oxabicyclo[2.2.1]heptane-2-carboxamide;

ethyl 4-((1R,2R,3R,4S)-3-(pyrazin-2-yl)-7-oxabicyclo[2.2.1]heptane-2-carboxamido)benzoate; and (1R,2S,3R,4S)—N-(4-cyanophenyl)-3-(pyridin-4-yl)-7-oxabicyclo[2.2.1]heptane-2-carboxamide.

16. A pharmaceutical composition comprising a pharmaceutically effective amount of a compound according to claim 1, or a salt, or a stereoisomer thereof, and a pharmaceutically acceptable excipient.

17. The composition according to claim 16 further comprising an agent selected from angiopoietin-like 3 protein (ANGPTL3), oral salmon calcitonin, SD-6010, vitamin D3, collagen hydrolyzate, FGF18, BMP7, rusalatide acetate, avocado soy unsaponifiables, a steroid, and a non-steroidal anti-inflammatory agent (NSAID) and hyaluronic acid.

18. The compound of claim 1, wherein the compound is Example 5 in Table 3, having the formula:

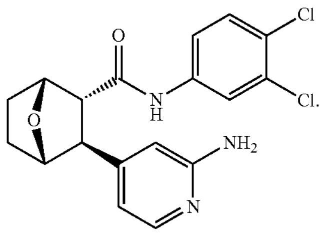 [SMILES: Nc1cc([C@@H]2[C@@H](C(=O)Nc3ccc(Cl)c(Cl)c3)[C@H]3CC[C@@H]2O3)ccn1]

19. The compound of claim 1, wherein the compound is Example 8 in Table 3, having the formula:

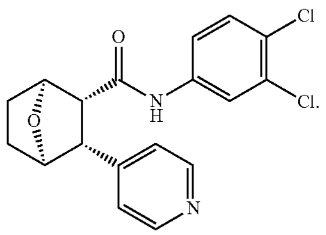 [SMILES: O=C(Nc1ccc(Cl)c(Cl)c1)[C@@H]1[C@H](c2ccncc2)[C@H]2CC[C@@H]1O2]

20. The compound of claim 1, wherein the compound is Example 10 of Table 3, having the formula:

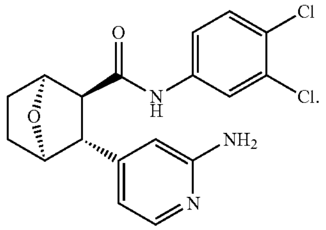 [SMILES: Nc1cc([C@H]2[C@H](C(=O)Nc3ccc(Cl)c(Cl)c3)[C@@H]3CC[C@H]2O3)ccn1]

21. The compound of claim 1, wherein the compound is Example 11 in Table 3, having the formula:

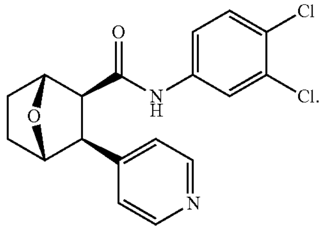 [SMILES: O=C(Nc1ccc(Cl)c(Cl)c1)[C@H]1[C@@H](c2ccncc2)[C@@H]2CC[C@H]1O2]

22. The compound of claim 1, wherein the compounds is Example 21 in Table I, having the formula:

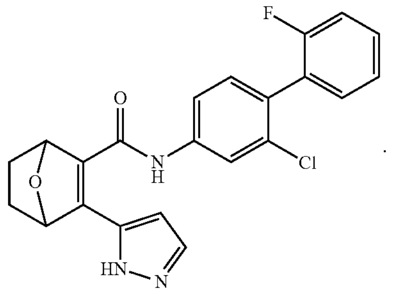 [SMILES: O=C(Nc1ccc(-c2ccccc2F)c(Cl)c1)C1=C(c2ccn[nH]2)C2CCC1O2]

23. The compound of claim 1, wherein the compound is Example 71 in Table 3 having the formula:

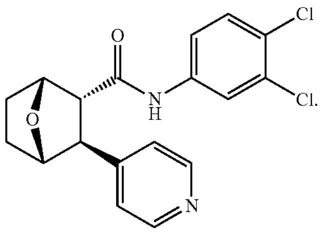 [SMILES: O=C(Nc1ccc(Cl)c(Cl)c1)[C@@H]1[C@@H](c2ccncc2)[C@@H]2CC[C@H]1O2]

24. The compound of claim 1, wherein the compound is Example 103 in Table 3 having the formula:

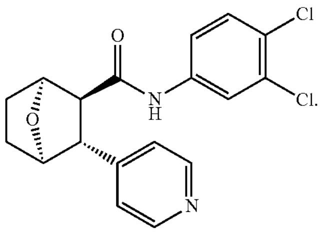 [SMILES: O=C(Nc1ccc(Cl)c(Cl)c1)[C@H]1[C@H](c2ccncc2)[C@H]2CC[C@@H]1O2]

25. The compound of claim 1, wherein the compound is Example 107 in Table 3 having the formula:

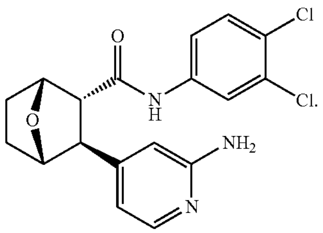 [SMILES: Nc1cc([C@@H]2[C@@H](C(=O)Nc3ccc(Cl)c(Cl)c3)[C@H]3CC[C@@H]2O3)ccn1]

26. The compound of claim 1, wherein the compound is Example 108 in Table 3 having the formula:

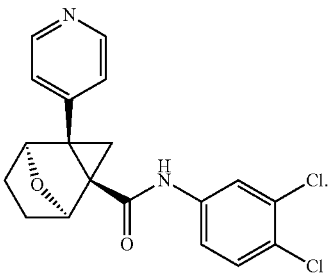 [SMILES: O=C(Nc1ccc(Cl)c(Cl)c1)[C@]12C[C@@]1(c1ccncc1)[C@@H]1CC[C@H]2O1]

27. The compound of claim 1, wherein the compound is Example 118 in Table 3 having the formula:

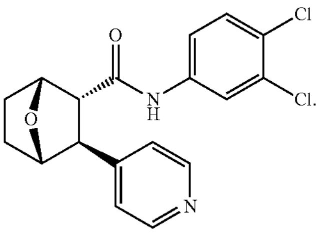 [SMILES: O=C(Nc1ccc(Cl)c(Cl)c1)[C@@H]1[C@@H](c2ccncc2)[C@@H]2CC[C@H]1O2]

28. The compound of claim 1, wherein the compound is Example 164 in Table 3 having the formula:

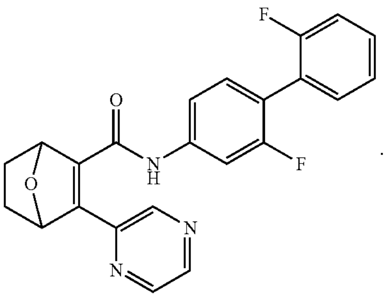 [SMILES: O=C(Nc1ccc(-c2ccccc2F)c(F)c1)C1=C(c2cnccn2)C2CCC1O2]

* * * * *

UNITED STATES PATENT AND TRADEMARK OFFICE

CERTIFICATE OF CORRECTION

PATENT NO. : 9,688,689 B2
APPLICATION NO. : 14/709852
DATED : June 27, 2017
INVENTOR(S) : Ha-Soon Choi et al.

It is certified that error appears in the above-identified patent and that said Letters Patent is hereby corrected as shown below:

In the Claims

In Claim 6, Column 165 Line 39, please delete "$R^3$ to L"; and add --$R^3$ to N--.

In Claim 14, Column 168 Line 59, please delete "$R^3$ to L"; and add --$R^3$ to N--.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*